(12) United States Patent
Bennett et al.

(10) Patent No.: US 7,759,342 B2
(45) Date of Patent: Jul. 20, 2010

(54) METHODS OF TREATMENT AND PREVENTION USING HALOARYL SUBSTITUTED AMINOPURINES

(75) Inventors: Brydon L. Bennett, San Diego, CA (US); Kate Blease, San Diego, CA (US); Brian Edwin Cathers, San Diego, CA (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 0 days.

(21) Appl. No.: 11/708,150

(22) Filed: Feb. 15, 2007

(65) Prior Publication Data

US 2008/0021048 A1 Jan. 24, 2008

Related U.S. Application Data

(63) Continuation-in-part of application No. 11/411,413, filed on Apr. 26, 2006, now Pat. No. 7,521,446, which is a continuation-in-part of application No. 11/332,617, filed on Jan. 12, 2006.

(60) Provisional application No. 60/643,796, filed on Jan. 13, 2005, provisional application No. 60/709,980, filed on Aug. 19, 2005.

(51) Int. Cl.
*A61P 11/00* (2006.01)
*C07D 473/32* (2006.01)
*C07D 239/50* (2006.01)
*C07D 239/48* (2006.01)
*A61K 31/53* (2006.01)
*A61P 3/10* (2006.01)

(52) U.S. Cl. .................. 514/234.2; 514/263.4
(58) Field of Classification Search .............. 514/234.2, 514/263.4

See application file for complete search history.

(56) References Cited

U.S. PATENT DOCUMENTS

| 5,332,744 | A | 7/1994 | Chakravarty et al. | |
|---|---|---|---|---|
| 6,552,192 | B1 | 4/2003 | Hanus et al. | |
| 7,256,196 | B1 | 8/2007 | Sabat et al. | |
| 2003/0187261 | A1 | 10/2003 | Havlicek et al. | |
| 2006/0287344 | A1* | 12/2006 | Albers et al. | 514/263.2 |
| 2007/0060598 | A1* | 3/2007 | Albers et al. | 514/263.23 |

FOREIGN PATENT DOCUMENTS

| WO | WO 00/43394 | 7/2000 |
|---|---|---|
| WO | WO 01/034618 | 5/2001 |
| WO | WO 01/049688 | 7/2001 |
| WO | WO 02/20495 | 3/2002 |
| WO | WO 02/22598 | 3/2002 |
| WO | WO 03/030909 | 4/2003 |
| WO | WO 2006/045828 | 5/2006 |

OTHER PUBLICATIONS

Hind et al. Eur Respir J 2004; 23:20-27.*
MDAdvice.com entry for Asthma <http://www.mdadvice.com/topics/asthma/info/1.htm> downloaded from the internet Jul. 30, 2008.*
Medline Medical Encyclopedia entry for Cystic fibrosis <http://www.nlm.nih.gov/medlineplus/ency/article/000107.htm> downloaded from the internet Jul. 30, 2008.*
Karin et al., Iubmb Life, vol. 57, Issue 4-5 (p. 283-295).*
Kracht, Anti-Inflammatory & Anti-Allergy Agents in Medicinal Chemistry, 2007, 6, 71-84.*
"JNK PAthway" <http://www.ambion.com/tools/pathway/pathway.php?pathway=JNK%20Pathway> Dowloaded from the internet, Nov. 5, 2009.*
Berven et al. *Immunol Cell Biol.* 78(4):447-51 (2000).
Bolen JB. *Oncogene* 8:2025-2031 (1993).
Cohen, *Eur. J. Biochem.*, 268:5001-5010 (2001).
Cohen, *Nature*, 1:309-315 (2002).
Das et al., *Breast Cancer Res. Treat.* 40:141 (1996).
Dutertre et al., *Oncogene* 21:6175-6183 (2002).
Fabbro et al., *Pharmacology & Therapeutics* 93:79-98 (2002).
Frodin and Gammeltoft, *Mol. Cell. Endocrinol.* 151:65-77 (1999).
Gross et al., *J. Biol. Chem.* 276(49): 46099-46103 (2001).
Hartwell et al., *Science*, 246: 629-634 (1989).
Hartwell et al., *Science*, 266: 1821-1828 (1994).
Hu et al., *Cell Growth Differ.* 11:191-200 (2000).
Hunter, *Cell* 100:113-127 (2000).
Kohn, *Mol. Biol. Cell* 10:2703-2734 (1999).
Li et al., *Mol. Cell. Biol.* 16:5947-5954 (1996).
Manoukian et al., *Adv Cancer Res.*;84:203-29, (2002).

(Continued)

*Primary Examiner*—Mark L Berch
(74) *Attorney, Agent, or Firm*—Jones Day

(57) ABSTRACT

Provided herein are Aminopurine Compounds having the following structure:

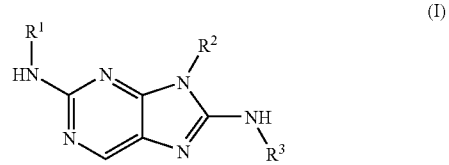

(I)

wherein $R^1$, $R^2$ and $R^3$ are as defined herein, compositions comprising an effective amount of an Aminopurine Compound and methods for treating or preventing cancer, a cardiovascular disease, a renal disease, an autoimmune condition, an inflammatory condition, macular degeneration, ischemia-reperfusion injury, pain and related syndromes, disease-related wasting, an asbestos-related condition, pulmonary hypertension or a condition treatable or preventable by inhibition of the JNK pathway comprising administering an effective amount of an Aminopurine Compound to a patient in need thereof.

7 Claims, No Drawings

OTHER PUBLICATIONS

Martinez et al. *Med Res Rev.*; 22(4):373-84 (2002).
Matter, A., *Drug Discov. Today* 6:1005-1023 (2001).
Morgan Do, *Ann. Rev. Cell Dev Biol.*,13:261-291 (1997).
Nasmyth K., *Science*, 274(5293)::1643-5 (1996).
Nurse, *Cell*, 91: 865-867 (1997).
O'Connor, *Cancer Surveys*, 29: 151-182 (1997).
Ohi and Gould, *Curr. Opin. Cell Biol.* 11:267-273 (1999).
Pap et al., *J. Biol Chem.*, 273(32):19929-32 (1998).
Park et al. *Cell* 101 (7), 777-787 (2000).
Pearson et al., *Prog. Cell Cycle Res.* 1:21-32 (1995).
Peng, et al., *Science* 277:1501-1505 (1997).
Pombo et al., *J. Biol. Chem.* 269:26546-26551 (1994).
Richards et al., *Curr. Biol.* 9:810-820 (1999).
Richards et al., *Mol. Cell. Biol.* 21:7470-7480 (2001).
Riento et al., *Nature Reviews Mol. Cell Biol.* 4:446-456 (2003).
Risau, W., *Nature* 386:671-674 (1997).
Robertson et al., *Trends Genet.* 16:265-271 (2000).
Robinson et al., *Oncogene* 19:5548-5557 (2000).
Sabat et al., *Bioorganic & Medicinal Chemistry Letters* 16:4360-4365 (2006).
Sridhar et al. *Pharmaceutical Research*, 17(11):1345-1353 (2000).
Virkamaki et al., *J. Clin. Invest.* 103:931-943 (1999).
Yang et al., *Immunity* 9(4):575-85 (1998).
Bauer E., *Xenobiotica* 16(7):625-633 (1986).
Gauldie and Kolb, 2008, "Animal models of pulmonary fibrosis: how far from effective reality?" *Am. J. Physiol. Lung Cell. Mol. Physiol.* 294:L151.
Nagase et al., 1999, "Matrix Metalloproteinases," *J. Biol. Chem.* 274(31):21491-21494.
Barnes, P.J., 2004, "Mediators of Chronic Obstructive Pulmonary Disease," *Pharmacol. Rev.* 56:515-548.
Decitre et al., 1998, "Lysyl Oxidase-Like Protein Localizes to Sites of De Novo Fibrinogenesis in Fibrosis and in the Early Stromal Reaction of Ductal Breast Carcinomas," *Laboratory Investigations* 78(2):143-151.
Pierce et al., 1995, "Elastin in lung development and disease," *Ciba Foundation Symposium* 192:199-214.
Cutroneo, K. R., 2003, "How is Type I Procollagen Synthesis Regulated at the Gene Level During Tissue Fibrosis," *J. Cell. Biochem.* 90:1-5.
Redington, A.E., 2000, "Airway fibrosis in asthma: mechanisms, consequences, and potential for therapeutic intervention," *Monaldi Arch. Chest. Dis.* 55(4):317-323.
Sacco et al., 2004, "Epithelial cells and fibroblasts: structural repair and remodelling in the airways," *Paediatr. Respir. Rev. 5 (Suppl. A)*:S35-S40.
Arndt et al., 2005, "Inhibition of c-Jun N-Terminal Kinase Limits Lipopolysaccharide-induced Pulmonary Neutrophil Influx," *Am. J. Respir. Crit. Care Med. 171*:978-986.
Barnes, P. J., 2007, "Molecular mechanisms in allergy and clinical immunology," *J. Allergy Clin. Immunol. 119*(5):1055-1062.
Togbe et al., 2007, "Toll-like receptor and tumour necrosis factor dependent endotoxin-induced acute lung injury," *Int. J. Exp. Path. 88*:387-391.
Underwood et al., 2000, B 239063, a p38 MAPK inhibitor, reduces neutrophilia, inflammatory cytokines, MMP-9, and fibrosis in lung, *Am. J. Physiol. Lung Cell. Mol. Physiol. 279*:L895-L902.

\* cited by examiner

METHODS OF TREATMENT AND PREVENTION USING HALOARYL SUBSTITUTED AMINOPURINES

This application is a continuation-in-part of U.S. application Ser. No. 11/411,413, filed Apr. 26, 2006 now U.S. Pat. No. 7,521,446, which is a continuation-in-part of U.S. application Ser. No. 11/332,617, filed Jan. 12, 2006, which claims the benefit of U.S. provisional application No. 60/643,796, filed Jan. 13, 2005, and U.S. provisional application No. 60/709,980, filed Aug. 19, 2005, the contents of each is incorporated by reference herein in their entirety.

1. FIELD

Provided herein are certain amino-substituted purine compounds, compositions comprising an effective amount of such compounds and methods for treating or preventing cancer, a cardiovascular disease, a renal disease, an autoimmune condition, an inflammatory condition, macular degeneration, ischemia-reperfusion injury, pain and related syndromes, disease-related wasting, an asbestos-related condition, pulmonary hypertension, central nervous system (CNS) injury/damage or a condition treatable or preventable by inhibition of a kinase pathway comprising administering an effective amount of such aminopurine compounds to a patient in need thereof.

2. BACKGROUND

The connection between abnormal protein phosphorylation and the cause or consequence of diseases has been known for over 20 years. Accordingly, protein kinases have become a very important group of drug targets. See Cohen, *Nature*, 1:309-315 (2002). Various protein kinase inhibitors have been used clinically in the treatment of a wide variety of diseases, such as cancer and chronic inflammatory diseases, including diabetes and stroke. See Cohen, *Eur. J. Biochem.*, 268:5001-5010 (2001).

The protein kinases are a large and diverse family of enzymes that catalyze protein phosphorylation and play a critical role in cellular signaling. Protein kinases may exert positive or negative regulatory effects, depending upon their target protein. Protein kinases are involved in specific signaling pathways which regulate cell functions such as, but not limited to, metabolism, cell cycle progression, cell adhesion, vascular function, apoptosis, and angiogenesis. Malfunctions of cellular signaling have been associated with many diseases, the most characterized of which include cancer and diabetes. The regulation of signal transduction by cytokines and the association of signal molecules with protooncogenes and tumor suppressor genes have been well documented. Similarly, the connection between diabetes and related conditions, and deregulated levels of protein kinases, has been demonstrated. See e.g., Sridhar et al. *Pharmaceutical Research*, 17(11):1345-1353 (2000). Viral infections and the conditions related thereto have also been associated with the regulation of protein kinases. Park et al. *Cell* 101 (7), 777-787 (2000).

Protein kinases can be divided into broad groups based upon the identity of the amino acid(s) that they target (serine/threonine, tyrosine, lysine, and histidine). For example, tyrosine kinases include receptor tyrosine kinases (RTKs), such as growth factors and non-receptor tyrosine kinases, such as the src kinase family. There are also dual-specific protein kinases that target both tyrosine and serine/threonine, such as cyclin dependent kinases (CDKs) and mitogen-activated protein kinases (MAPKs). Any particular cell contains many protein kinases, some of which phosphorylate other protein kinases. Some protein kinases phosphorylate many different proteins, others phosphorylate only a single protein. Not surprisingly, there are numerous classes of protein kinases. Upon receiving a signal, some proteins may also undergo auto-phosphorylation.

The protein tyrosine kinases (PTKs) compose a large family of kinases that regulate cell to cell signals involved in growth, differentiation, adhesion, motility, and death. Robinson et al., *Oncogene* 19:5548-5557 (2000). Members of the tyrosine kinase include, but are not limited to, Yes, BMX, Syk, EphA1, FGFR3, RYK, MUSK, JAK1 and EGFR. Tyrosine kinases are distinguished into two classes, i.e., the receptor type and non-receptor type tyrosine kinases. Interestingly, the entire of family of tyrosine kinases is quite large—consisting of at least 90 characterized kinases with at least 58 receptor type and at least 32 nonreceptor type kinases comprising at least 30 total subfamilies. Robinson et al., *Oncogene* 19:5548-5557 (2000). Tyrosine kinases have been implicated in a number of diseases in humans, including diabetes and cancer. Robinson et al. at page 5548. Tyrosine kinases are often involved in most forms of human malignancies and have been linked to a wide variety of congenital syndromes. Robertson et al., *Trends Genet.* 16:265-271 (2000).

The non-receptor tyrosine kinases represent a group of intracellular enzymes that lack extracellular and transmembrane sequences. Currently, over 32 families of non-receptor tyrosine kinases have been identified. Robinson et al., *Oncogene* 19:5548-5557 (2000). Examples are Src, Btk, Csk, ZAP70, Kak families. In particular, the Src family of non-receptor tyrosine kinase family is the largest, consisting of Src, Yes, Fyn, Lyn, Lck, Blk, Hck, Fgr and Yrk protein tyrosine kinases. The Src family of kinases have been linked to oncogenesis, cell proliferation and tumor progression. A detailed discussion of non-receptor protein tyrosine kinases is available in *Oncogene* 8:2025-2031 (1993). Many of these protein tyrosine kinases have been found to be involved in cellular signaling pathways involved in various pathological conditions including but not limited to cancer and hyperproliferative disorders and immune disorders.

The cyclin dependent kinases CDKs represent a group of intracellular enzymes that control progression through the cell cycle and have essential roles in cell proliferation. See Cohen, *Nature*, 1:309-315 (2002). Examples of CDKs include, but are not limited to, cyclin dependent kinase 2 (CDK2), cyclin dependent kinase 7 (CDK7), cyclin dependent kinase 6 (CDK6) and cell division control 2 protein (CDC2). CDKs have been implicated in the regulation of transitions between different phases of the cell cycle, such as the progression from a quiescent stage in $G_1$ (the gap between mitosis and the onset of DNA replication for a new round of cell division) to S (the period of active DNA synthesis), or the progression from $G_2$ to M phase, in which active mitosis and cell division occur. See e.g., the articles compiled in *Science*, vol. 274 (1996), pp. 1643-1677; and *Ann. Rev. Cell Dev Biol.*, vol. 13 (1997), pp. 261-291. CDK complexes are formed through association of a regulatory cyclin subunit (e.g., cyclin A, B1, B2, D1, D2, D3, and E) and a catalytic kinase subunit (e.g., cdc2 (CDK1), CDK2, CDK4, CDK5, and CDK6). As the name implies, CDKs display an absolute dependence on the cyclin subunit in order to phosphorylate their target substrates, and different kinase/cyclin pairs function to regulate progression through specific portions of the cell cycle. CDKs have been implicated in various disease states, including but not limited to, those displaying the cancer phenotype, various neoplastic disorders and in neurological disorders. Hunter, *Cell* 100:113-127 (2000).

The mitogen activated protein (MAP) kinases participate in the transduction of signals to the nucleus of the cell in response to extracellular stimuli. Examples of MAP kinases include, but are not limited to, mitogen activated protein kinase 3 (MAPK3), mitogen-activated protein kinase 1 (ERK2), mitogen-activated protein kinase 7 (MAPK7), mitogen-activated protein kinase 8 (JNK1), mitogen-activated protein kinase 14 (p38 alpha), mitogen-activated protein kinase 10 (MAPK10), JNK3 alpha protein kinase, stress-activated protein kinase JNK2 and mitogen-activated protein kinase 14 (MAPK14). MAP kinases are a family of proline-directed serine/threonine kinases that mediate signal transduction from extracellular receptors or heath shock, or UV radiation. See Sridhar et al., *Pharmaceutical Research,* 17:11 1345-1353 (2000). MAP kinases activate through the phosphorylation of theonine and tyrosine by dual-specificity protein kinases, including tyrosine kinases such as growth factors. Cell proliferation and differentiation have been shown to be under the regulatory control of multiple MAP kinase cascades. See Sridhar et al., *Pharmaceutical Research,* 17:11 1345-1353 (2000). As such, the MAP kinase pathway plays critical roles in a number of disease states. For example, defects in activities of MAP kinases have been shown to lead to aberrant cell proliferation and carcinogenesis. See Hu et al., *Cell Growth Differ.* 11:191-200 (2000); and Das et al., *Breast Cancer Res. Treat.* 40:141 (1996). Moreover, MAP kinase activity has also been implicated in insulin resistance associated with type-2 diabetes. See Virkamaki et al., *J. Clin. Invest.* 103:931-943 (1999).

The p90 ribosomal S6 kinases (Rsk) are serine/threonine kinases. The Rsk family members function in mitogen-activated cell growth and proliferation, differentiation, and cell survival. Examples of members of the Rsk family of kinases include, but are not limited to, ribosomal protein S6 kinase, 90 kDa, polypeptide 2 (Rsk3), ribosomal protein S6 kinase, 90 kDa, polypeptide 6 (Rsk4), ribosomal protein S6 kinase, 90 kDa, polypeptide 3 (Rsk2) and ribosomal protein S6 kinase, 90 kDa, polypeptide 1 (Rsk1/p90Rsk). The Rsk family members are activated by extracellular signal-related kinases 1/2 and phosphoinositide-dependent protein kinase 1. Frodin and Gammeltoft, *Mol. Cell. Endocrinol.* 151:65-77 (1999). Under basal conditions, RSK kinases are localized in the cytoplasm of cells and upon stimulation by mitogens, the activated (phosphorylated by extracellular-related kinase) RSK transiently translocates to the plasma membrane where they become fully activated. The fully activated RSK phosphorylates substrates that are involved in cell growth, proliferation, differentiation, and cell survival. Richards et al., *Curr. Biol.* 9:810-820 (1999); Richards et al., *Mol. Cell. Biol.* 21:7470-7480 (2001). RSK signaling pathways have also been associated with the modulation of the cell cycle. Gross et al., *J. Biol. Chem.* 276(49): 46099-46103 (2001). Current data suggests that small molecules that inhibit Rsk may be useful therapeutic agents for the prevention and treatment of cancer and inflammatory diseases.

Members of the checkpoint protein kinase family are serine/threonine kinases that play an important role in cell cycle progression. Examples of members of the checkpoint family include, but are not limited to, CHK1 and CHK2. Checkpoints are control systems that coordinate cell cycle progression by influencing the formation, activation and subsequent inactivation of the cyclin-dependent kinases. Checkpoints prevent cell cycle progression at inappropriate times, maintain the metabolic balance of cells while the cell is arrested, and in some instances can induce apoptosis (programmed cell death) when the requirements of the checkpoint have not been met. See e.g., O'Connor, *Cancer Surveys,* 29: 151-182 (1997); Nurse, *Cell,* 91: 865-867 (1997); Hartwell et al., *Science,* 266: 1821-1828 (1994); Hartwell et al., *Science,* 246: 629-634 (1989). Members of the checkpoint family of kinases have been implicated in cell proliferative disorders, cancer phenotypes and other diseases related to DNA damage and repair. Kohn, *Mol. Biol. Cell* 10:2703-2734 (1999); Ohi and Gould, *Curr. Opin. Cell Biol.* 11:267-273 (1999); Peng, et al., *Science* 277:1501-1505 (1997).

Aurora kinases are a family of multigene mitotic serine-threonine kinases that functions as a class of novel oncogenes. These kinases comprise aurora-A and aurora-B members. Aurora kinases are hyperactivated and/or overexpressed in several solid tumors including but not limited to, breast, ovary, prostate, pancreas, and colorectal cancers. In particular aurora-A is a centrosome kinase that plays an important role cell cycle progression and cell proliferation. Aurora-A is located in the 20q13 chromosome region that is frequently amplified in several different types of malignant tumors such as colorectal, breast and bladder cancers. There is also a high correlation between aurora-A and high histo-prognostic grade aneuploidy, making the kinase a potential prognostic vehicle. Inhibition of aurora kinase activity could help to reduce cell proliferation, tumor growth and potentially tumorigenesis. A detailed description of aurora kinase function is reviewed in *Oncogene* 21:6175-6183 (2002).

The Rho-associated coiled-coil-containing protein serine/threonine kinases ROCK-I and ROCK-II are thought to play a major role in cytoskeletal dynamics by serving as downstream effectors of the Rho/Rac family of cytokine- and growth factor-activated small GTPases. ROCKs phosphorylate various substrates, including, but not limited to, myosin light chain phosphatase, myosin light chain, ezrin-radixin-moesin proteins and LIM (for Lin11, Isl1 and Mec3) kinases. ROCKs also mediate the formation of actin stress fibers and focal adhesions in various cell types. ROCKs have an important role in cell migration by enhancing cell contractility. They are required for tail retraction of monocytes and cancer cells, and a ROCK inhibitor has been used to reduce tumor-cell dissemination in vivo. Recent experiments have defined new functions of ROCKs in cells, including centrosome positioning and cell-size regulation, which might contribute to various physiological and pathological states. See *Nature Reviews Mol. Cell. Biol.* 4, 446-456 (2003). The ROCK family members are attractive intervention targets for a variety of pathologies, including cancer and cardiovascular disease. For example, Rho kinase inhibitors can be useful therapeutic agents for hypertension, angina pectoris, and asthma. Furthermore, Rho is expected to play a role in peripheral circulation disorders, arteriosclerosis, inflammation, and autoimmune disease and as such, is a useful target for therapy.

The 70 kDa ribosomal S6 kinase (p70S6K) is activated by numerous mitogens, growth factors and hormones. Activation of p70S6K occurs through phosphorylation at a number of sites and the primary target of the activated kinase is the 40S ribosomal protein S6, a major component of the machinery involved in protein synthesis in mammalian cells. In addition to its involvement in regulating translation, p70S6K activation has been implicated in cell cycle control, neuronal cell differentiation, regulation of cell motility and a cellular response that is important in tumor metastases, immunity and tissue repair. Modulation of p70S6 kinase activity may have therapeutic implications in disorders such as cancer, inflammation, and various neuropathies. A detailed discussion of p70S6K kinases can be found in *Prog. Cell Cycle Res.* 1:21-32 (1995), and *Immunol Cell Biol.* 78(4):447-51 (2000).

Glycogen synthase kinase 3 (GSK-3) is a ubiquitously expressed constitutively active serine/threonine kinase that phosphorylates cellular substrates and thereby regulates a wide variety of cellular functions, including development, metabolism, gene transcription, protein translation, cytoskeletal organization, cell cycle regulation, and apoptosis. GSK-3 was initially described as a key enzyme involved in glycogen metabolism, but is now known to regulate a diverse array of cell functions. Two forms of the enzyme, GSK-3α and GSK-3β, have been previously identified. The activity of GSK-3β is negatively regulated by protein kinase B/Akt and by the Wnt signaling pathway. Small molecules inhibitors of GSK-3 may, therefore, have several therapeutic uses, including the treatment of neurodegenerative diseases, diabetes type II, bipolar disorders, stroke, cancer, and chronic inflammatory disease. Reviewed in Role of glycogen synthase kinase-3 in cancer: regulation by Wnts and other signaling pathways (*Adv Cancer Res.;* 84:203-29, 2002); Glycogen synthase kinase 3 (GSK-3) inhibitors as new promising drugs for diabetes, neurodegeneration, cancer, and inflammation (*Med Res Rev.;* 22(4):373-84, 2002); Role of glycogen synthase kinase-3 in the phosphatidylinositol 3-Kinase/Akt cell survival pathway. (*J. Biol. Chem.,* 273(32):19929-32, 1998).

Because protein kinases regulate nearly every cellular process, including metabolism, cell proliferation, cell differentiation, and cell survival, they are attractive targets for therapeutic intervention for various disease states. For example, cell-cycle control and angiogenesis, in which protein kinases play a pivotal role are cellular processes associated with numerous disease conditions such as but not limited to cancer, inflammatory diseases, abnormal angiogenesis and diseases related thereto, atherosclerosis, macular degeneration, diabetes, obesity, and pain.

Protein kinases have become attractive targets for the treatment of cancers. Fabbro et al., *Pharmacology & Therapeutics* 93:79-98 (2002). It has been proposed that the involvement of protein kinases in the development of human malignancies may occur, by: (1) genomic rearrangements (e.g., BCR-ABL in chronic myelogenous leukemia), (2) mutations leading to constitutively active kinase activity, such as acute myelogenous leukemia and gastrointestinal tumors, (3) deregulation of kinase activity by activation of oncogenes or loss of tumor suppressor functions, such as in cancers with oncogenic RAS, (4) deregulation of kinase activity by over-expression, as in the case of EGFR and (5) ectopic expression of growth factors that can contribute to the development and maintenance of the neoplastic phenotype. Fabbro et al., *Pharmacology & Therapeutics* 93:79-98 (2002).

Certain cancers are associated with angiogenesis. Angiogenesis is the growth of new capillary blood vessels from pre-existing vasculature. Risau, W., *Nature* 386:671-674 (1997). It has been shown that protein kinases can contribute to the development and maintenance of the neoplastic phenotype. Fabbro et al., *Pharmacology & Therapeutics* 93:79-98 (2002). For example, VEGF A-D and their four receptors have been implicated in phenotypes that involve neovascularization and enhanced vascular permeability, such as tumor angiogenesis and lymphangiogenesis. Matter, A., *Drug Discov. Today* 6:1005-1023 (2001).

Cardiovascular disease ("CVD") accounts for nearly one quarter of total annual deaths worldwide. Vascular disorders such as atherosclerosis and restenosis result from dysregulated growth of the vessel walls and the restriction of blood flow to vital organs. Various kinase pathways, e.g. JNK, are activated by atherogenic stimuli and regulated through local cytokine and growth factor production in vascular cells. Yang et al., *Immunity* 9:575 (1998). Ischemia and ischemia coupled with reperfusion in the heart, kidney or brain result in cell death and scar formation, which can ultimately lead to congestive heart failure, renal failure or cerebral dysfunction. In organ transplantation, reperfusion of previously ischemic donor organs results in acute leukocyte-mediated tissue injury and delay of graft function. Ischemia and reperfusion pathways are mediated by various kinases. For example, the JNK pathway has been linked to leukocyte-mediated tissue damage. Li et al., *Mol. Cell. Biol.* 16:5947-5954 (1996). Finally, enhanced apoptosis in cardiac tissues has also been linked to kinase activity. Pombo et al., *J. Biol. Chem.* 269:26546-26551 (1994).

The elucidation of the intricacy of protein kinase pathways and the complexity of the relationship and interaction among and between the various protein kinases and kinase pathways highlights the importance of developing pharmaceutical agents capable of acting as protein kinase modulators, regulators or inhibitors that have beneficial activity on multiple kinases or multiple kinase pathways.

It has therefore been suggested that due to the complexity of intracellular signaling cascades of protein kinase pathways, agents that affect multiple pathways simultaneously may be required for meaningful clinical activity. Indeed, it is known that some kinase drugs, such as Gleevec®, do target several kinases at once. Gleevec® primarily targets a mutant fusion protein containing the abl kinase, which is created by a 9:22 chromosomal translocation event; Gleevec® also targets c-kit, a tyrosine kinase implicated in gastrointestinal stromal tumors (GIST). However, in recent clinical trials, patients have developed resistance to Gleevec® or have shown incomplete response to treatment.

Accordingly, there remains a need for new kinase modulators.

Citation or identification of any reference in Section 2 of this application is not to be construed as an admission that the reference is prior art to the present application.

3. SUMMARY

Provided herein are compounds having the following formula (I):

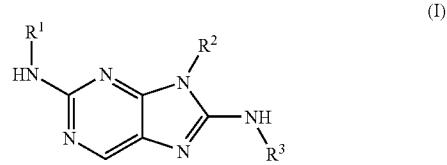

and pharmaceutically acceptable salts, polymorphs, clathrates, solvates, hydrates, stereoisomers and prodrugs thereof, wherein $R^1$, $R^2$ and $R^3$ are as defined herein.

A compound of formula (I) or a pharmaceutically acceptable salt, clathrate, solvate, hydrate, stereoisomer or prodrug thereof (each being referred to herein as an "Aminopurine Compound") is useful for treating or preventing cancer, a cardiovascular disease, a renal disease, an autoimmune condition, an inflammatory condition, macular degeneration, ischemia-reperfusion injury, pain and related syndromes, disease-related wasting, an asbestos-related condition, pulmonary hypertension, central nervous system (CNS) injury/damage or a condition treatable or preventable by inhibition of a kinase pathway, in one embodiment, the JNK pathway.

Further provided herein are compositions comprising an effective amount of an Aminopurine Compound and compositions comprising an effective amount of an Aminopurine Compound and a pharmaceutically acceptable carrier or vehicle. The compositions are useful for treating or preventing cancer, a cardiovascular disease, a renal disease, an autoimmune condition, an inflammatory condition, macular degeneration, ischemia-reperfusion injury, pain and related syndromes, disease-related wasting, an asbestos-related condition, pulmonary hypertension, central nervous system (CNS) injury/damage or a condition treatable or preventable by inhibition of a kinase pathway, in one embodiment, the JNK pathway.

Further provided herein are methods for treating or preventing cancer, a cardiovascular disease, a renal disease, an inflammatory condition, a metabolic condition, an autoimmune condition, macular degeneration, ischemia-reperfusion injury, pain and related syndromes, disease-related wasting, an asbestos-related condition, pulmonary hypertension, central nervous system (CNS) injury/damage or a condition treatable or preventable by inhibition of a kinase pathway, in one embodiment, the JNK pathway, comprising administering an effective amount of an Aminopurine Compound to a patient in need of the treating or preventing.

In one embodiment, the Aminopurine Compound targets two or more of the following: kinases from the src kinase family, kinases from the Rsk kinase family, kinases from the CDK family, kinases from the MAPK kinase family, and tyrosine kinases such as Fes, Lyn, and Syk kinases. The agent may target two or more kinases of the same family, or may target kinases representing two or more kinase families or classes.

Further provided herein are stents (e.g., stent graft) containing or coated with an amount of an Aminopurine Compound effective for treating or preventing a cardiovascular disease or renal disease.

The present embodiments can be understood more fully by reference to the detailed description and examples, which are intended to exemplify non-limiting embodiments.

4. DETAILED DESCRIPTION

4.1 Definitions

A "$C_{1-6}$alkyl" group is a saturated straight chain or branched non-cyclic hydrocarbon having from 1 to 6 carbon atoms. Representative—($C_{1-6}$alkyls) include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, 2-methylpentyl, 3-methylpentyl, 4-methylpentyl, 2,3-dimethylbutyl and the like. A —($C_{1-6}$alkyl) group can be substituted or unsubstituted.

An "alkoxy" group is an —O—($C_{1-6}$alkyl) group, wherein $C_{1-6}$alkyl is defined above, including —OCH$_3$, —OCH$_2$CH$_3$, —O(CH$_2$)$_2$CH$_3$, —O(CH$_2$)$_3$CH$_3$, —O(CH$_2$)$_4$CH$_3$, —O(CH$_2$)$_5$CH$_3$, and the like.

An "alkoxyalkyl" group is a —($C_{1-6}$alkylene)-O—($C_{1-6}$alkyl) group, wherein each $C_{1-6}$alkyl is independently a $C_{1-6}$alkyl group defined above, including —CH$_2$OCH$_3$, —CH$_2$OCH$_2$CH$_3$, —(CH$_2$)$_2$OCH$_2$CH$_3$, —(CH$_2$)$_2$O(CH$_2$)$_2$CH$_3$, and the like.

An "alkylamino" group is a mono-alkylamino or di-alkylamino group, such as —NH($C_{1-6}$alkyl), —N($C_{1-6}$alkyl)($C_{1-6}$alkyl), —NH($C_{3-10}$cycloalkyl), —N($C_{3-10}$cycloalkyl)($C_{3-10}$cycloalkyl) or —N($C_{1-6}$alkyl)($C_{3-10}$cycloalkyl) wherein each $C_{1-6}$alkyl and $C_{3-10}$cycloalkyl is independently as defined herein, including, but not limited to, —NHCH$_3$, —NHCH$_2$CH$_3$, —NH(CH$_2$)$_2$CH$_3$, —NH(CH$_2$)$_3$CH$_3$, —NH(CH$_2$)$_4$CH$_3$, —NH(CH$_2$)$_5$CH$_3$, —N(CH$_3$)$_2$, —N(CH$_2$CH$_3$)$_2$, —N((CH$_2$)$_2$CH$_3$)$_2$, and —N(CH$_3$)(CH$_2$CH$_3$).

An "aminocarbonyl" group is a —C(O)NR$_2$ group, wherein each R is independently hydrogen or a $C_{1-6}$alkyl group defined above, wherein each $C_{1-6}$alkyl group can be optionally substituted.

An "acylamino" group is a —NHC(O)R group, wherein R is independently hydrogen or a $C_{1-6}$alkyl group defined above, wherein each $C_{1-6}$alkyl group can be optionally substituted.

An "aminoalkyl" group is a $C_{1-6}$alkyl group substituted with one or more NR$_2$ groups, wherein R is hydrogen or a $C_{1-6}$alkyl group defined above, wherein each $C_{1-6}$alkyl group can be optionally further substituted.

An "alkanesulfonylamino" group is a —NR—SO$_2$—C$_{1-6}$ alkyl group, wherein R is hydrogen or a $C_{1-6}$alkyl group defined above, wherein each $C_{1-6}$alkyl group can be optionally substituted.

A "$C_{3-10}$cycloalkyl" group is a cyclic alkyl group of from 3 to 10 carbon atoms having a single cyclic ring or multiple condensed or bridged rings which can be optionally substituted with from 1 to 3 alkyl groups. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as adamantanyl and the like. A —($C_{3-10}$cycloalkyl) group can be substituted or unsubstituted. Such substituted cycloalkyl groups include, by way of example, cyclohexanone and the like.

A "carboxyl" or "carboxy" is a —COOH group.

A "halogen" is fluorine, chlorine, bromine or iodine.

An "aryl" group is an unsaturated aromatic carbocyclic group of from 6 to 14 carbon atoms having a single ring (e.g., phenyl) or multiple condensed rings (e.g., naphthyl or anthryl). Particular aryls include phenyl, biphenyl, naphthyl and the like. An aryl group can be substituted or unsubstituted.

A "$C_{3-10}$heteroaryl" group is an aryl ring system having one to four heteroatoms as ring atoms in a heteroaromatic ring system, wherein the remainder of the atoms are carbon atoms. Suitable heteroatoms include oxygen, sulfur and nitrogen. In certain embodiments, the heterocyclic ring system is monocyclic or bicyclic. Non-limiting examples include the following:

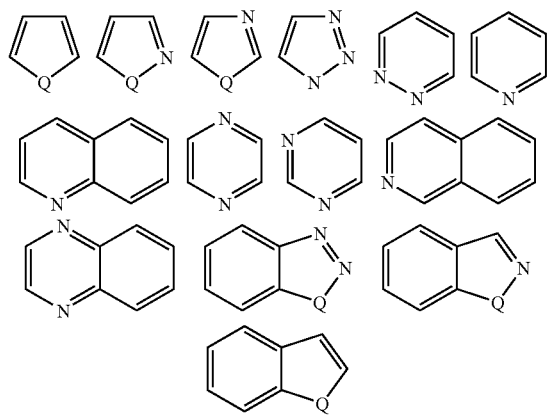

wherein Q is CH$_2$, C=CH$_2$, O, S or NH. A —($C_{3-10}$heteroaryl) group can be substituted or unsubstituted.

A "$C_{3-10}$heterocycle" is an aromatic or non-aromatic cycloalkyl having from 3 to 10 ring atoms in which one to four of the ring carbon atoms are independently replaced with a heteroatom from the group consisting of O, S and N. Representative examples of a heterocycle include, but are not limited to, azetidine, benzofuranyl, benzothiophene, indolyl, benzopyrazolyl, coumarinyl, isoquinolinyl, morpholinyl, pyrrolyl, pyrrolidinyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl, (1,4)-dioxane, (1,3)-dioxolane, 4,5-dihydro-1H-imidazolyl, tetrahydropyran, tetrahydrofuran and tetrazolyl. Additional non-limiting examples include the following:

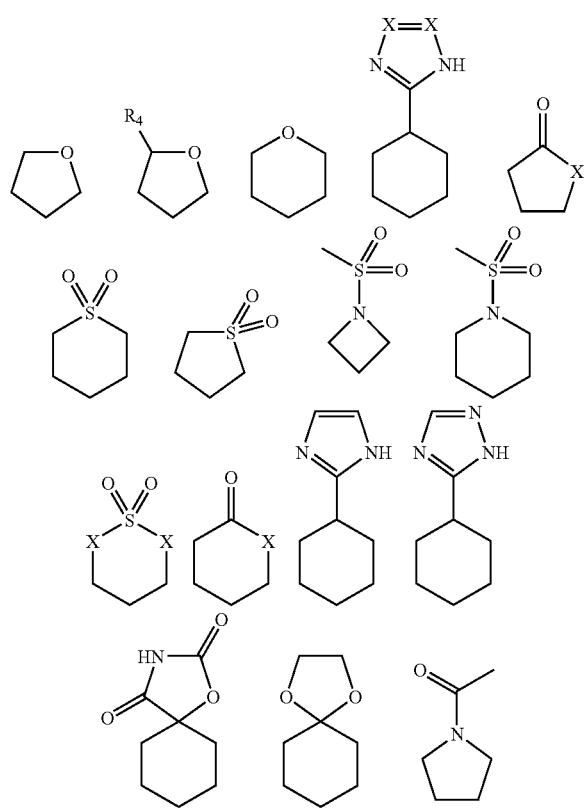

including stereoisomers and enantiomers thereof, wherein each occurrence of X is independently $CH_2$, O, S or N and $R^4$ is H, substituted or unsubstituted $C_{1-6}$alkyl, substituted or unsubstituted aryl, substituted or unsubstituted $C_{3-10}$cycloalkyl, substituted or unsubstituted $C_{3-10}$heterocycle or substituted or unsubstituted $C_{3-10}$heteroaryl. A —($C_{3-10}$heteroaryl) group can be substituted or unsubstituted. A —($C_{3-10}$heterocycle) group can be substituted or unsubstituted.

A "heterocyclocarbonyl" group is a —C(O)—$C_{3-10}$heterocycle group, wherein $C_{3-10}$heterocycle is as described herein, wherein the $C_{3-10}$heterocycle group can be optionally substituted.

A "hydroxyalkyl" group is an alkyl group as described above substituted with one or more hydroxy groups.

In one embodiment, when the groups described herein are said to be "substituted," they may be substituted with any substituent or substituents that do not adversely affect the activity of the Aminopurine Compound. Examples of substituents are those found in the exemplary compounds and embodiments disclosed herein, as well as halogen (chloro, iodo, bromo, or fluoro); $C_{1-6}$ alkyl; $C_{2-6}$ alkenyl; $C_{2-6}$ alkynyl; hydroxyl; $C_{1-6}$ alkoxyl; amino; nitro; thiol; thioether; imine; cyano; amido; phosphonato; phosphine; carboxyl; thiocarbonyl; sulfonyl; sulfonamide; ketone; aldehyde; ester; oxygen (=O); haloalkyl (e.g., trifluoromethyl); $B(OH)_2$, carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); O-lower alkyl; O-aryl, aryl; aryl-lower alkyl; $CO_2CH_3$; $CONH_2$; $OCH_2CONH_2$; $NH_2$; $SO_2NH_2$; $OCHF_2$; $CF_3$; $OCF_3$.

"JNK" means a protein or an isoform thereof expressed by a JNK 1, JNK 2, or JNK 3 gene (Gupta, S., Barrett, T., Whitmarsh, A. J., Cavanagh, J., Sluss, H. K., Derijard, B. and Davis, R. J. *The EMBO J.* 15:2760-2770 (1996)).

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the Aminopurine Compounds include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine(N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, *Remington's Pharmaceutical Sciences*, 18th eds., Mack Publishing, Easton Pa. (1990) or *Remington: The Science and Practice of Pharmacy*, 19th eds., Mack Publishing, Easton Pa. (1995).

As used herein, the term "polymorph(s)" and related terms herein refer to solid forms of the Aminopurine Compounds having different physical properties as a result of the order of the molecules in the crystal lattice. The differences in physical properties exhibited by solid forms affect pharmaceutical parameters such as storage stability, compressibility and density (important in formulation and product manufacturing), and dissolution rates (an important factor in determining bioavailability). Differences in stability can result from changes in chemical reactivity (e.g., differential oxidation, such that a dosage form discolors more rapidly when comprised of one solid form than when comprised of another solid form) or mechanical changes (e.g., tablets crumble on storage as a kinetically favored polymorph converts to thermodynamically more stable solid form) or both (e.g., tablets of one solid form are more susceptible to breakdown at high humidity). As a result of solubility/dissolution differences, in the extreme case, some solid form transitions may result in lack of potency or, at the other extreme, toxicity. In addition, the physical properties of the crystal may be important in processing, for example, one solid form might be more likely to form solvates or might be difficult to filter and wash free of impurities (i.e., particle shape and size distribution might be different between one solid form relative to the other).

As used herein and unless otherwise indicated, the term "clathrate" means an Aminopurine Compound, or a salt thereof, in the form of a crystal lattice that contains spaces (e.g., channels) that have a guest molecule (e.g., a solvent or water) trapped within or a crystal lattice wherein an Aminopurine Compound is a guest molecule.

As used herein and unless otherwise indicated, the term "hydrate" means an Aminopurine Compound, or a salt thereof, that further includes a stoichiometric or non-stoichiometric amount of water bound by non-covalent intermolecular forces.

As used herein and unless otherwise indicated, the term "solvate" means an Aminopurine Compound, or a salt thereof, that further includes a stoichiometric or non-stoichiometric amount of a solvent bound by non-covalent intermolecular forces.

As used herein and unless otherwise indicated, the term "prodrug" means an Aminopurine Compound derivative that can hydrolyze, oxidize, or otherwise react under biological conditions (in vitro or in vivo) to provide an active compound, particularly an Aminopurine Compound. Examples of prodrugs include, but are not limited to, derivatives and metabolites of an Aminopurine Compound that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* 6th ed. (Donald J. Abraham ed., 2001, Wiley) and *Design and Application of Prodrugs* (H. Bundgaard ed., 1985, Harwood Academic Publishers Gmfh).

As used herein and unless otherwise indicated, the term "stereoisomer" or "stereomerically pure" means one stereoisomer of an Aminopurine Compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The Aminopurine Compounds can have chiral centers and can occur as racemates, individual enantiomers or diastereomers, and mixtures thereof. All such isomeric forms are included within the embodiments disclosed herein, including mixtures thereof.

Various Aminopurine Compounds contain one or more chiral centers, and can exist as racemic mixtures of enantiomers, mixtures of diastereomers or enantiomerically or optically pure compounds. The use of stereomerically pure forms of such Aminopurine Compounds, as well as the use of mixtures of those forms are encompassed by the embodiments disclosed herein. For example, mixtures comprising equal or unequal amounts of the enantiomers of a particular Aminopurine Compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the Aminopurine Compounds include E and Z isomers, or a mixture thereof, and cis and trans isomers or a mixture thereof. In certain embodiments, the Aminopurine Compounds are isolated as either the E or Z isomer. In other embodiments, the Aminopurine Compounds are a mixture of the E and Z isomers.

The term "effective amount" in connection with an Aminopurine Compound can mean an amount capable of treating or preventing a disease disclosed herein, such as cancer, a cardiovascular disease, a renal disease, an autoimmune condition, an inflammatory condition, macular degeneration, ischemia-reperfusion injury, pain and related syndromes, disease-related wasting, an asbestos-related condition, pulmonary hypertension, central nervous system (CNS) injury/damage or a condition treatable or preventable by inhibition of a kinase pathway, in one embodiment, the JNK pathway.

As used herein, the term "macular degeneration" encompasses all forms of macular degenerative diseases regardless of a patient's age, although some macular degenerative diseases are more common in certain age groups. These include, but are not limited to, Best's disease or vitelliform (most common in patients under about seven years of age); Stargardt's disease, juvenile macular dystrophy or fundus flavimaculatus (most common in patients between about five and about 20 years of age); Behr's disease, Sorsby's disease, Doyne's disease or honeycomb dystrophy (most common in patients between about 30 and about 50 years of age); and age-related macular degeneration (most common in patients of about 60 years of age or older). In one embodiment, the cause of the macular degenerative disease is genetic. In another embodiment, the cause of the macular degenerative disease is physical trauma. In another embodiment, the cause of the macular degenerative disease is diabetes. In another embodiment, the cause of the macular degenerative disease is malnutrition. In another embodiment, the cause of the macular degenerative disease is infection.

As used herein, the phrase "ischemia-reperfusion injury" includes injury that occurs during or as a result of surgery, including, but not limited to, coronary artery bypass graft surgery, percutaneous transluminal coronary angioplasty, orthopedic surgery, organ/vessel surgery, plaque/tumor removal surgery or organ/tissue transplant surgery (donor or recipient). The phrase "ischemia-reperfusion injury" also includes injury that occurs to an organ or tissue ex vivo prior to transplant.

As used herein, the phrase "pain and related syndromes" includes nociceptive pain, such as that resulting from physical trauma (e.g., a cut or contusion of the skin; or a chemical or thermal burn), osteoarthritis, rheumatoid arthritis or tendonitis; myofascial pain; neuropathic pain, such as that associated with stroke, diabetic neuropathy, luetic neuropathy, postherpetic neuralgia, trigeminal neuralgia, fibromyalgia, or painful neuropathy induced iatrogenically by drugs such as vincristine, velcade or thalidomide; or mixed pain (i.e., pain with both nociceptive and neuropathic components). Further types of pain that can be treated or prevented by administering an effective amount of an Aminopurine Compound to a patient in need thereof include, but are not limited to, visceral pain; headache pain (e.g., migraine headache pain); CRPS; CRPS type I; CRPS type II; RSD; reflex neurovascular dystrophy; reflex dystrophy; sympathetically maintained pain syndrome; causalgia; Sudeck atrophy of bone; algoneurodystrophy; shoulder hand syndrome; post-traumatic dystrophy; autonomic dysfunction; cancer-related pain; phantom limb pain; chronic fatigue syndrome; post-operative pain; spinal cord injury pain; central post-stroke pain; radiculopathy; sensitivity to temperature, light touch or color change to the skin (allodynia); pain from hyperthermic or hypothermic conditions; and other painful conditions (e.g., diabetic neuropathy, luetic neuropathy, postherpetic neuralgia, trigeminal neuralgia).

The term "disease-related wasting" means wasting (e.g., a loss of physical bulk through the breakdown of bodily tissue) associated with a disease such as HIV, AIDS, cancer, end-stage renal disease, kidney failure, chronic heart disease, obstructive pulmonary disease, tuberculosis, rheumatoid arthritis, a chronic inflammatory disease (e.g., scleroderma or mixed connective tissue disease) or a chronic infectious disease (e.g., osteoarthritis or bacterial endocarditis).

The term "asbestos-related disease" includes diseases and disorders such as malignant mesothelioma, asbestosis, malignant pleural effusion, benign pleural effusion, pleural plaque, pleural calcification, diffuse pleural thickening, round atelectasis, and bronchogenic carcinoma, as well as symptoms of asbestos-related diseases and disorders such as dyspnea, obliteration of the diaphragm, radiolucent sheet-like encasement of the pleura, pleural effusion, pleural thickening, decreased size of the chest, chest discomfort, chest pain, easy fatigability, fever, sweats and weight loss.

The term "pulmonary hypertension" includes diseases characterized by sustained elevations of pulmonary artery pressure as well as symptoms associated with pulmonary hypertension such as dyspnea, fatigue, weakness, chest pain, recurrent syncope, seizures, light-headedness, neurologic deficits, leg edema and palpitations.

The term "central nervous system (CNS) injury/damage" includes, but is not limited to, primary brain injury, secondary brain injury, traumatic brain injury, focal brain injury, diffuse axonal injury, head injury, concussion, post-concussion syndrome, cerebral contusion and laceration, subdural hematoma, epidermal hematoma, post-traumatic epilepsy, chronic vegetative state, complete SCI, incomplete SCI, acute SCI, subacute SCI, chronic SCI, central cord syndrome, Brown-Sequard syndrome, anterior cord syndrome, conus medullaris syndrome, cauda equina syndrome, neurogenic shock, spinal shock, altered level of consciousness, headache, nausea, emesis, memory loss, dizziness, diplopia, blurred vision, emotional liability, sleep disturbances, irritability, inability to concentrate, nervousness, behavioral impairment, cognitive deficit, and seizure.

The term "patient" includes an animal, including, but not limited to, an animal such a cow, monkey, horse, sheep, pig, chicken, turkey, quail, cat, dog, mouse, rat, rabbit or guinea pig, in one embodiment a mammal, in another embodiment a human.

4.2 Aminopurine Compounds

Provided herein are Aminopurine Compounds having the following formula (I):

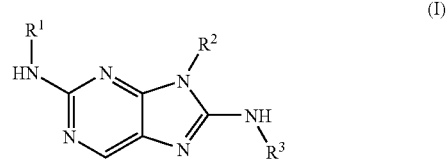

and pharmaceutically acceptable salts, polymorphs, clathrates, solvates, hydrates, stereoisomers, enantiomers and prodrugs thereof, wherein:

$R^1$ is substituted or unsubstituted $C_{1-6}$alkyl, substituted or unsubstituted aryl, substituted or unsubstituted $C_{3-10}$cycloalkyl, substituted or unsubstituted $C_{3-10}$heterocycle or substituted or unsubstituted $C_{3-10}$heteroaryl;

$R^2$ is H, substituted or unsubstituted $C_{1-6}$alkyl, substituted or unsubstituted aryl, substituted or unsubstituted $C_{3-10}$cycloalkyl, substituted or unsubstituted $C_{3-10}$heterocycle or substituted or unsubstituted $C_{3-10}$heteroaryl; and $R^3$ is aryl substituted with one or more halogens or $C_{3-10}$heteroaryl substituted with one or more halogens, wherein the aryl or $C_{3-10}$heteroaryl group is optionally further substituted with one or more $C_{1-6}$alkyl, hydroxyl, hydroxyalkyl, alkoxy, alkoxyalkyl, amino, alkylamino, carboxy, aminocarbonyl, cyano, acylamino, alkanesulfonylamino, tetrazolyl, triazolyl or imidazolyl groups.

In one embodiment, the Aminopurine Compounds of formula (I) are those wherein $R^1$ is phenyl.

In another embodiment, the Aminopurine Compounds of formula (I) are those wherein $R^1$ is substituted phenyl, in one embodiment alkoxy substituted phenyl, in one embodiment p-alkoxy substituted phenyl, and in one embodiment p-methoxy substituted phenyl.

In another embodiment, the Aminopurine Compounds of formula (I) are those wherein $R^1$ is m-alkoxy substituted phenyl, in one embodiment m-methoxy substituted phenyl.

In another embodiment, the Aminopurine Compounds of formula (I) are those wherein $R^1$ is trifluoromethyl substituted phenyl, in one embodiment p-trifluoromethyl substituted phenyl.

In another embodiment, the Aminopurine Compounds of formula (I) are those wherein $R^1$ is $C_{1-6}$alkyl, in one embodiment isopropyl.

In another embodiment, the Aminopurine Compounds of formula (I) are those wherein $R^1$ is p-halo substituted phenyl, in one embodiment p-fluoro substituted phenyl.

In another embodiment, the Aminopurine Compounds of formula (I) are those wherein $R^1$ is p-$C_{1-6}$alkyl substituted phenyl, in one embodiment p-methyl substituted phenyl.

In another embodiment, the Aminopurine Compounds of formula (I) are those wherein $R^1$ is o-halo substituted phenyl, in one embodiment o-fluoro substituted phenyl.

In another embodiment, the Aminopurine Compounds of formula (I) are those wherein $R^1$ is m,p-dihalo substituted phenyl, in one embodiment m,p-dichloro substituted phenyl.

In another embodiment, the Aminopurine Compounds of formula (I) are those wherein $R^1$ is m-cyano substituted phenyl.

In another embodiment, the Aminopurine Compounds of formula (I) are those wherein $R^1$ is p-$C_{3-10}$heterocycle substituted phenyl, in one embodiment p-morpholino substituted phenyl.

In another embodiment, the Aminopurine Compounds of formula (I) are those wherein $R^1$ is p-sulfonyl substituted phenyl.

In another embodiment, the Aminopurine Compounds of formula (I) are those wherein $R^1$ is $C_{3-10}$heteroaryl, in one embodiment pyridine or pyridinone.

In another embodiment, the Aminopurine Compounds of formula (I) are those wherein $R^1$ is $C_{3-10}$heterocycle, in one embodiment piperidine, piperidin-2-one, pyrrolidinone or tetrahydropyran.

In another embodiment, the Aminopurine Compounds of formula (I) are those wherein $R^1$ is N-substituted piperidine, in one embodiment N-sulfonyl substituted piperidine.

In another embodiment, the Aminopurine Compounds of formula (I) are those wherein $R^1$ is $C_{3-10}$cycloalkyl, in one embodiment cyclohexyl, cyclopentyl or cyclopropyl.

In another embodiment, the Aminopurine Compounds of formula (I) are those wherein $R^1$ is substituted $C_{3-10}$cycloalkyl, in one embodiment $C_{3-10}$cycloalkyl substituted with one or more $C_{1-6}$alkyl, hydroxy, hydroxyalkyl, alkoxy, alkoxyalkyl, amino, alkylamino, carboxy, heterocyclocarbonyl, aminocarbonyl, cyano, acylamino, alkanesulfonylamino, tetrazolyl, triazolyl or imidazolyl groups.

In another embodiment, the Aminopurine Compounds of formula (I) are those wherein $R^1$ is substituted $C_{3-10}$cycloalkyl, in one embodiment $C_{3-10}$cycloalkyl substituted with one or more alkyl, hydroxy, hydroxyalkyl, alkoxy, alkoxyalkyl, amino, aminoalkyl, amido, amidoalkyl, carboxy, heterocyclocarbonyl, sulfonamide or sulfonaminoalkyl groups. Cyclohexyl and cyclopentyl are particular $C_{3-10}$cycloalkyl groups.

In another embodiment, the Aminopurine Compounds of formula (I) are those wherein $R^1$ is cyclohexyl substituted with one or more alkyl, hydroxy, hydroxyalkyl, alkoxy, alkoxyalkyl, amino, aminoalkyl, amido, amidoalkyl, carboxy, heterocyclocarbonyl, sulfonamide or sulfonaminoalkyl groups.

In another embodiment, the Aminopurine Compounds of formula (I) are those wherein $R^1$ is $C_{1-6}$alkyl, in one embodiment methyl, ethyl, propyl (e.g., n-propyl or isopropyl) or butyl (e.g., isobutyl).

In another embodiment, the Aminopurine Compounds of formula (I) are those wherein $R^1$ is substituted $C_{1-6}$alkyl, in one embodiment phenyl, hydroxy, $C_{3-10}$cycloalkyl, or oxirane substituted $C_{1-6}$alkyl.

In another embodiment, the Aminopurine Compounds of formula (I) are those wherein $R^1$ is benzyl.

In another embodiment, the Aminopurine Compounds of formula (I) are those wherein $R^1$ is substituted $C_{1-6}$alkyl, in one embodiment $C_{3-10}$heterocycle (e.g., piperidine or pyrrolidine substituted $C_{1-6}$alkyl.

In another embodiment, the Aminopurine Compounds of formula (I) are those wherein $R^2$ is substituted or unsubstituted $C_{1-6}$alkyl, substituted or unsubstituted aryl, substituted or unsubstituted $C_{3-10}$heterocycle or substituted or unsubstituted $C_{3-10}$heteroaryl.

In another embodiment, the Aminopurine Compounds of formula (I) are those wherein $R^2$ is substituted or unsubstituted $C_{3-10}$cycloalkyl, in one embodiment cyclohexyl, cyclopentyl, cyclobutyl or cyclopropyl. Cyclohexyl and cyclopentyl are specific $C_{3-10}$cycloalkyl groups. In one embodiment, $C_{3-10}$cycloalkyl substitutents include $C_{1-6}$alkyl, hydroxy, hydroxyalkyl, alkoxy, alkoxyalkyl, amino, aminoalkyl, amido, amidoalkyl, carboxy, heterocyclocarbonyl, sulfonamide and sulfonaminoalkyl groups.

In another embodiment, the Aminopurine Compounds of formula (I) are those wherein $R^2$ is cyclohexyl or cyclopentyl substituted with one or more $C_{1-6}$alkyl, hydroxy, hydroxyalkyl, alkoxy, alkoxyalkyl, amino, aminoalkyl, amido, amidoalkyl, carboxy, heterocyclocarbonyl, sulfonamide or sulfonaminoalkyl groups.

In another embodiment, the Aminopurine Compounds of formula (I) are those wherein $R^2$ is cyclohexyl or cyclopentyl substituted with one or more $C_{1-6}$alkyl, hydroxy, hydroxyalkyl, alkoxy, alkoxyalkyl, amino, alkylamino, carboxy, heterocyclocarbonyl, aminocarbonyl, cyano, acylamino, alkanesulfonylamino, tetrazolyl, triazolyl or imidazolyl groups.

In another embodiment, the Aminopurine Compounds of formula (I) are those wherein $R^2$ is $C_{1-6}$alkyl, in one embodiment butyl (e.g., n-butyl, isobutyl or t-butyl), propyl (e.g., isopropyl), ethyl or methyl.

In another embodiment, the Aminopurine Compounds of formula (I) are those wherein $R^2$ is substituted $C_{1-6}$alkyl, in one embodiment cyano, $C_{3-10}$cycloalkyl or hydroxy substituted $C_{1-6}$alkyl.

In another embodiment, the Aminopurine Compounds of formula (I) are those wherein $R^2$ is substituted $C_{1-6}$alkyl, in one embodiment $C_{3-10}$heterocycle (e.g., piperidine or pyrrolidine) hydroxy or amido substituted $C_{1-6}$alkyl.

In another embodiment, the Aminopurine Compounds of formula (I) are those wherein $R^2$ is aryl, in one embodiment phenyl.

In another embodiment, the Aminopurine Compounds of formula (I) are those wherein $R^2$ is $C_{3-10}$heterocycle, in one embodiment piperidine, piperidin-2-one, tetrahydropyran, tetrahydrofuran or azetidine.

In another embodiment, the Aminopurine Compounds of formula (I) are those wherein $R^2$ is $C_{3-10}$heterocycle, in one embodiment a sulfur containing $C_{3-10}$heterocycle, including but not limited to 4-(1,1-dioxo)thiopyranyl and 3-(1,1-dioxo)thiofuranyl. In a particular embodiment, $R^2$ is a sulfur, sulfonyl or sulfonamido containing $C_{3-10}$heterocycle.

In another embodiment, the Aminopurine Compounds of formula (I) are those wherein $R^2$ is substituted $C_{3-10}$heterocycle, in one embodiment acetyl substituted piperidine.

In another embodiment, the Aminopurine Compounds of formula (I) are those wherein $R^2$ is substituted or unsubstituted 3-oxetanyl, 3-tetrahydrofuranyl, 4-tetrahydropyranyl, 4-piperidinyl, 4-(1-acy)-piperidinyl, 4-(1-alkanesulfonyl)piperidinyl, 3-pyrrolidinyl, 3-(1-acyl)pyrrolidinyl or 3-(1-alkanesulfonyl)pyrrolidinyl.

In another embodiment, the Aminopurine Compounds of formula (I) are those wherein $R^3$ is o-halo substituted phenyl, in one embodiment o-fluoro or chloro substituted phenyl.

In another embodiment, the Aminopurine Compounds of formula (I) are those wherein $R^3$ is m-halo substituted phenyl, in one embodiment m-fluoro or chloro substituted phenyl.

In another embodiment, the Aminopurine Compounds of formula (I) are those wherein $R^3$ is p-halo substituted phenyl, in one embodiment p-fluoro or chloro substituted phenyl.

In another embodiment, the Aminopurine Compounds of formula (I) are those wherein $R^3$ is m,p-dihalo substituted phenyl, in one embodiment m,p-difluoro or dichloro substituted phenyl.

In another embodiment, the Aminopurine Compounds of formula (I) are those wherein $R^3$ is o,m-dihalo substituted phenyl, in one embodiment o,m-difluoro substituted phenyl.

In another embodiment, the Aminopurine Compounds of formula (I) are those wherein R³ is o,p-dihalo substituted phenyl, in one embodiment o,p-difluoro substituted phenyl, o-fluoro-p-bromo substituted phenyl or o-fluoro-p-chloro substituted phenyl.

In another embodiment, the Aminopurine Compounds of formula (I) are those wherein R³ is o,o-dihalo substituted phenyl, in one embodiment o,o-difluoro substituted phenyl or o-chloro-o-fluoro substituted phenyl.

In another embodiment, the Aminopurine Compounds of formula (I) are those wherein R³ is 2,4,6-trihalo substituted phenyl, in one embodiment trifluoro substituted phenyl.

In another embodiment, the Aminopurine Compounds of formula (I) are those wherein R³ is o-halo substituted, in one embodiment o-fluoro or chloro substituted, and m-trifluoromethyl substituted phenyl.

In another embodiment, the Aminopurine Compounds of formula (I) are those wherein R³ is halo substituted $C_{3-10}$heteroaryl, in one embodiment halo substituted pyridine.

In another embodiment, the Aminopurine Compounds of formula (I) are those wherein R² is not aminoethyl.

In another embodiment, the Aminopurine Compounds of formula (I) are those wherein R² is not a five-membered heterocyclic ring.

In another embodiment, the Aminopurine Compounds of formula (I) are those wherein R² is not a five-membered N-containing heterocyclic ring.

In another embodiment, the Aminopurine Compounds of formula (I) are those wherein R² is not a five-membered O-containing heterocyclic ring.

In another embodiment, the Aminopurine Compounds of formula (I) are those wherein R² is not 2-tetrahydrofuranyl.

In another embodiment, the Aminopurine Compounds of formula (I) are those wherein R² is not 2-pyrrolidinyl.

In a further embodiment, provided herein are Aminopurine Compounds of formula (I), and pharmaceutically acceptable salts, polymorphs, clathrates, solvates, hydrates, stereoisomers and prodrugs thereof, wherein:

R¹ is substituted or unsubstituted $C_{1-6}$alkyl, substituted or unsubstituted aryl, substituted or unsubstituted $C_{3-10}$cycloalkyl, substituted or unsubstituted $C_{3-10}$heterocycle or substituted or unsubstituted $C_{3-10}$heteroaryl;

R² is:

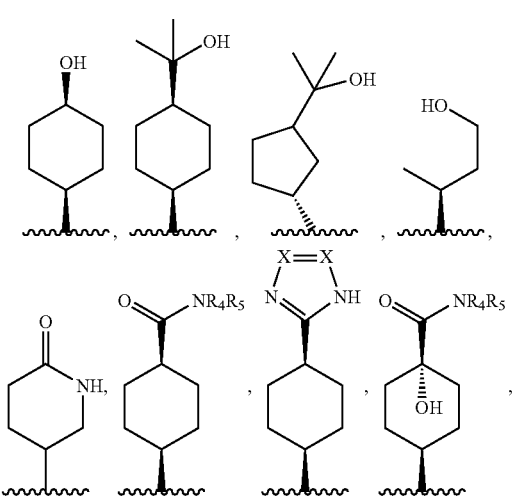

-continued

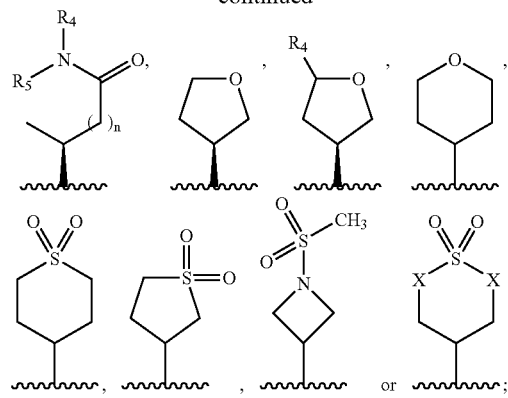

R³ is aryl or $C_{3-10}$heteroaryl, each being substituted with one or more halogens;

X is at each occurrence independently $CH_2$, O, S or N;

R⁴ and R⁵ are at each occurrence independently H, substituted or unsubstituted $C_{1-6}$alkyl, substituted or unsubstituted aryl, substituted or unsubstituted $C_{3-10}$cycloalkyl, substituted or unsubstituted $C_{3-10}$heterocycle or substituted or unsubstituted $C_{3-10}$heteroaryl; or R⁴ and R⁵ taken together with the N atom to which they are attached form a substituted or unsubstituted 5-7 membered heterocycle; and n is at each occurrence independently an integer ranging from 0 to 3.

In a another embodiment, the Aminopurine Compounds of formula (I) are those wherein R³ is:

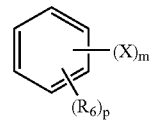

wherein:

X is at each occurrence independently F, Cl, Br or I;

$R_6$ is $C_{1-6}$alkyl, hydroxyl, hydroxyalkyl, alkoxy, alkoxyalkyl, amino, alkylamino, carboxy, aminocarbonyl, cyano, acylamino, alkanesulfonylamino, tetrazolyl, triazolyl or imidazolyl;

m is an integer ranging from 1 to 5; and p is an integer ranging from 0 to 4.

In a further embodiment, p is an integer ranging from 1 to 4.

In a further embodiment, provided herein are Aminopurine Compounds having the following formula (II):

(II)

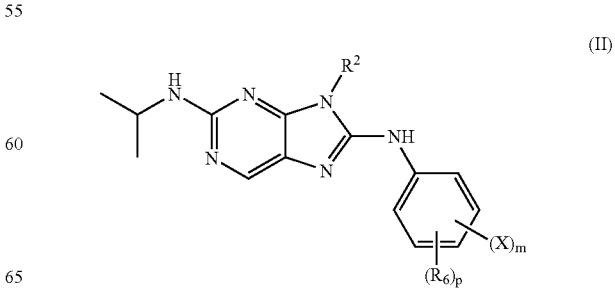

and pharmaceutically acceptable salts, polymorphs, clathrates, solvates, hydrates, stereoisomers, enantiomers and prodrugs thereof, wherein:

X is at each occurrence independently F, Cl, Br or I;

$R^2$ is:

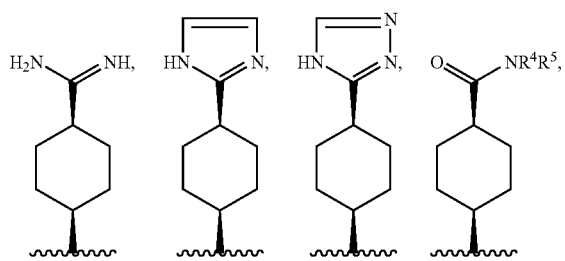

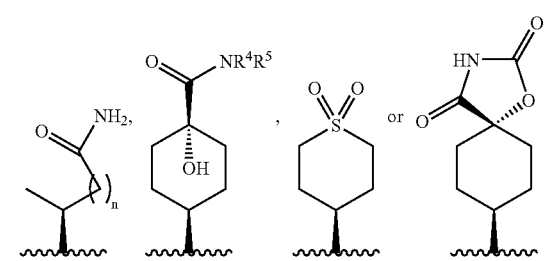

$R^4$ and $R^5$ are at each occurrence independently H, substituted or unsubstituted $C_{1-6}$alkyl, substituted or unsubstituted aryl, substituted or unsubstituted $C_{3-10}$cycloalkyl, substituted or unsubstituted $C_{3-10}$heterocycle or substituted or unsubstituted $C_{3-10}$heteroaryl; or $R^4$ and $R^5$ taken together with the N atom to which they are attached form a substituted or unsubstituted 5-7 membered heterocycle;

$R_6$ is $C_{1-6}$alkyl, hydroxyl, hydroxyalkyl, alkoxy, alkoxyalkyl, amino, alkylamino, carboxy, aminocarbonyl, cyano, acylamino, alkanesulfonylamino, tetrazolyl, triazolyl or imidazolyl;

m is an integer ranging from 1 to 5;

n is at each occurrence independently an integer ranging from 0 to 3; and p is an integer ranging from 0-4.

In one embodiment, the Aminopurine Compounds of formula (II) are those wherein X is fluoro.

In another embodiment, the Aminopurine Compounds of formula (II) are those wherein X is fluoro and m is 3.

In another embodiment, p is 0.

In another embodiment, p is an integer ranging from 1 to 4.

In a further embodiment, provided herein are Aminopurine Compounds having the following formula (III):

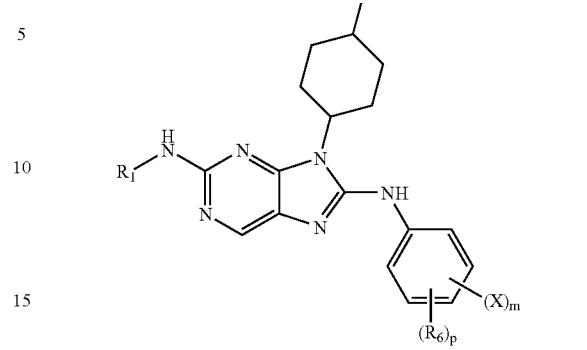

and pharmaceutically acceptable salts, polymorphs, clathrates, solvates, hydrates, stereoisomers, enantiomers and prodrugs thereof, wherein:

X is at each occurrence independently F, Cl, Br or I;

m is an integer ranging from 1 to 5;

p is an integer ranging from 0-4;

$R^1$ is:

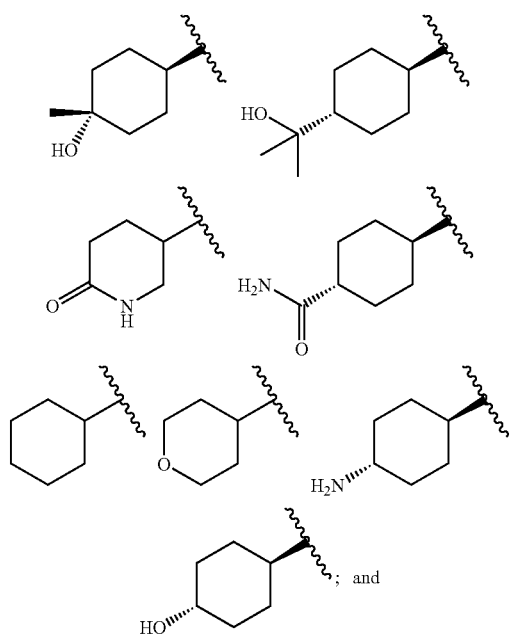

$R_6$ is $C_{1-6}$alkyl, hydroxyl, hydroxyalkyl, alkoxy, alkoxyalkyl, amino, alkylamino, carboxy, aminocarbonyl, cyano, acylamino, alkanesulfonylamino, tetrazolyl, triazolyl or imidazolyl.

In one embodiment, the Aminopurine Compounds of formula (III) are those wherein X is fluoro.

In another embodiment, the Aminopurine Compounds of formula (III) are those wherein X is fluoro and m is 3.

In another embodiment, p is 0.

In another embodiment, p is an integer ranging from 1 to 4.

In one embodiment, provided herein are Aminopurine Compounds having the following formula (IV):

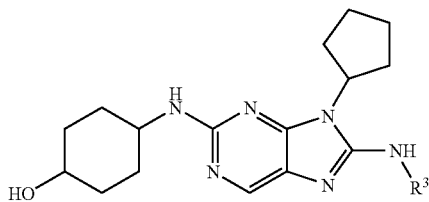

(IV)

and pharmaceutically acceptable salts, polymorphs, clathrates, solvates, hydrates, stereoisomers, enantiomers and prodrugs thereof,
wherein:
R³ is:

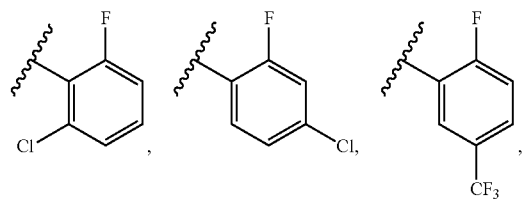

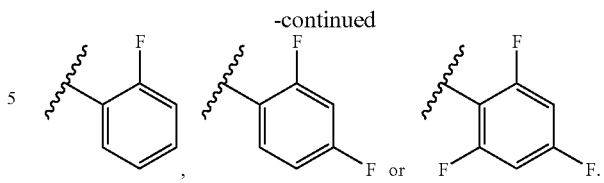

The following HPLC methods were used to characterized the compounds of Table 1, below.

Method A=5→70% acetonitrile/water (0.1% TFA) over 20 minutes.

Method B=20→100% acetonitrile/water (0.1% TFA) over 20 minutes.

Method C=5→50% acetonitrile/water (0.1% TFA) over 20 minutes.

Method D=0→75% acetonitrile/water (0.1% TFA) over 20 minutes.

Method E: 0-75% Acetonitrile/Water (0.1% Formic Acid) over 5 minutes then hold at 75% Acetonitrile/Water (0.1% Formic Acid) for 2 minutes.

Method F: 10% Acetonitrile/Water (0.1% Formic Acid) for first two 10-100% Acetonitrile/Water (0.1% Formic Acid) from 2 minutes to 25 minutes.

Representative Aminopurine Compounds are set forth in Table 1, below.

TABLE 1

| Compound | M + 1 HPLC (min/method) |
|---|---|
| 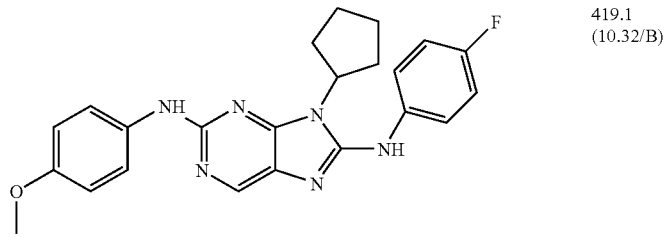<br>1 | 419.1<br>(10.32/B) |
| 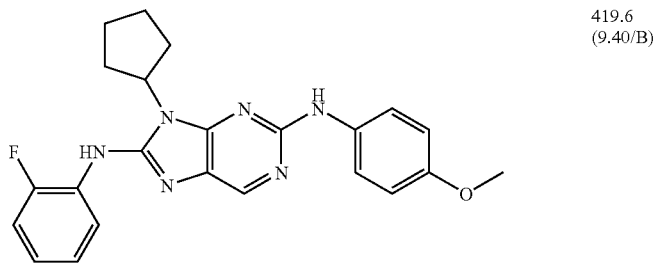<br>2 | 419.6<br>(9.40/B) |

TABLE 1-continued
| Compound | M + 1 HPLC (min/method) |
|---|---|
| 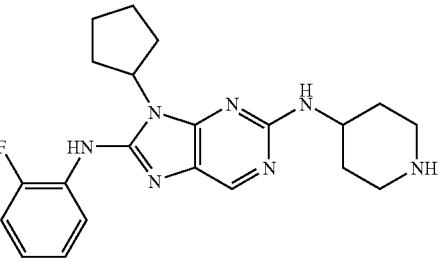 3 | 396.2 (2.51/E) |
| 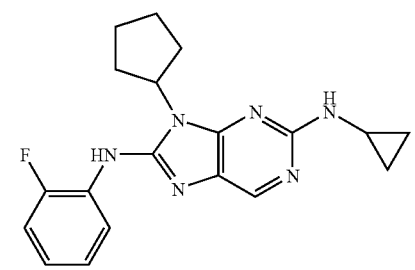 4 | 353.41 (3.49/E) |
| 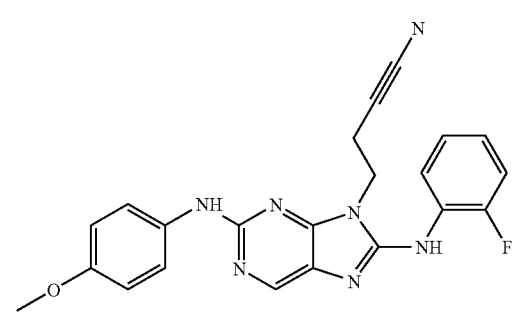 5 | 403.7 (15.98/D) |
| 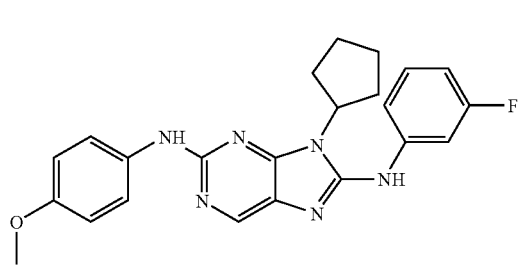 6 | 419.1 (10.57/B) |

TABLE 1-continued
| Compound | M + 1 HPLC (min/method) |
|---|---|
| 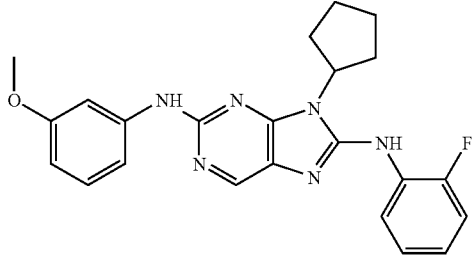<br>7 | 419.4 (9.517/B) |
| 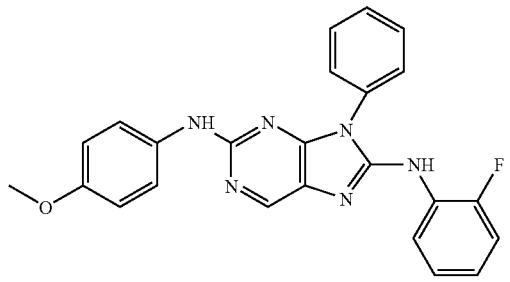<br>8 | 427.2 (9.3/B) |
| 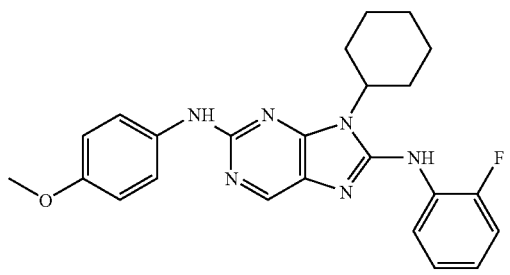<br>9 | 433.5 (9.817/B) |
| 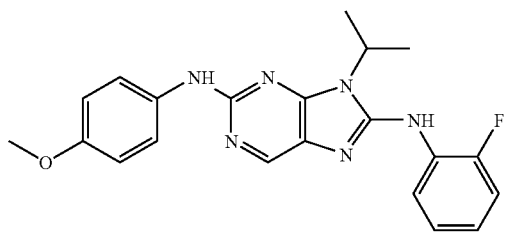<br>10 | 393.3 (8.950/B) |
| 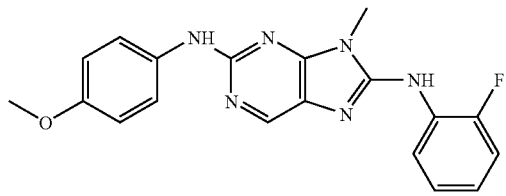<br>11 | 365.4 (8.083/B) |

TABLE 1-continued

| Compound | M + 1 HPLC (min/method) |
|---|---|
| 12 | 379.5 (8.517/B) |
| 13 | 351.1 (8.98/B) |
| 14 | 449.5 (7.967/B) |
| 15 | 434.4 (6.283/B) |

TABLE 1-continued
| Compound | M + 1 HPLC (min/method) |
|---|---|
| 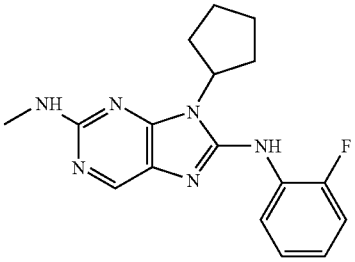<br>16 | 327.3 (8.433/B) |
| 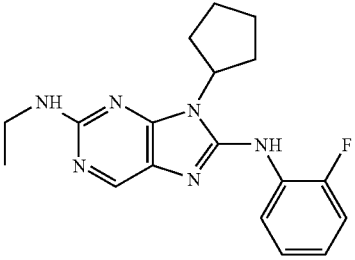<br>17 | 341.2 (8.883/B) |
| 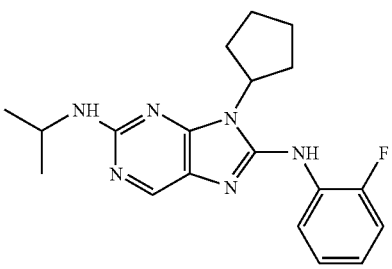<br>18 | 355.3 (9.267/B) |
| 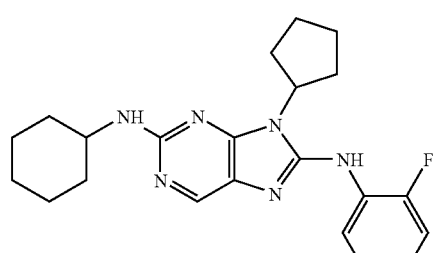<br>19 | 395.4 (10.183/B) |
| 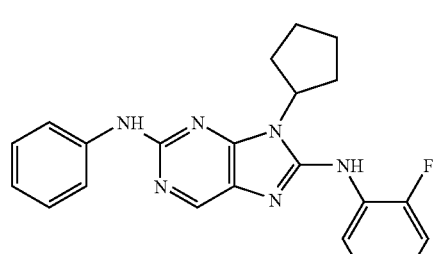<br>20 | 389.3 (9.533/B) |

TABLE 1-continued
| Compound | M + 1 HPLC (min/method) |
|---|---|
| 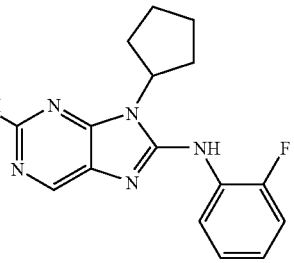<br>21 | 437.2 (9.37/B) |
| 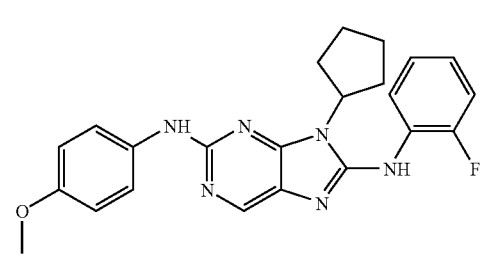<br>22 | 435.2 (10.89/B) |
| 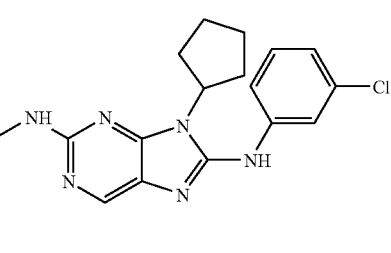<br>23 | 435.2 (10.89/B) |
| 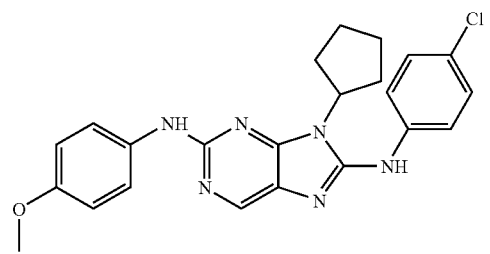<br>24 | 435.2 (10.89/B) |
| 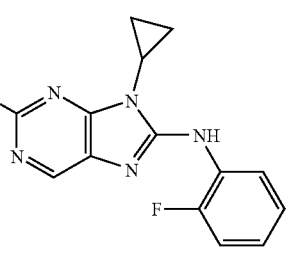<br>25 | 390.42 (8.717/B) |

TABLE 1-continued
| Compound | M + 1 HPLC (min/method) |
|---|---|
| 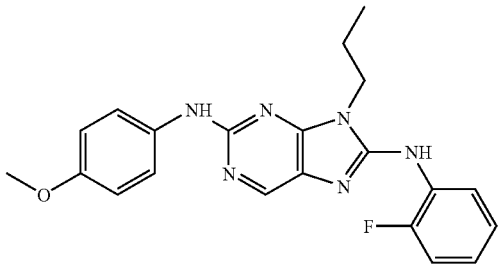 26 | 393.1 (8.917/B) |
| 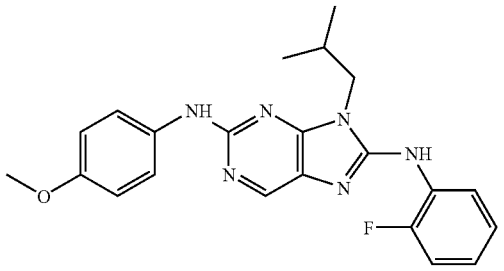 27 | 407.5 (9.317/B) |
| 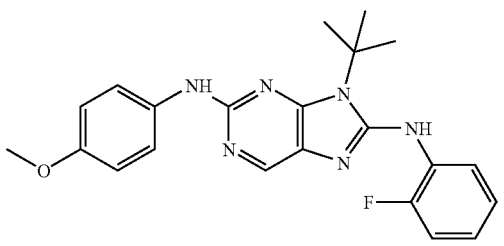 28 | 407.5 (9.467/B) |
| 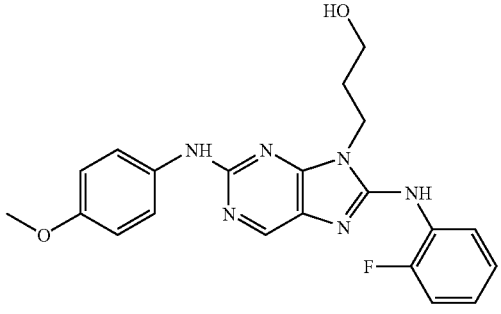 29 | 409.4 (10.583/A) |

TABLE 1-continued
| Compound | M + 1 HPLC (min/method) |
|---|---|
| 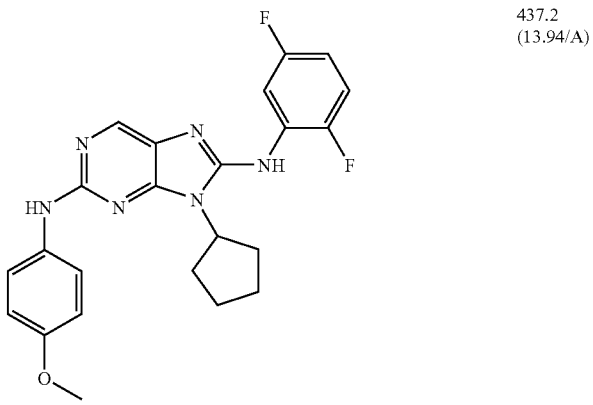<br>30 | 437.2 (13.94/A) |
| 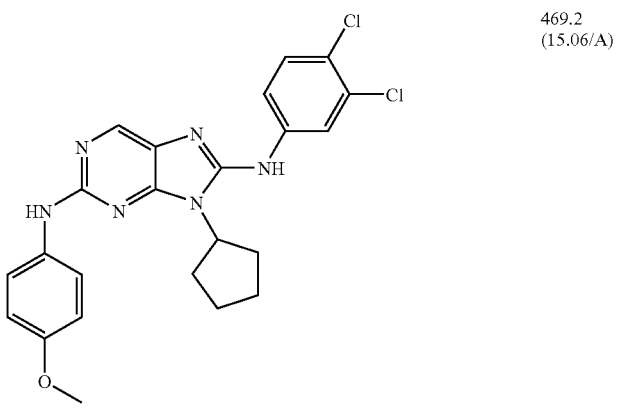<br>31 | 469.2 (15.06/A) |
| 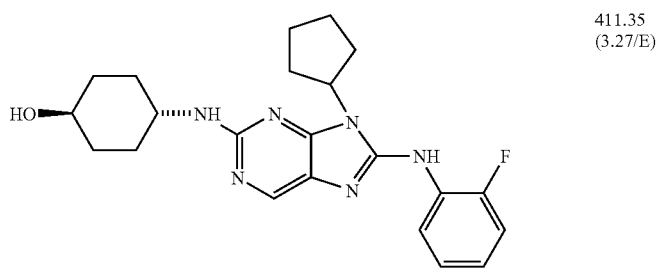<br>32 | 411.35 (3.27/E) |
| 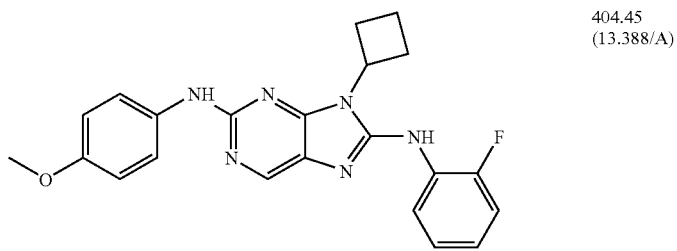<br>33 | 404.45 (13.388/A) |

TABLE 1-continued
| Compound | M + 1 HPLC (min/method) |
|---|---|
| 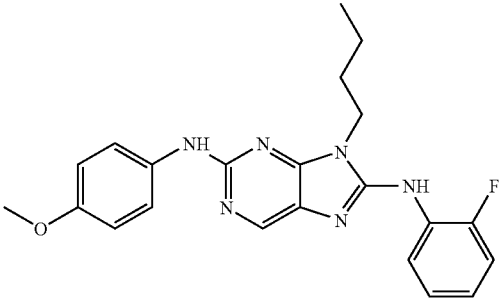 34 | 407.5 (10.315/B) |
| 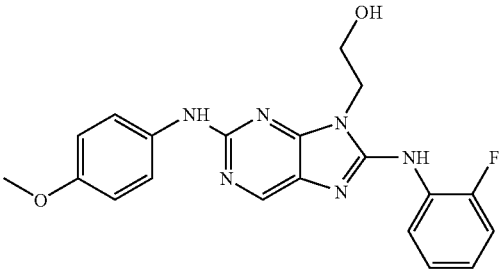 35 | 395.2 (12.1/A) |
| 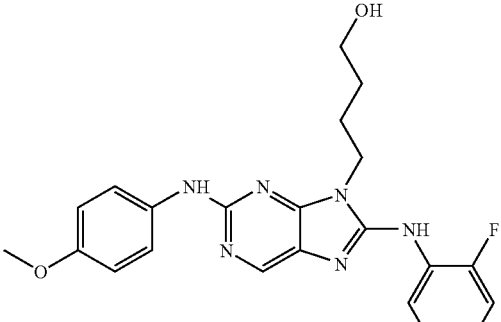 36 | 423.4 (11.68/A) |
| 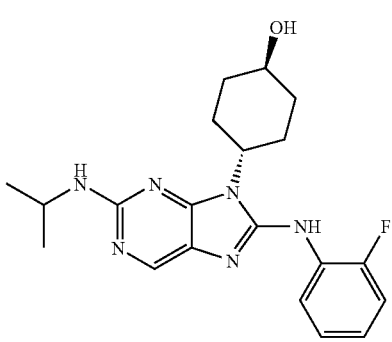 37 | 385.4 (11.164/A) |

TABLE 1-continued
| Compound | M + 1 HPLC (min/method) |
|---|---|
| 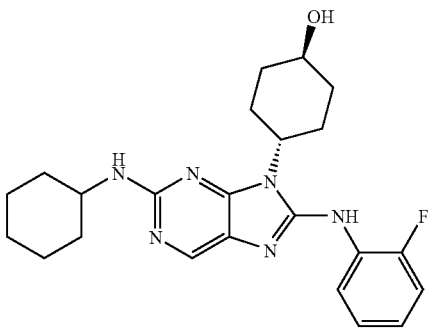 38 | 425.4 (8.25/B) |
| 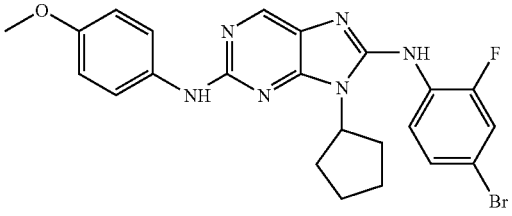 39 | 497.2 (18.04/B) |
| 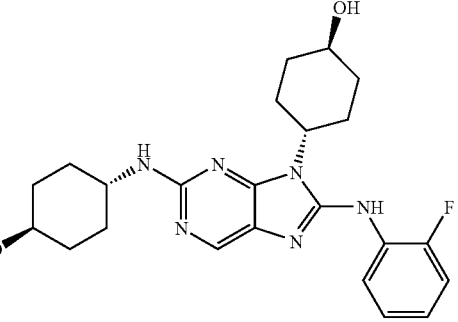 40 | 441.3 (13.557/B) |
| 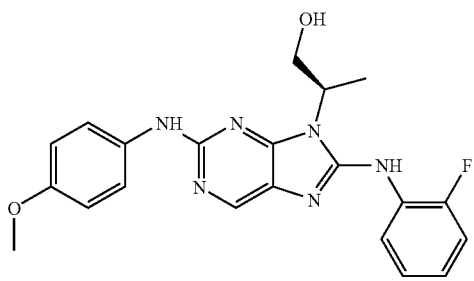 41 | 409.2 (9.216/B) |

TABLE 1-continued
| Compound | M + 1 HPLC (min/method) |
|---|---|
| 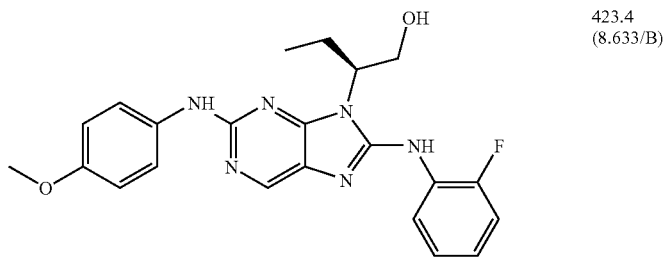<br>42 | 423.4 (8.633/B) |
| 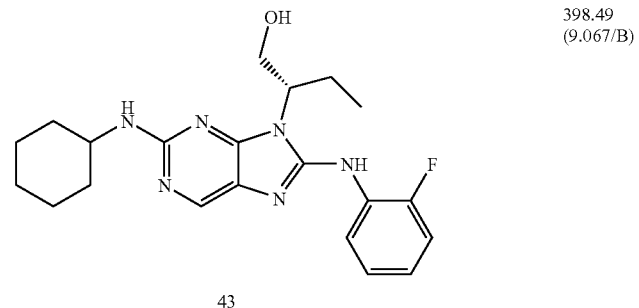<br>43 | 398.49 (9.067/B) |
| 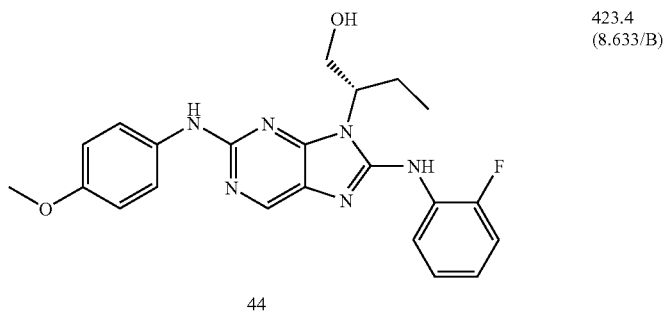<br>44 | 423.4 (8.633/B) |
| 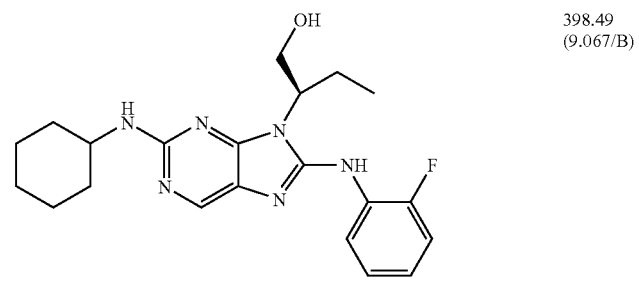<br>45 | 398.49 (9.067/B) |

TABLE 1-continued
| Compound | M + 1 HPLC (min/method) |
|---|---|
| 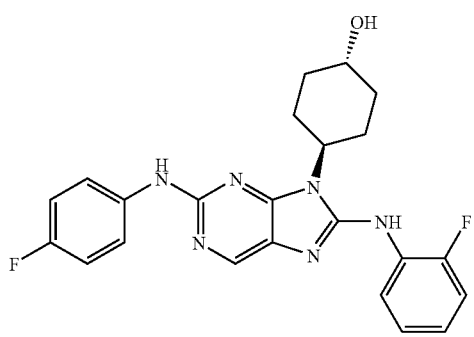<br>46 | 437 (8.82/B) |
| 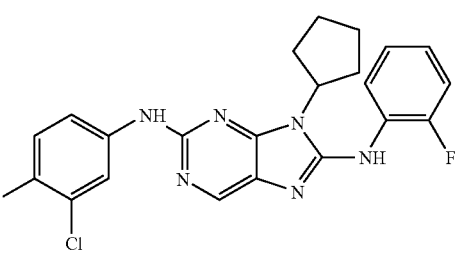<br>47 | 457.3 (11.82/B) |
| 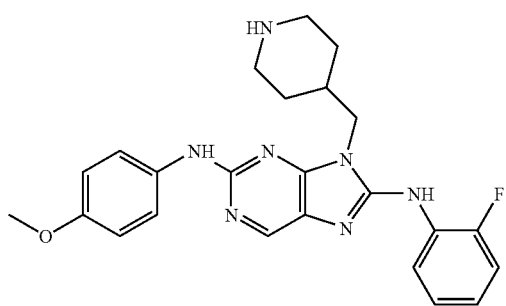<br>48 | 448.3 (8.867/A) |
| 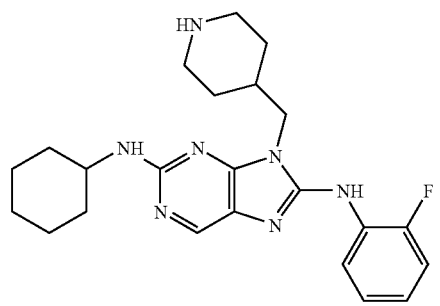<br>49 | 424.5 (9.083/B) |

TABLE 1-continued
| Compound | M + 1 HPLC (min/method) |
|---|---|
| 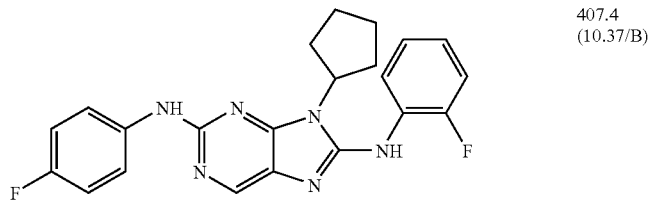 50 | 407.4 (10.37/B) |
| 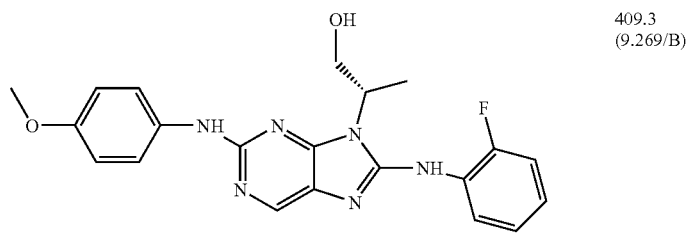 51 | 409.3 (9.269/B) |
| 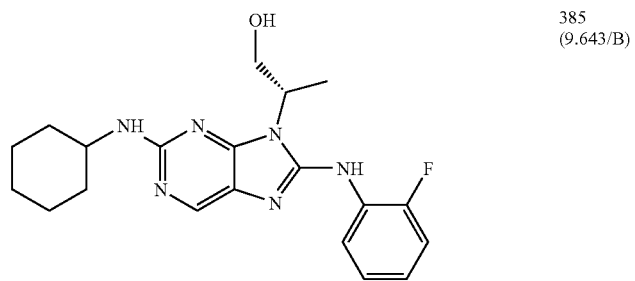 52 | 385 (9.643/B) |
| 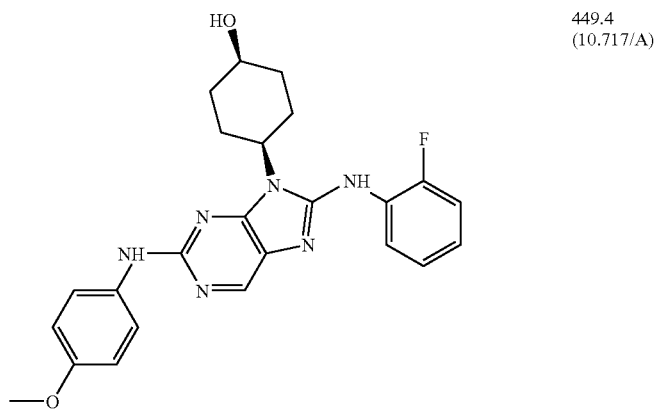 53 | 449.4 (10.717/A) |

TABLE 1-continued
| Compound | M + 1 HPLC (min/method) |
|---|---|
| 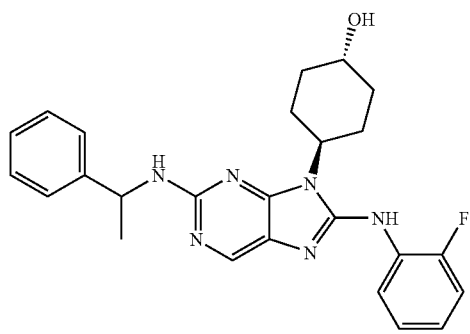  54 | 447.4 (11.63/A) |
| 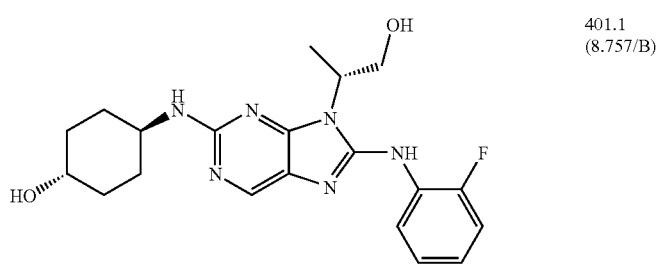  55 | 401.1 (8.757/B) |
| 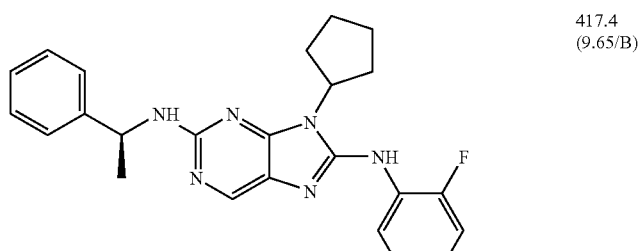  56 | 417.4 (9.65/B) |
| 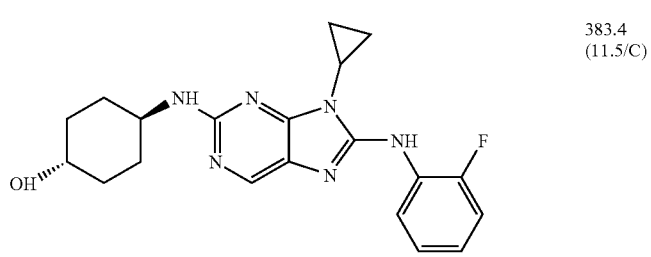  57 | 383.4 (11.5/C) |

TABLE 1-continued
| Compound | M + 1 HPLC (min/method) |
|---|---|
| 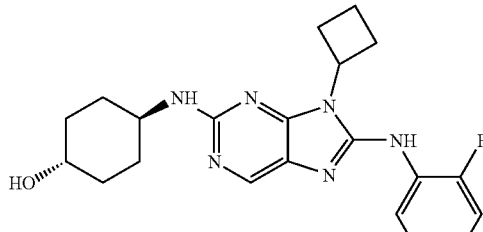<br>58 | 397.2 (12.286/C) |
| 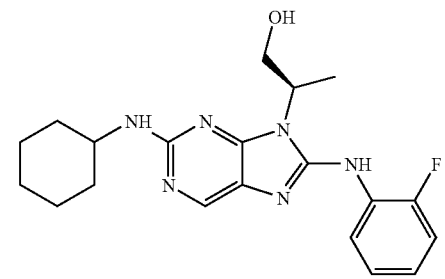<br>59 | 385.1 (10.496/B) |
| 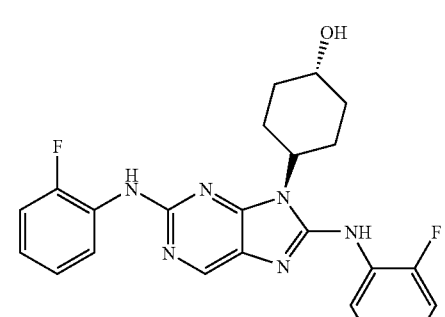<br>60 | 437.1 (7.58/B) |
| 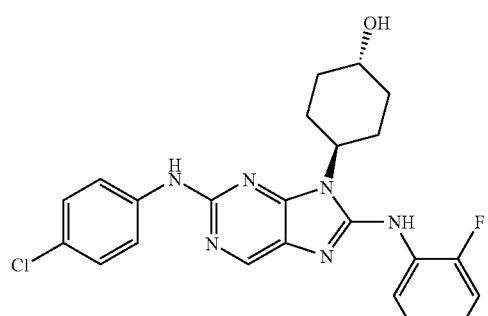<br>61 | 453.22 (8.28/B) |

TABLE 1-continued
| Compound | M + 1 HPLC (min/method) |
|---|---|
| 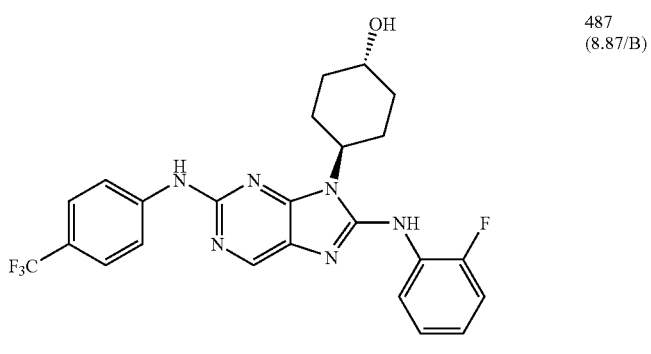<br>62 | 487<br>(8.87/B) |
| 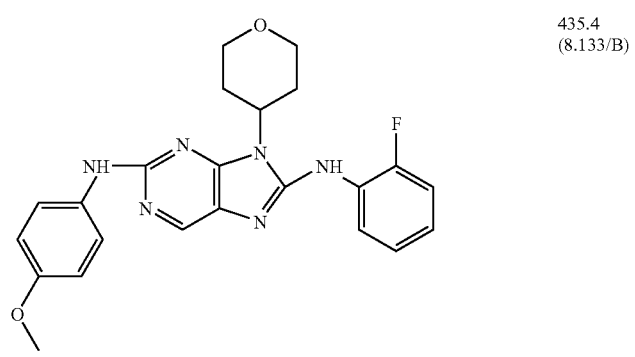<br>63 | 435.4<br>(8.133/B) |
| 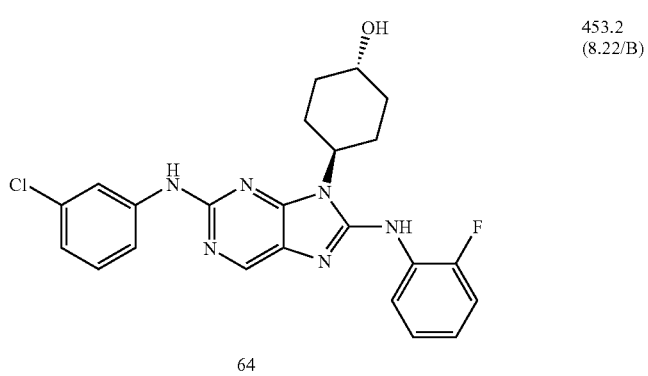<br>64 | 453.2<br>(8.22/B) |
| 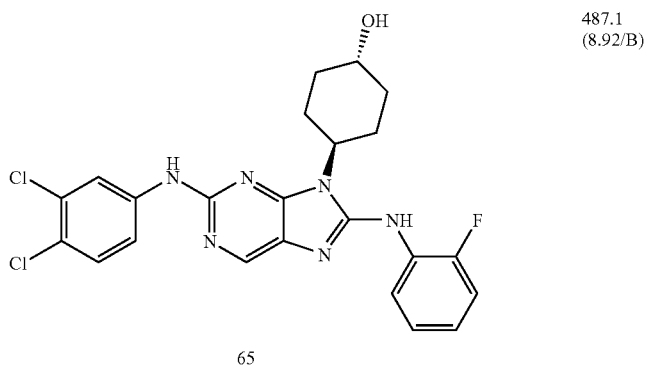<br>65 | 487.1<br>(8.92/B) |

TABLE 1-continued
| Compound | M + 1 HPLC (min/method) |
|---|---|
| 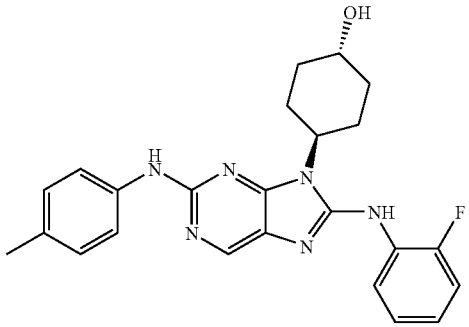<br>66 | 433.2 (7.93/B) |
| 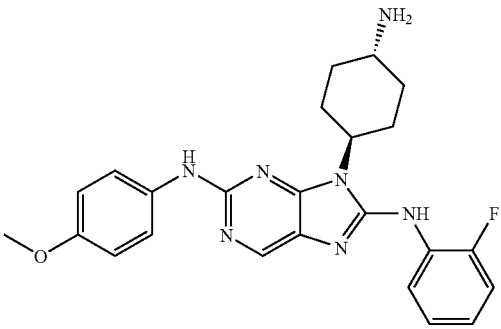<br>67 | 448.3 (8.85/A) |
| 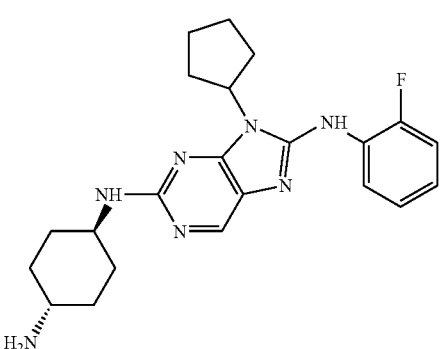<br>68 | 410.6 (9.517/A) |

TABLE 1-continued
| Compound | M + 1 HPLC (min/method) |
|---|---|
| 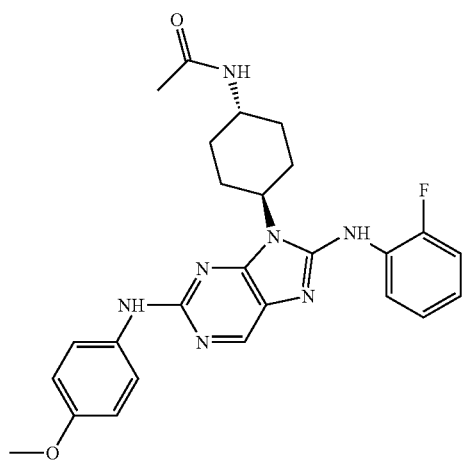 69 | 490.5 (7.617/B) |
| 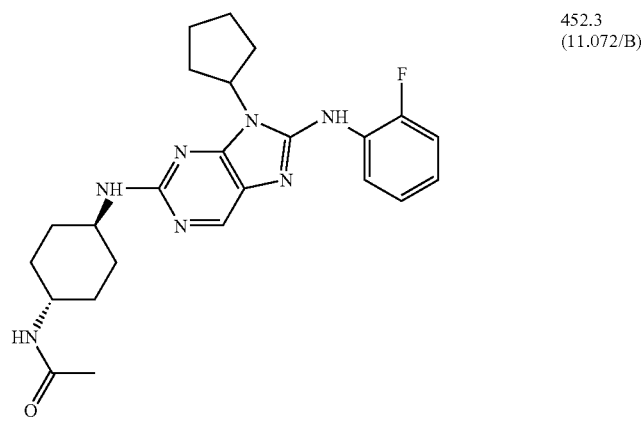 70 | 452.3 (11.072/B) |
| 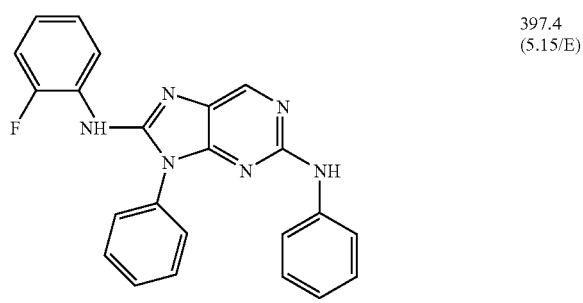 71 | 397.4 (5.15/E) |

TABLE 1-continued

| Compound | M + 1 HPLC (min/method) |
|---|---|
| 72 | 476.4 (8.983/A) |
| 73 | 438.6 (9.25/A) |
| 74 | 419.4 (7.53/B) |
| 75 | 526.5 (9.056/B) |

TABLE 1-continued
| Compound | M + 1 HPLC (min/method) |
|---|---|
| 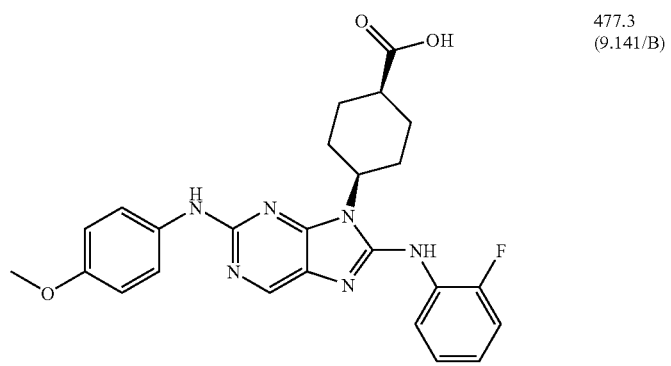<br>76 | 488.4<br>(10.741/B) |
| 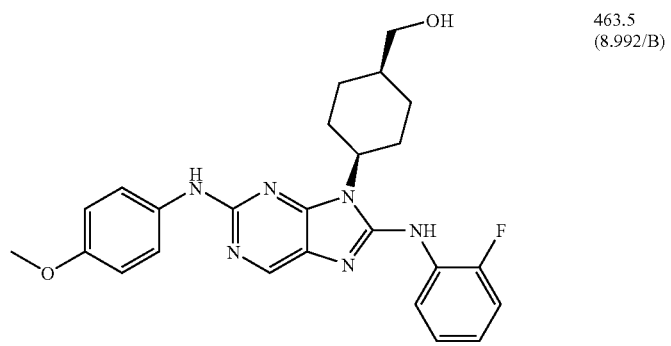<br>77 | 477.3<br>(9.141/B) |
| 78 | 463.5<br>(8.992/B) |

TABLE 1-continued
| Compound | M + 1 HPLC (min/method) |
|---|---|
| 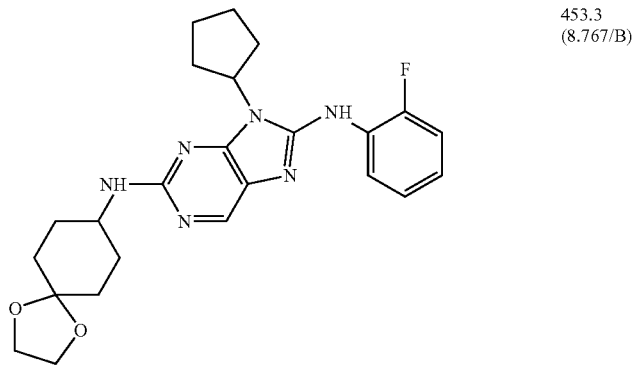<br>79 | 453.3 (8.767/B) |
| 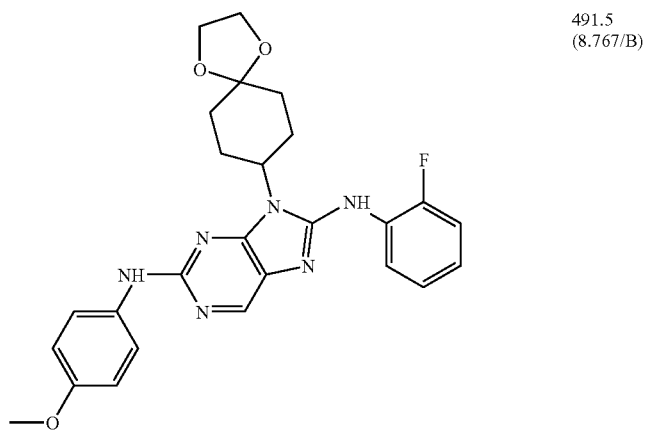<br>80 | 491.5 (8.767/B) |
| 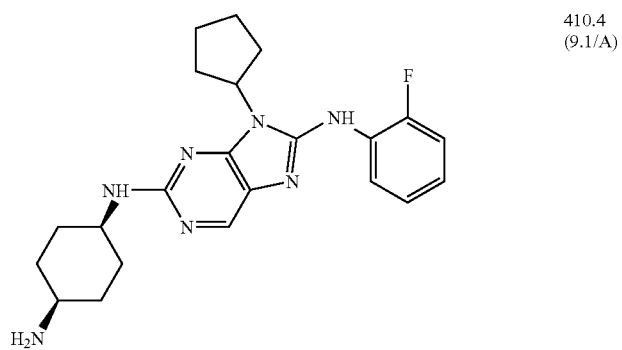<br>81 | 410.4 (9.1/A) |

TABLE 1-continued
| Compound | M + 1 HPLC (min/method) |
|---|---|
| 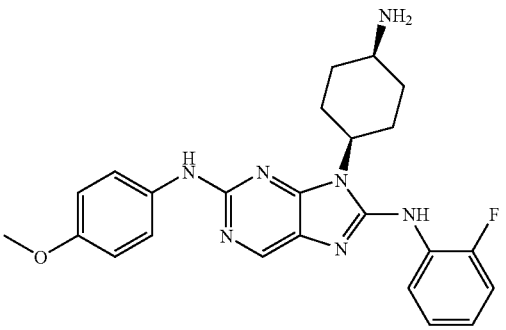 82 | 448.4 (8.8/A) |
| 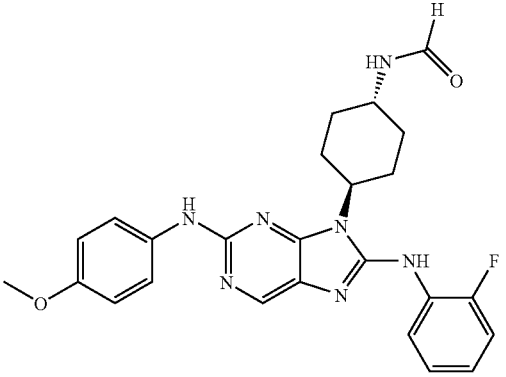 83 | 476.7 (7.55/B) |
| 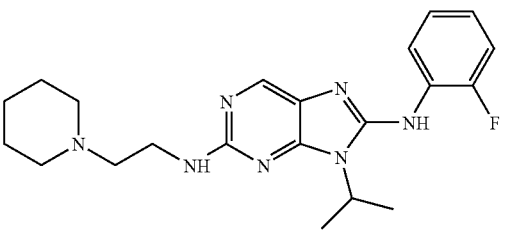 84 | 398.4 (8.72/A) |
| 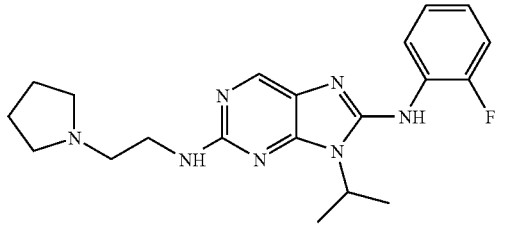 85 | 384.2 (11.75/A) |

TABLE 1-continued
| Compound | M + 1 HPLC (min/method) |
|---|---|
| 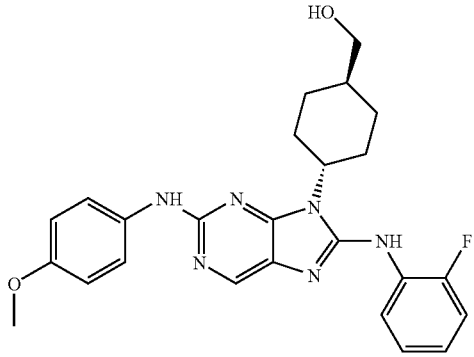<br>86 | 463<br>(9.941/B) |
| 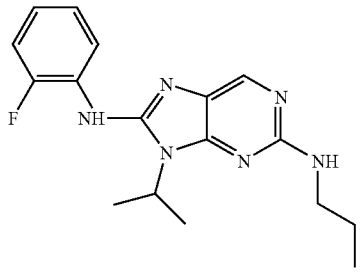<br>87 | 329.15<br>(3.41/E) |
| 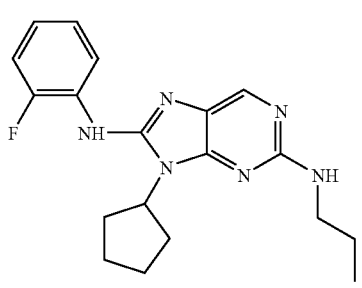<br>88 | 355.25<br>(3.72/E) |
| 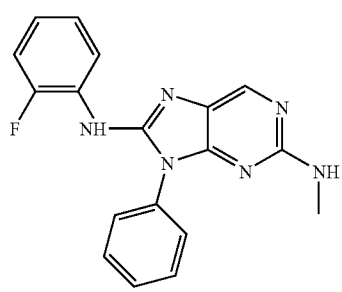<br>89 | 335.15<br>(3.25/E) |

TABLE 1-continued

| Compound | M + 1 HPLC (min/method) |
|---|---|
| 90 | 315.4 (3.24/E) |
| 91 | 329.4 (3.25/E) |
| 91 | 343.25 (3.62/E) |
| 93 | 414.4 (9.27/B) |

TABLE 1-continued

| Compound | M + 1 HPLC (min/method) |
|---|---|
| 94 | 361.4 (3.37/E) |
| 95 | 504.5 (10.98/A) |
| 96 | 427.1 (9.183/B) |
| 97 | 540.6 (13.3/C) |

TABLE 1-continued
| Compound | M + 1 HPLC (min/method) |
|---|---|
| 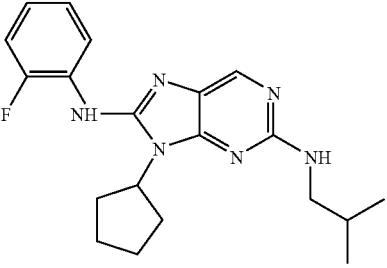 98 | 369.45 (3.9/E) |
| 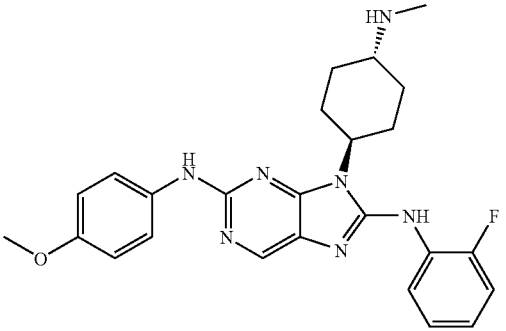 99 | 462.3 (9.02/A) |
| 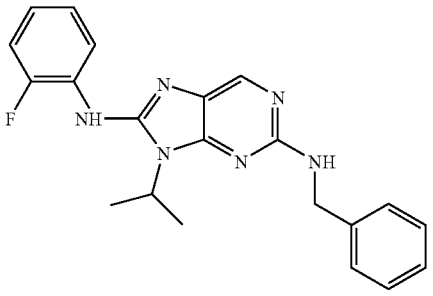 100 | 377.4 (11.02/F) |
| 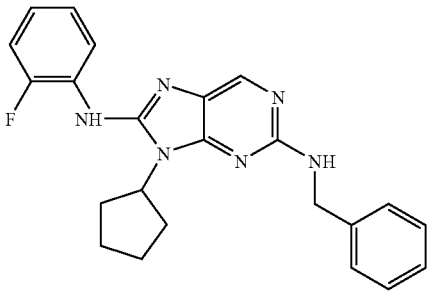 101 | 403.4 (12.16/F) |

TABLE 1-continued
| Compound | M + 1 HPLC (min/method) |
|---|---|
| 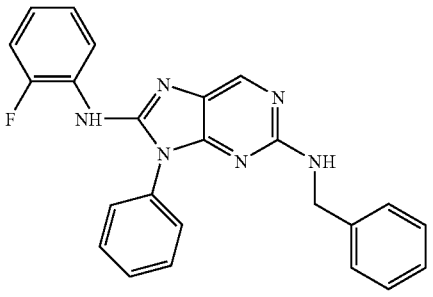 102 | 411.4 (12.84/F) |
| 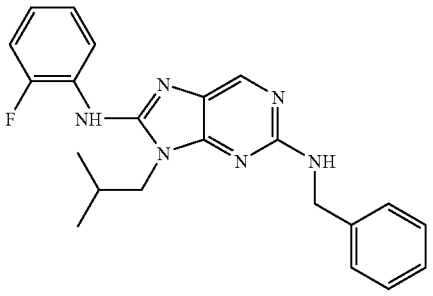 103 | 391.4 (11.85/F) |
| 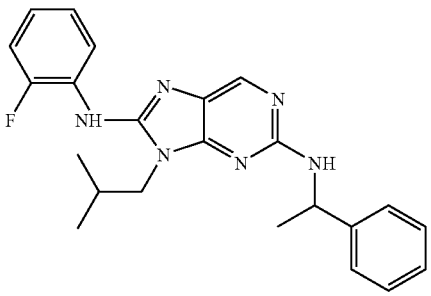 104 | 405.4 (12.39/F) |
| 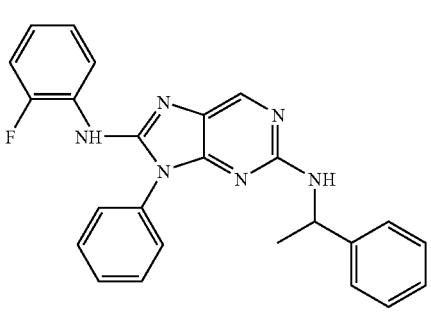 105 | 425.4 (13.54/F) |

TABLE 1-continued

| Compound | M + 1 HPLC (min/method) |
|---|---|
| 106 | 383.4 (4.04/E) |
| 107 | 418.4 (6.12/F) |
| 108 | 432.5 (6.48/F) |
| 109 | 331.4 (7.7/F) |

TABLE 1-continued

| Compound | M + 1 HPLC (min/method) |
|---|---|
| 110 | 345.4 (8.63/F) |
| 111 | 426.2 (8.550/A) |
| 112 | 518.6 (8.48/B) |
| 113 | 532.6 (8.82/B) |

TABLE 1-continued
| Compound | M + 1 HPLC (min/method) |
|---|---|
| 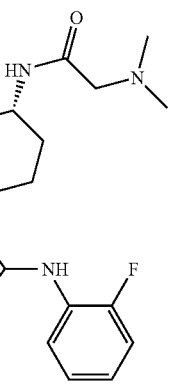  114 | 533.5 (6.53/B) |
| 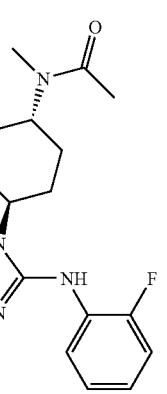  115 | 504.6 (8.00/B) |
| 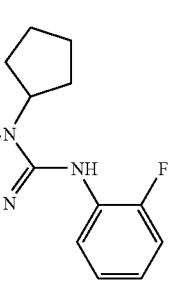  116 | 397.4 (8.12/B) |
| 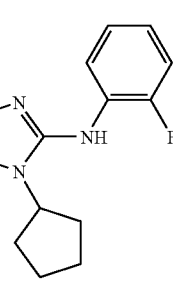  117 | 432.1 (7.60/B) |

TABLE 1-continued
| Compound | M + 1 HPLC (min/method) |
|---|---|
| 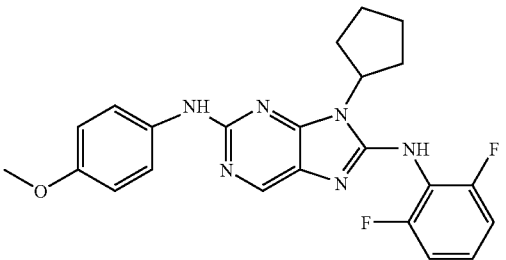 118 | 437.4 (11.040/B) |
| 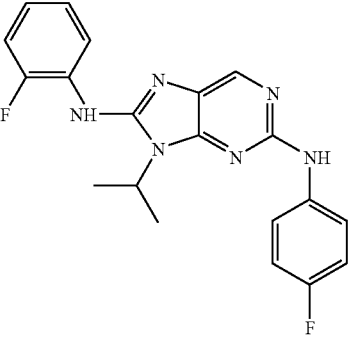 119 | 381.05 (4.55/E) |
| 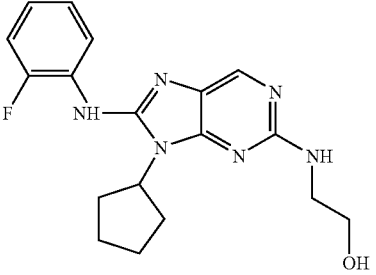 120 | 357.4 (8.84/F) |
| 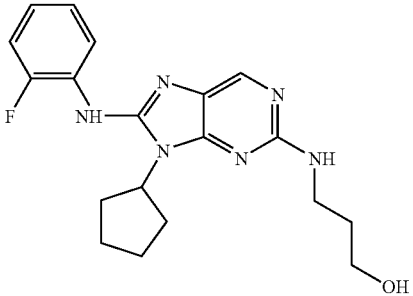 121 | 371.4 (9.09/F) |

TABLE 1-continued
| Compound | M + 1 HPLC (min/method) |
|---|---|
| 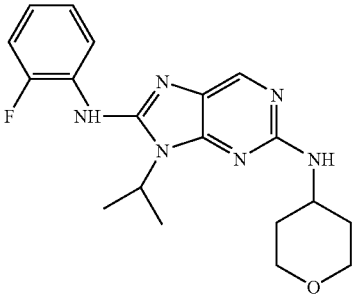
122 | 371.15 (3.17/E) |
| 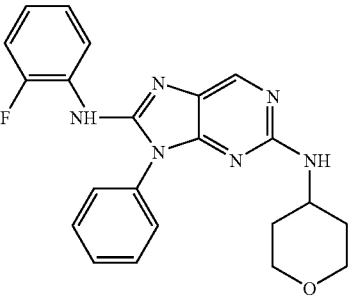
123 | 405.4 (10.3/F) |
| 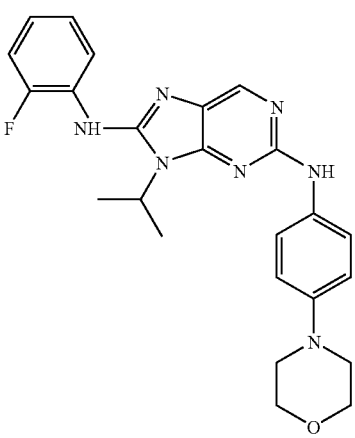
124 | 448.1 (3.72/E) |

TABLE 1-continued
| Compound | M + 1 HPLC (min/method) |
|---|---|
| 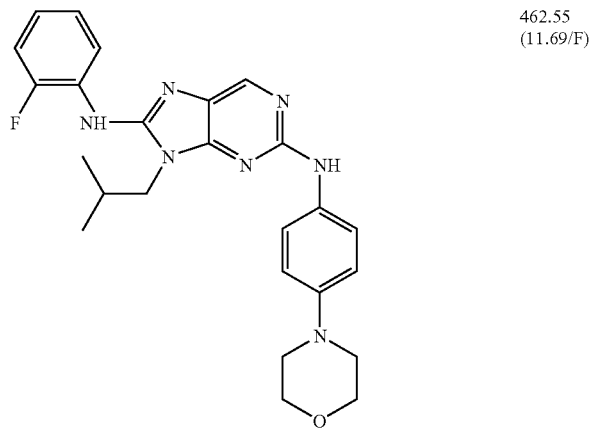<br>125 | 462.55 (11.69/F) |
| 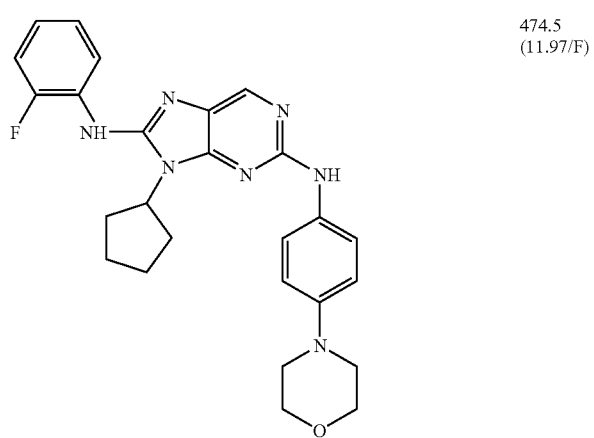<br>126 | 474.5 (11.97/F) |
| 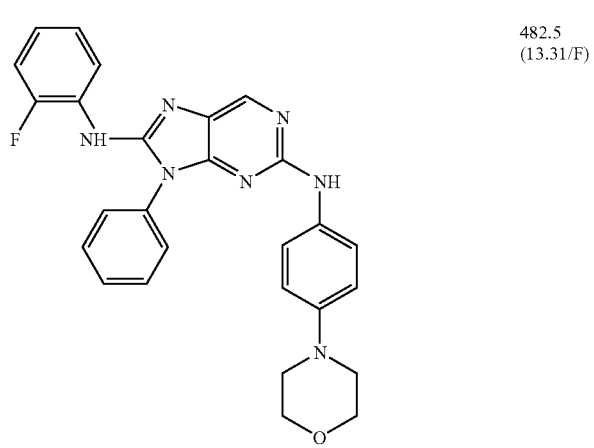<br>127 | 482.5 (13.31/F) |

TABLE 1-continued
| Compound | M + 1 HPLC (min/method) |
|---|---|
| 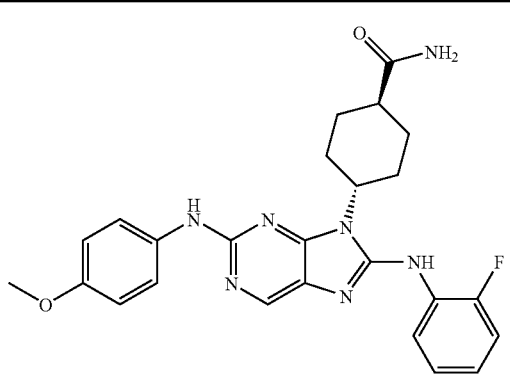<br>128 | 476.6 (11.019/B) |
| 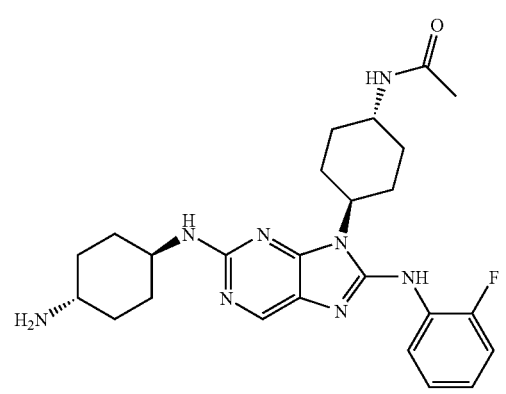<br>129 | 481.3 (8.67/A) |
| 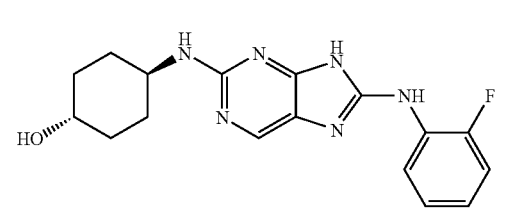<br>130 | 343.4 (6.25/B) |
| 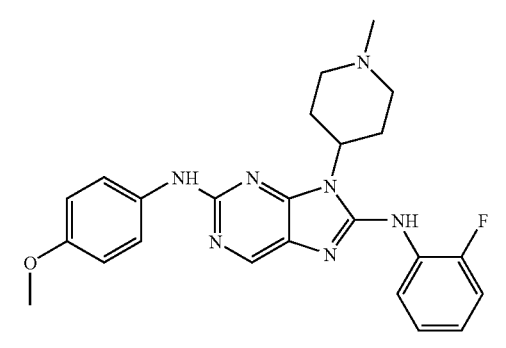<br>131 | 448.6 (10.733/A) |

TABLE 1-continued
| Compound | M + 1 HPLC (min/method) |
|---|---|
| 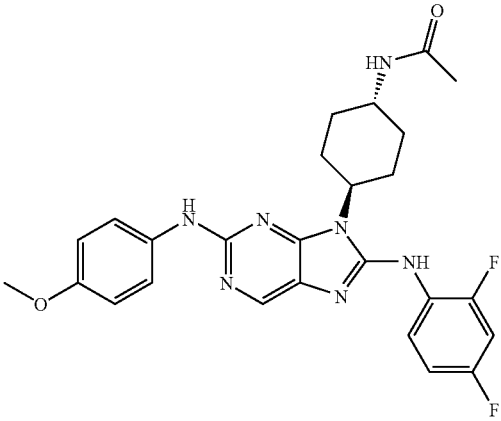 132 | 508.3 (8.517/B) |
|  133 | 489.56 |
| 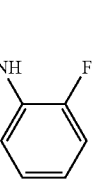 134 | 342.4 (8.05/A) |
| 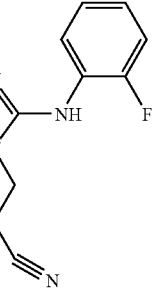 135 | 396 (6.33/B) |

TABLE 1-continued

| Compound | M + 1 HPLC (min/method) |
|---|---|
| 136 | 426.1 (9.707/B) |
| 137 | 488.5 (9.045/B) |
| 138 | 415.3 (8.22/B) |
| 139 | 367.4 (3.76/E) |

TABLE 1-continued

| Compound | M + 1 HPLC (min/method) |
|---|---|
| 140 | 399.5 (3.23/E) |
| 141 | 419.45 (3.31/E) |
| 142 | 363.35 (4.39/E) |
| 143 | 355.4 (3.67/E) |

TABLE 1-continued

| Compound | M + 1 HPLC (min/method) |
|---|---|
| 144 | 385.4 (3.05/E) |
| 145 | 413.5 (8.62/B) |
| 146 | 385.1 (3.28/E) |
| 147 | 384.2 (9.58/A) |

TABLE 1-continued
| Compound | M + 1 HPLC (min/method) |
|---|---|
| 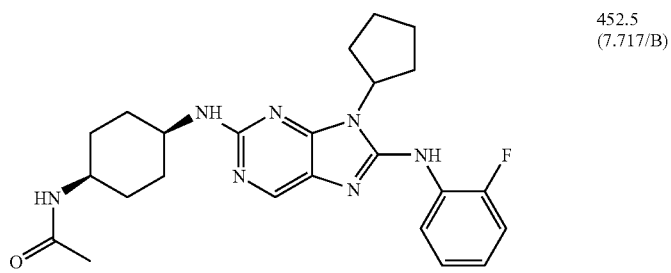 148 | 452.5 (7.717/B) |
| 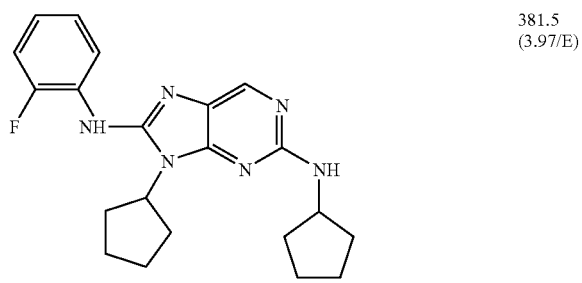 149 | 381.5 (3.97/E) |
| 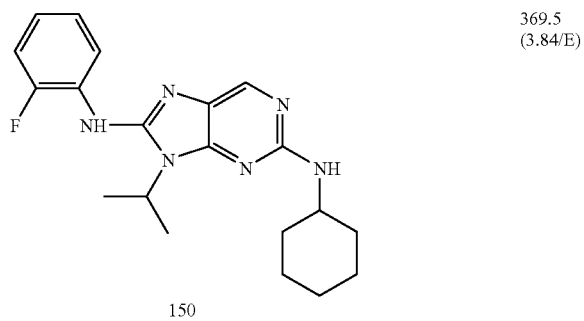 150 | 369.5 (3.84/E) |
| 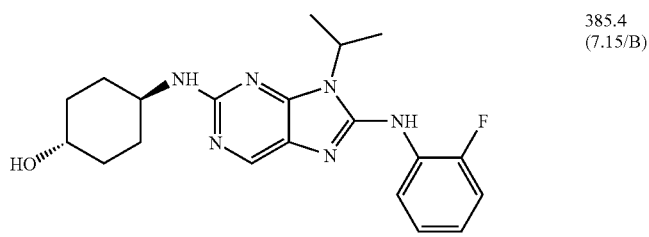 151 | 385.4 (7.15/B) |

TABLE 1-continued

| Compound | M + 1 HPLC (min/method) |
|---|---|
| 152 | 403.3 (7.28/B) |
| 153 | 402.1 (6.18/B) |
| 154 | 382.4 (2.23/E) |
| 155 | 496.1 (7.87/B) |

TABLE 1-continued

| Compound | M + 1 HPLC (min/method) |
|---|---|
| 156 | 506.5 (8.40/B) |
| 157 | 495.4 (11.467/B) |
| 158 | 482.5 (9.48/A) |

TABLE 1-continued
| Compound | M + 1 HPLC (min/method) |
|---|---|
| 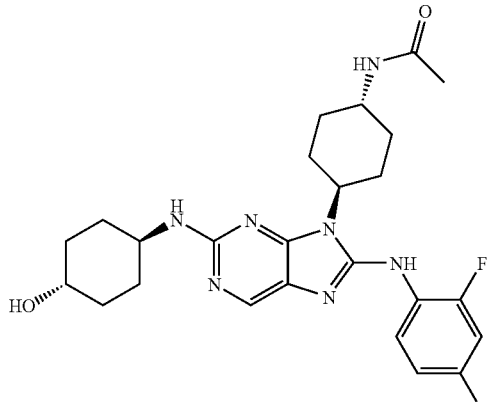159 | 500.4 (10.52/A) |
| 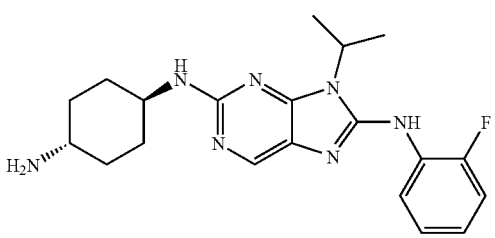160 | 384.5 (8.65/A) |
| 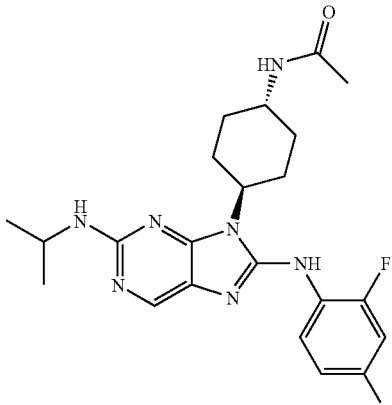161 | 444.3 (10.837/B) |

TABLE 1-continued

| Compound | M + 1 HPLC (min/method) |
|---|---|
| 162 | 476.5 (7.417/B) |
| 163 | 401.1 (9.97/A) |
| 164 | 419.2 (10.13/A) |
| 165 | 423.3 (8.37/A) |

TABLE 1-continued
| Compound | M + 1 HPLC (min/method) |
|---|---|
| 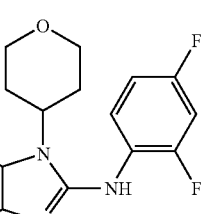 166 | 441.3 (8.82/B) |
| 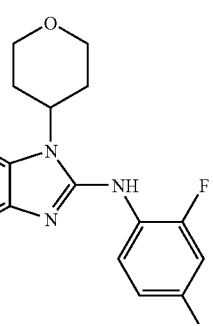 167 | 445.4 (6.800/B) |
| 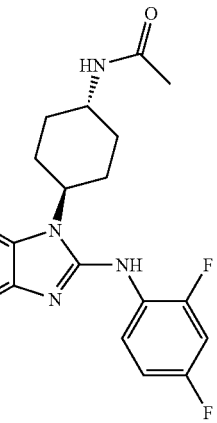 168 | 499.5 (8.83/A) |
| 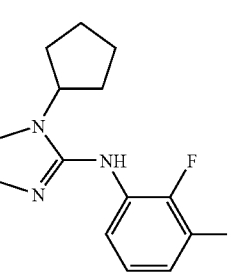 169 | 437.4 (12.757/B) |

TABLE 1-continued
| Compound | M + 1 HPLC (min/method) |
|---|---|
| 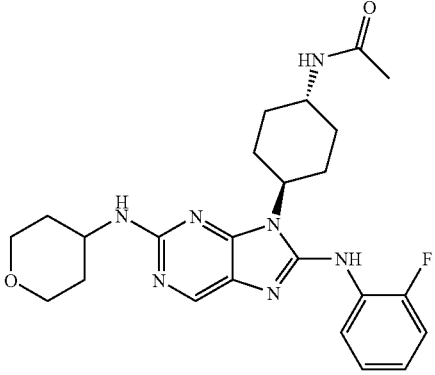<br>170 | 468.4 (9.50/A) |
| 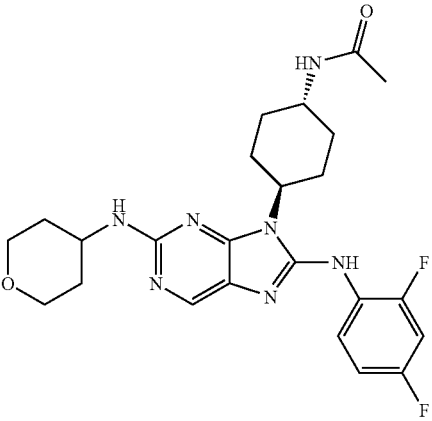<br>171 | 486.5 (9.67/A) |
| 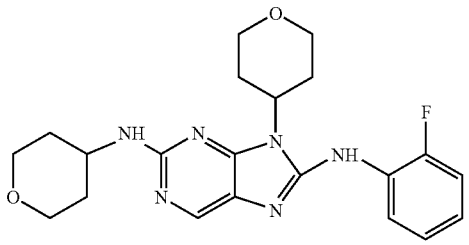<br>172 | 413.2 (11.061/B) |
| 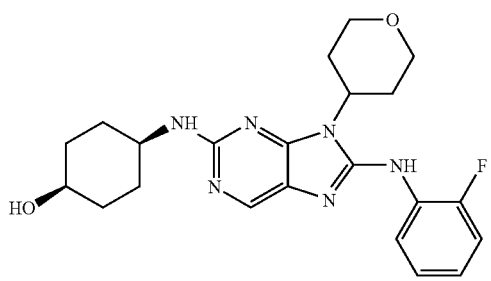<br>173 | 427.2 (11.072/B) |

TABLE 1-continued

| Compound | M + 1 HPLC (min/method) |
|---|---|
| 174 | 429 (10.67/A) |
| 175 | 559.2 (9.85/A) |
| 176 | 577.5 (10.02/A) |

TABLE 1-continued
| Compound | M + 1 HPLC (min/method) |
|---|---|
| 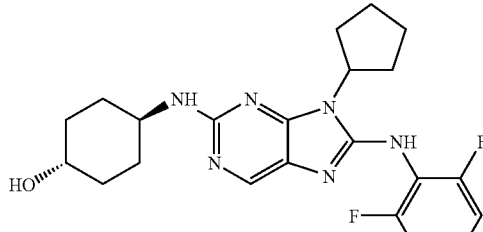 177 | 429.4 (10.57/A) |
| 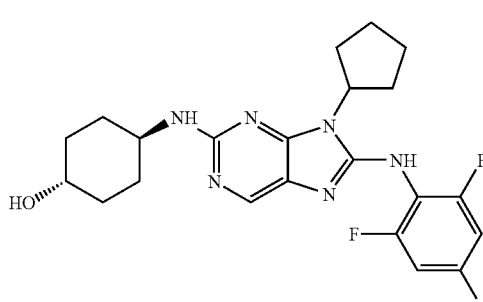 178 | 447.4 (10.80/A) |
| 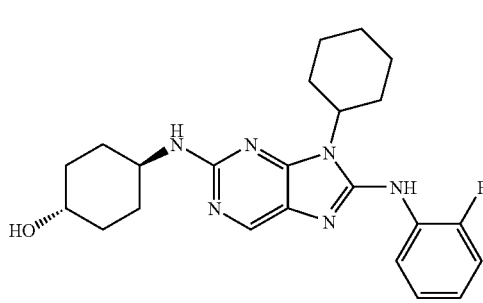 179 | 425.4 (8.067/A) |
| 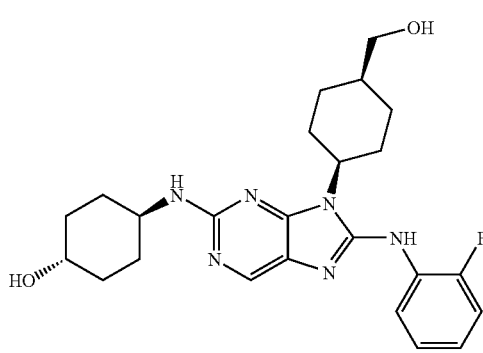 180 | 455.1 (7.100/B) |

TABLE 1-continued

| Compound | M + 1 HPLC (min/method) |
|---|---|
| 181 | 425.3 (11.78/A) |
| 182 | 467.4 (11.45/A) |
| 183 | 441.5 (7.563/B) |
| 184 | 518.5 (6.967/B) |

TABLE 1-continued
| Compound | M + 1 HPLC (min/method) |
|---|---|
| 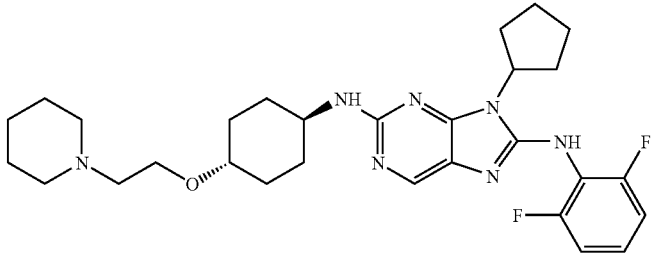 185 | 540.3 (10.1/A) |
| 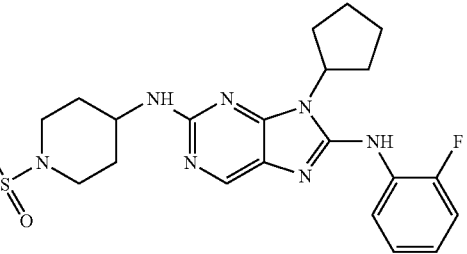 186 | 474.3 (15.381/B) |
| 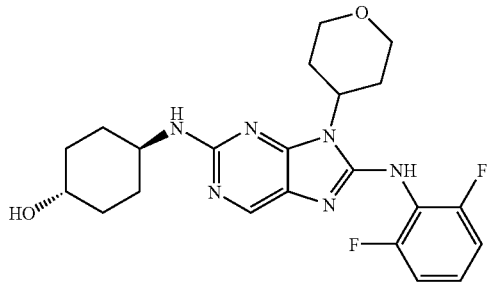 187 | 445.4 (10.944/B) |
| 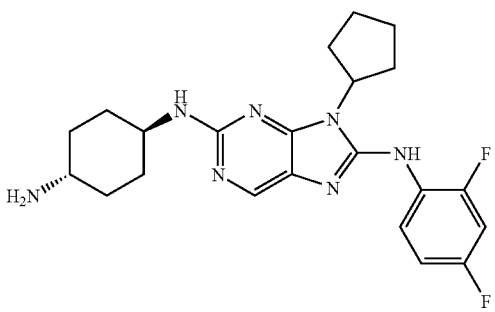 188 | 428.4 (9.17/A) |

TABLE 1-continued
| Compound | M + 1 HPLC (min/method) |
|---|---|
| 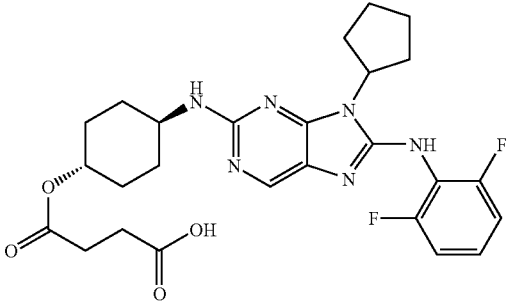<br>189 | 529 (16.526/B) |
| 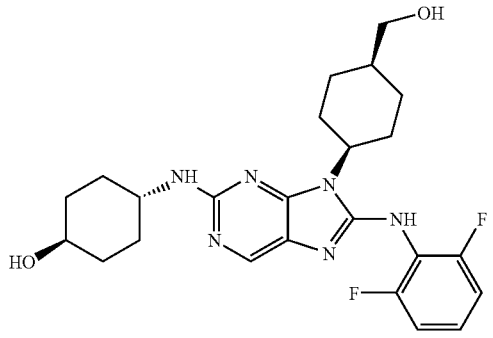<br>190 | 473.4 (14.624/B) |
| 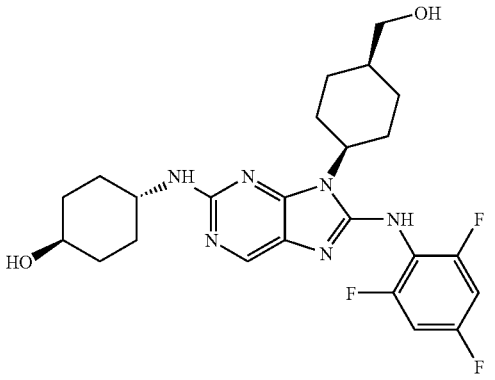<br>191 | 473.4 (14.624/B) |
| 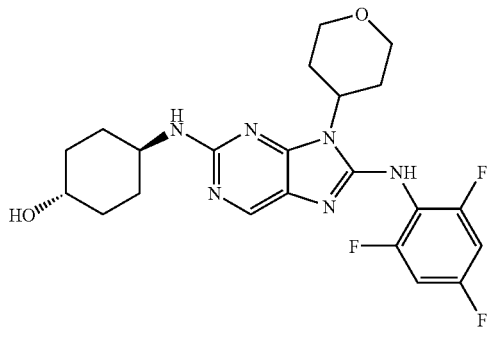<br>192 | 463.4 (7.050/B) |

TABLE 1-continued

| Compound | M + 1 HPLC (min/method) |
|---|---|
| 193 | 428.4 (9.05/A) |
| 194 | 446.4 (9.30/A) |
| 195 | 426.4 (5.600/A) |
| 196 | 455.4 (9.617/A) |

TABLE 1-continued
| Compound | M + 1 HPLC (min/method) |
|---|---|
| 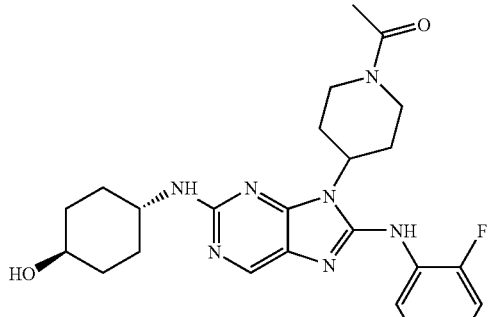 197 | 468.5 (6.567/B) |
| 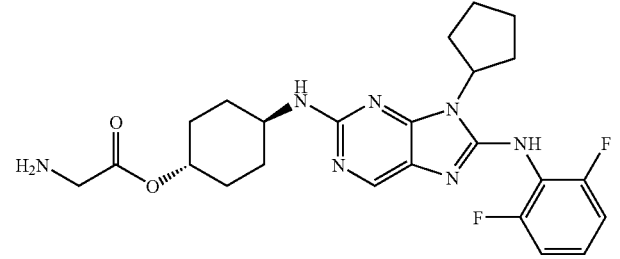 198 | 486 (9.467/A) |
| 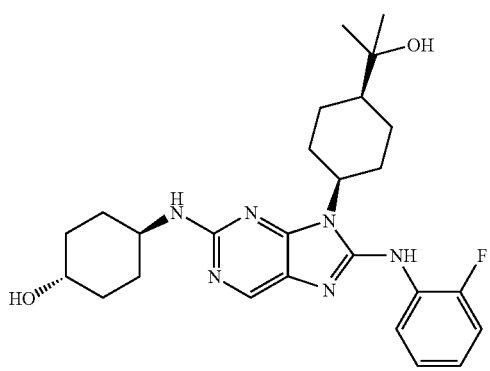 199 | 483.5 (7.58/B) |
| 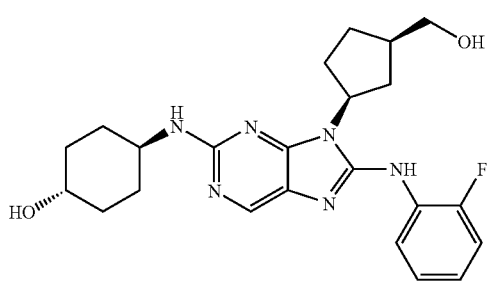 200 | 441.3 (9.483/A) |

TABLE 1-continued

| Compound | M + 1 HPLC (min/method) |
|---|---|
| 201 | 441.5 (9.433/A) |
| 202 | 469.3 (8.533/B) |
| 203 | 487.5 (10.66/A) |
| 204 | 505.5 (8.017/B) |

TABLE 1-continued

| Compound | M + 1 HPLC (min/method) |
|---|---|
| 205 | 443.4 (8.156/B) |
| 206 | 457 (8.000/B) |
| 207 | 551.6 (9.95/C) |
| 208 | 390.2 (7.10/B) |

TABLE 1-continued

| Compound | M + 1 HPLC (min/method) |
|---|---|
| 209 | 408.4 (8.52/B) |
| 210 | 534.4 (7.52/) |
| 211 | 459 (7.983/B) |

TABLE 1-continued
| Compound | M + 1 HPLC (min/method) |
|---|---|
| 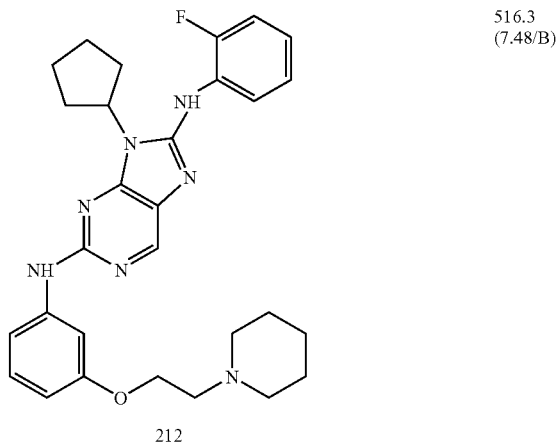 212 | 516.3 (7.48/B) |
| 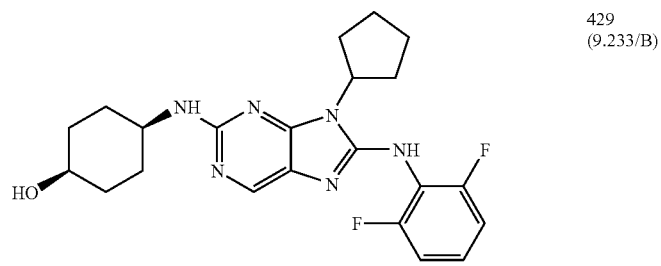 213 | 429 (9.233/B) |
| 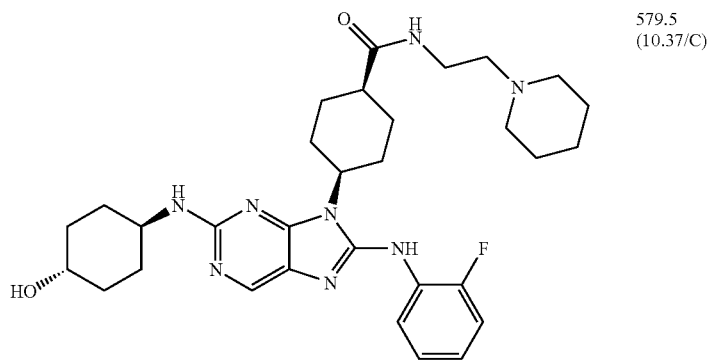 214 | 579.5 (10.37/C) |

TABLE 1-continued
| Compound | M + 1 HPLC (min/method) |
|---|---|
| 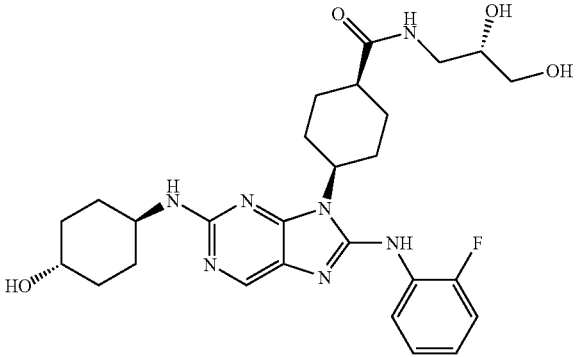 215 | 542.4 (10.57/C) |
| 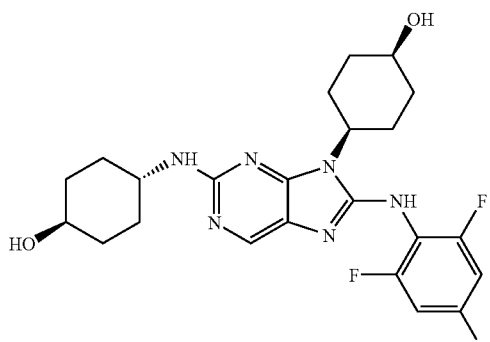 216 | 477.5 (8.233/B) |
| 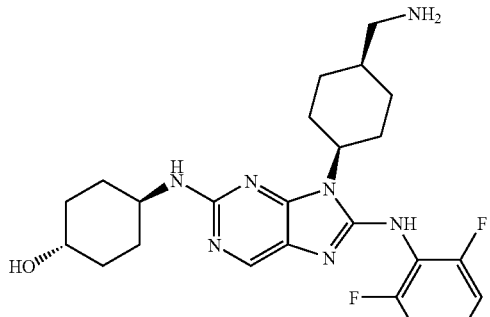 217 | 472.5 (8.467/A) |

TABLE 1-continued
| Compound | M + 1 HPLC (min/method) |
|---|---|
| 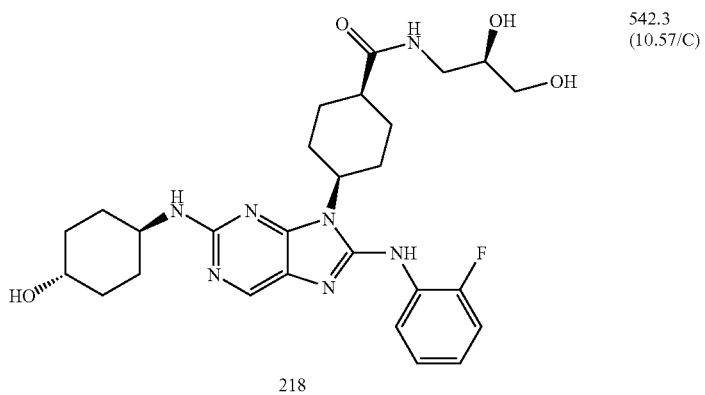 218 | 542.3 (10.57/C) |
| 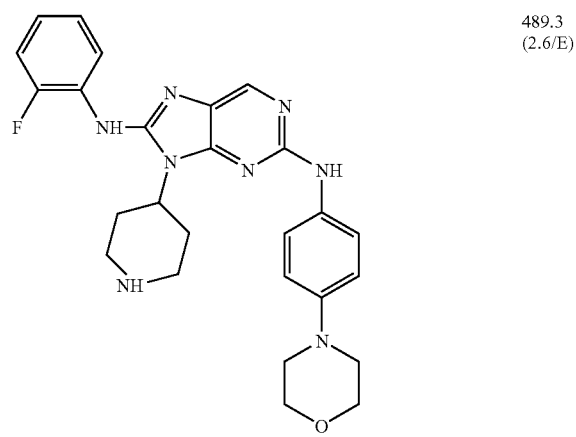 219 | 489.3 (2.6/E) |
| 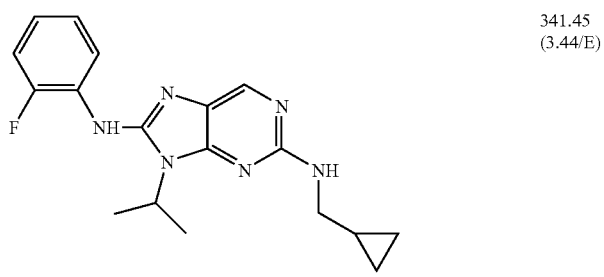 220 | 341.45 (3.44/E) |

TABLE 1-continued
| Compound | M + 1 HPLC (min/method) |
|---|---|
| 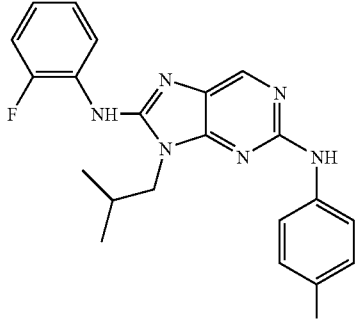 221 | 395.15 (4.87/E)) |
| 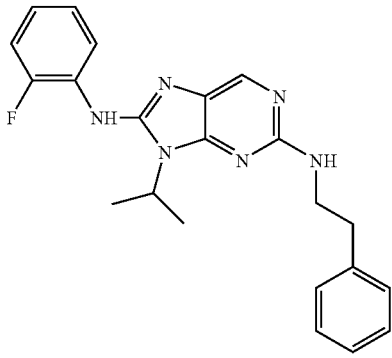 222 | 391.1 (3.87/E) |
| 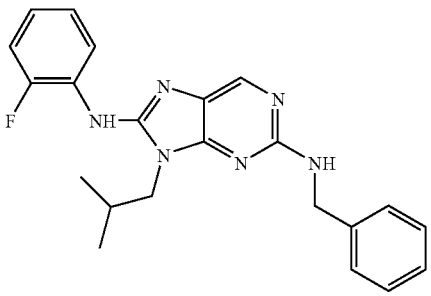 223 | 392.4 (8.12/F) |
| 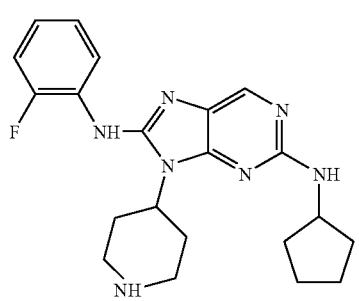 224 | 396.5 (2.32/E) |

TABLE 1-continued
| Compound | M + 1 HPLC (min/method) |
|---|---|
| 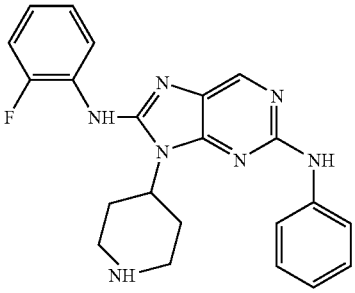 225 | 404.45 (2.71/E) |
| 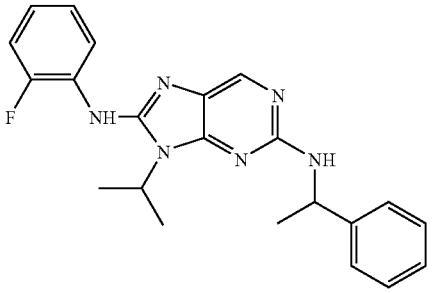 226 | 391.4 (11.67/F) |
| 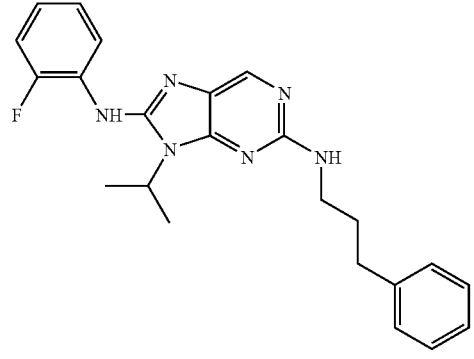 227 | 405.2 (4.02/E) |
| 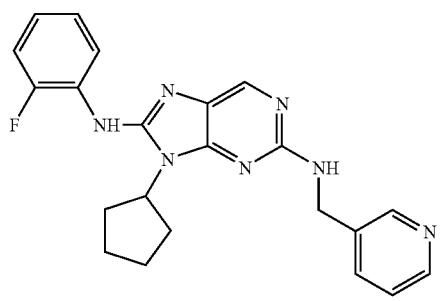 228 | 404.4 (8.42/F) |

TABLE 1-continued

| Compound | M + 1 HPLC (min/method) |
| --- | --- |
| 229 | 439.1 (4.37/E) |
| 230 | 422.15 (2.82/E) |
| 231 | 431.5 (4.27/E) |
| 232 | 412.1 (3.08/E) |

TABLE 1-continued
| Compound | M + 1 HPLC (min/method) |
|---|---|
| 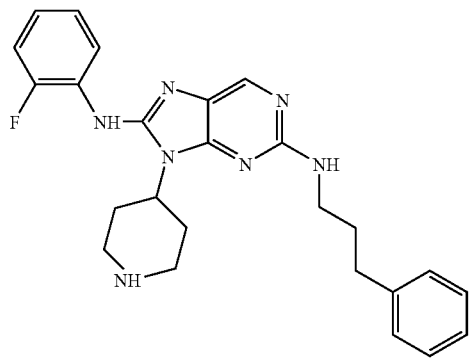 233 | 446.15 (2.68/E) |
| 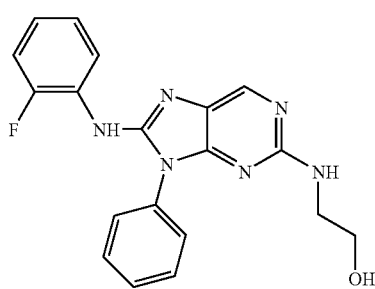 234 | 365.4 (8.85/F) |
| 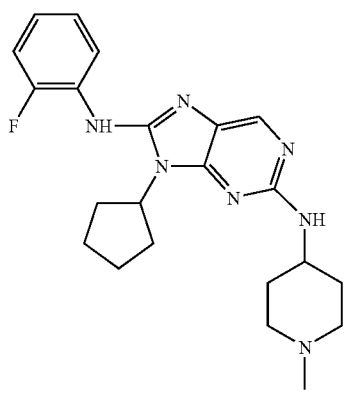 235 | 410.15 (2.53/E) |
| 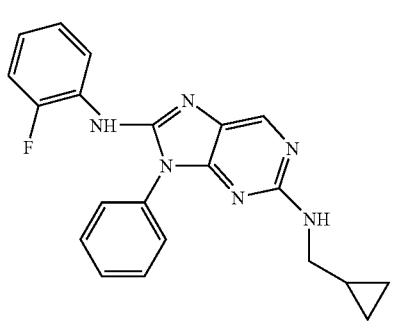 236 | 375.35 (3.76/E) |

TABLE 1-continued
| Compound | M + 1 HPLC (min/method) |
|---|---|
| 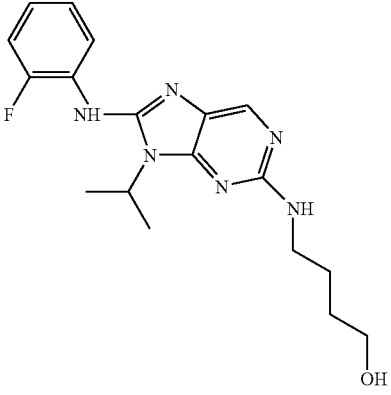
237 | 359.15 (3.00/E) |
| 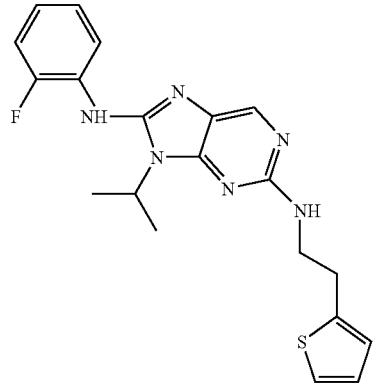
238 | 397.1 (3.82/E) |
| 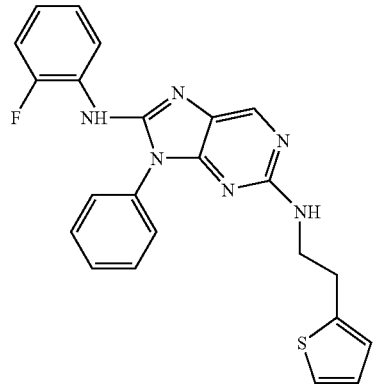
239 | 431.5 (12.84/F) |

TABLE 1-continued
| Compound | M + 1 HPLC (min/method) |
|---|---|
| 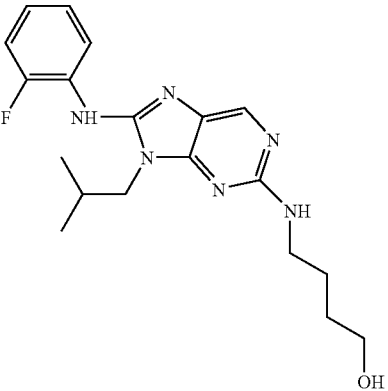240 | 373.1 (3.21/E) |
| 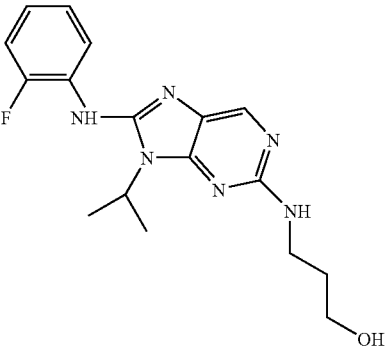241 | 345.4 (8.05/F) |
| 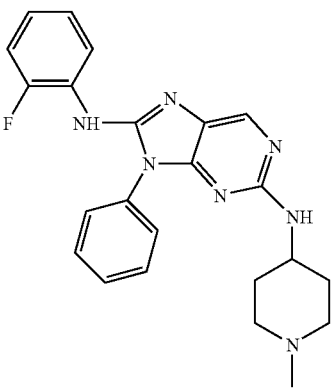242 | 418.1 (2.64/E) |

TABLE 1-continued
| Compound | M + 1 HPLC (min/method) |
|---|---|
| 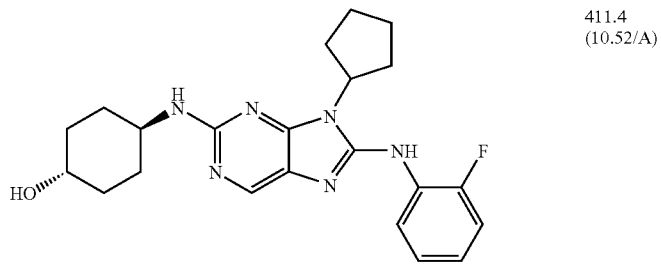 243 | 411.4 (10.52/A) |
| 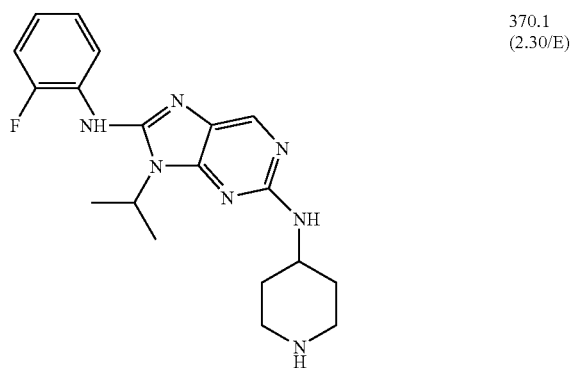 244 | 370.1 (2.30/E) |
| 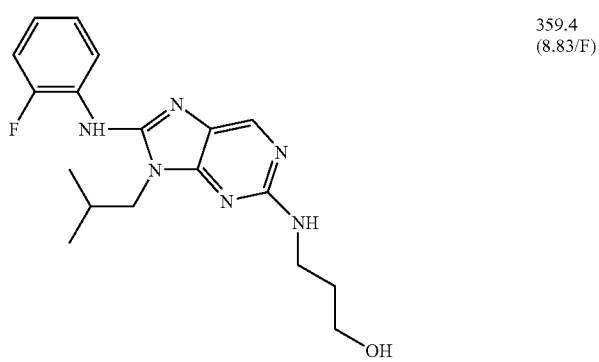 245 | 359.4 (8.83/F) |

TABLE 1-continued

| Compound | M + 1 HPLC (min/method) |
|---|---|
| 246 | 417.2 (4.14/E) |
| 247 | 384.2 (2.51E) |
| 248 | 405.2 (4.07/E) |

TABLE 1-continued
| Compound | M + 1 HPLC (min/method) |
|---|---|
| 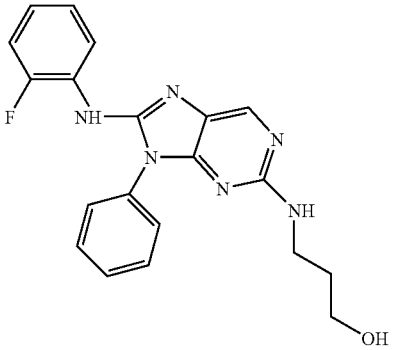<br>249 | 379.4<br>(9.03/F) |
| 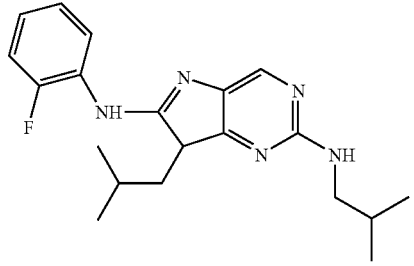<br>250 | 357<br>(11.41/F) |
| 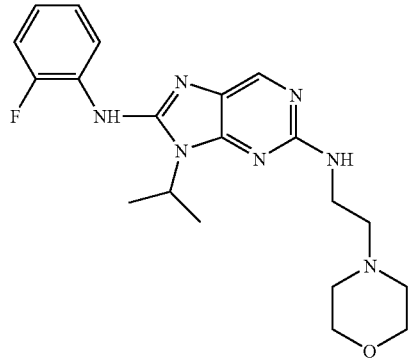<br>251 | 400.1<br>(2.33/E) |
| 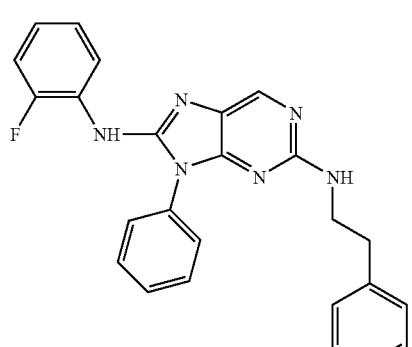<br>252 | 425.15<br>(4.25/E) |

TABLE 1-continued

| Compound | M + 1 HPLC (min/method) |
|---|---|
| 253 | 369.5 (3.86/E) |
| 254 | 432.2 (2.54/E) |
| 255 | 414.2 (2.55/E) |
| 256 | 385.4 (9.83/F) |

TABLE 1-continued

| Compound | M + 1 HPLC (min/method) |
|---|---|
| 257 | 389.45 (3.97/E) |
| 258 | 419.15 (4.19/E) |
| 259 | 423.05 (4.09/E) |
| 260 | 426.9 (6.84/F) |

TABLE 1-continued

| Compound | M + 1 HPLC (min/method) |
|---|---|
| 261 | 403.4 (4.18/E) |
| 262 | 384.2 (2.32/E) |
| 263 | 434.15 (2.67/E) |
| 264 | 438.05 (2.49/E) |

TABLE 1-continued
| Compound | M + 1 HPLC (min/method) |
|---|---|
| 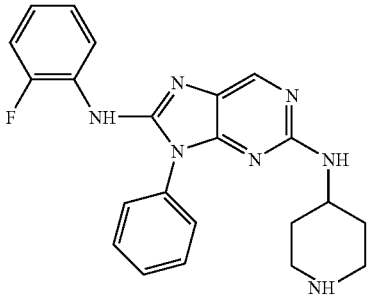 265 | 404.15 (2.61/E) |
| 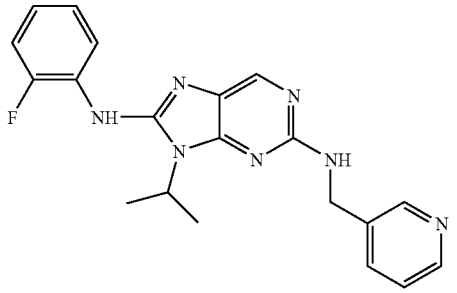 266 | 378.4 (7.18/F) |
| 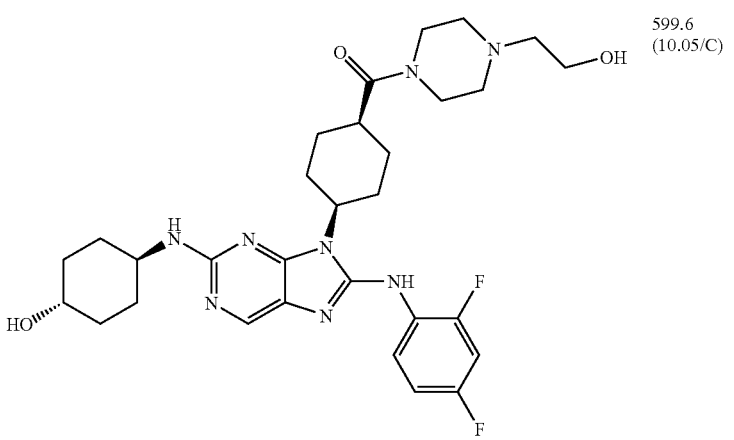 267 | 599.6 (10.05/C) |

TABLE 1-continued

| Compound | M + 1 HPLC (min/method) |
|---|---|
| 268 | 393.5 (3.25/E) |
| 269 | 508 (9.467/A) |
| 270 | 508 (9.433/A) |
| 271 | 526 (9.700/A) |

TABLE 1-continued
| Compound | M + 1 HPLC (min/method) |
|---|---|
| 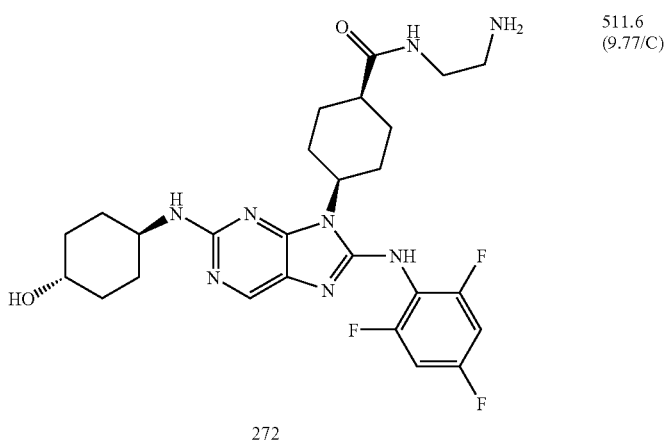 272 | 511.6 (9.77/C) |
| 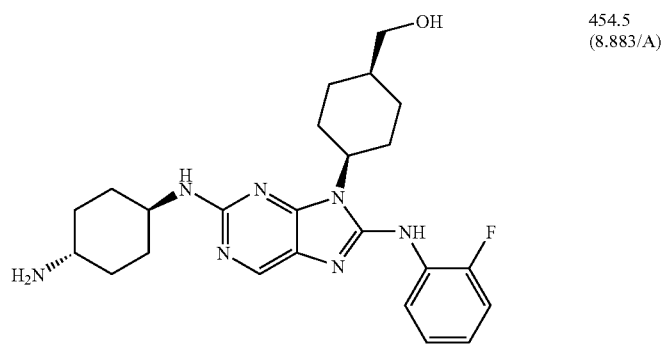 273 | 454.5 (8.883/A) |
| 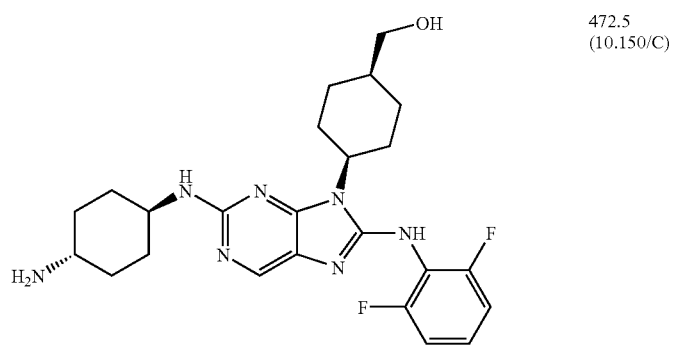 274 | 472.5 (10.150/C) |

TABLE 1-continued
| Compound | M + 1 HPLC (min/method) |
|---|---|
| 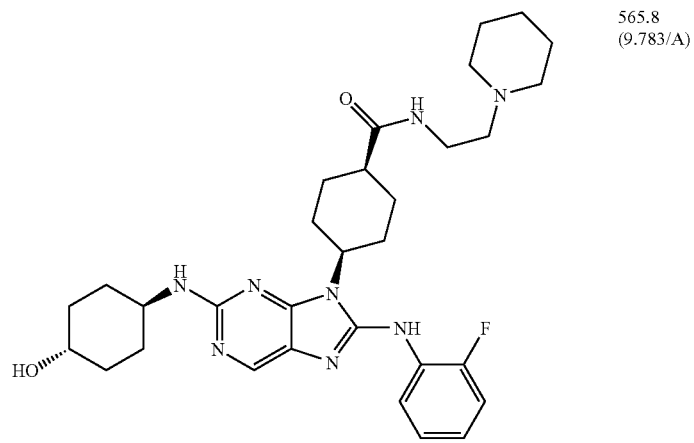 275 | 565.8 (9.783/A) |
| 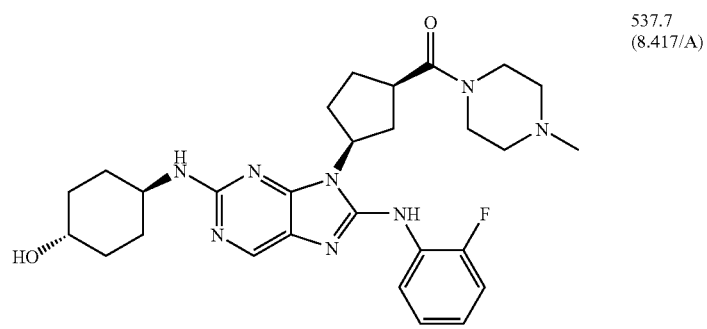 276 | 537.7 (8.417/A) |
| 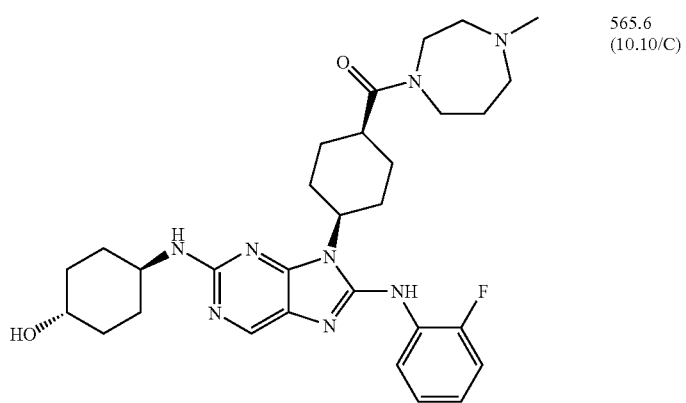 277 | 565.6 (10.10/C) |

TABLE 1-continued
| Compound | M + 1 HPLC (min/method) |
|---|---|
| 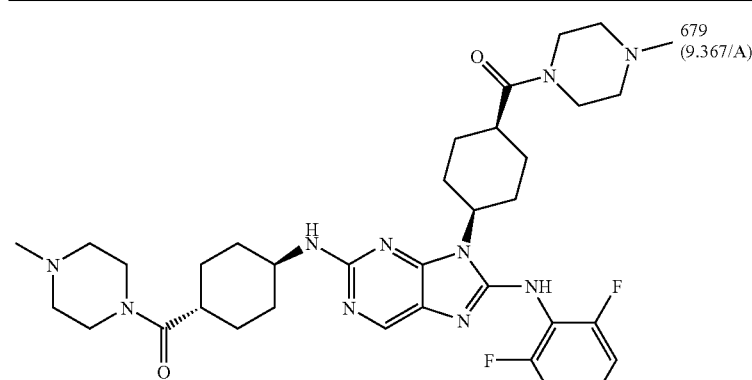 278 | 679 (9.367/A) |
| 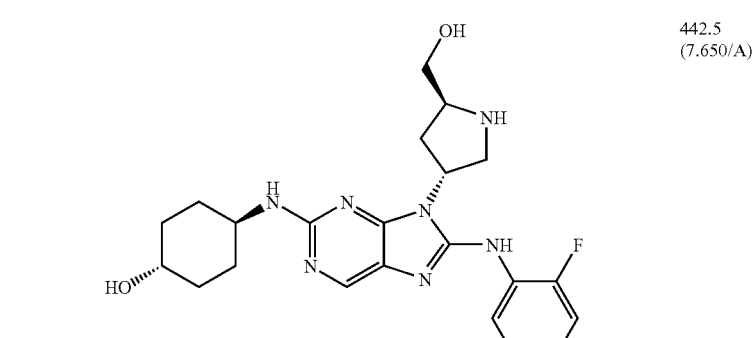 279 | 442.5 (7.650/A) |
| 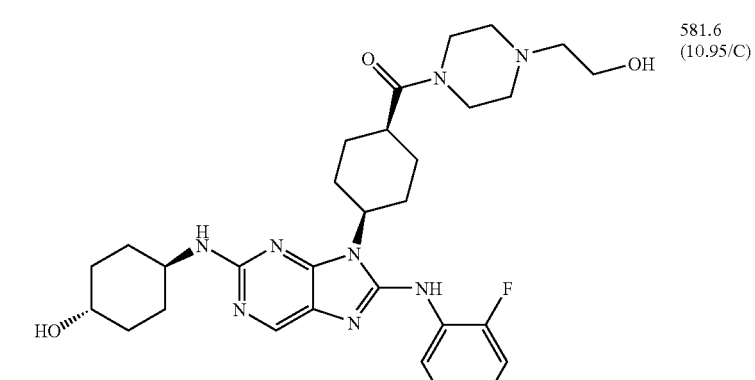 280 | 581.6 (10.95/C) |

TABLE 1-continued
| Compound | M + 1 HPLC (min/method) |
|---|---|
| 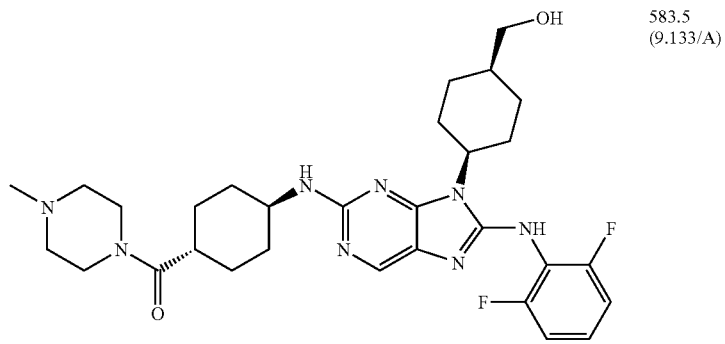 281 | 583.5 (9.133/A) |
| 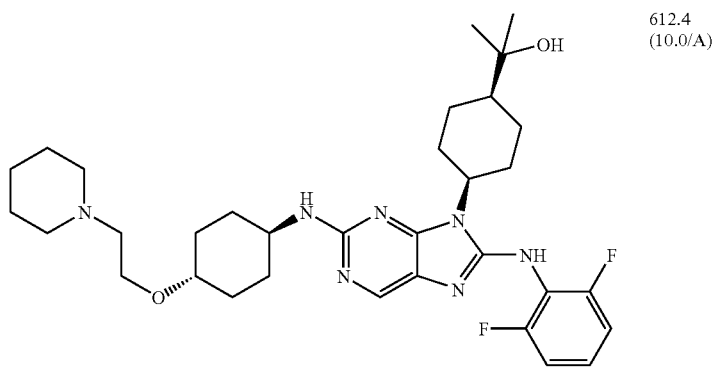 282 | 612.4 (10.0/A) |
| 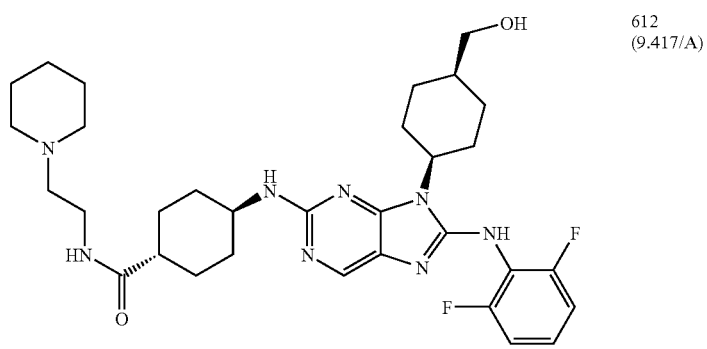 283 | 612 (9.417/A) |

TABLE 1-continued
| Compound | M + 1 HPLC (min/method) |
|---|---|
| 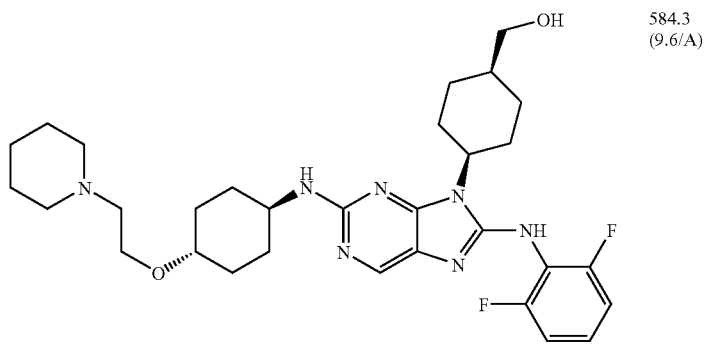 284 | 584.3 (9.6/A) |
| 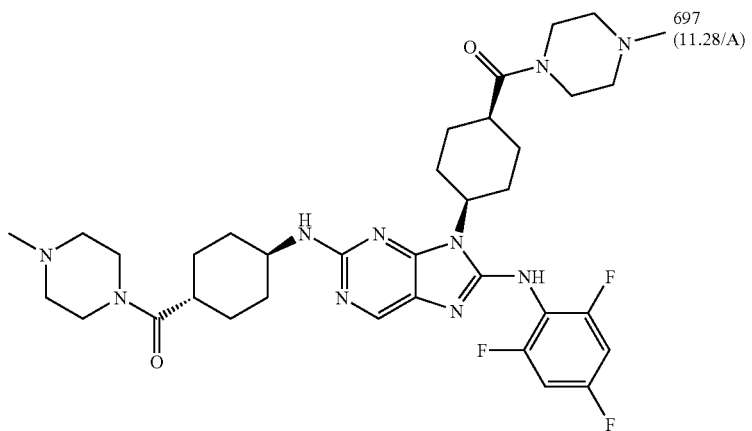 285 | 697 (11.28/A) |
| 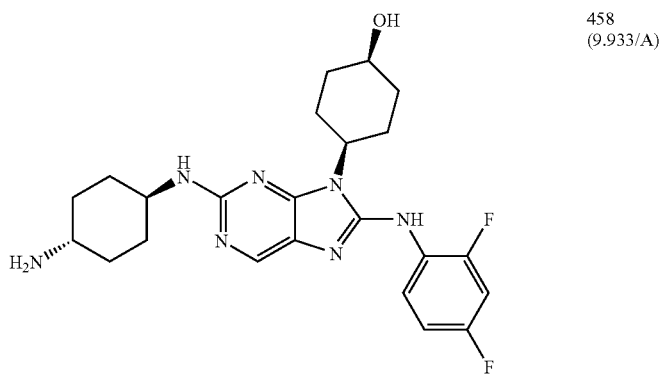 286 | 458 (9.933/A) |

TABLE 1-continued
| Compound | M + 1 HPLC (min/method) |
|---|---|
| 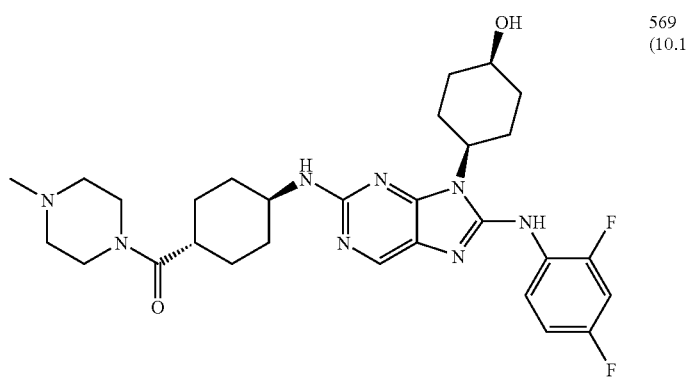 287 | 569 (10.167/A) |
| 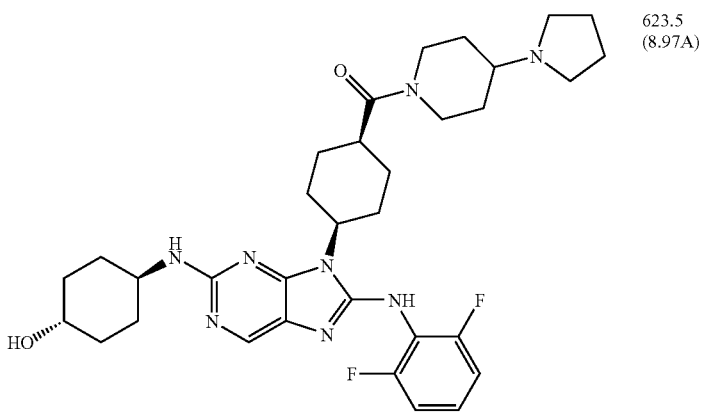 288 | 623.5 (8.97A) |
| 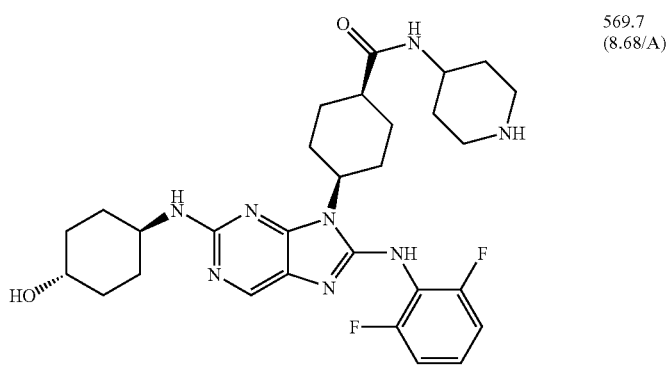 289 | 569.7 (8.68/A) |

TABLE 1-continued
| Compound | M + 1 HPLC (min/method) |
|---|---|
| 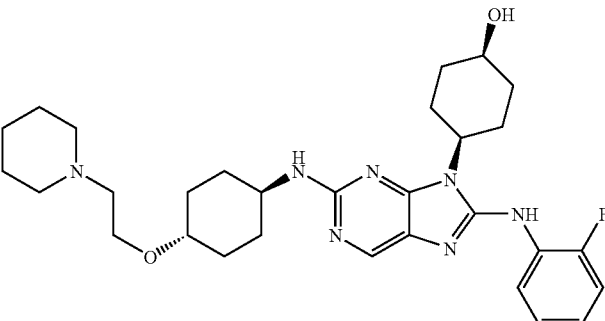 290 | 570.5 (10.50/A) |
| 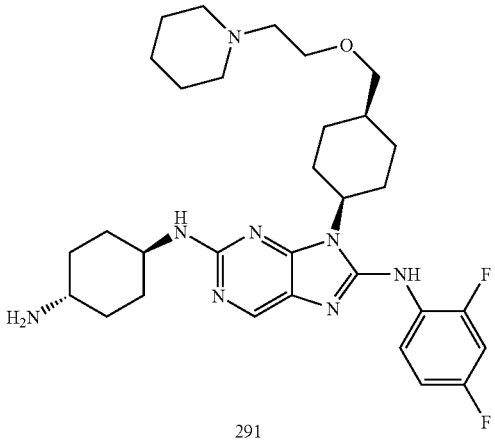 291 | 583.8 (9.92/A) |
| 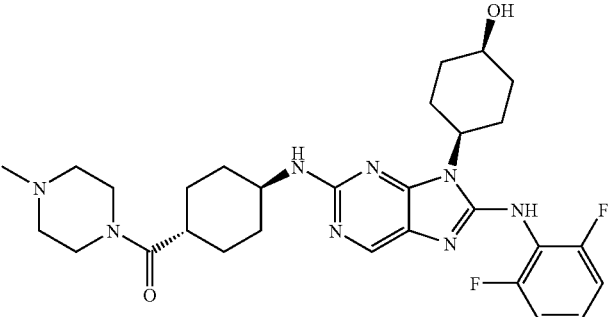 292 | 587 (10.217/A) |

TABLE 1-continued
| Compound | M + 1 HPLC (min/method) |
|---|---|
| 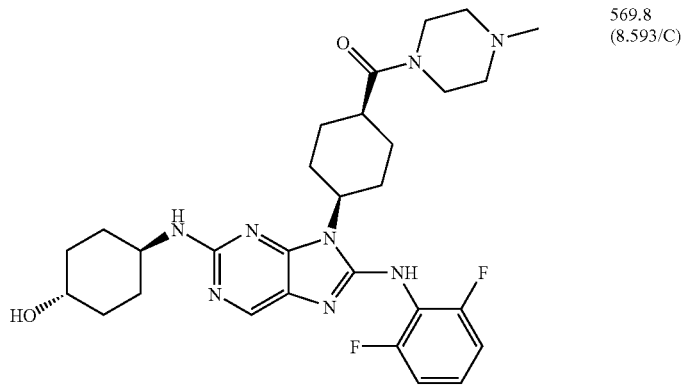 293 | 569.8 (8.593/C) |
| 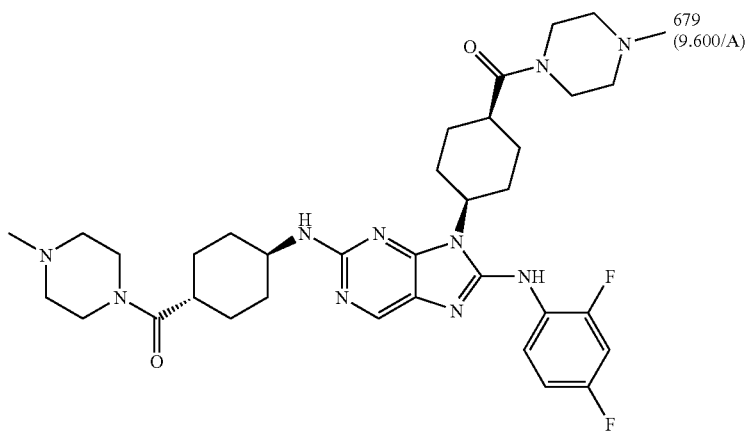 294 | 679 (9.600/A) |
| 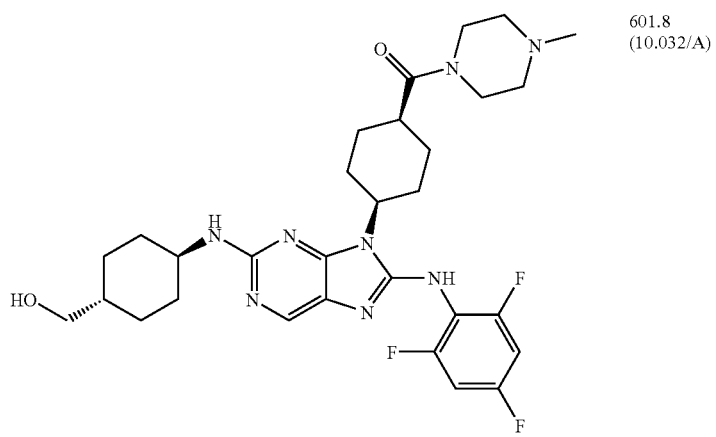 295 | 601.8 (10.032/A) |

TABLE 1-continued
| Compound | M + 1 HPLC (min/method) |
|---|---|
| 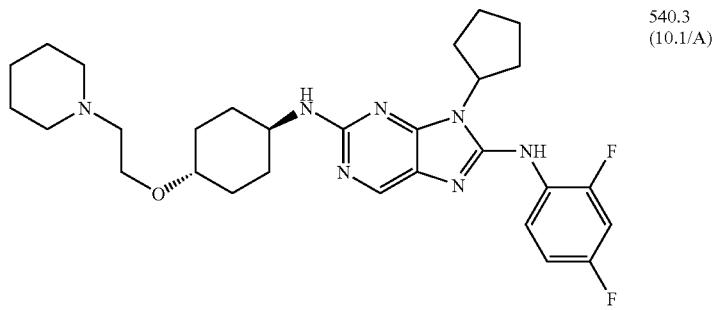 296 | 540.3 (10.1/A) |
| 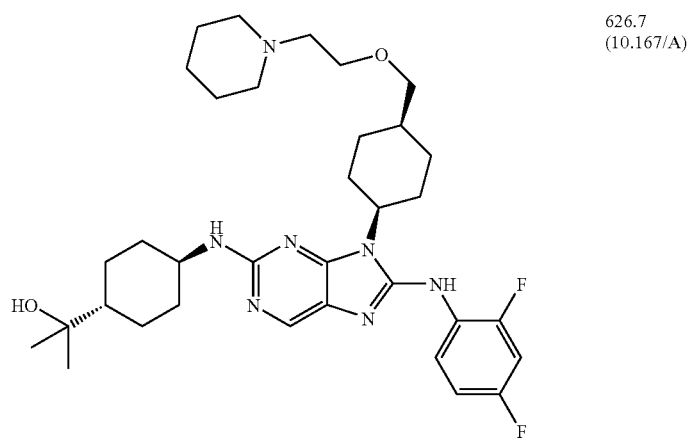 297 | 626.7 (10.167/A) |
| 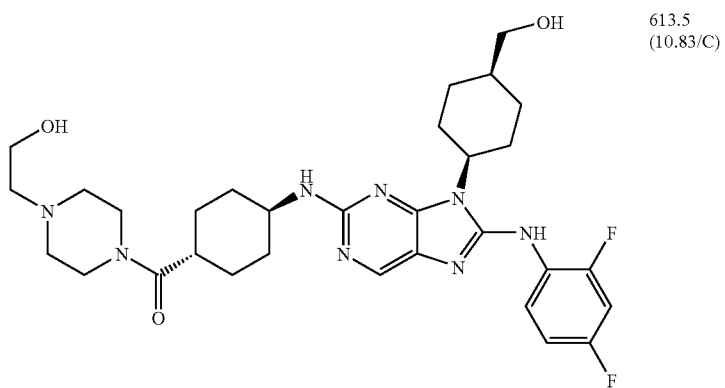 298 | 613.5 (10.83/C) |

TABLE 1-continued
| Compound | M + 1 HPLC (min/method) |
|---|---|
| 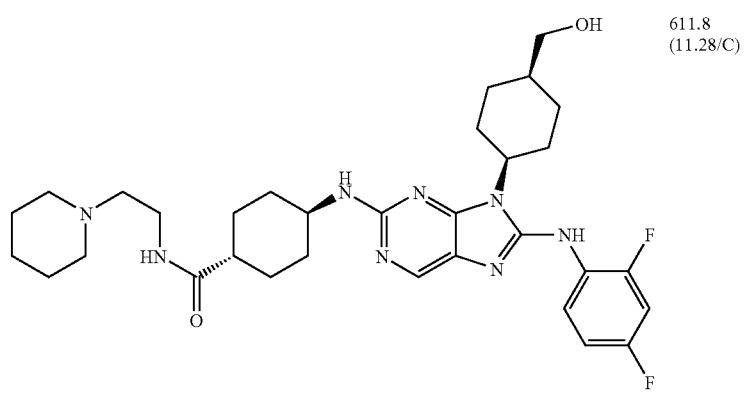 299 | 611.8 (11.28/C) |
| 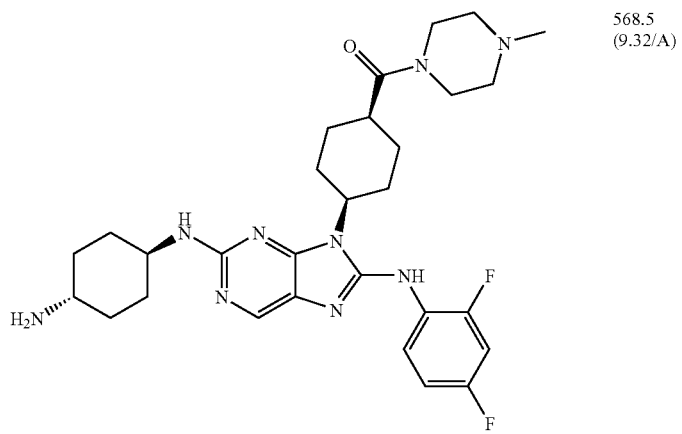 300 | 568.5 (9.32/A) |
| 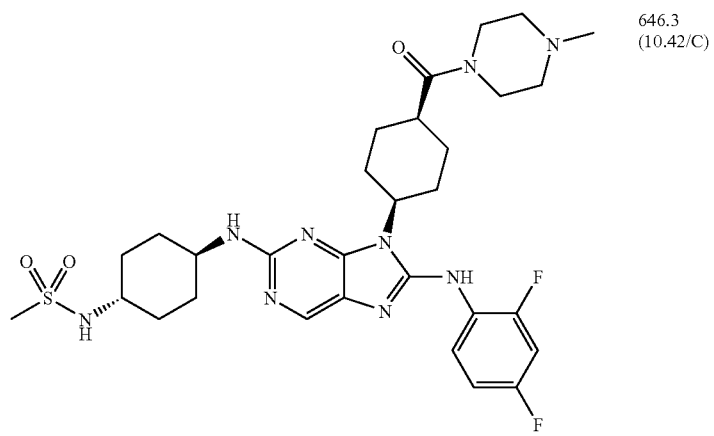 301 | 646.3 (10.42/C) |

TABLE 1-continued
| Compound | M + 1 HPLC (min/method) |
|---|---|
| 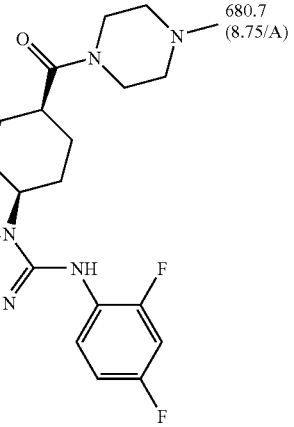 302 | 680.7 (8.75/A) |
| 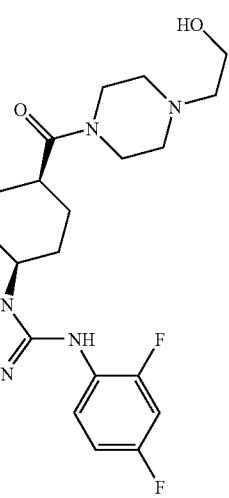 303 | 598.7 (9.184/A) |
| 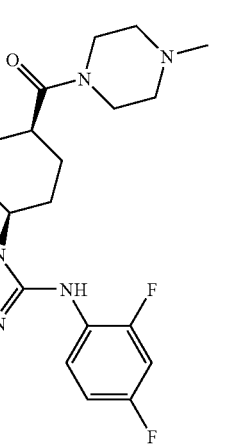 304 | 611.5 (10.360/A) |

TABLE 1-continued
| Compound | M + 1 HPLC (min/method) |
|---|---|
| 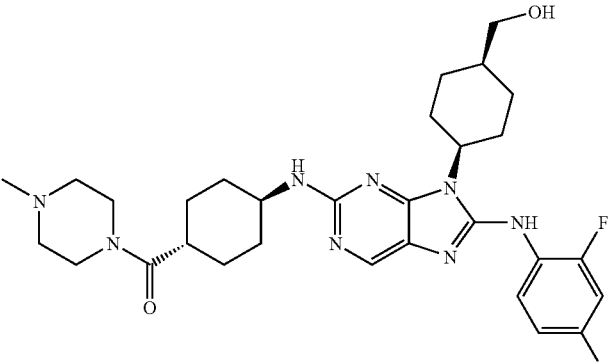 305 | 583.5 (10.92/C) |
| 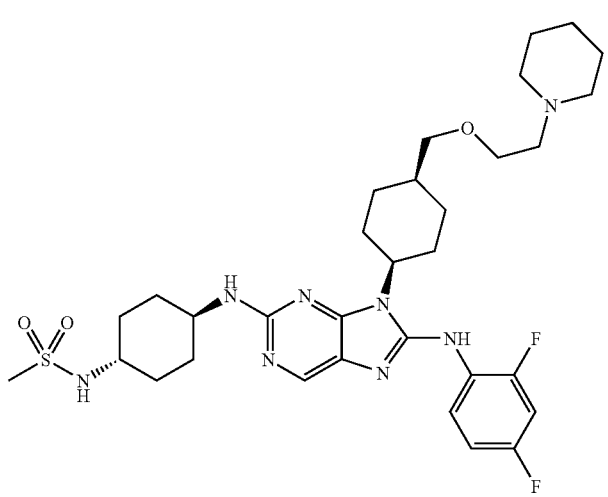 306 | 661.5 (11.65/C) |
| 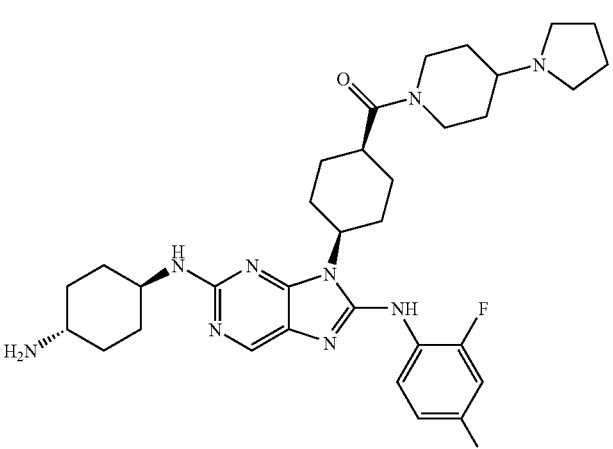 307 | 622.7 (9.484/A) |

TABLE 1-continued
| Compound | M + 1 HPLC (min/method) |
|---|---|
| 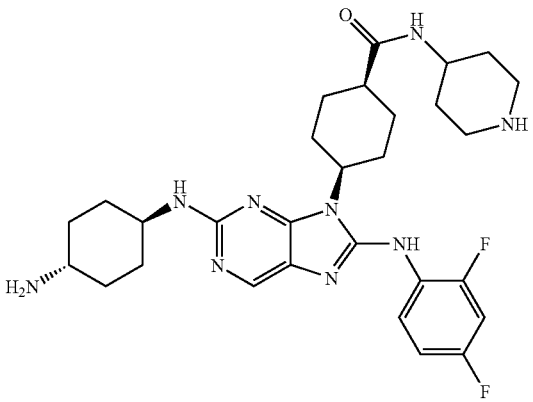308 | 568.5 (9.256/A) |
| 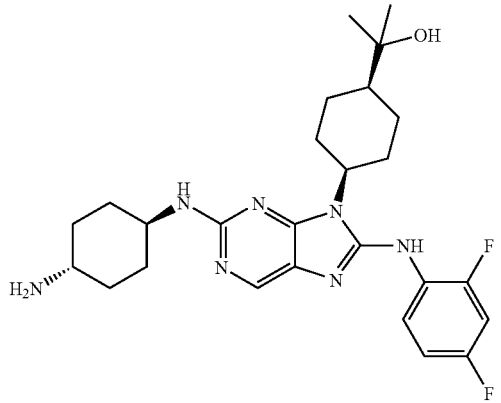309 | 500.4 (10.436/A) |
| 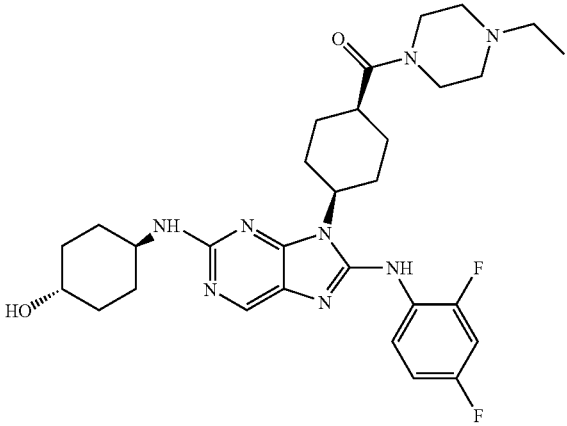310 | 583.5 (C) |

TABLE 1-continued

| Compound | M + 1 HPLC (min/method) |
|---|---|
| 311 | 623.8 (C) |
| 312 | 556.4 (C) |
| 313 | 583.7 (C) |

TABLE 1-continued
| Compound | M + 1 HPLC (min/method) |
|---|---|
| 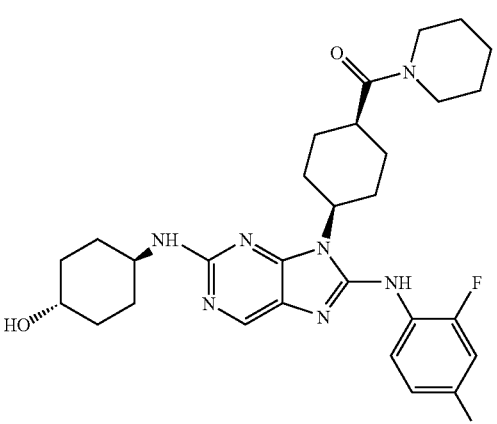 314 | 554.6 (C) |
| 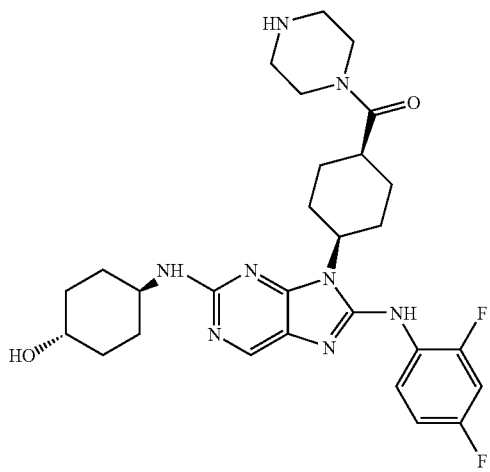 315 | 555.5 (C) |
| 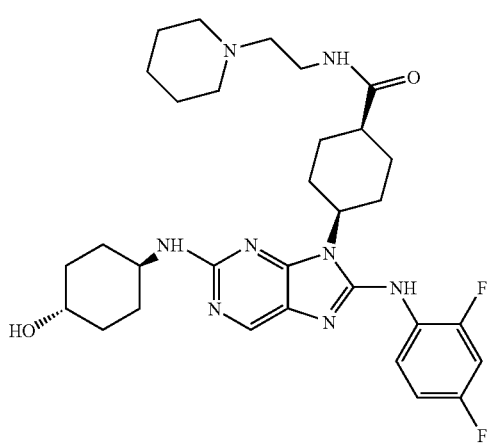 316 | 598.5 (A) |

TABLE 1-continued
| Compound | M + 1 HPLC (min/method) |
|---|---|
| 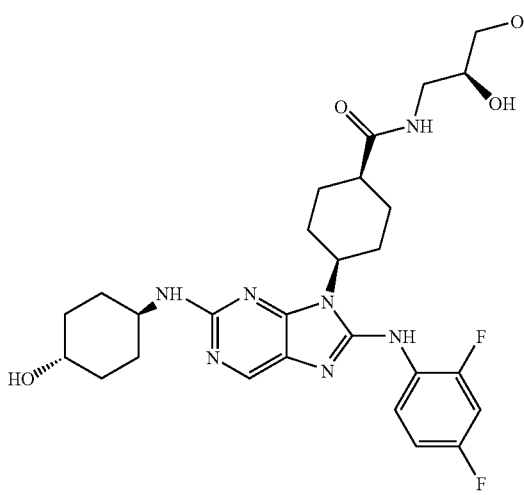 317 | 560.5 (B) |
| 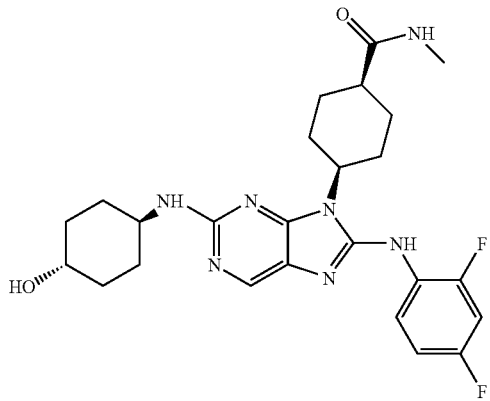 318 | 500.4 (B) |
| 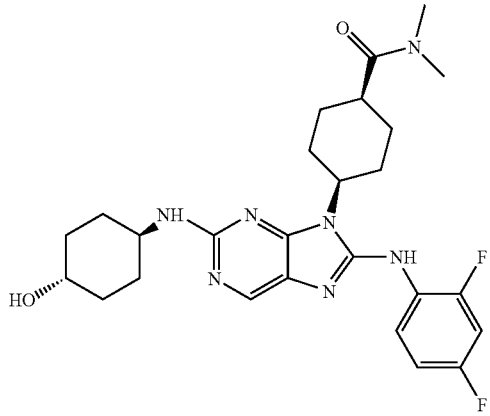 319 | 514.5 (B) |

TABLE 1-continued
| Compound | M + 1 HPLC (min/method) |
|---|---|
| 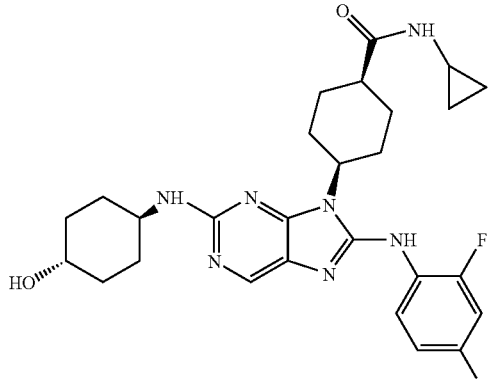 320 | 526.6 (B) |
| 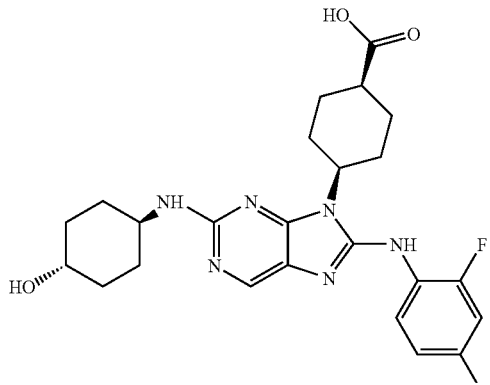 321 | 487.1 (A) |
| 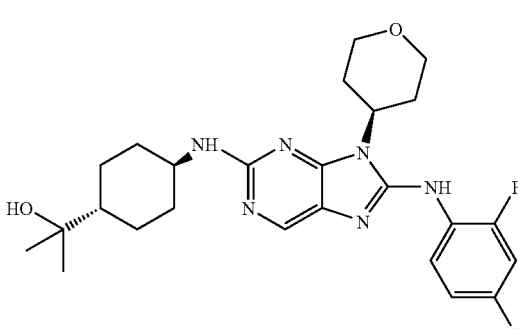 322 | 487.1 (A) |

TABLE 1-continued
| Compound | M + 1 HPLC (min/method) |
|---|---|
| 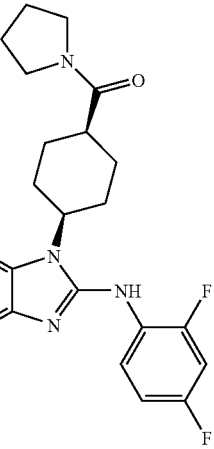 323 | 485.6 (A) |
| 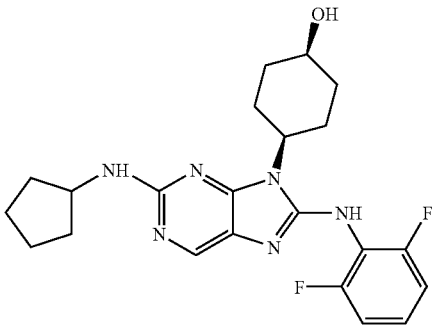 324 | 429.4 (B) |
| 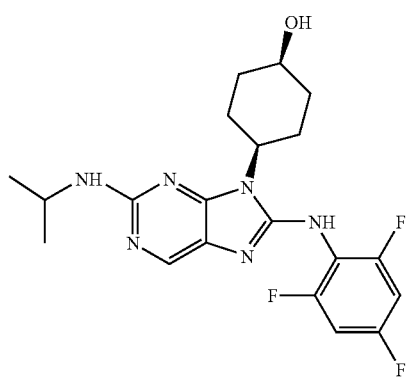 325 | 421.4 (B) |

TABLE 1-continued
| Compound | M + 1 HPLC (min/method) |
|---|---|
| 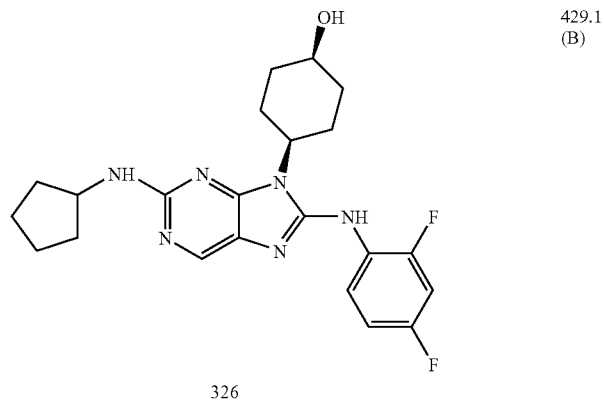 326 | 429.1 (B) |
| 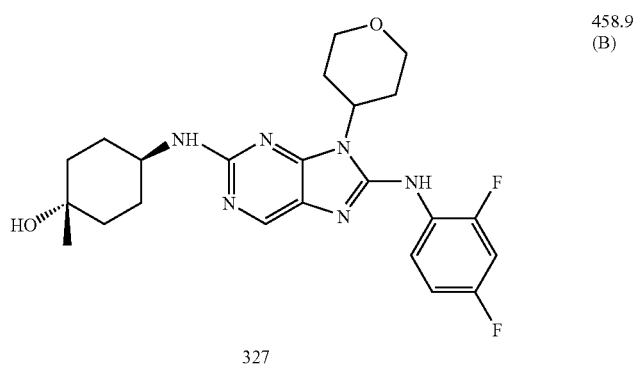 327 | 458.9 (B) |
| 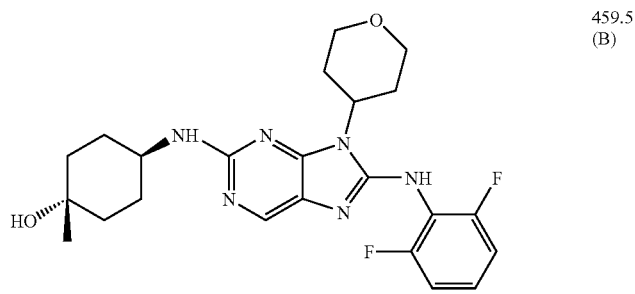 328 | 459.5 (B) |

TABLE 1-continued
| Compound | M + 1 HPLC (min/method) |
|---|---|
| 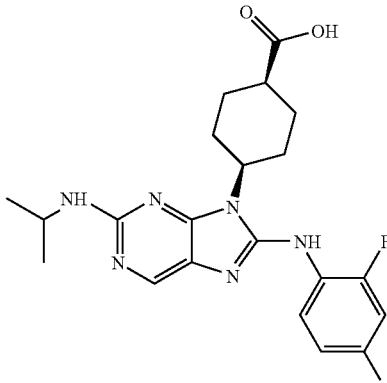 329 | 431.3 (B) |
| 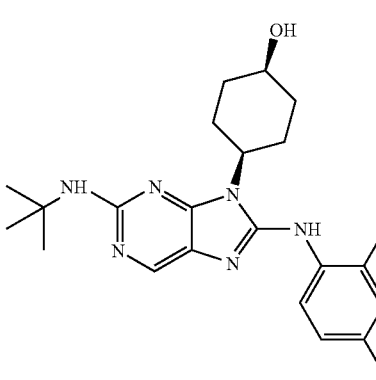 330 | 417.6 (B) |
| 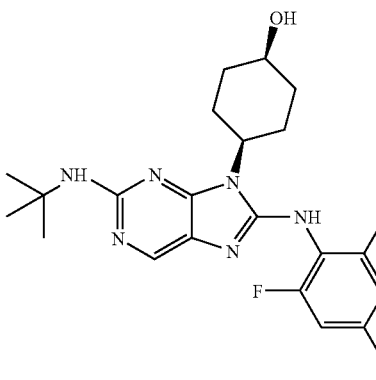 331 | 435.3 (B) |

TABLE 1-continued
| Compound | M + 1 HPLC (min/method) |
|---|---|
| 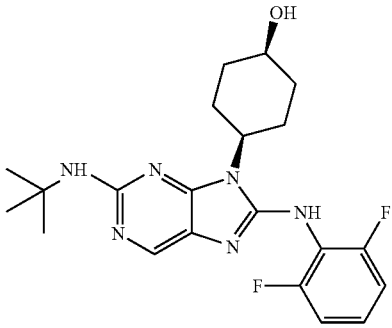 332 | 417.3 (B) |
| 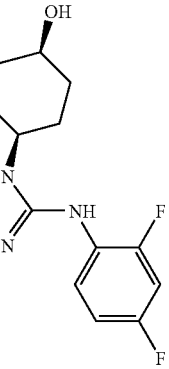 333 | 401 (B) |
| 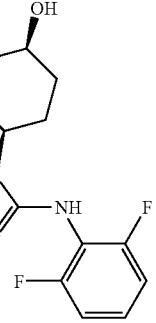 334 | 445 (A) |

TABLE 1-continued
| Compound | M + 1 HPLC (min/method) |
|---|---|
| 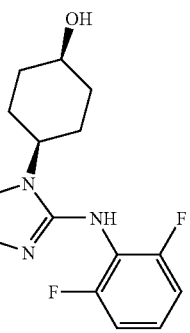 335 | 414 (A) |
| 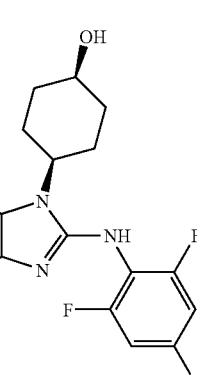 336 | 463 (A) |
| 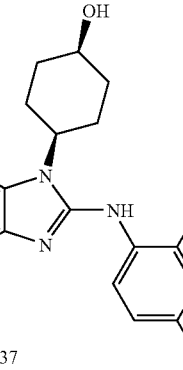 337 | 445 (A) |
| 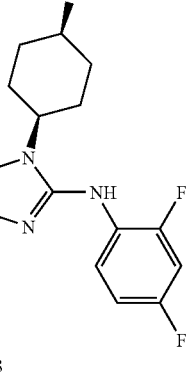 338 | 414 (A) |

TABLE 1-continued
| Compound | M + 1 HPLC (min/method) |
|---|---|
| 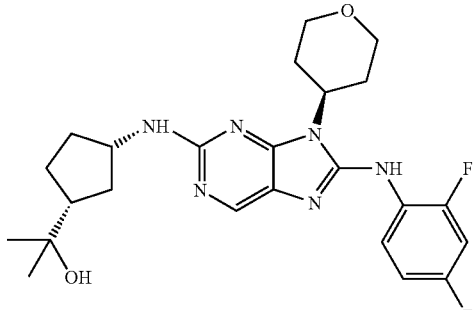<br>339 | 473 (A) |
| 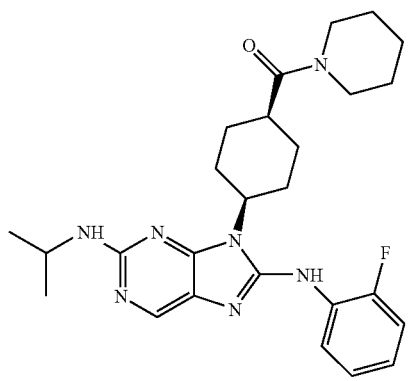<br>340 | 500.5 (A) |
| 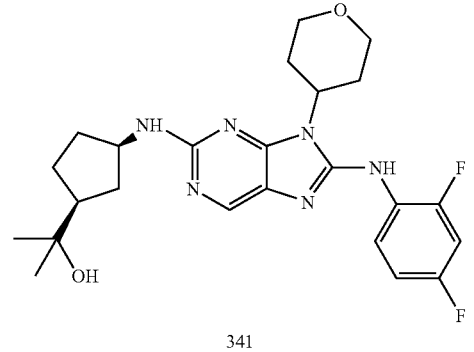<br>341 | 473 (A) |
| 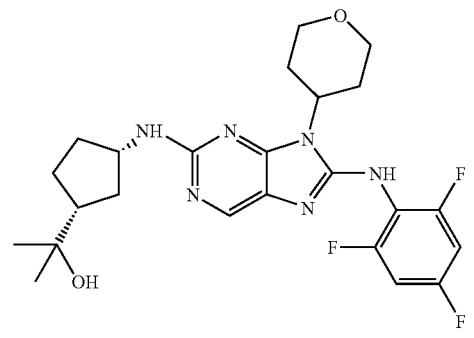<br>342 | 491 (A) |

TABLE 1-continued
| Compound | M + 1 HPLC (min/method) |
|---|---|
| 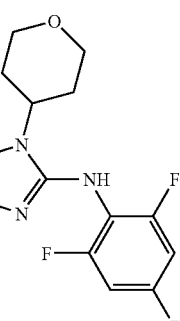 343 | 491 (A) |
| 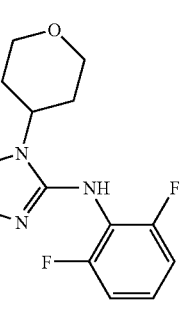 344 | 473 (A) |
| 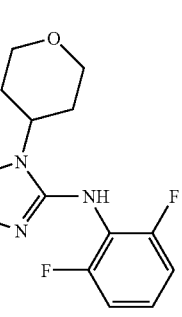 345 | 473 (A) |
| 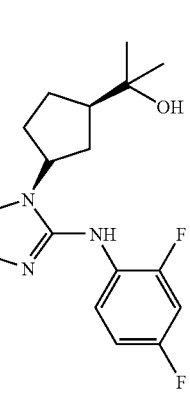 346 | 487 (A) |

TABLE 1-continued

| Compound | M + 1 HPLC (min/method) |
|---|---|
| 347 | 487 (A) |
| 348 | 487 (A) |
| 349 | 487 (A) |
| 350 | 505 (A) |

TABLE 1-continued
| Compound | M + 1 HPLC (min/method) |
|---|---|
| 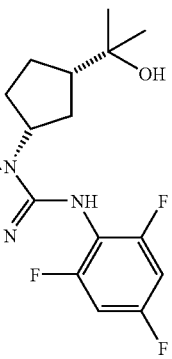<br>351 | 505 (A) |
| 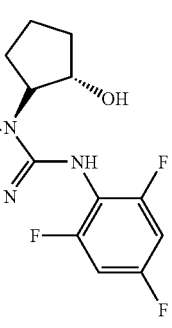<br>352 | 463 (A) |
| 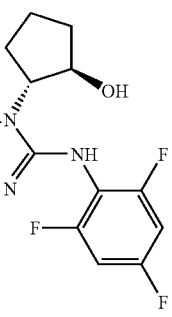<br>353 | 463 (A) |
| 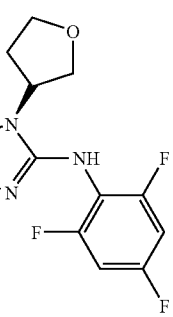<br>354 | 546 (A) |

TABLE 1-continued

| Compound | M + 1 HPLC (min/method) |
|---|---|
| 355 | 530 (A) |
| 356 | 547 (A) |
| 357 | 547 (A) |
| 358 | 520 (A) |

TABLE 1-continued

| Compound | M + 1 HPLC (min/method) |
|---|---|
| 358 | 560 (A) |
| 360 | 520 (A) |
| 361 | 546 (A) |
| 362 | 448 (A) |

TABLE 1-continued
| Compound | M + 1 HPLC (min/method) |
|---|---|
| 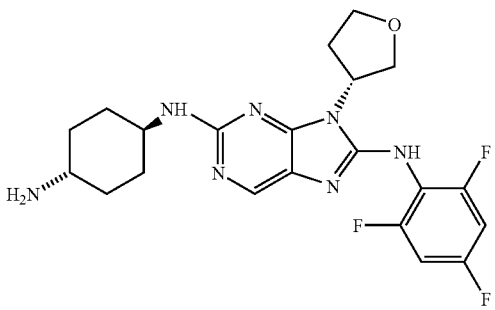<br>363 | 448 (A) |
| 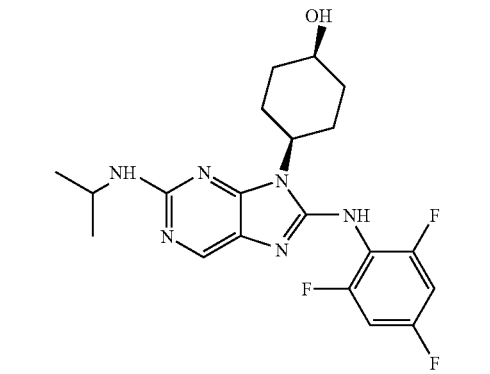<br>364 | 403.5 (B) |
| 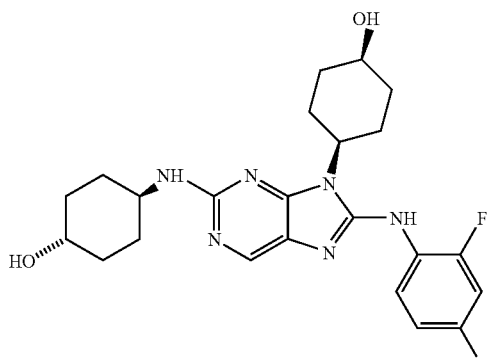<br>365 | 459.6 (A) |

TABLE 1-continued

| Compound | M + 1 HPLC (min/method) |
|---|---|
| 365 | 403.5 (A) |
| 367 | 501.6 (A) |
| 368 | 471.6 (A) |

TABLE 1-continued
| Compound | M + 1 HPLC (min/method) |
|---|---|
| 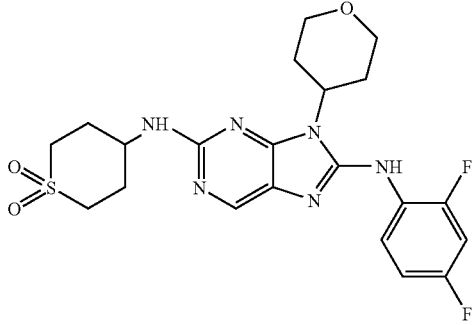<br>369 | 479.4 (A) |
| 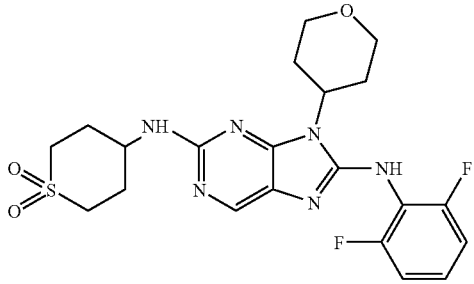<br>370 | 479.5 (A) |
| 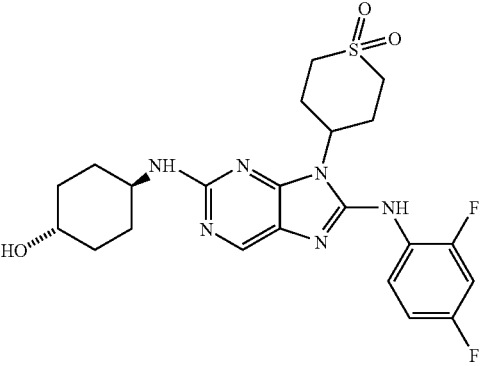<br>371 | 493.5 (A) |
| 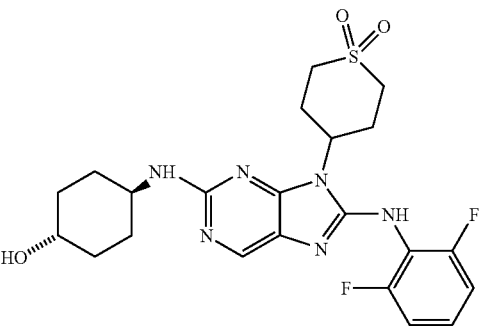<br>372 | 493.5 (A) |

TABLE 1-continued

| Compound | M + 1 HPLC (min/method) |
|---|---|
| 373 | 437.4 (A) |
| 374 | 405.5 (A) |
| 375 | 437.4 (A) |
| 376 | 463.5 (A) |

TABLE 1-continued
| Compound | M + 1 HPLC (min/method) |
|---|---|
| 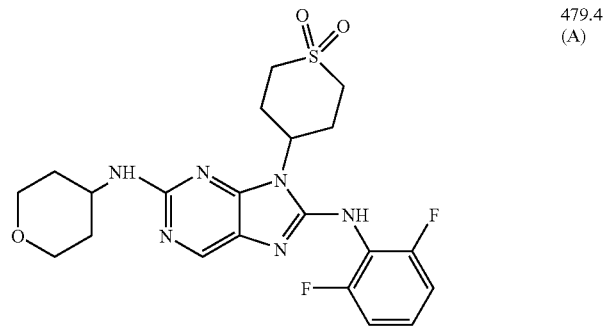 377 | 479.4 (A) |
| 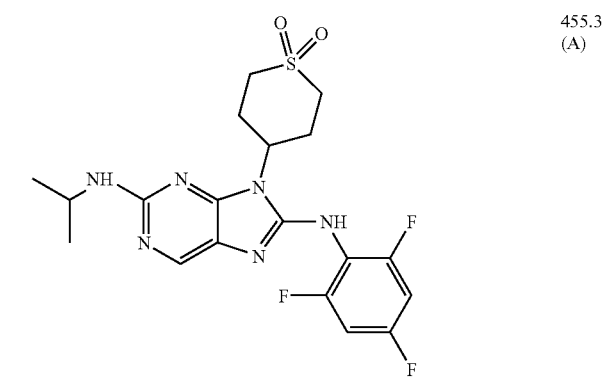 378 | 455.3 (A) |
| 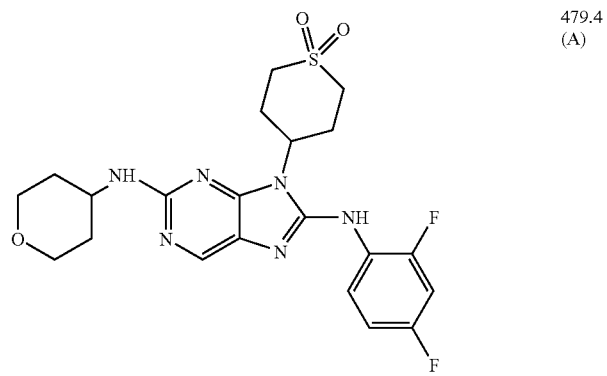 379 | 479.4 (A) |

TABLE 1-continued
| Compound | M + 1 HPLC (min/method) |
|---|---|
| 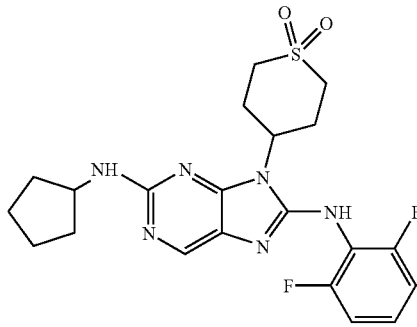 380 | 463.5 (A) |
| 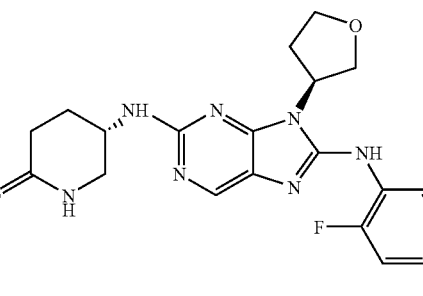 381 | 448.3 (A) |
| 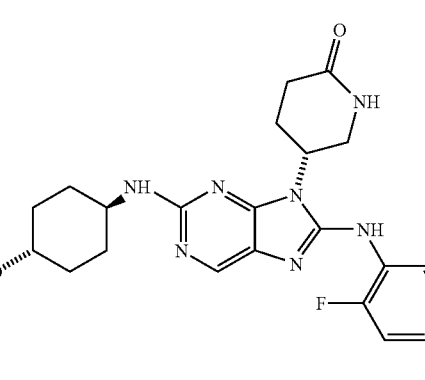 382 | 476.3 (A) |

TABLE 1-continued
| Compound | M + 1 HPLC (min/method) |
|---|---|
| 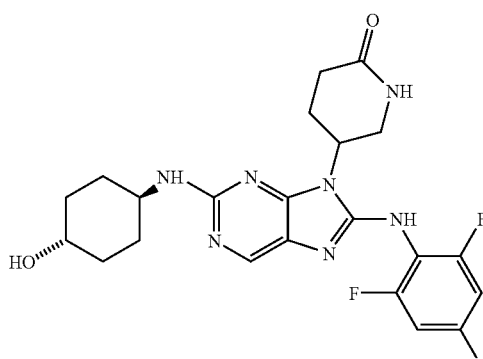 383 | 476.4 (A) |
| 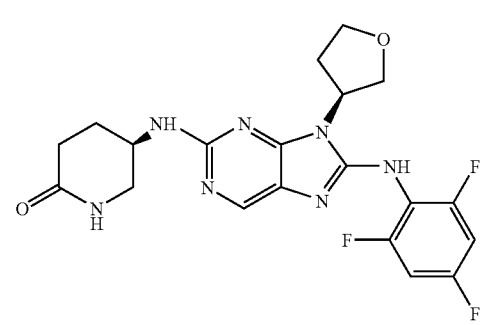 384 | 448.3 (A) |
| 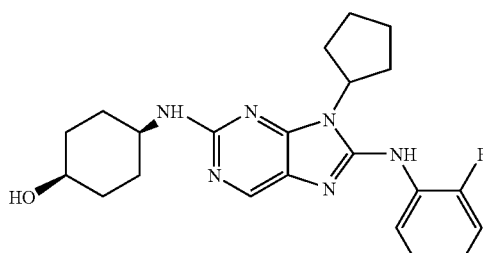 385 | 411.3 (A) |
| 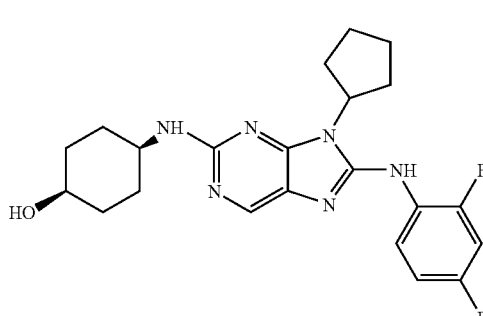 386 | 429.3 (A) |

TABLE 1-continued
| Compound | M + 1 HPLC (min/method) |
|---|---|
| 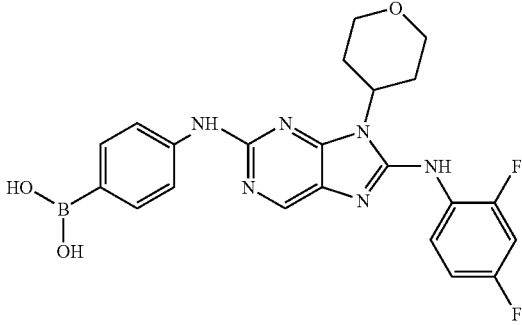 387 | 467.5 (A) |
| 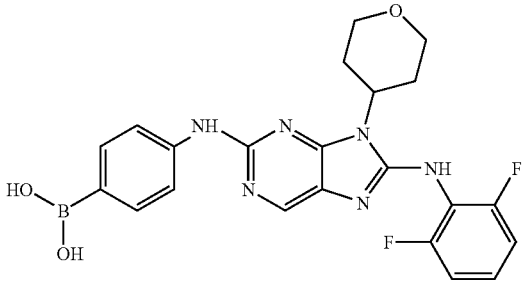 388 | 467.5 (A) |
| 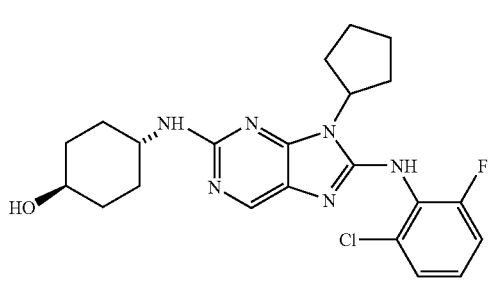 389 | 445.5 (A) |
| 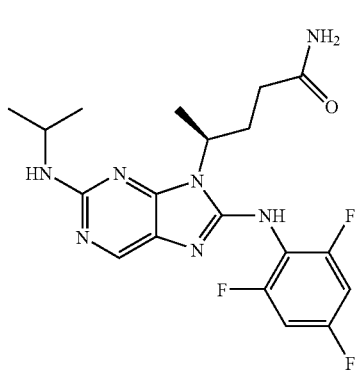 390 | 422.3 (A) |

TABLE 1-continued
| Compound | M + 1 HPLC (min/method) |
|---|---|
| 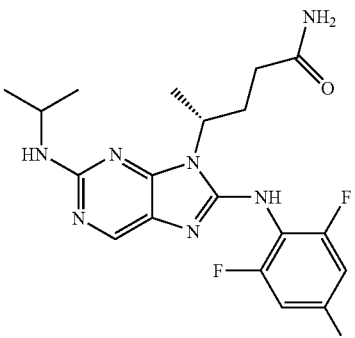 391 | 422.3 (11.33/A) |
| 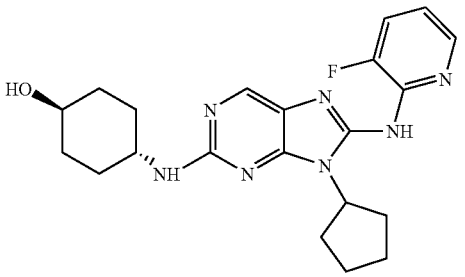 392 | 412.4 (A) |
| 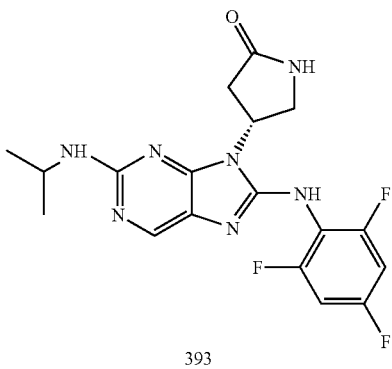 393 | 406.5 (A) |
| 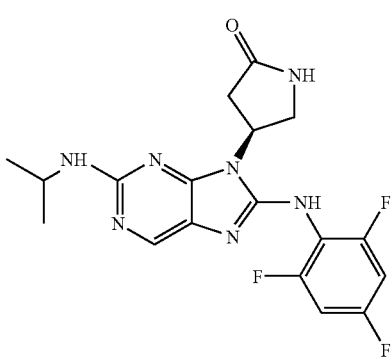 394 | 406.5 (A) |

TABLE 1-continued
| Compound | M + 1 HPLC (min/method) |
|---|---|
| 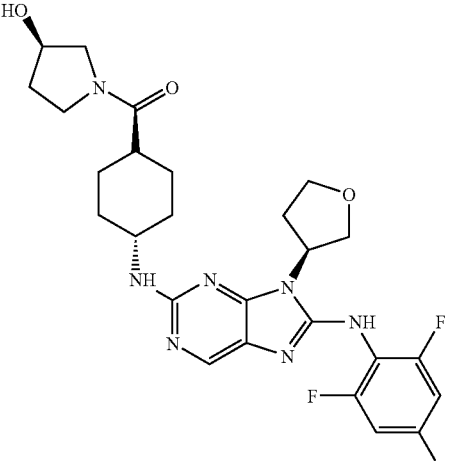<br>395 | 546.3 (A) |
| 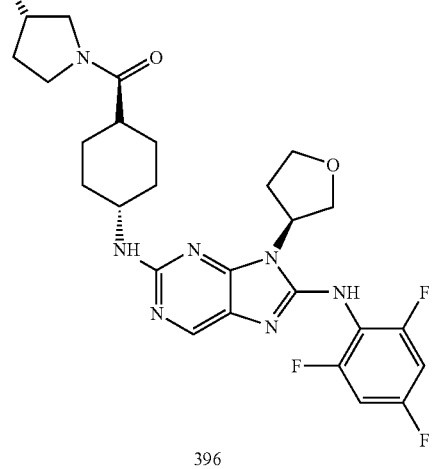<br>396 | 546.3 (A) |
| 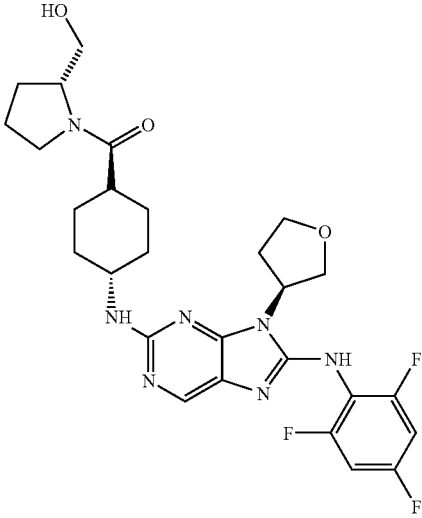<br>397 | 560.5 (A) |

TABLE 1-continued
| Compound | M + 1 HPLC (min/method) |
|---|---|
| 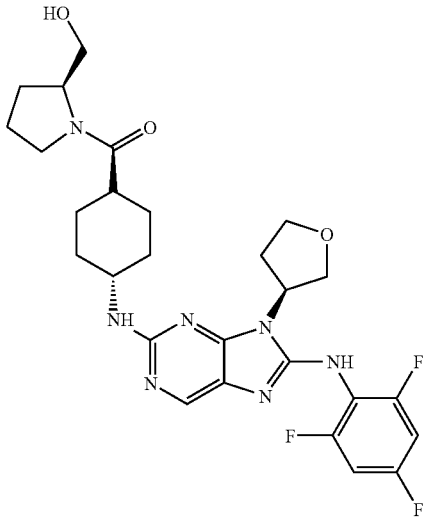<br>398 | 560.5 (A) |
| 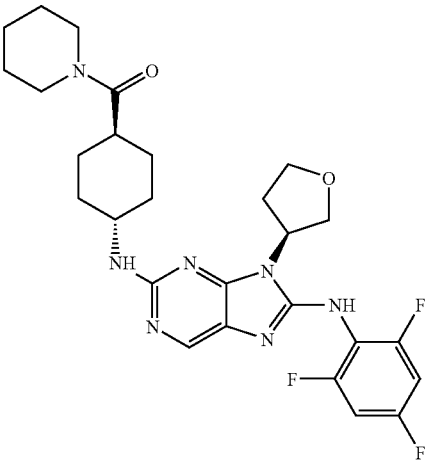<br>399 | 544.4 (A) |
| 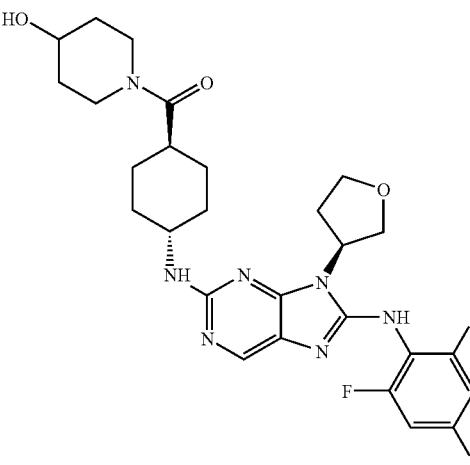<br>400 | 560.4 (A) |

TABLE 1-continued
| Compound | M + 1 HPLC (min/method) |
|---|---|
| 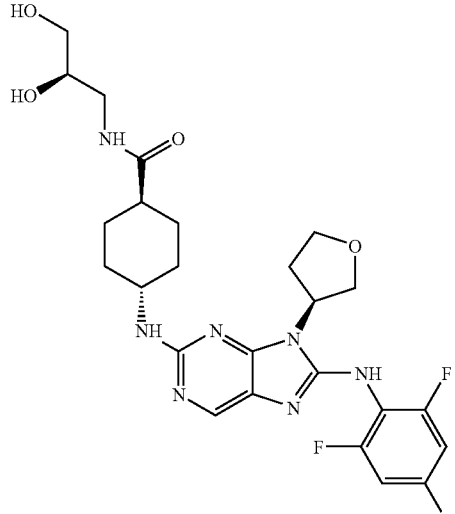 401 | 550.5 (A) |
| 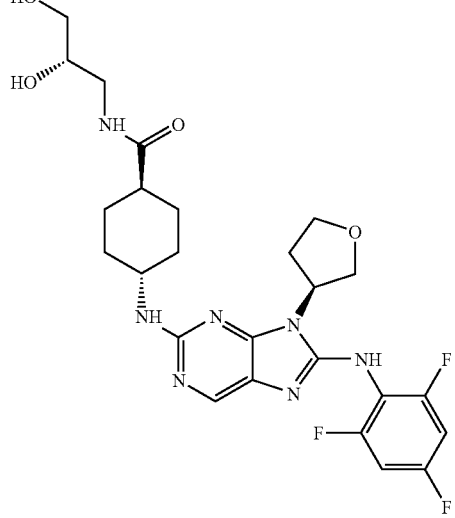 402 | 550.5 (A) |
| 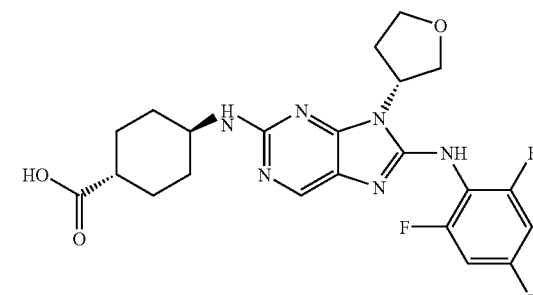 403 | 477.3 (A) |

TABLE 1-continued
| Compound | M + 1 HPLC (min/method) |
|---|---|
| 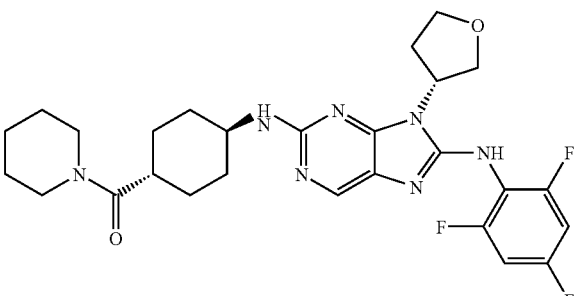 404 | 544.4 (A) |
| 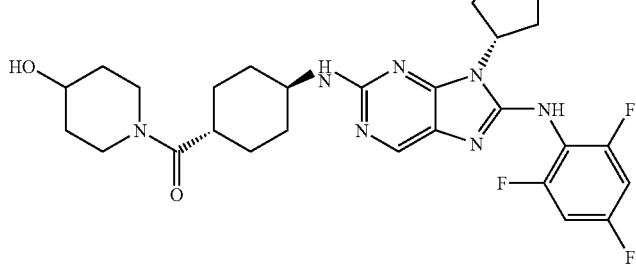 405 | 560.5 (A) |
| 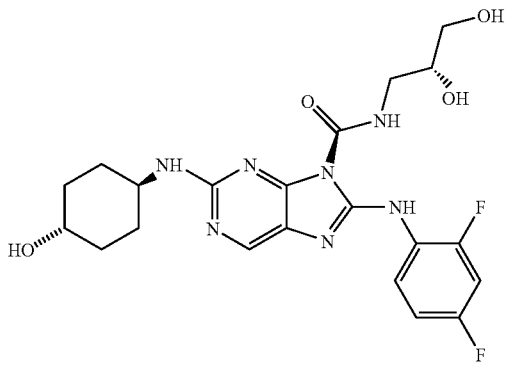 406 | 560.5 (A) |
| 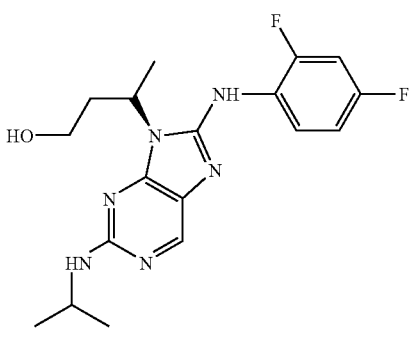 407 | 377.1 (A) |

TABLE 1-continued
| Compound | M + 1 HPLC (min/method) |
|---|---|
| 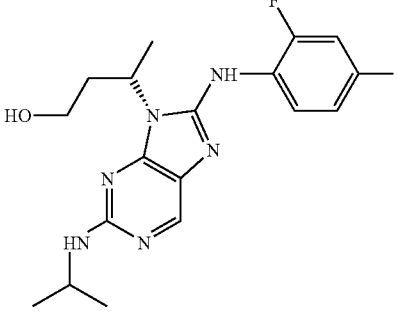<br>408 | 377<br>(A) |
| 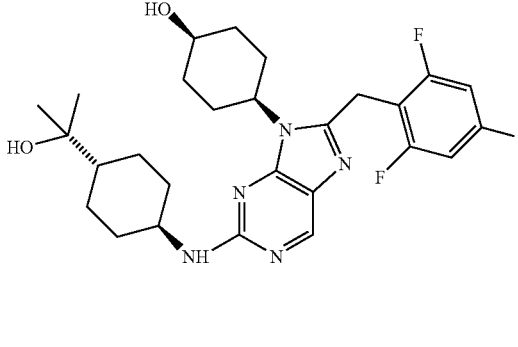<br>409 | 519.4<br>(B) |
| 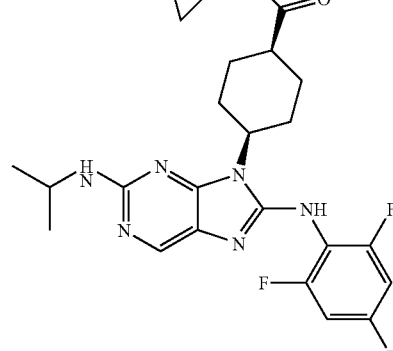<br>410 | 488.5<br>(A) |

TABLE 1-continued
| Compound | M + 1 HPLC (min/method) |
|---|---|
| 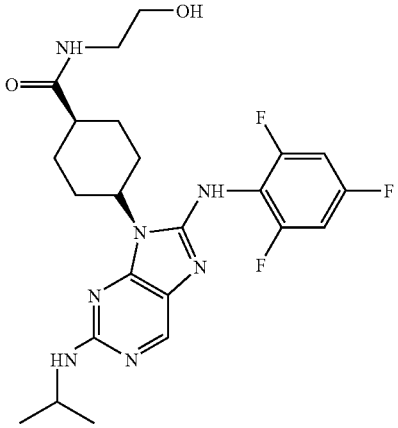 411 | 492.5 (A) |
| 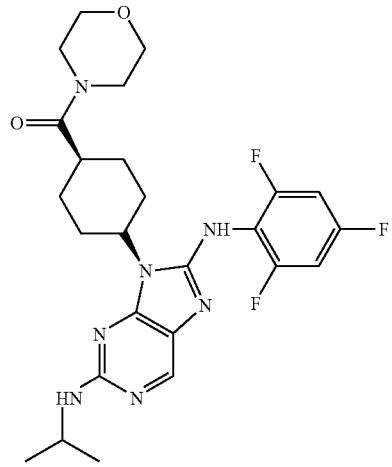 412 | 418.5 (A) |
| 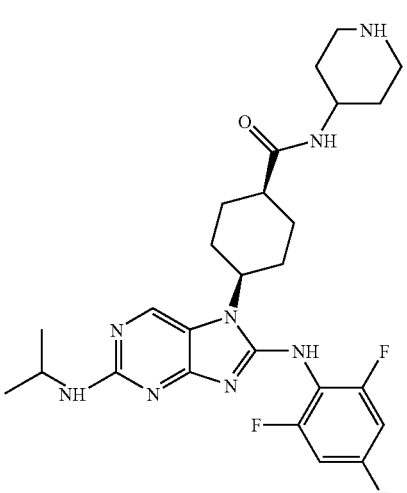 413 | 531.4 (A) |

TABLE 1-continued
| Compound | M + 1 HPLC (min/method) |
|---|---|
| 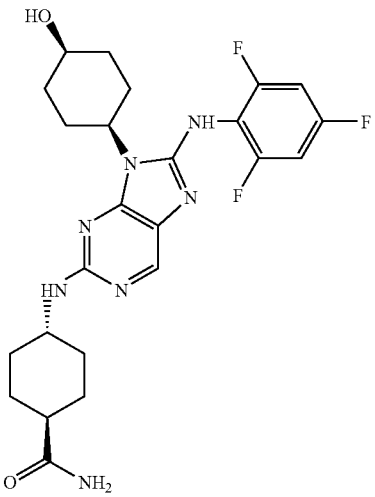 414 | 504.5 (A) |
| 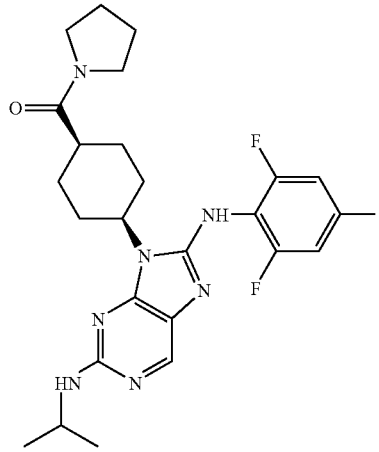 415 | 502.5 (A) |
| 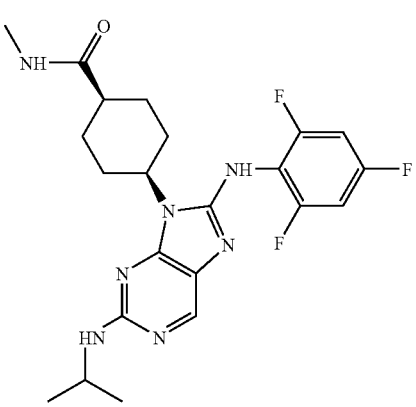 416 | 461.9 (A) |

TABLE 1-continued
| Compound | M + 1 HPLC (min/method) |
|---|---|
| 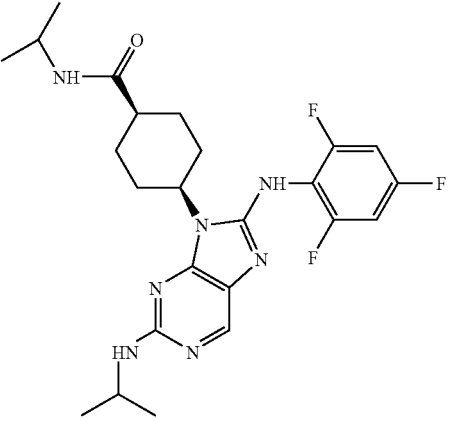<br>417 | 490.1 (A) |
| 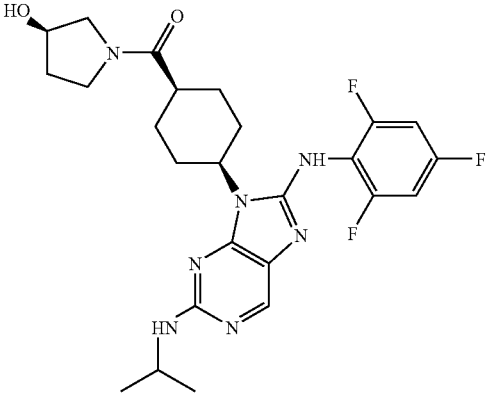<br>418 | 518.3 (A) |
| 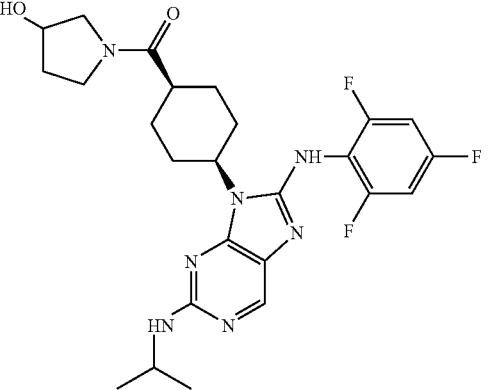<br>419 | 518.3 (A) |

TABLE 1-continued
| Compound | M + 1 HPLC (min/method) |
|---|---|
| 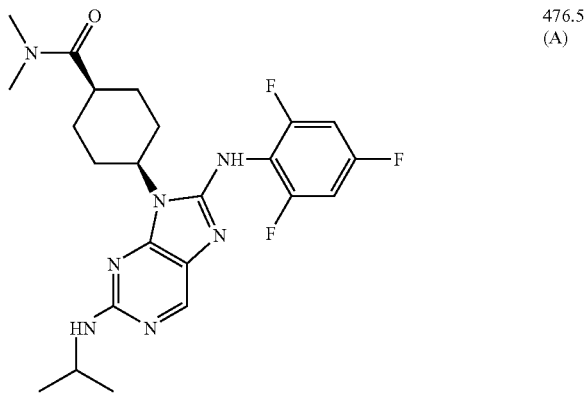 420 | 476.5 (A) |
| 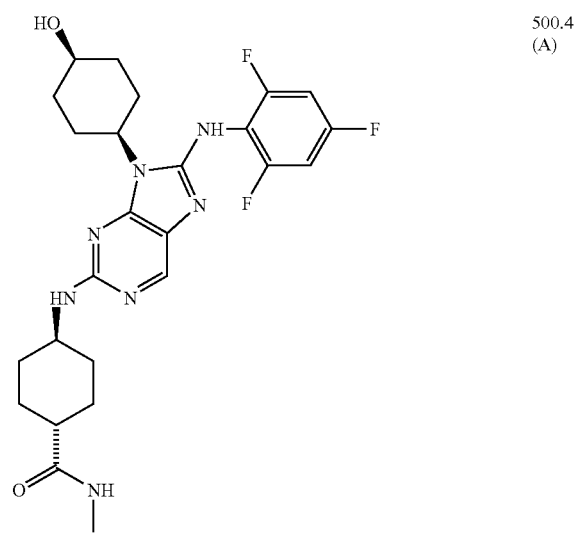 421 | 500.4 (A) |

TABLE 1-continued
| Compound | M + 1 HPLC (min/method) |
|---|---|
| 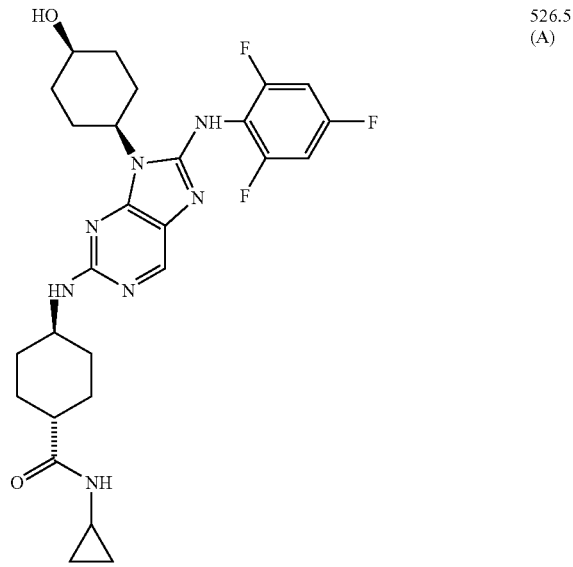 422 | 526.5 (A) |
| 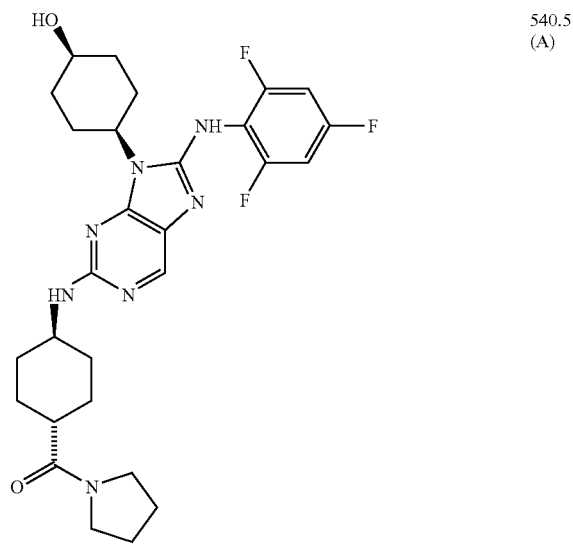 423 | 540.5 (A) |

TABLE 1-continued

| Compound | M + 1 HPLC (min/method) |
|---|---|
| 424 | 449.5 (A) |
| 425 | 449.3 (A) |
| 426 | 449.3 (A) |
| 427 | 367.3 (A) |

TABLE 1-continued
| Compound | M + 1 HPLC (min/method) |
|---|---|
| 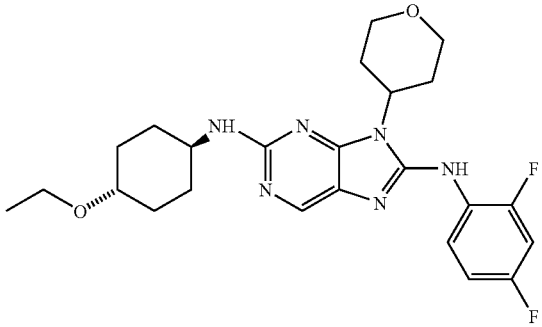 428 | 473 (A) |
| 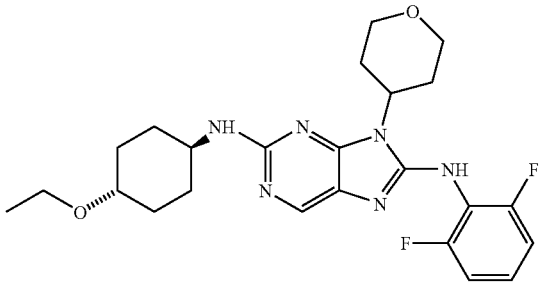 429 | 473 (A) |
| 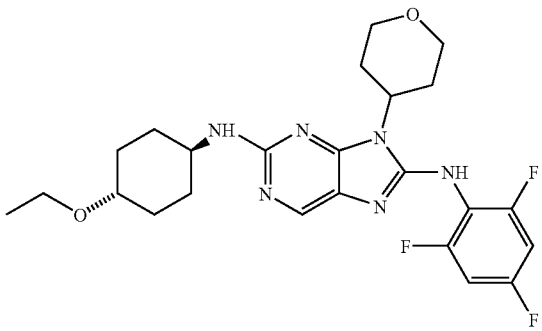 430 | 491 (A) |
| 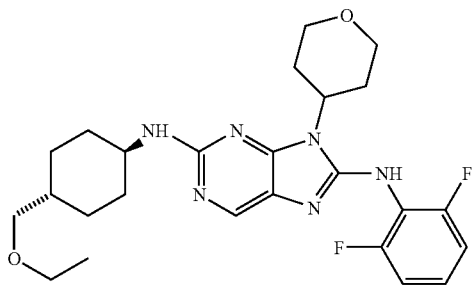 431 | 487 (A) |

TABLE 1-continued
| Compound | M + 1 HPLC (min/method) |
|---|---|
| 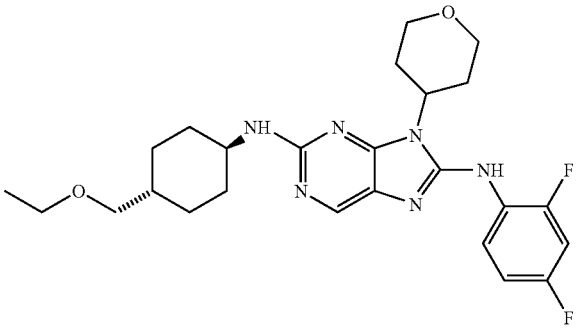<br>432 | 487<br>(A) |
| 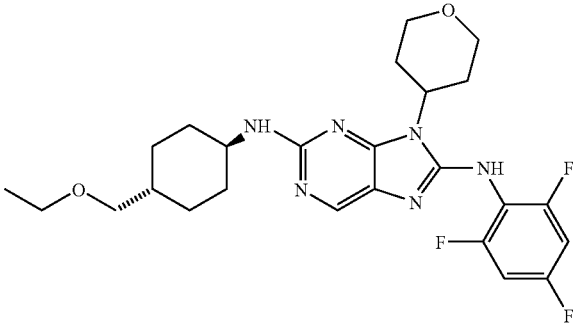<br>433 | 505<br>(A) |
| 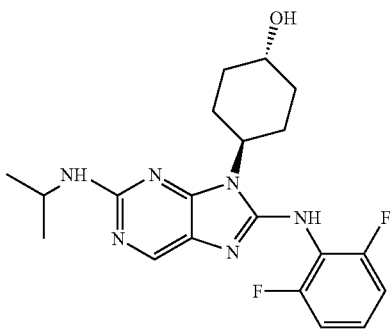<br>434 | 403<br>(A) |

TABLE 1-continued
| Compound | M + 1 HPLC (min/method) |
|---|---|
| 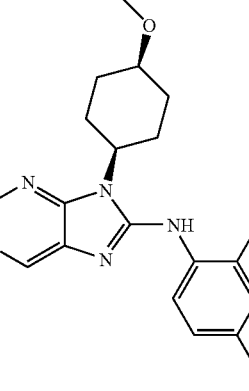  435 | 431 (A) |
| 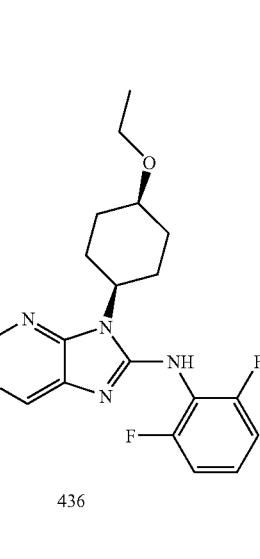  436 | 431 (A) |
| 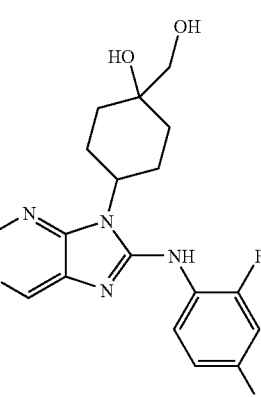  437 | 433 (A) |

TABLE 1-continued
| Compound | M + 1 HPLC (min/method) |
|---|---|
| 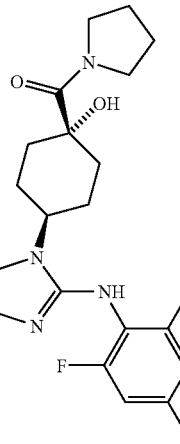 438 | 518 (B) |
| 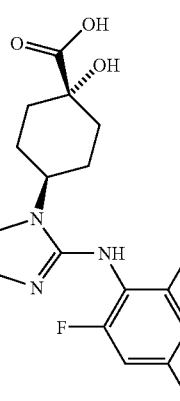 439 | 465.1 (A) |
| 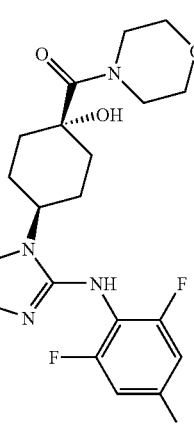 440 | 534 (A) |

TABLE 1-continued
| Compound | M + 1 HPLC (min/method) |
|---|---|
| 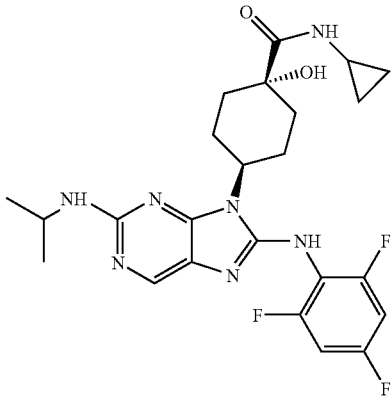<br>441 | 504 (A) |
| 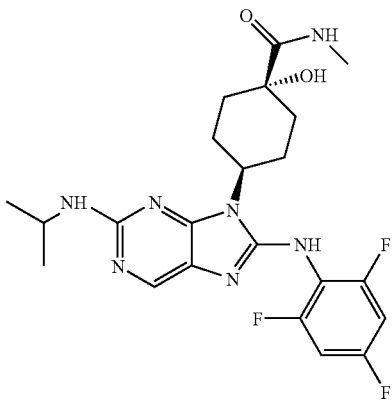<br>442 | 478 (A) |
| 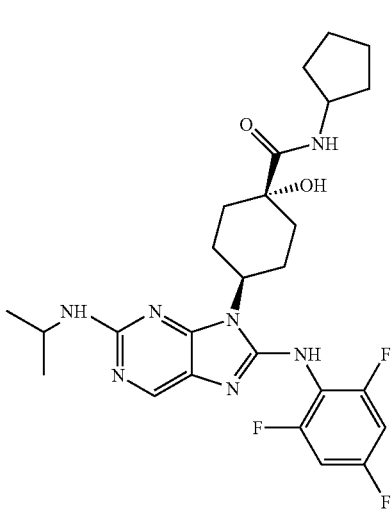<br>443 | 532 (A) |

TABLE 1-continued
| Compound | M + 1 HPLC (min/method) |
|---|---|
| 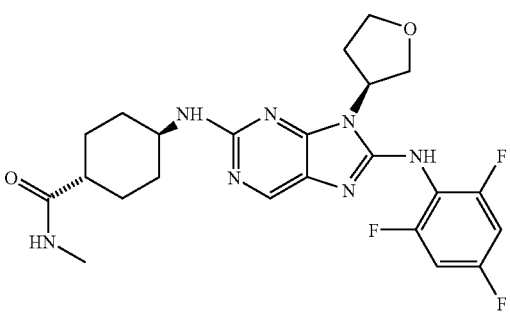<br>444 | 90 (A) |
| 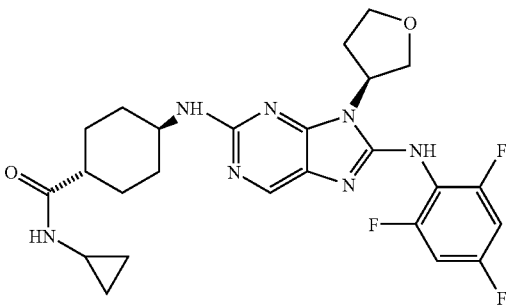<br>445 | 516 (A) |
| 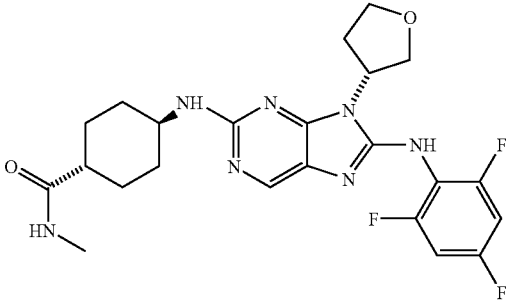<br>446 | 490 (A) |
| 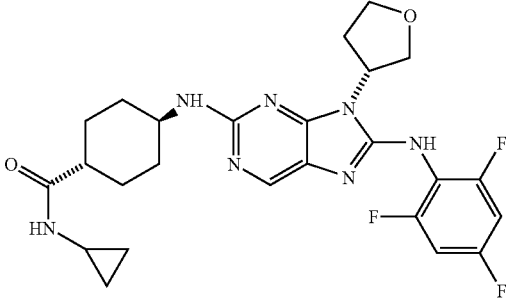<br>447 | 516 (A) |

TABLE 1-continued
| Compound | M + 1 HPLC (min/method) |
|---|---|
| 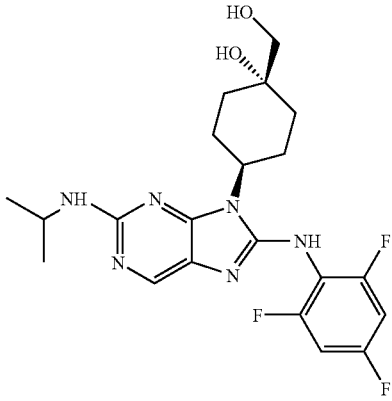 448 | 451 (A) |
| 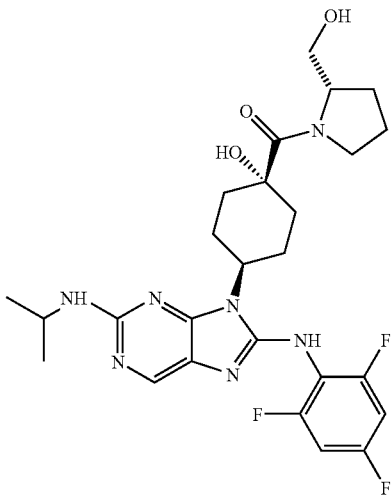 449 | 548 (A) |
| 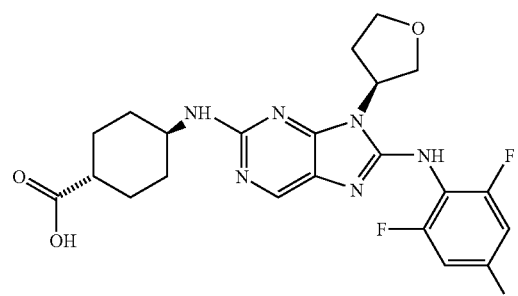 450 | 477 (B) |

TABLE 1-continued

| Compound | M + 1 HPLC (min/method) |
|---|---|
| 451 | 522.5 (A) |
| 452 | 540.5 (A) |
| 453 | 522.1 (A) |
| 454 | 419.5 (A) |

TABLE 1-continued

| Compound | M + 1 HPLC (min/method) |
|---|---|
| 455 | 431.5 (A) |
| 456 | 431.5 (A) |
| 457 | 431.5 (A) |
| 458 | 431.5 (A) |

TABLE 1-continued

| Compound | M + 1 HPLC (min/method) |
|---|---|
| 459 | 449.4 (A) |
| 460 | 449.4 (A) |
| 461 | 472.5 (A) |

TABLE 1-continued

| Compound | M + 1 HPLC (min/method) |
|---|---|
| 462 | 472.5 (A) |
| 463 | 419.5 (A) |
| 464 | 437.4 (A) |

TABLE 1-continued
| Compound | M + 1 HPLC (min/method) |
|---|---|
| 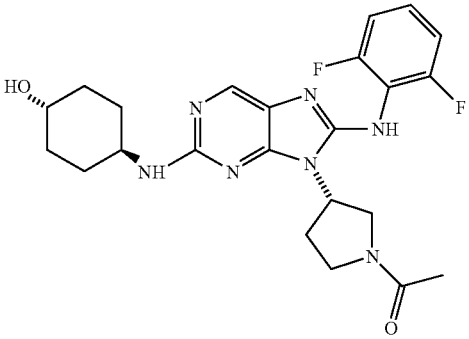 465 | 472.5 (A) |
| 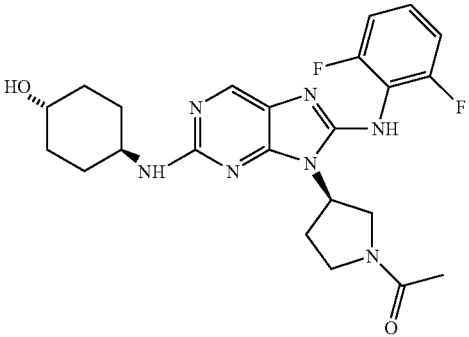 466 | 472.6 (A) |
| 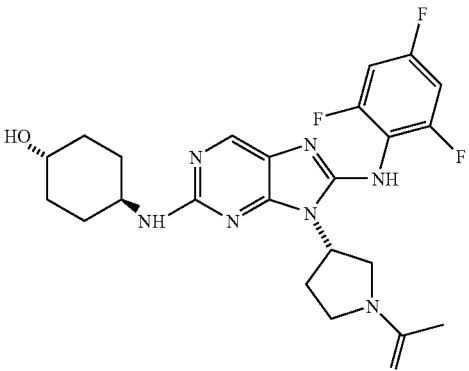 467 | 490.5 (A) |

TABLE 1-continued

| Compound | M + 1 HPLC (min/method) |
|---|---|
| 468 | 490.3 (A) |
| 469 | 375.3 (A) |
| 470 | 375.3 (A) |

TABLE 1-continued
| Compound | M + 1 HPLC (min/method) |
|---|---|
| 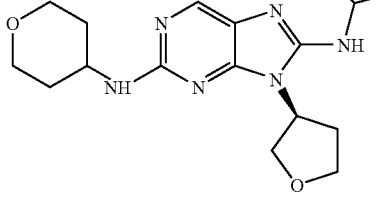<br>471 | 417.5 (A) |
| 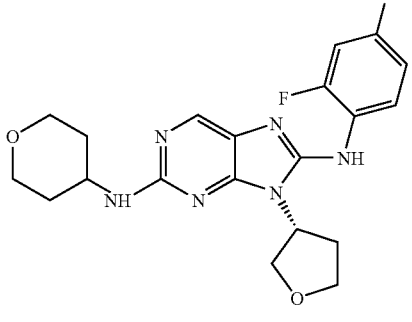<br>472 | 417.5 (A) |
| 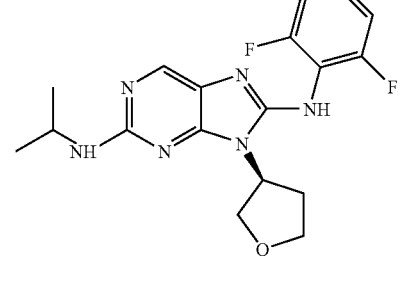<br>473 | 375.3 (A) |
| 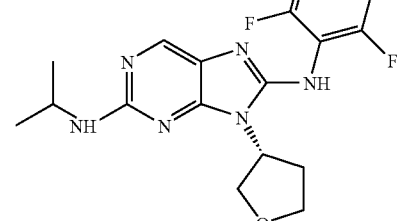<br>474 | 375.2 (A) |

TABLE 1-continued

| Compound | M + 1 HPLC (min/method) |
|---|---|
| 475 | 417 (A) |
| 476 | 417.5 (A) |
| 477 | 491.5 (A) |
| 478 | 491.5 (B) |

TABLE 1-continued
| Compound | M + 1 HPLC (min/method) |
|---|---|
| 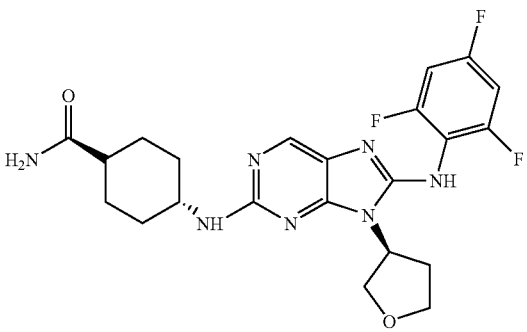 479 | 476.4 (A) |
| 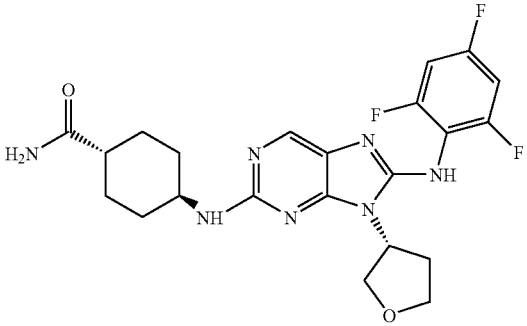 480 | 476.4 (A) |
| 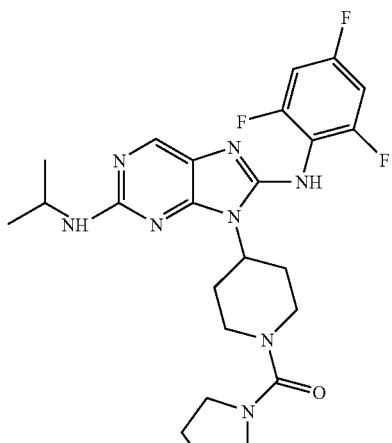 481 | 503.3 (A) |

TABLE 1-continued
| Compound | M + 1 HPLC (min/method) |
|---|---|
| 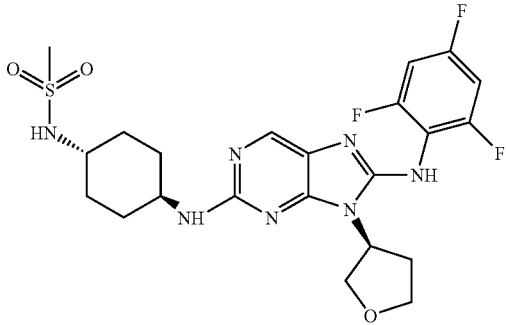 482 | 526.3 (A) |
| 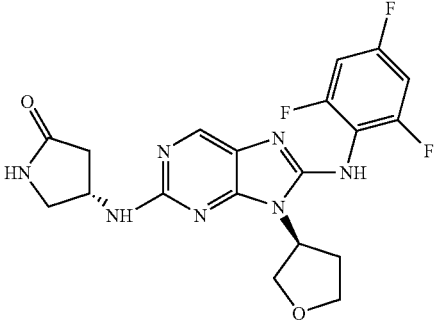 483 | 434.1 (A) |
| 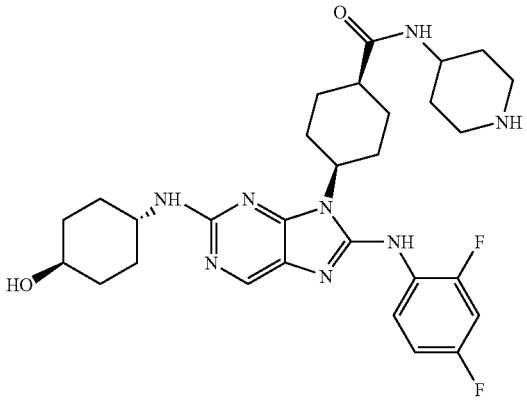 484 | 569.7 (A) |

TABLE 1-continued
| Compound | M + 1 HPLC (min/method) |
|---|---|
| 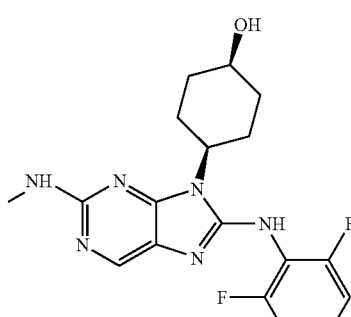 485 | 375 (B) |
| 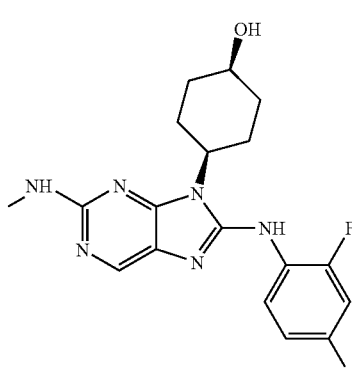 486 | 375.3 (A) |
| 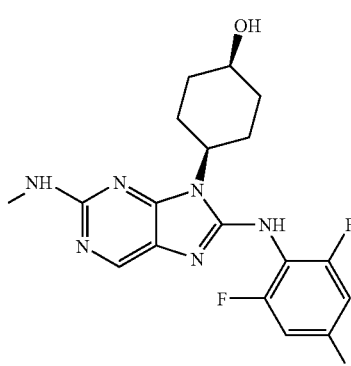 487 | 393.1 (A) |

TABLE 1-continued
| Compound | M + 1 HPLC (min/method) |
|---|---|
| 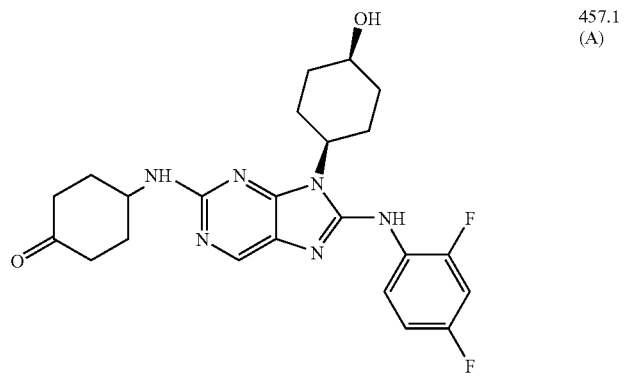<br>488 | 457.1<br>(A) |
| 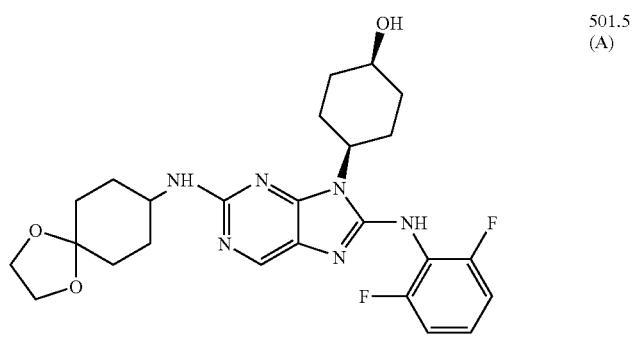<br>489 | 501.5<br>(A) |
| 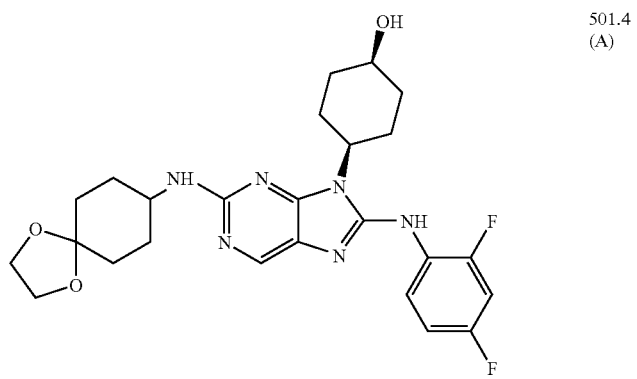<br>490 | 501.4<br>(A) |

TABLE 1-continued
| Compound | M + 1 HPLC (min/method) |
|---|---|
| 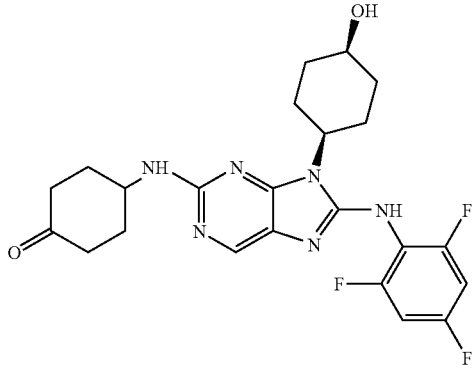 491 | 476.5 (A) |
| 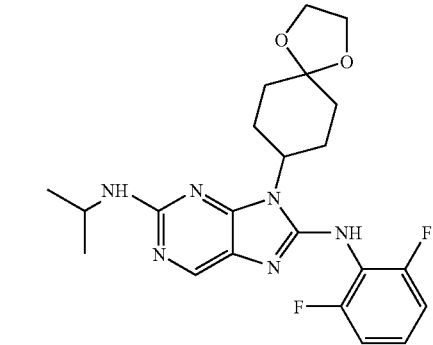 492 | 445.5 (A) |
| 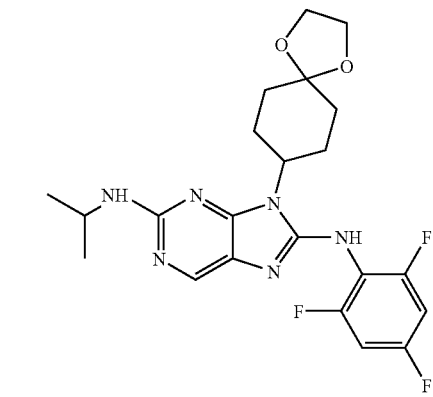 493 | 463.4 (A) |

TABLE 1-continued
| Compound | M + 1 HPLC (min/method) |
|---|---|
| 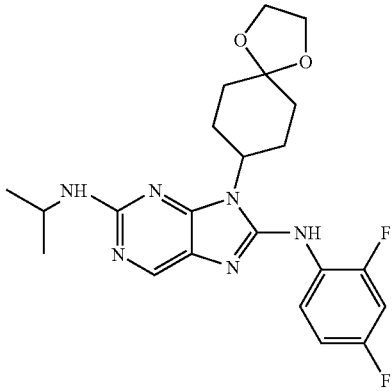 494 | 445 (A) |
| 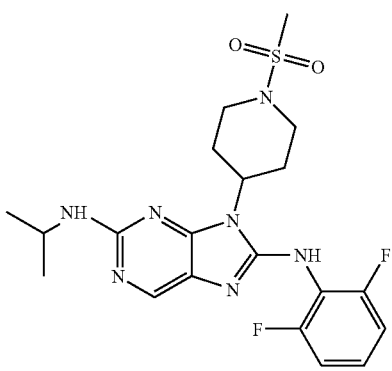 495 | 466.1 (A) |
| 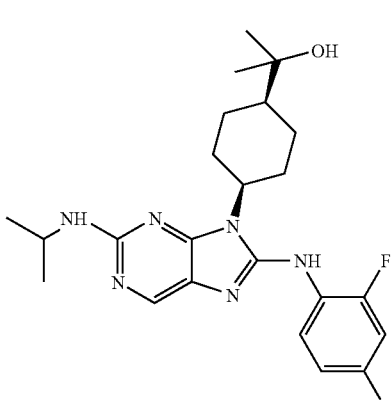 496 | 445.3 (A) |

TABLE 1-continued

| Compound | M + 1 HPLC (min/method) |
|---|---|
| 497 | 448.4 (A) |
| 498 | 448.4 (A) |
| 499 | 516.3 (A) |

TABLE 1-continued
| Compound | M + 1 HPLC (min/method) |
|---|---|
| 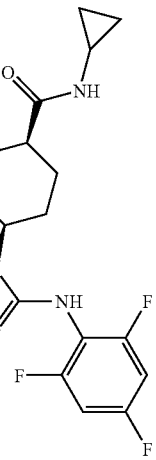 500 | 516.3 (A) |
| 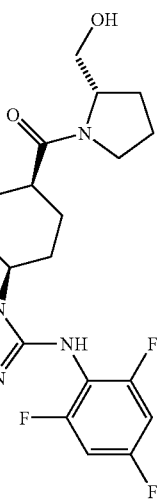 501 | 560.5 (A) |
| 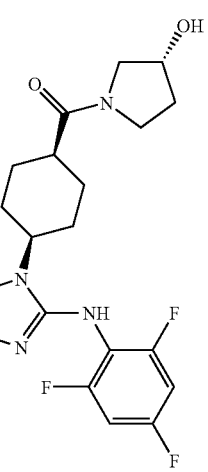 502 | 546.5 (A) |

TABLE 1-continued

| Compound | M + 1 HPLC (min/method) |
|---|---|
| 503 | 4615 (A) |
| 504 | 375.8 (A) |
| 505 | 376 (A) |
| 506 | 376.1 (A) |

TABLE 1-continued

| Compound | M + 1 HPLC (min/method) |
|---|---|
| 507 | 375.8 (A) |
| 508 | 479.3 (A) |
| 509 | 445.3 (A) |
| 510 | 408.1 (A) |

TABLE 1-continued
| Compound | M + 1 HPLC (min/method) |
|---|---|
| 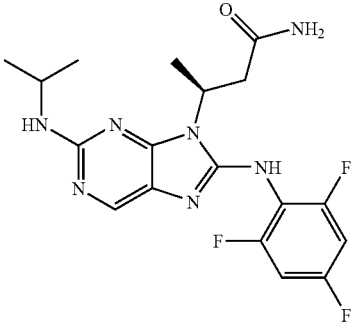<br>511 | 408.4 (A) |
| 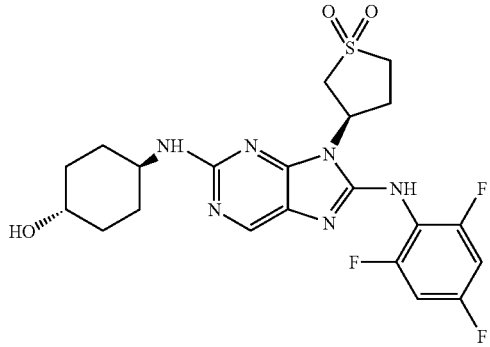<br>512 | 497 (A) |
| 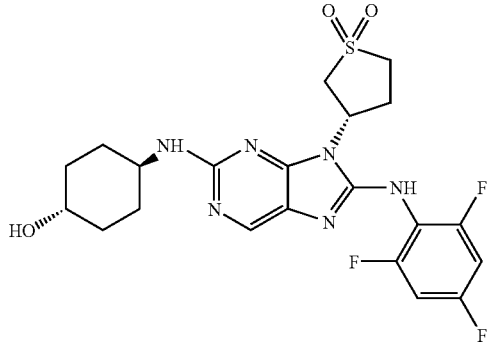<br>513 | 497 (A) |
| 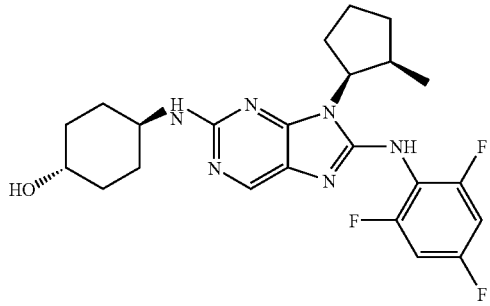<br>514 | 461.4 (A) |

TABLE 1-continued

| Compound | M + 1 HPLC (min/method) |
|---|---|
| 515 | 461.4 (A) |
| 516 | 417.6 (A) |
| 517 | 417.6 (A) |

TABLE 1-continued
| Compound | M + 1 HPLC (min/method) |
|---|---|
| 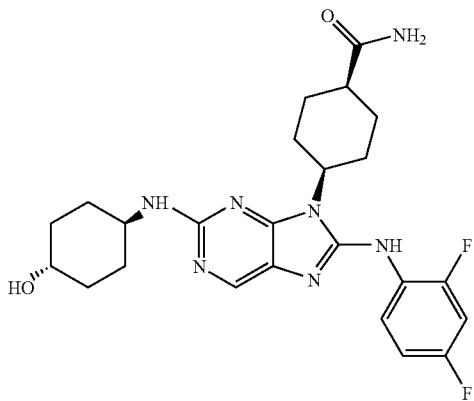　518 | 486.6 (A) |
| 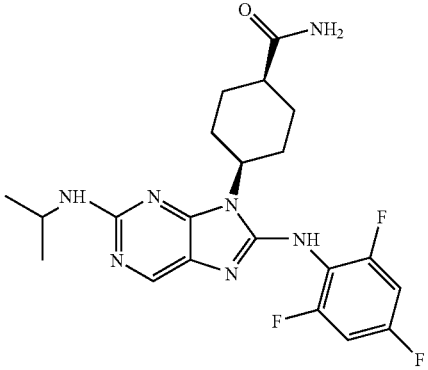　519 | 448.4 (A) |
| 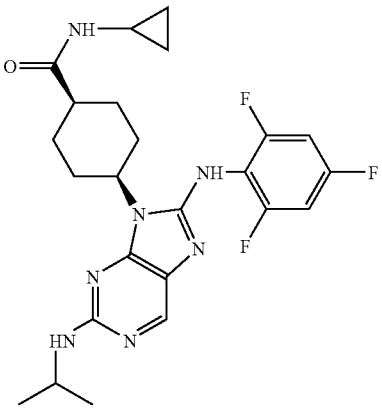　520 | 488.4 (A) |

TABLE 1-continued
| Compound | M + 1 HPLC (min/method) |
|---|---|
| 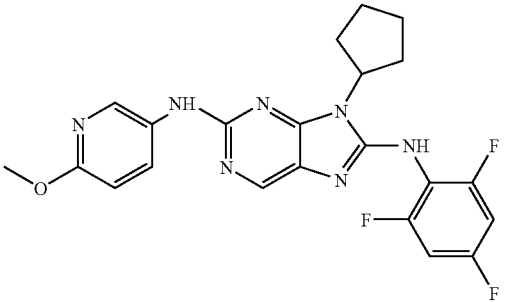 521 | 456.4 (A) |
| 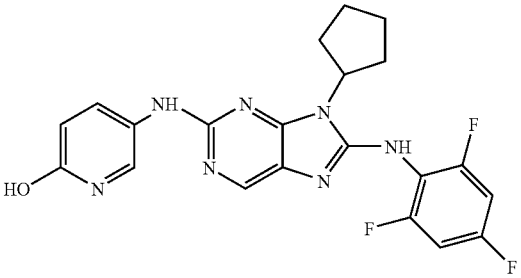 522 | 442.4 (A) |
| 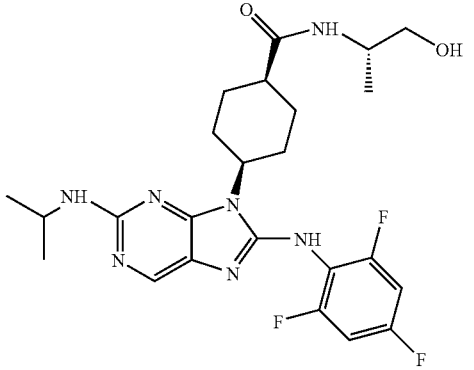 523 | 506 (A) |
| 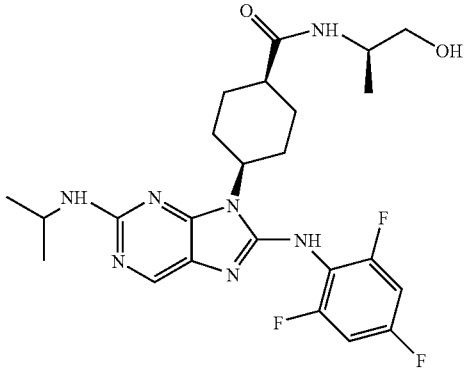 524 | 506 (A) |

TABLE 1-continued
| Compound | M + 1 HPLC (min/method) |
|---|---|
| 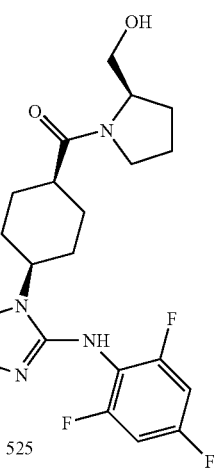 525 | 532.3 (A) |
| 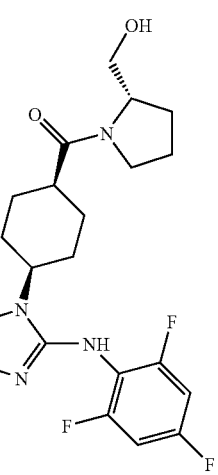 526 | 532.3 (A) |
| 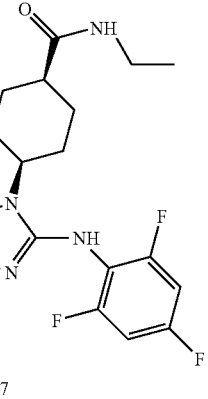 527 | 476.5 (A) |

TABLE 1-continued
| Compound | M + 1 HPLC (min/method) |
|---|---|
| 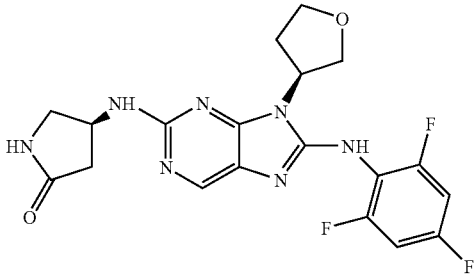 528 | 434.4 (A) |
| 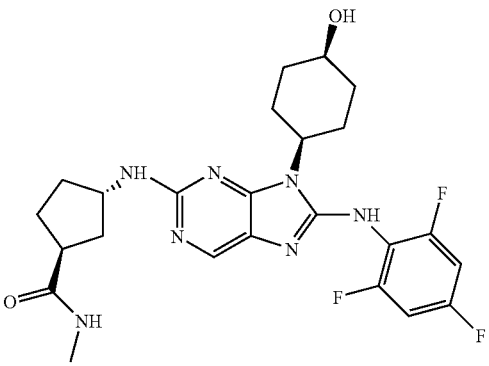 529 | 518.6 (A) |
| 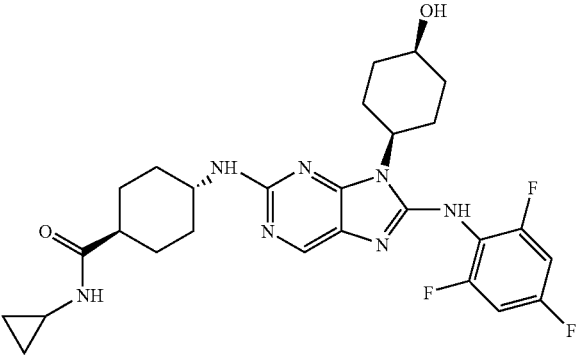 530 | 544.4 (A) |

TABLE 1-continued

| Compound | M + 1 HPLC (min/method) |
|---|---|
| 531 | 558 (A) |
| 532 | 514.6 (A) |
| 533 | 514.7 (A) |

TABLE 1-continued

| Compound | M + 1 HPLC (min/method) |
|---|---|
| 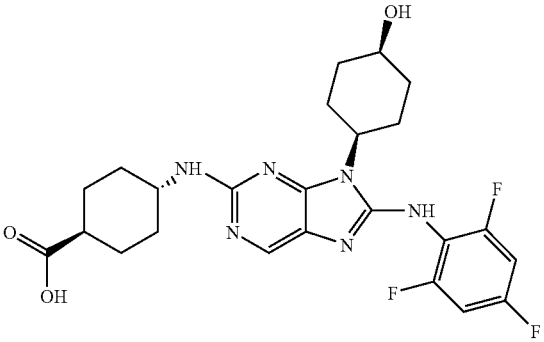 534 | 505.3 (A) |
| 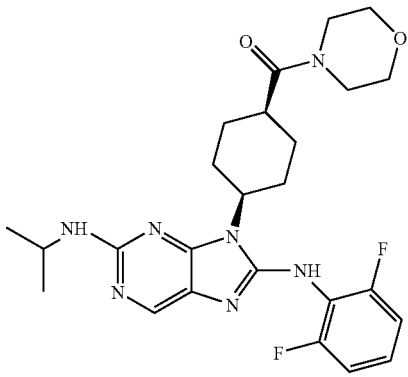 535 | 500.5 (A) |
| 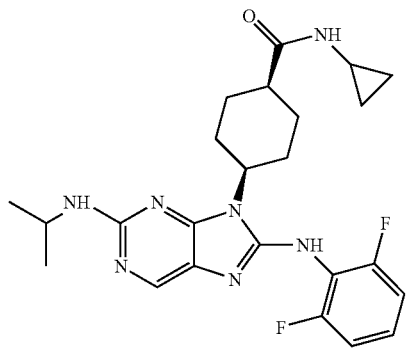 536 | 470.6 (A) |

The compounds of Table 1 were purified by HPLC using one of the conditions A-F described above. The mass spectrometry data (M+1 ion) for each compound is also set forth.

Aminopurine Compounds set forth in Table 1 were tested in the JNK inhibitor assays described herein and were found to have activity as JNK inhibitors.

4.3 Methods for Making Aminopurine Compounds

The Aminopurine Compounds can be made using conventional organic syntheses. By way of example and not limitation, an Aminopurine Compound can be prepared as outlined in Schemes 1 and 2 shown below as well as in Examples 5.1 to 5.53.

Scheme 1:

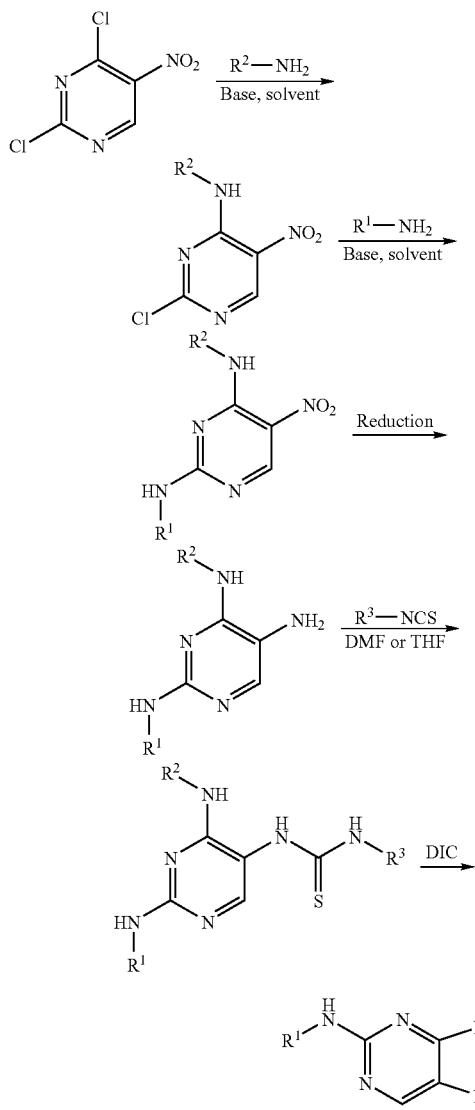

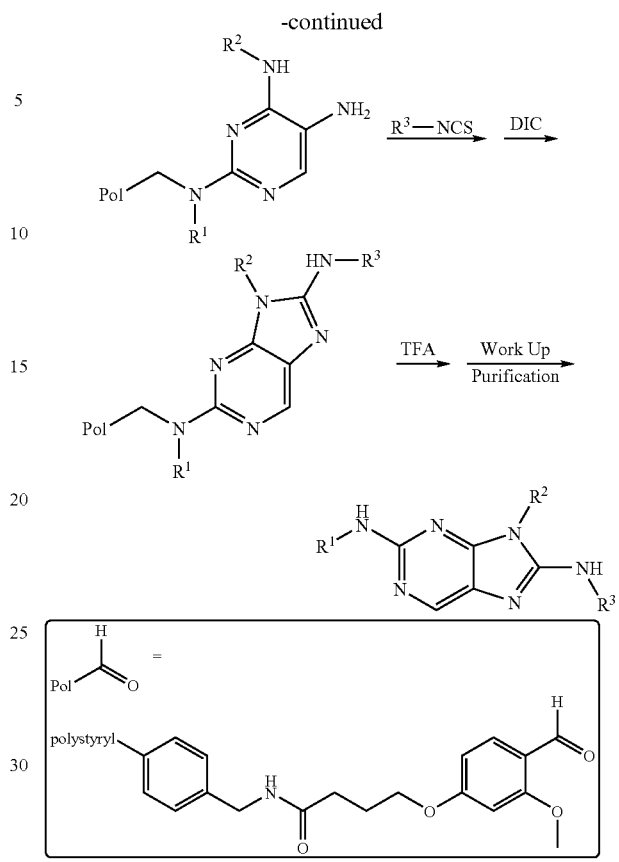

Solid-phase reactions can be performed in, for example, 250 mL polypropylene bottles for large reactions (>50 mL) or in 20 mL fritted polypropylene syringes (<20 mL). All solvents used for washings are HPLC grade unless otherwise stated. Each wash cycle is carried out with 100 mL of solvent for the large vessels or 10 mL of solvent for small vessels over 3-5 minutes unless otherwise stated. The reactions are shaken using a Lab-Line Instruments Titer Plate Shaker.

Synthesis of (2-Chloro-5-nitropyrimidin-4-yl)-$R^2$amines

Scheme 2:

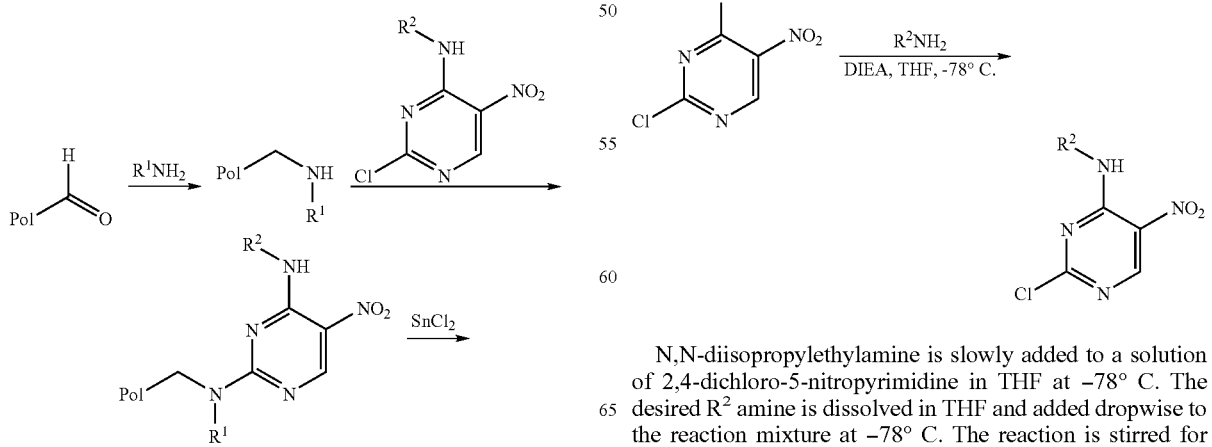

N,N-diisopropylethylamine is slowly added to a solution of 2,4-dichloro-5-nitropyrimidine in THF at −78° C. The desired $R^2$ amine is dissolved in THF and added dropwise to the reaction mixture at −78° C. The reaction is stirred for about 1 hour at −78° C. and then allowed to slowly warm to room temperature overnight. Dichloromethane is added and the organics are washed with water (500 mL) followed by NaHCO$_3$ (sat. aq., 2×500 mL). The organics are dried (MgSO$_4$), filtered, and the solvent is removed in vacuo to provide the crude (2-chloro-5-nitropyrimidin-4-yl)-R$^2$amine. The crude products are used without further purification.

Reductive Amination with R$^1$ Amin

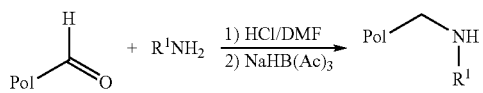

A solution of R$^1$ amine and HCl (a 4 M solution in dioxane) in 5% AcOH/DMF is added to 4-(4-formyl-3-methoxyphenoxy)butyryl AM resin in, for example, a 250 mL polypropylene tube. The resin suspension is agitated on a shaker for about 3 h and sodium triacetoxyborohydride is added. Following shaking for about 1 h with periodic venting, the resin is washed twice with 5% AcOH/DMF using, for example, a polypropylene gas-dispersion tube under vacuum to aspirate off the solvent. A second solution of R$^1$ amine is added followed by agitation for 1 h. Sodium triacetoxyborohydride is added and the suspension is shaken overnight at room temperature with venting of the reaction vessel for about the first 1 h. The reaction vessel is drained and the resin is washed with DMF (2×), 50% MeOH/DMF (2×), DMF (3×) and CH$_2$Cl$_2$ (4×). The resin is then split into five, for example, 20 mL fritted polypropylene syringes using a suspension in DMF.

N-Arylation with (2-Chloro-5-nitropyrimidin-4-yl)-R$^2$amine

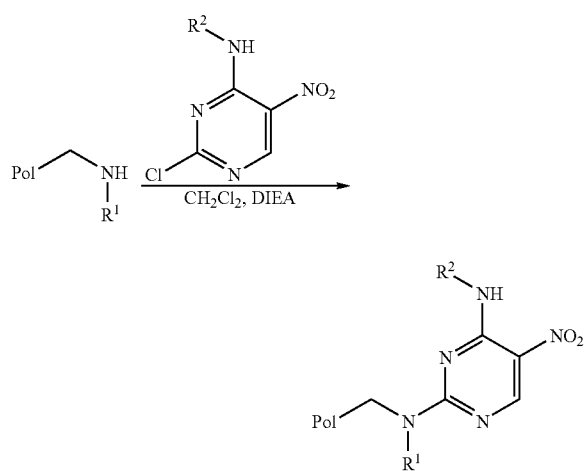

A solution of crude (2-chloro-5-nitropyrimidin-4-yl)-R$^2$amine and NAN-diisopropylethylamine in CH$_2$Cl$_2$ is added to each syringe containing a different resin-bound secondary R$^1$ amine. After shaking the mixture overnight, the reaction solution is drained and the resin is washed with DMF (5×) and CH$_2$Cl$_2$ (7×).

Nitro Reduction

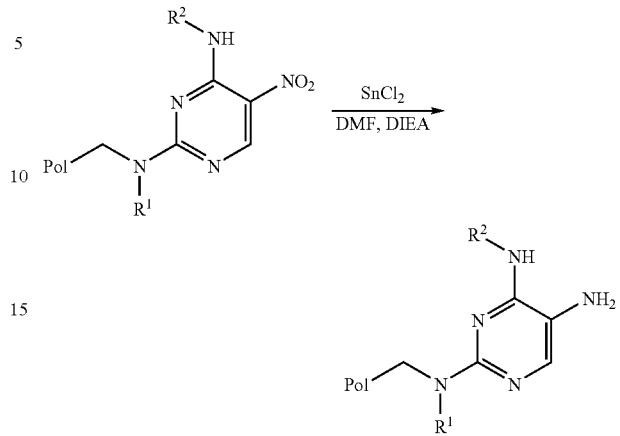

A solution of SnCl$_2$ dihydrate in nitrogen-purged DMF is prepared in, for example, a graduated 1 L glass bottle. N,N-Diisopropylethylamine is added, the volume is adjusted to 1 L with nitrogen saturated DMF, and the solution is purged for about 30 min. with a gentle stream of nitrogen. The SnCl$_2$ solution is added to each resin-bound 5-nitropyrimidine in, for example, a 20 mL fritted polypropylene syringe. The reactions are capped and shaken overnight. The reaction solutions are expelled, the resin is washed with nitrogen-purged DMF (3×) and freshly prepared SnCl$_2$ solution is added. After shaking overnight, the reaction solutions are expelled and the resin is washed with nitrogen-purged DMF (3×). Following a third treatment with SnCl$_2$ solution overnight, the reaction solutions are expelled, the resin is washed with DMF (3×) followed by alternating washes with 50% DMF/H$_2$O and DMF (3× each). This is followed by washing the resin with MeOH (2×), DMF (2×) and CH$_2$Cl$_2$ (7×). Each resin is split into four, for example, 20 mL fritted polypropylene syringes using a suspension in DMF.

Aminopurine Formation

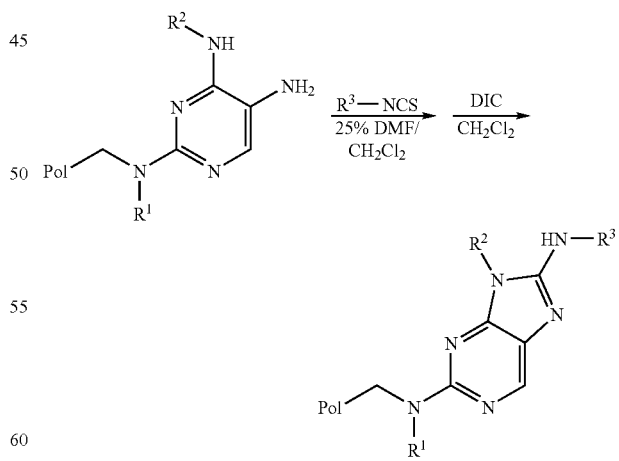

The desired isothiocyanate is added to a suspension of each resin-bound 5-aminopyrimidine in DMF and CH$_2$Cl$_2$. The 20 mL fritted polypropylene syringes containing the resin suspension are capped and allowed to shake overnight. The reaction solutions are expelled, followed by the addition of a solution of DIC in CH$_2$Cl$_2$. The reactions are allowed to shake for about 4 days, the reaction solutions are expelled and the resin is washed with DMF (5×) and CH$_2$Cl$_2$ (7×). The resulting resin-bound aminopurines are dried in vacuo.

Cleavage from Resin

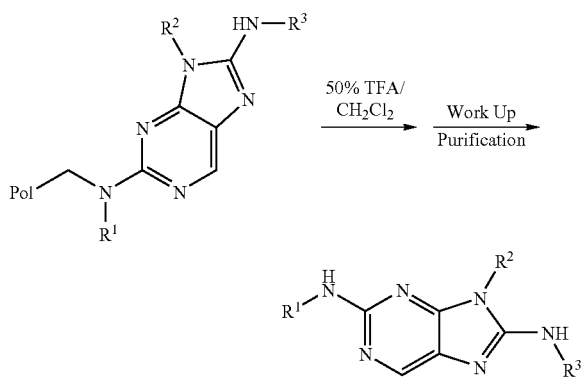

A 50% v/v TFA/CH$_2$Cl$_2$ solution is added to the resin-bound aminopurines in, for example, 20 mL fritted polypropylene syringes. The resulting resin suspensions are allowed to shake overnight, the reaction solutions are collected and dried in vacuo. The residues are partitioned between EtOAc and saturated aq. Na$_2$CO$_3$. After further extracting with EtOAc (2×4 mL) the organic layers are collected, passed through polyethylene frits and dried in vacuo. The residues are dissolved in DMSO, passed through a silica plug and purified using preparative HPLC to provide the desired aminopurine.

Illustrative examples of Schemes 1 and 2 are set forth in Examples 5.1 to 5.14, below.

Pharmaceutically acceptable salts of the Aminopurine Compounds can be formed by conventional and known techniques, such as by reacting a Aminopurine Compound with a suitable acid as disclosed above. Such salts are typically formed in high yields at moderate temperatures, and often are prepared by merely isolating the compound from a suitable acidic wash in the final step of the synthesis. The salt-forming acid may dissolved in an appropriate organic solvent, or aqueous organic solvent, such as an alkanol, ketone or ester. On the other hand, if the Aminopurine Compound is desired in the free base form, it may be isolated from a basic final wash step, according to known techniques. For example, a typical technique for preparing hydrochloride salt is to dissolve the free base in a suitable solvent, and dry the solution thoroughly, as over molecular sieves, before bubbling hydrogen chloride gas through it.

4.4 Methods of Use

The Aminopurine Compounds have utility as pharmaceuticals to heal or prevent disease in animals or humans. Further, the Aminopurine Compounds are active against protein kinases including those involved in cancer, cardiovascular disease, inflammatory diseases, autoimmune diseases and metabolic disorders. Accordingly, provided herein are many uses of the Aminopurine Compounds, including the treatment or prevention of those diseases set forth below. The methods provided herein comprise the administration of an effective amount of an Aminopurine Compound to a patient in need thereof.

Representative autoimmune conditions that the Aminopurine Compounds are useful for treating or preventing include, but are not limited to, rheumatoid arthritis, rheumatoid spondylitis, osteoarthritis, multiple sclerosis, lupus, inflammatory bowel disease, ulcerative colitis, Crohn's disease, myasthenia gravis, Grave's disease and diabetes (e.g., Type I diabetes).

Representative inflammatory conditions that the Aminopurine Compounds are useful for treating or preventing include, but are not limited to, asthma and allergic rhinitis, bronchitis, chronic obstructive pulmonary disease, cystic fibrosis, inflammatory bowel disease, irritable bowel syndrome, Crohn's disease, mucous colitis, ulcerative colitis, diabetes (e.g., Type I diabetes and Type II diabetes) and obesity.

Representative metabolic conditions that the Aminopurine Compounds are useful for treating or preventing include, but are not limited to, obesity and diabetes (e.g., Type II diabetes).

In a particular embodiment, provided herein are methods for the treatment or prevention of insulin resistance. In certain embodiments, provided herein are methods for the treatment or prevention of insulin resistance that leads to diabetes (e.g., Type II diabetes).

In another embodiment, provided herein are methods for the treatment or prevention of syndrome X or metabolic syndrome.

In another embodiment, provide herein are methods for the treatment or prevention of diabetes.

In another embodiment, provide herein are methods for the treatment or prevention of Type II diabetes, Type I diabetes, slow-onset Type I diabetes, diabetes insipidus (e.g., neurogenic diabetes insipidus, nephrogenic diabetes insipidus, dipsogenic diabetes insipidus, or gestagenic diabetes insipidus), diabetes mellitus, gestational diabetes mellitus, polycystic ovarian syndrome, maturity-onset diabetes, juvenile diabetes, insulin-dependant diabetes, non-insulin dependant diabetes, malnutrition-related diabetes, ketosis-prone diabetes, pre-diabetes (e.g., imparied glucose metabolism), cystic fibrosis related diabetes, hemochromatosis and ketosis-resistant diabetes.

In another embodiment, provided herein are methods for the treatment or prevention of fibrotic diseases and disorders. In a particular embodiment, provided herein are methods for the treatment or prevention of idiopathic pulmonary fibrosis, myelofibrosis, hepatic fibrosis, steatofibrosis and steatohepatitis.

Representative cardiovascular diseases that the Aminopurine Compounds are useful for treating or preventing include, but are not limited to, stroke, myocardial infarction or ischemic damage to the heart, lung, gut, kidney, liver, pancreas, spleen or brain.

Representative cardiovascular and renal diseases that an Aminopurine Compound containing or coated stent or stent graft is useful for treating or preventing include atherosclerosis and the treatment or prevention of restenosis after vascular intervention such as angioplasty.

In another embodiment, provided herein are methods for improved processing of beta-islet cells (e.g., human) for transplantation.

In another embodiment, provided herein are methods for improved culturing of beta-islet cells (e.g., human) for transplantation.

In another embodiment, provided herein are methods for improved viability of beta-islet cells (e.g., human) for transplantation.

In another embodiment, provided herein are methods for improved graft-survival of beta-islet cells (e.g., human) for transplantation.

In another embodiment, provided herein are methods for improved processing, culturing, viability and graft-survival of beta-islet cells (e.g., human) for transplantation.

An Aminopurine Compound containing or coated stent or stent graft can further comprise an effective amount of another active agent useful for treating or preventing a cardiovascular or renal disease, including, but are not limited to, an anticoagulant agent, an antimetabolite agent, an anti-inflammatory agent, an antiplatelet agent, an antithrombin agent, an antimitotic agent, a cytostatic agent or an antiproliferative agent.

The Aminopurine Compounds are also useful for treating or preventing ischemia/reperfusion injury in general. Accordingly, the Aminopurine Compounds are useful for treating or preventing acute or chronic organ transplant rejection and for the preservation of tissue and organs.

Representative cancers that the Aminopurine Compounds are useful for treating or preventing include, but are not limited to, cancers of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, and brain or central nervous system.

Cancers within the scope of the methods provided herein include those associated with BCR-ABL, and mutants or isoforms thereof, as well as kinases from the src kinase family, kinases from the Rsk kinase family, kinases from the CDK family, kinases from the MAPK kinase family, and tyrosine kinases such as Fes, Lyn, and Syk kinases, and mutants or isoforms thereof.

In a particular embodiment, provided herein are methods for the treatment or prevention of a disease or disorder associated with the modulation, for example inhibition, of a kinase, including, but not limited to, tyrosine-protein kinase (SYK), tyrosine-protein kinase (ZAP-70), protein tyrosine kinase 2 beta (PYK2), focal adhesion kinase 1 (FAK), B lymphocyte kinase (BLK), hemopoietic cell kinase (HCK), v-yes-1 Yamaguchi sarcoma viral related oncogene homolog (LYN), T cell-specific protein-tyrosine kinase (LCK), proto-oncogene tyrosine-protein kinase (YES), proto-oncogene tyrosine-protein kinase (SRC), proto-oncogene tyrosine-protein kinase (FYN), proto-oncogene tyrosine-protein kinase (FGR), proto-oncogene tyrosine-protein kinase (FER), proto-oncogene tyrosine-protein kinase (FES), C-SRC kinase, protein-tyrosine kinase (CYL), tyrosine protein kinase (CSK), megakaryocyte-associated tyrosine-protein kinase (CTK), tyrosine-protein kinase receptor (EPH), Ephrin type-A receptor 1, Ephrin type-A receptor 4 (EPHA4), Ephrin type-B receptor 3 (EPHB3), Ephrin type-A receptor 8 (EPHA8), neurotrophic tyrosine kinase receptor, type 1 (NTRK1), protein-tyrosine kinase (PTK2), syk-related tyrosine kinase (SRK), protein tyrosine kinase (CTK), tyro3 protein tyrosine kinase (TYRO3), bruton agammaglobulinemia tyrosine kinase (BTK), leukocyte tyrosine kinase (LTK), protein-tyrosine kinase (SYK), protein-tyrosine kinase (STY), tek tyrosine kinase (TEK), elk-related tyro sine kinase (ERK), tyrosine kinase with immunoglobulin and egf factor homology domains (TIE), protein tyrosine kinase (TKF), neurotrophic tyrosine kinase, receptor, type 3 (NTRK3), mixed-lineage protein kinase-3 (MLK3), protein kinase, mitogen-activated 4 (PRKM4), protein kinase, mitogen-activated 1 (PRKM 1), protein tyrosine kinase (PTK7), protein tyrosine kinase (EEK), minibrain (drosophila) homolog (MNBH), bone marrow kinase, x-linked (BMX), eph-like tyrosine kinase 1 (ETK1), macrophage stimulating I receptor (MST1R), btk-associated protein, 135 kd, lymphocyte-specific protein tyrosine kinase (LCK), fibroblast growth factor receptor-2 (FGFR2), protein tyrosine kinase-3 (TYK3), protein tyrosine kinase (TXK), tec protein tyrosine kinase (TEC), protein tyrosine kinase-2 (TYK2), eph-related receptor tyrosine kinase ligand 1 (EPLG1), t-cell tyrosine kinase (EMT), eph tyrosine kinase 1 (EPHT1), zona pellucida receptor tyrosine kinase, 95 kd (ZRK), protein kinase, mitogen-activated, kinase 1 (PRKMK1), eph tyrosine kinase 3 (EPHT3), growth arrest-specific gene-6 (GAS6), kinase insert domain receptor (KDR), axl receptor tyrosine kinase (AXL), fibroblast growth factor receptor-1 (FGFR1), v-erb-b2 avian erythroblastic leukemia viral oncogene homolog 2 (ERBB2), fms-like tyrosine kinase-3 (FLT3), neuroepithelial tyrosine kinase (NEP), neurotrophic tyrosine kinase receptor-related 3 (NTRKR3), eph-related receptor tyrosine kinase ligand 5 (EPLG5), neurotrophic tyrosine kinase, receptor, type 2 (NTRK2), receptor-like tyrosine kinase (RYK), tyrosine kinase, b-lymphocyte specific (BLK), eph tyrosine kinase 2 (EPHT2), eph-related receptor tyrosine kinase ligand 2 (EPLG2), glycogen storage disease VIII, eph-related receptor tyrosine kinase ligand 7 (EPLG7), janus kinase 1 (JAK1), fms-related tyrosine kinase-1 (FLT1), protein kinase, camp-dependent, regulatory, type I, alpha (PRKAR1A), wee-1 tyrosine kinase (WEE1), eph-like tyrosine kinase 2 (ETK2), receptor tyrosine kinase musk, insulin receptor (INSR), janus kinase 3 (JAK3), fms-related tyrosine kinase-3 ligand protein kinase c, beta 1 (PRKCB1), tyrosine kinase-type cell surface receptor (HER3), janus kinase 2 (JAK2), lim domain kinase 1 (LIMK1), dual specificity phosphatase 1 (DUSP1), hemopoietic cell kinase (HCK), tyrosine 3-monooxygenase/tryptophan 5-monooxygenase activation protein, eta polypeptide (YWHAH), ret proto-oncogene (RET), tyrosine 3-monooxygenase/tryptophan 5-monooxygenase activation protein, zeta polypeptide (YWHAZ), tyrosine 3-monooxygenase/tryptophan 5-monooxygenase activation protein, beta polypeptide (YWHAB), hepatoma transmembrane kinase (HTK), map kinase kinase 6, phosphatidylinositol 3-kinase, catalytic, alpha polypeptide (PIK3CA), cyclin-dependent kinase inhibitor 3 (CDKN3), diacylglycerol kinase, delta, 130 kd, protein-tyrosine phosphatase, nonreceptor type, 13 (PTPN13), abelson murine leukemia viral oncogene homolog 1 (ABL1), diacylglycerol kinase, alpha (DAGK1), focal adhesion kinase 2, epithelial discoidin domain receptor 1 (EDDR1), anaplastic lymphoma kinase (ALK), phosphatidylinositol 3-kinase, catalytic, gamma polypeptide (PIK3CG), phosphatidylinositol 3-kinase regulatory subunit, (PIK3R1), eph homology kinase-1 (EHK1), v-kit hardy-zuckerman 4 feline sarcoma viral oncogene homolog (KIT), fibroblast growth factor receptor-3 (FGFR3), vascular endothelial growth factor c (VEGFC), epidermal growth factor receptor (EGFR), oncogene (TRK), growth factor receptor-bound protein-7 (GRB7), ras p21 protein activator (RASA2), met proto-oncogene (MET), src-like adapter (SLA), vascular endothelial growth factor (VEGF), vascular endothelial growth factor receptor (VEGFR), nerve growth factor receptor (NGFR), platelet derived growth factor receptor (PDGFR), platelet derived growth factor receptor beta (PDGFRB), dual-specificity tyrosine-(Y)-phosphorylation regulated kinase 2 (DYRK2), dual-specificity tyrosine-(Y)-phosphorylation regulated kinase 3 (DYRK3), dual-specificity tyrosine-(Y)-phosphorylation regulated kinase 4 (DYRK4), dual-specificity tyrosine-(Y)-phosphorylation regulated kinase 1A (DYRK1A), dual-specificity tyrosine-(Y)-phosphorylation regulated kinase 1B (DYRK1B), CDC-like kinase 1 (CLK1), protein tyrosine kinase STY, CDC-like kinase 4 (CLK4), CDC-like kinase 2 (CLK2) or CDC-like kinase 3 (CLK3).

In another embodiment, provided herein are methods for the treatment or prevention of a disease or disorder associated with the modulation, for example inhibition, of serine/threonine kinases or related molecules, including, but not limited to, cyclin-dependent kinase 7 (CDK7), rac serine/threonine protein kinase, serine-threonine protein kinase n (PKN), serine/threonine protein kinase 2 (STK2), zipper protein kinase (ZPK), protein-tyrosine kinase (STY), bruton agammaglobulinemia tyrosine kinase (BTK), mkn28 kinase, protein kinase, x-linked (PRKX), elk-related tyrosine kinase (ERK), ribosomal protein s6 kinase, 90 kd, polypeptide 3 (RPS6KA3), glycogen storage disease VIII, death-associated protein kinase 1 (DAPK1), pctaire protein kinase 1 (PCTK1), protein kinase, interferon-inducible double-stranded ma (PRKR), activin a receptor, type II-like kinase 1 (ACVRLK1), protein kinase, camp-dependent, catalytic, alpha (PRKACA), protein kinase, y-linked (PRKY), G protein-coupled receptor kinase 2 (GPRK21), protein kinase c, theta form (PRKCQ), lim domain kinase 1 (LIMK1), phosphoglycerate kinase 1 PGK1), lim domain kinase 2 (LIMK2), c-jun kinase, activin a receptor, type II-like kinase 2 (ACVRLK2), janus kinase 1 (JAK1), elk1 motif kinase (EMK1), male germ cell-associated kinase (MAK), casein kinase 2, alpha-prime subunit (CSNK2A2), casein kinase 2, beta polypeptide (CSNK2B), casein kinase 2, alpha 1 polypeptide (CSNK2A1), ret proto-oncogene (RET), hematopoietic progenitor kinase 1, conserved helix-loop-helix ubiquitous kinase (CHUK), casein kinase 1, delta (CSNK1D), casein kinase 1, epsilon (CSNK1E), v-akt murine thymoma viral oncogene homolog 1 (AKT1), tumor protein p53 (TP53), protein phosphatase 1, regulatory (inhibitor) subunit 2 (PPP1R2), oncogene pim-1 (PIM1), transforming growth factor-beta receptor, type II (TGFBR2), transforming growth factor-beta receptor, type I (TGFBR1), v-raf murine sarcoma viral oncogene homolog b1 (BRAF), bone morphogenetic receptor type II (BMPR2), v-raf murine sarcoma 3611 viral oncogene homolog 1 (ARAF1), v-raf murine sarcoma 3611 viral oncogene homolog 2 (ARAF2), protein kinase C (PKC), v-kit hardy-zuckerman 4 feline sarcoma viral oncogene homolog (KIT) or c-KIT receptor (KITR).

In another embodiment, provided herein are methods for the treatment or prevention of a disease or disorder associated with the modulation, for example inhibition, of a MAP kinase, including, but not limited to, mitogen-activated protein kinase 3 (MAPK3), p44erk1, p44mapk, mitogen-activated protein kinase 3 (MAP kinase 3; p44), ERK1, PRKM3, P44ERK1, P44MAPK, mitogen-activated protein kinase 1 (MAPK1), mitogen-activated protein kinase kinase 1 (MEK1), MAP2K1protein tyrosine kinase ERK2, mitogen-activated protein kinase 2, extracellular signal-regulated kinase 2, protein tyrosine kinase ERK2, mitogen-activated protein kinase 2, extracellular signal-regulated kinase 2, ERK, p38, p40, p41, ERK2, ERT1, MAPK2, PRKM1, PRKM2, P42MAPK, p41mapk, mitogen-activated protein kinase 7 (MAPK7), BMK1 kinase, extracellular-signal-regulated kinase 5, BMK1, ERK4, ERK5, PRKM7, nemo-like kinase (NLK), likely ortholog of mouse nemo like kinase, mitogen-activated protein kinase 8 (MAPK8), protein kinase JNK1, JNK1 beta protein kinase, JNK1 alpha protein kinase, c-Jun N-terminal kinase 1, stress-activated protein kinase JNK1, JNK, JNK1, PRKM8, SAPK1, JNK1A2, JNK21B1/2, mitogen-activated protein kinase 10 (MAPK10), c-Jun kinase 3, JNK3 alpha protein kinase, c-Jun N-terminal kinase 3, stress activated protein kinase JNK3, stress activated protein kinase beta, mitogen-activated protein kinase 9 (MAPK9), MAP kinase 9, c-Jun kinase 2, c-Jun N-terminal kinase 2, stress-activated protein kinase JNK2, JNK2, JNK2A, JNK2B, PRKM9, JNK-55, JNK2BETA, p54aSAPK, JNK2ALPHA, mitogen-activated protein kinase 14 (MAPK14), p38 MAP kinase, MAP kinase Mxi2, Csaids binding protein, MAX-interacting protein 2, stress-activated protein kinase 2A, p38 mitogen activated protein kinase, cytokine suppressive anti-inflammatory drug binding protein, RK, p38, EXIP, Mxi2, CSBP1, CSBP2, CSPB1, PRKM14, PRKM15, SAPK2A, p38ALPHA, mitogen-activated protein kinase 11 (MAPK11), stress-activated protein kinase-2, stress-activated protein kinase-2b, mitogen-activated protein kinase p38-2, mitogen-activated protein kinase p38beta, P38B, SAPK2, p38-2, PRKM11, SAPK2B, p38Beta, P38BETA2, mitogen-activated protein kinase 13 (MAPK13), stress-activated protein kinase 4, mitogen-activated protein kinase p38 delta, SAPK4, PRKM13, p38delta, mitogen-activated protein kinase 12 (MAPK12), p38gamma, stress-activated protein kinase 3, mitogen-activated protein kinase 3, ERK3, ERK6, SAPK3, PRKM12, SAPK-3, P38GAMMA, mitogen-activated protein kinase 6 (MAPK6), MAP kinase isoform p97, mitogen-activated 5 protein kinase, mitogen-activated 6 protein kinase, extracellular signal-regulated kinase 3, extracellular signal-regulated kinase, p97, ERK3, PRKM6, p97MAPK, mitogen-activated protein kinase 4 (MAPK4), Erk3-related protein kinase, mitogen-activated 4 protein kinase (MAP kinase 4; p63), PRKM4, p63MAPK, ERK3-RELATED or Extracellular signal-regulated kinase 8 (ERK7).

More particularly, cancers and related disorders that can be treated or prevented by methods and compositions provided herein include but are not limited to the following: Leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome (or a symptom thereof such as anemia, thrombocytopenia, neutropenia, bicytopenia or pancytopenia), refractory anemia (RA), RA with ringed sideroblasts (RARS), RA with excess blasts (RAEB), RAEB in transformation (RAEB-T), preleukemia and chronic myelomonocytic leukemia (CMML), chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, non-seminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypemephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine*, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

Accordingly, the methods and compositions provided herein are also useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal orignin, including fibrosarcoma and rhabdomyosarcoma; other tumors, including melanoma, seminoma, teratocarcinoma, neuroblastoma and glioma; tumors of the central and peripheral nervous system, including astrocytoma, glioblastoma multiforme, neuroblastoma, glioma, and schwannomas; solid and blood born tumors; tumors of mesenchymal origin, including fibrosarcoma, rhabdomyoscarama, and osteosarcoma; and other tumors, including melanoma, xenoderoma pegmentosum, keratoctanthoma, seminoma, thyroid follicular cancer and teratocarcinoma. It is also contemplated that cancers caused by aberrations in apoptosis would also be treated by the methods and compositions disclosed herein. Such cancers may include but not be limited to follicular lymphomas, carcinomas with p53 mutations, hormone dependent tumors of the breast, prostate and ovary, and pre-cancerous lesions such as familial adenomatous polyposis, and myelodysplastic syndromes. In specific embodiments, malignancy or dysproliferative changes (such as metaplasias and dysplasias), or hyperproliferative disorders, are treated or prevented in the ovary, bladder, breast, colon, lung, skin, pancreas, or uterus. In other specific embodiments, sarcoma, melanoma, or leukemia is treated or prevented.

In another embodiment, the methods and compositions provided herein are also useful for administration to patients in need of a bone marrow transplant to treat a malignant disease (e.g., patients suffering from acute lymphocytic leukemia, acute myelogenous leukemia, chronic myelogenous leukemia, chronic lymphocytic leukemia, myelodysplastic syndrome ("preleukemia"), monosomy 7 syndrome, non-Hodgkin's lymphoma, neuroblastoma, brain tumors, multiple myeloma, testicular germ cell tumors, breast cancer, lung cancer, ovarian cancer, melanoma, glioma, sarcoma or other solid tumors), those in need of a bone marrow transplant to treat a non-malignant disease (e.g., patients suffering from hematologic disorders, congenital immunodeficiencies, mucopolysaccharidoses, lipidoses, osteoporosis, Langerhan's cell histiocytosis, Lesch-Nyhan syndrome or glycogen storage diseases), those undergoing chemotherapy or radiation therapy, those preparing to undergo chemotherapy or radiation therapy and those who have previously undergone chemotherapy or radiation therapy.

In another embodiment, provided herein are methods for the treatment of myeloproliferative disorders or myelodysplastic syndromes, comprising administering to a patient in need thereof an effective amount of an Aminopurine Compound or a composition thereof. In certain embodiments, the myeloproliferative disorder is polycythemia rubra vera; primary thrombocythemia; chronic myelogenous leukemia; acute or chronic granulocytic leukemia; acute or chronic myelomonocytic leukemia; myelofibro-erythroleukemia; or agnogenic myeloid metaplasia.

In another embodiment, provided herein are methods for the treatment of cancer or tumors resistant to other kinase inhibitors such as imatinib mesylate (STI-571 or Gleevec™) treatment, comprising administering to a patient in need thereof an effective amount of an Aminopurine Compound or a composition thereof. In a particular embodiment, provided herein are methods for the treatment of leukemias, including, but not limited to, gastrointestinal stromal tumor (GIST), acute lymphocytic leukemia or chronic myelocytic leukemia resistant to imatinib mesylate (STI-571 or Gleevec™) treatment, comprising administering to a patient in need thereof an effective amount of an Aminopurine Compound or a composition thereof.

In a particular embodiment, provided herein are methods for the treatment or prevention of airway hyperresponsiveness (AHR) and lung inflammation comprising administering an effective amount of an Aminopurine Compound to a patient in need thereof.

In another embodiment, provided herein are methods for the treatment or prevention of a disease or disorder caused, induced or exacerbated by an agonist including, but not limited to, ozone, cold or exercise, comprising administering an effective amount of an Aminopurine Compound to a patient in need thereof. In a specific embodiment, provided herein are methods for the treatment or prevention of asthma, bronchitis, rhinitis, COPD, lung inflammation and AHR caused, induced or exacerbated by an agonist including, but not limited to, ozone, cold or exercise, comprising administering an effective amount of an Aminopurine Compound to a patient in need thereof.

In another embodiment, provided herein are methods for the treatment or prevention of ozone-induced effects (e.g., adverse effects) on a lung, comprising administering an effective amount of an Aminopurine Compound to a patient in need thereof.

In another embodiment, provided herein are methods for modulating inflammatory cell recruitment and/or inflammatory gene expression in the lungs comprising administering an effective amount of an Aminopurine Compound to a patient in need thereof.

In another embodiment, provided herein are methods for inhibiting neutrophil accumulation in bronchioalveolar lavage fluid comprising administering an effective amount of an Aminopurine Compound to a patient in need thereof.

In another embodiment, provided herein are methods for modulating (i.e., inducing or inhibiting) expression of genes involved in oxidative stress response comprising administering an effective amount of an Aminopurine Compound to a patient in need thereof.

In another embodiment, provided herein are methods for modulating (i.e., inducing or inhibiting) expression of genes modulated by ozone comprising administering an effective amount of an Aminopurine Compound to a patient in need thereof. In a specific embodiment, provided herein are methods for modulating (i.e., inducing or inhibiting) expression of the following genes comprising administering an effective amount of an Aminopurine Compound to a patient in need thereof: Interleukin 6; Chemokine (C-X-C motif) ligand 1; A disintegrin-like and metalloprotease (reprolysin type) with thrombospondin type 1 motif, 4; Metallothionein 1; Chemokine (C-X-C motif) ligand 2; Interleukin 1 receptor, type II; Small chemokine (C—C motif) ligand 11; Pentaxin related gene; Hemopexin; Matrix metalloproteinase 8; Tumor necrosis factor alpha induced protein 6; Cyclin-dependent kinase inhibitor 1A (P21); FK506 binding protein 5; Protease, serine, 22; DNA-damage-inducible transcript 4; Similar to mPLZF(B)=promyelocytic leukemia zinc finger protein {alternatively spliced} (LOC235320), mRNA; Cyclin-dependent kinase inhibitor 1A (P21); Double C2, beta; Suppressor of cytokine signaling 3; Metallothionein 2; Angiopoietin; Solute carrier family 27 (fatty acid transporter), member 3; wingless-related MMTV integration site 7A; BB224790 RIKEN full-length enriched, adult male aorta and vein *Mus musculus* mRNA sequence; Calcitonin receptor-like; Glia maturation factor, beta; RIKEN full-length enriched library, clone:D230030K09; Mp78a12.x1 Soares_thymus_2NbMT *Mus musculus* cDNA clone IMAGE:575326 mRNA sequence; cDNA sequence BC025076; Interleukin 6 signal transducer; Myc target 1; Tripartite motif protein 37; Frizzled homolog 2 (Drosophila); DNA segment, Chr 4, Wayne State University 53, expressed; Stromal antigen 2; HLA-B associated transcript 8; RIKEN cDNA 1110014P06 gene; GATA binding protein 3; AV218922 RIKEN full-length enriched, mRNA sequence; and PDZ domain containing, X chromosome.

In one embodiment, provided herein are methods for treating or preventing a disease or disorder treatable or preventable by modulating a kinase pathway, in one embodiment, the JNK pathway, comprising administering an effective amount of an Aminopurine Compound to a patient in need of the treating or preventing. Particular diseases which are treatable or preventable by modulating, for example, inhibiting, a kinase pathway, in one embodiment, the JNK pathway, include, but are not limited to, rheumatoid arthritis; rheumatoid spondylitis; osteoarthritis; gout; asthma, bronchitis; allergic rhinitis; chronic obstructive pulmonary disease; cystic fibrosis; inflammatory bowel disease; irritable bowel syndrome; mucous colitis; ulcerative colitis; Crohn's disease; Huntington's disease; gastritis; esophagitis; hepatitis; pancreatitis; nephritis; multiple sclerosis; lupus erythematosus; Type II diabetes; obesity; atherosclerosis; restenosis following angioplasty; left ventricular hypertrophy; myocardial infarction; stroke; ischemic damages of heart, lung, gut, kidney, liver, pancreas, spleen and brain; acute or chronic organ transplant rejection; preservation of the organ for transplantation; organ failure or loss of limb (e.g., including, but not limited to, that resulting from ischemia-reperfusion injury, trauma, gross bodily injury, car accident, crush injury or transplant failure); graft versus host disease; endotoxin shock; multiple organ failure; psoriasis; burn from exposure to fire, chemicals or radiation; eczema; dermatitis; skin graft; ischemia; ischemic conditions associated with surgery or traumatic injury (e.g., vehicle accident, gunshot wound or limb crush); epilepsy; Alzheimer's disease; Parkinson's disease; immunological response to bacterial or viral infection; cachexia; angiogenic and proliferative diseases; solid tumor; and cancers of a variety of tissues such as colon, rectum, prostate, liver, lung, bronchus, pancreas, brain, head, neck, stomach, skin, kidney, cervix, blood, larynx, esophagus, mouth, pharynx, urinary bladder, ovary or uterine.

4.5 Pharmaceutical Compositions and Routes of Administration

The Aminopurine Compounds can be administered to a patient orally or parenterally in the conventional form of preparations, such as capsules, microcapsules, tablets, granules, powder, troches, pills, suppositories, injections, suspensions and syrups. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g., sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the Aminopurine Compounds in the pharmaceutical composition may be at a level that will exercise the desired effect; for example, about 0.005 mg/kg of a patient's body weight to about 10 mg/kg of a patient's body weight in unit dosage for both oral and parenteral administration.

The dose of an Aminopurine Compound to be administered to a patient is rather widely variable and can be subject to the judgment of a health-care practitioner. In general, the Aminopurine Compounds can be administered one to four times a day in a dose of about 0.005 mg/kg of a patient's body weight to about 10 mg/kg of a patient's body weight in a patient, but the above dosage may be properly varied depending on the age, body weight and medical condition of the patient and the type of administration. In one embodiment, the dose is about 0.01 mg/kg of a patient's body weight to about 5 mg/kg of a patient's body weight, about 0.05 mg/kg of a patient's body weight to about 1 mg/kg of a patient's body weight, about 0.1 mg/kg of a patient's body weight to about 0.75 mg/kg of a patient's body weight or about 0.25 mg/kg of a patient's body weight to about 0.5 mg/kg of a patient's body weight. In one embodiment, one dose is given per day. In any given case, the amount of the Aminopurine Compound administered will depend on such factors as the solubility of the active component, the formulation used and the route of administration.

In another embodiment, provided herein are methods for the treatment or prevention of a disease or disorder comprising the administration of about 0.375 mg/day to about 750 mg/day, about 0.75 mg/day to about 375 mg/day, about 3.75 mg/day to about 75 mg/day, about 7.5 mg/day to about 55 mg/day or about 18 mg/day to about 37 mg/day of an Aminopurine Compound to a patient in need thereof.

In another embodiment, provided herein are methods for the treatment or prevention of a disease or disorder comprising the administration of about 1 mg/day to about 1200 mg/day, about 10 mg/day to about 1200 mg/day, about 100 mg/day to about 1200 mg/day, about 400 mg/day to about 1200 mg/day, about 600 mg/day to about 1200 mg/day, about 400 mg/day to about 800 mg/day or about 600 mg/day to about 800 mg/day of an Aminopurine Compound to a patient in need thereof. In a particular embodiment, the methods disclosed herein comprise the administration of 400 mg/day, 600 mg/day or 800 mg/day of an Aminopurine Compound to a patient in need thereof.

In another embodiment, provided herein are unit dosage formulations that comprise between about 1 mg and 200 mg, about 35 mg and about 1400 mg, about 125 mg and about 1000 mg, about 250 mg and about 1000 mg, or about 500 mg and about 1000 mg of an Aminopurine Compound.

In a particular embodiment, provided herein are unit dosage formulation comprising about 100 mg or 400 mg of an Aminopurine compound.

In another embodiment, provided herein are unit dosage formulations that comprise 1 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of an Aminopurine Compound.

An Aminopurine Compound can be administered once, twice, three, four or more times daily. In a particular embodiment, doses of 600 mg or less are administered as a a once daily dose and doses of more than 600 mg are administered twice daily in an amount equal to one half of the total daily dose.

An Aminopurine Compound can be administered orally for reasons of convenience. In one embodiment, when administered orally, an Aminopurine Compound is administered with a meal and water. In another embodiment, the Aminopurine Compound is dispersed in water or juice (e.g., apple juice or orange juice) and administered orally as a suspension.

The Aminopurine Compound can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing an Aminopurine Compound without an additional carrier, excipient or vehicle.

In another embodiment, provided herein are compositions comprising an effective amount of an Aminopurine Compound and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing an Aminopurine Compound with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the die. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer an Aminopurine Compound as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the Aminopurine Compound can be delayed or prolonged by proper formulation. For example, a slowly soluble pellet of the Aminopurine Compound can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the Aminopurine Compound in oily or emulsified vehicles that allow it to disperse slowly in the serum.

5. EXAMPLES

The following Examples are presented by way of illustration, not limitation.

Example 5.1

Synthesis of 4-({8-[(2,6-Difluorophenyl)amino]-9-cyclopentylpurin-2-yl}amino)trans-cyclohexan-1-ol

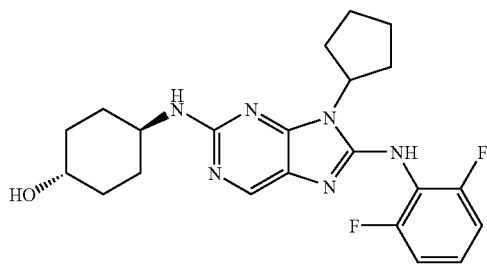

1. (2-Chloro-5-nitropyrimidin-4-yl)cyclopentylamine 2,4-Dichloro-5-nitropyrimidine (10.31 mmol, 2 g) and cyclopentylamine (10.31 mmol, 1.02 mL) were dissolved in THF (60 mL) and cooled to −78° C. N,N-diisopropylethylamine (10.31 mmol, 1.8 mL) was added dropwise. The reaction mixture was stirred at −78° C. for about 45 minutes. The cooling bath was removed and the reaction mixture was stirred at room temperature for about 16 hours. After removal of the solvent the residue was redissolved in EtOAc and washed with water and brine. The organic phase was dried over $MgSO_4$ and the solvent evaporated. The residue was purified using column chromatography ($SiO_2$, 9:1 n-hexanes/ethyl acetate) to give the desired product (2.11 g, 84% yield). ES-MS: 242 (M+1). When the hydrochloride salt of an amine is used in place of the cyclopentylamine described above, 2 to 3 equivalents of N,N-diisopropylethylamine and dichloromethane are used as solvent.

2. 4-{[4-(Cyclopentylamino)-5-nitropyrimidin-2-yl]amino}trans-cyclohexan-1-ol (2-Chloro-5-nitropyrimidin-4-yl)cyclopentylamine (6.18 mmol, 1.5 g) and trans-4-aminocyclohexan-1-ol (7.42 mmol, 854 mg mL) were mixed in DMF (18 mL) and N,N-diisopropylethylamine (7.42 mmol, 1.29 mL) was added. The reaction mixture was stirred overnight. Solvent was removed in vacuo and the residue purified using column chromatography ($SiO_2$, 1:1 n-hexanes/ethyl acetate→7:3 n-hexanes/ethyl acetate→ethyl acetate) to give the desired product (1.75 g, 88% yield). ES-MS: 322 (M+1). When the hydrochloride salt of an amine is used in place of the trans-4-aminocyclohexan-1-ol described above, 2 to 3 equivalents of N,N-diisopropylethylamine or sodium bicarbonate and tetrahydrofuran or acetonitrile were used as solvent.

3. 4-{[5-Amino-4-(cyclopentylamino)pyrimidin-2-yl]amino}trans-cyclohexan-1-ol

4-{[4-(Cyclopentylamino)-5-nitropyrimidin-2-yl]amino}trans-cyclohexan-1-ol (2.18 mmol, 700 mg) was dissolved in 20 ml EtOH and hydrogenated overnight at 1 bar with Pd/C (10%) as catalyst. The catalyst was filtered and the solvent evaporated to give the desired product (635 mg, 100% yield) which was carried on to the next step without further purification. ES-MS: 292 (M+1). This reduction can be also accomplished using the following procedure: $Na_2S_2O_4$ (140.0 mmol, 14 eq.) is dissolved in 150 mL water and 75 mL dioxane and 7.5 mL $NH_4OH$ solution are added. The corresponding nitro compound (10.0 mmol, 1 eq.) is added and the reaction mixture is stirred for 12 to 72 hours. Dioxane is evaporated and the product is extracted by using EtOAc or brine/THF. The organic phase is dried over $MgSO_4$ and evaporated to give the desired product.

4. 4-({8-[(2,6-Difluorophenyl)amino]-9-cyclopentylpurin-2-yl}amino)trans-cyclohexan-1-ol 4-{[5-Amino-4-(cyclopentylamino)pyrimidin-2-yl]amino}trans-cyclohexan-1-ol (1.13 mmol, 330 mg) was dissolved in DMF (8.5 mL) and 2,6-difluorophenyl-isothiocyanate (1.13 mmol, 0.146 mL) was added. The reaction mixture was stirred at room temperature for about 90 minutes. Ethanol (2.5 mL) was added and the reaction mixture was stirred for about an additional 30 minutes. N,N-Diisopropylcarbodiimide (3.40 mmol, 0.532 mL) was added and the reaction mixture was stirred overnight. Solvent was removed and the residue was purified using column chromatography ($SiO_2$, 1:1 n-hexanes/ethyl acetate→ethyl acetate→1% methanol/ethyl acetate) to give the desired product (222.5 mg, 46% yield). ES-MS: 429 (M+1). Tetrahydrofuran can also be used as solvent in this step.

Example 5.2

Synthesis of trans-(4-Aminocyclohexyl){8-[2,4-difluorophenyl)amino]-9-cyclopentylpurin-2-yl}amine

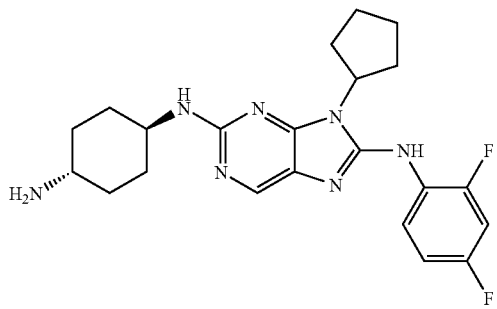

1. trans-(4-Aminocyclohexyl){8-[2,4-difluorophenyl)amino]-9-cyclopentylpurin-2-yl}amine N-[4-({8-[(2,4-difluorophenyl)amino]-9-cyclopentylpurin-2-yl}amino)trans-cyclohexyl](tert-butoxy)carboxamide (0.71 mmol, 375 mg) was dissolved in ethanol (6 mL) and cooled to 0° C. Acetyl chloride (3 mL) was added dropwise and the reaction was allowed to reach room temperature and stirred overnight. The precipitate was filtered off, washed with ethyl ether and dried under high vacuum to yield 372 mg (98% yield) as a trihydrochloride salt. ES-MS: 428 (M+1).

Alternatively, N-[4-({8-[(2,4-difluorophenyl)amino]-9-cyclopentylpurin-2-yl}amino)trans-cyclohexyl](tert-butoxy)carboxamide can be dissolved in 9 mL of methylene chloride followed by the addition of 2.25 mL of TFA. The reaction mixture is stirred for about 2 hours. Solvent is removed in vacuo, the residue is redissolved in methylene chloride and neutralized with ammonium hydroxide. The solution is then washed with a saturated solution of sodium carbonate. The organic layer is separated and the aqueous layer is further extracted with methylene chloride. Combined organic layers are dried over sodium sulfate, filtered and the solvent removed in vacuo to yield the amine.

Example 5.3

Synthesis of 8-(2-Fluorophenylamino)-2-(4-methoxyphenylamino)-9-(trans-4-(methylamino)cyclohexyl)-9H-purine

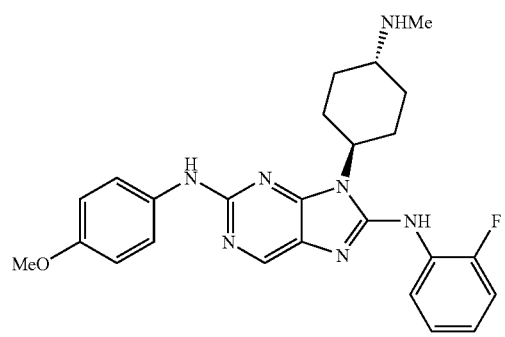

Boc-protected amine (481 mg, 0.88 mmol) was dissolved in THF (6 mL) and lithium aluminum hydride (1.0 M solution in THF, 2.64 mL, 2.64 mmol) added. The reaction mixture was heated at about 65° C. overnight. The reaction mixture was cooled to 0° C. and quenched dropwise with water until no further evolution of hydrogen was observed. The precipitate was filtered off and washed extensively with ethyl acetate. The solvent was removed in vacuo and the residue was purified using semi-preparative HPLC (20% acetonitrile/water (0.1% TFA)→80% acetonitrile/water (0.1% TFA) over 30 min) to yield 191 mg of product.

Example 5.4

Synthesis of 9-(trans-4-(Dimethylamino)cyclohexyl)-8-(2-fluorophenyl)-2-(4-methoxyphenyl)-9H-purine

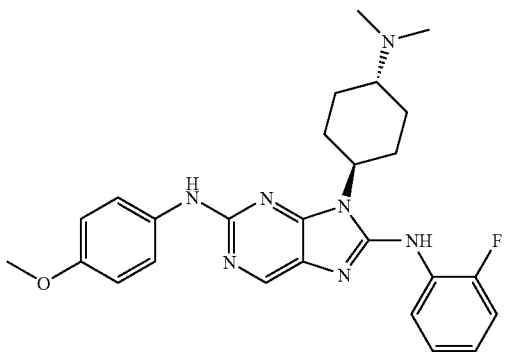

Amine (200 mg, 0.359 mmol) was dissolved in a 1:1 mixture THF/methylene chloride (4 mL) and a solution of formaldehyde (37% in water, 53 µL, 0.718 mmol) in THF (1 mL) was added dropwise, followed by sodium triacetoxyborohydride (761 mg, 3.59 mmol). The reaction mixture was stirred at room temperature for 1 hour. The solvent was removed in vacuo and the residue was dissolved in DMSO/methanol (1:1 mixture) and purified by semipreparative HPLC (20→70% acetonitrile/water (0.1% TFA) over 30 min). Fractions containing product were quenched with ammonium hydroxide. After standing overnight, a precipitate formed and it was filtered and dried under high vacuum, to yield 108 mg of the dimethylamino compound (63% yield).

Example 5.5

Synthesis of (4-{8-[(2-Fluorophenyl)amino]-2-[(4-methoxyphenyl)amino]purin-9-yl}trans-cyclohexyl)methan-1-ol

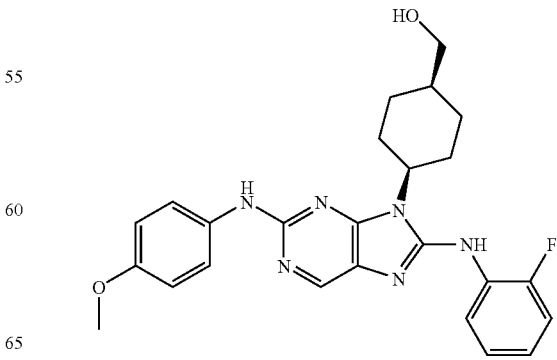

Ethyl 4-{8-[(2-fluorophenyl)amino]-2-[(4-methoxyphenyl)amino]purin-9-yl}-trans-cyclohexanecarboxylate (0.28 g, 0.55 mmol) was dissolved in 9 mL of THF and cooled to 0° C. (under nitrogen atmosphere). 1.38 mL of 1.0M LiAlH$_4$ in THF was added dropwise. The solution turned a dark orange as the LiAlH$_4$ was added. The reaction mixture was stirred for about 5 h and quenched by the addition of 40 mL of water. The reaction was extracted three times with ethyl acetate. Organics were combined and dried with magnesium sulfate, filtered and the solvent was removed in vacuo. The crude reaction mixture was then purified using reverse-phase preparative HPLC (20-80% acetonitrile/water (0.1% TFA) over 30 min) to obtain 0.126 g of the desired product (50% yield) after neutralization of the TFA salt. ES-MS: 463 (M+1).

Example 5.6

Synthesis of trans-4-{8-[(2-Fluorophenyl)amino]-9-[cis-4-(1-hydroxy-isopropyl)cyclohexyl]purin-2-yl}amino)cyclohexan-1-ol

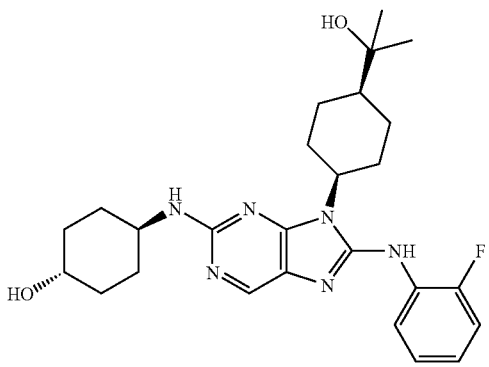

Ethyl cis-4-{8-[(2-fluorophenyl)amino]-2-[trans-(4-hydroxycyclohexyl)amino]purin-9-yl}cyclohexane carboxylate (0.200 g, 0.4 mmol) was dissolved in 4 mL of dry THF. Methyl magnesium bromide (0.6 mL, 3.0M solution in diethyl ether, 4.0 equivalents) was added dropwise at room temperature. The reaction mixture turned bright yellow and was stirred at room temperature for about 1 hour. The completion of the reaction was monitored by LC-MS. An additional 4 equivalents of methyl magnesium grignard solution were added and the reaction mixture was heated overnight at about 30° C.

The reaction mixture was then cooled to room temperature and was quenched slowly with saturated aqueous ammonium chloride solution. The crude was extracted in ethyl acetate and the extracts were dried over Na$_2$SO$_4$. The product was purified using column chromatography on silica gel using 1-4% (ethanol/ammonium hydroxide: 8:1) in dichloromethane. The compound was isolated as a light pink solid (57 mg, 29% yield).

Example 5.7

Synthesis of cis-4-[8-[(2,6-Difluorophenyl)amino]-2-trans-({4-[4-methylpiperazinyl)carbonyl]cyclohexyl)amino}purin-9-ylcyclohexanecarboxylic acid N-(4-methylpiperazinyl)amide

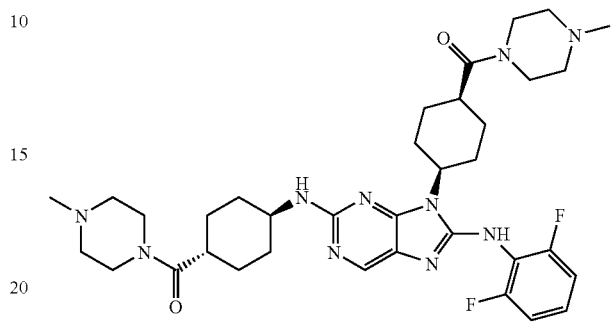

Diester (10.0 mmol, 1 eq.) was dissolved in 100 mL THF and LiOH (200.0 mmol, 20 eq.) (as a 1M aqueous solution) was added. The reaction mixture was heated at about 60° C. overnight. After cooling to room temperature, the pH was adjusted to 4 by adding 6N HCl. Brine was added and phases were separated. The aqueous phase was extracted with THF and the combined organic phases were dried over MgSO$_4$. The solvent was evaporated to give the desired product.

Diacid (10.0 mmol, 1 eq.), HOBT (20.0 mmol, 2 eq.) and EDCI (24.0 mmol, 2.4 eq.) were mixed in 100 mL DMF and stirred for 15 minutes. Amine (24.0 mmol, 2.4 eq.) was added and the reaction mixture was stirred overnight. The solvent was evaporated and the residue was purified using HPLC.

Example 5.8

Synthesis of 4-({9-[cis-4-(aminomethyl)cyclohexyl]-8-{(2,6-difluorophenyl)amino]purin-2-yl}trans-amino)cyclohexan-1-ol

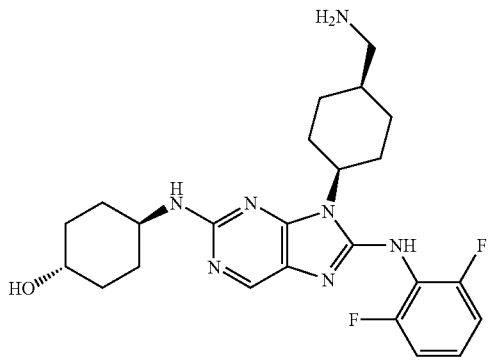

1. cis-4-[(tert-Butoxy)carbonylamino]cyclohexane carboxylic acid cis-4-Aminocyclohexyl carboxylic acid (2.0 g, 13.96 mmol) was dissolved in 40 mL of 1,4-dioxane. Two equivalents of di-tert-butyl-dicarbonate (6.094 g, 27.92 mmol) were added followed by 3 equivalents of sodium bicarbonate (4.06 g, 41.88 mmol) dissolved in 40 mL of water. The reaction mixture was stirred at room temperature for about 12 hours. The completion of the reaction was monitored by LC-MS. Saturated aqueous $KHSO_4$ was added dropwise, until gas evolution stopped. The solvent was then removed under reduced pressure and the crude product was extracted in ethyl acetate. The combined organic extracts were washed with aqueous saturated $KHSO_4$ and dried over $Na_2SO_4$. The solvent was removed under reduced pressure, yielding 2.6 g of product. Based on $^1H$ NMR, the product was pure and used in subsequent steps without further purification. ES-MS (m/z) 244.

2. cis-(tert-Butoxy)-N-[4-(hydroxymethyl)cyclohexyl]carboxamide cis-4-[(tert-Butoxy)carbonylamino]cyclohexane carboxylic acid (2.6 g, 10.68 mmol) was dissolved in THF (20 mL) and cooled to −10° C. (MeOH-ice). N-Methyl morpholine was added followed by isobutyl chloroformate (1.175 mL, 10.68 mmol). After 10 min, $NaBH_4$ was added as a solid in one portion (1.213 g, 32.06 mmol). The reaction mixture was warmed to 0° C. and methanol was added dropwise (13.35 mL). After 30 min, the reaction was quenched with 5% aqueous $KHSO_4$. The reaction was monitored by LC-MS until complete. The crude product was extracted with ethyl acetate and the combined extracts were dried over $Na_2SO_4$. A colorless oil was obtained and solidified slowly at room temperature. The product and purity were assessed by LC-MS and $^1H$ NMR. No further purification was necessary. (quantitative yield) ES-MS (m/z) 230.

3. cis-(tert-Butoxy)-N-{4-[(1,3-dioxobenzo[c]azolidin-2-yl)methyl]cyclohexyl}carboxamide cis-(tert-Butoxy)-N-[4-(hydroxymethyl)cyclohexyl]carboxamide (0.5 g, 2.18 mmol) and resin-bound triphenyl phosphine (1.453 g, 4.36 mmol, 3 mmol/g resin) were suspended in 15 mL of dry THF. Phthalimide was added in 5 mL of THF followed by diisopropyl azodicarboxylate (DIAD) (0.858 mL, 4.36 mmol). The reaction was stirred at room temperature and monitored by LC-MS. After overnight stirring at room temperature, the resin was removed by filtration and washed multiple times with 5 mL portions of THF. The filtrate combined with washings was concentrated under reduced pressure. The product was purified using column chromatography on silica gel using 10% ethyl acetate in hexanes as eluent. The product was isolated as a white solid (0.486 g, 1.35 mmol, 62% yield) ES-MS (m/z) 359.

4. cis-2-[(4-Aminocyclohexyl)methyl]benzo[c]azolidine-1,3-dione cis-(tert-Butoxy)-N-{4-[(1,3-dioxobenzo[c]azolidin-2-yl)methyl]cyclohexyl}carboxamide (0.486 g, 1.35 mmol) was suspended in ethanol (5 mL) and reacted with acetyl chloride (1 mL). The reaction mixture was stirred at room temperature for about 4 hours. The completion of the deprotection was monitored by LC-MS. The solvent was removed under reduced pressure and the product was isolated as its HCl salt as a white solid and used without further purification in the subsequent addition to 2,4-dichloro-5-nitropyrimidine: ES-MS (m/z) 259.

5. 4-({9-[cis-4-(Aminomethyl)cyclohexyl]-8-{(2,6-difluorophenyl)amino]purin-2-yl}trans-amino)cyclohexan-1-ol 2-[(4-{8-[(2,6-difluorophenyl)amino]-2-[trans-(4-hydroxycyclohexyl)-amino]purin-9-yl}cyclohexylmethyl]benzo[c]azolidine-1,3-dione (0.318 g, 0.52 mmol) was dissolved in ethanol (4.5 mL) and reacted with hydrazine (42 µL, 2.4 eq) at reflux temperature for about 5 hours. A white precipitate formed that was removed by filtration. The filtrate combined with washings of the precipitate, was concentrated under reduced pressure. The product was purified using column chromatography on silica gel using 5-10% (ethanol/$NH_4OH$: 8/1) in dichloromethane as the eluent. The product was isolated as a white solid (198 mg, 80% yield).

Example 5.9

Synthesis of 3-((trans-4-(8-(2,6-Difluorophenylamino)-9-cyclopentyl-9H-purin-2-ylamino)cyclohexyloxy)carbonyl)propanoic acid

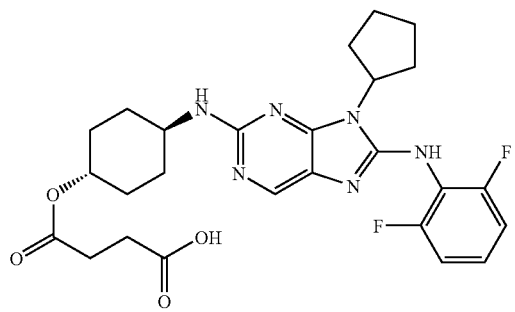

trans-4-(8-(2,6-Difluorophenylamino)-9-cyclopentyl-9H-purin-2-ylamino)cyclohexanol (1 mmol, 1 eq.) and succinic anhydride (10 mmol, 10 eq.) were mixed in 25 mL pyridine and stirred at room temperature for 3 days. The mixture was heated at 50° C. for about 10 hours and the solvent was subsequently evaporated. The residue was recrystallized from acetone/MeOH to give the desired product.

Example 5.10

Synthesis of trans-4-(8-(2,6-Difluorophenylamino)-9-cyclopentyl-9H-purin-2-ylamino)cyclohexyl 2-aminoacetate

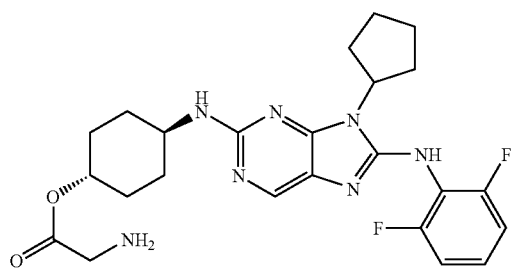

trans-4-(8-(2,6-Difluorophenylamino)-9-cyclopentyl-9H-purin-2-ylamino)cyclohexanol (1 mmol, 1 eq.) DCC (2 mmol, 2 eq.), BOC-glycine (1.12 mmol, 1.12 eq.) and DMAP (1.12 mmol, 1.12 eq.) were mixed in 20 mL DCM and stirred at room temperature for 2 days. Water and EtOAc were added, the phases were separated and the organic phase was dried over MgSO₄. Solvent was evaporated and the residue was purified using column chromatography to give the desired Boc protected product.

The Boc protected product (1 mmol, 1 eq.) was dissolved in 15 mL DCM and 4 ml TFA were added. The reaction mixture was stirred for about one hour and the solvent was evaporated. EtOAc and sat. NaHCO₃ solution were added and the phases separated. The organic phase was dried over MgSO₄ and the solvent was evaporated. The residue was purified using column chromatography/HPLC to give the desired product.

Example 5.11

Synthesis of 3-(8-(2-Fluorophenylamino)-9-cyclopentyl-9H-purin-2-ylamino)benzamide

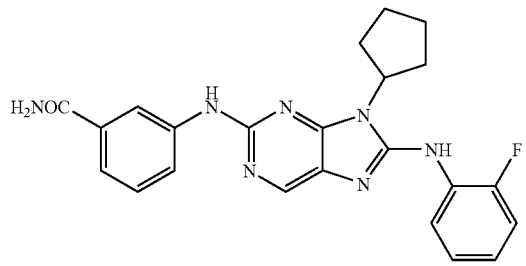

To a cooled solution (0° C.) of the cyano compound (100 mg, 0.24 mmol) in ethanol (1 mL), sodium hydroxide (18 mg, 0.46 mmol) and hydrogen peroxide (30%, 53 μL, 0.48 mmol) were added. The reaction mixture was stirred for about 4 h at room temperature. Only starting material was observed by LCMS. Another 18 mg of sodium hydroxide and 53 μL of hydrogen peroxide were added and the reaction mixture was stirred for about another 8 h. Still only starting material was observed. The reaction was heated to 60° C. for about 4 h. Product formation was observed together with traces of carboxylic acid. The reaction was quenched to pH=7 with 6N HCl. The crude reaction mixture was purified using semi-preparative reverse-phase HPLC (15% acetonitrile/water (0.1% TFA)→80% acetonitrile/water (0.1% TFA) over 30 min) to yield 35 mg of amide as a solid after neutralization of the TFA salt. LRMS (ES) m/e 432 [MH]⁺.

Example 5.12

Synthesis of 2-((3-(2-(Piperidin-1-yl)ethoxy)phenyl)amino)-9-cyclopentyl-8-((2-fluorophenyl)amino)-9H-purine

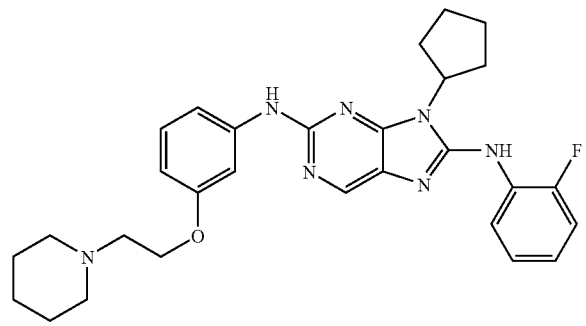

In a round bottom flask, sodium hydroxide (0.585 g, 14.6 mmol) was dissolved in 10 mL of water. THF (20 mL), 3-{[4-(cyclopentylamino)-5-nitropyridin-2-yl]amino}phenol (1.15 g, 3.66 mmol), and piperidyl ethyl chloride hydrochloride (0.81 g, 4.39 mmol) were added. The reaction mixture was heated at about 55° C. overnight. The reaction was monitored by LC-MS. The reaction mixture was poured in aqueous sodium bicarbonate solution and the crude was extracted in ethyl acetate. The combined organic were dried over sodium sulfate and evaporated to dryness. The desired product was isolated as a solid (1.538 g, 98% yield) ES-MS (m/z) 427.3.

Example 5.13

Synthesis of 8-((2-Fluorophenyl)amino)-2-((4-methoxyphenyl)amino)-9H-purine

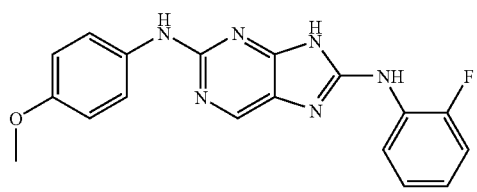

The cyanoethyl substituted compound (0.17 mmol) was dissolved in a mixture of THF:H₂O (8:2, 10 mL) and lithium hydroxide (1.05 mmol) was added. The reaction mixture was stirred at about 50° C. for about 72 h. The solvent was removed in vacuo and the residue was purified using column chromatography (SiO₂) or reverse-phase HPLC.

Example 5.14

Synthesis of 4-({9-(2H-3,4,5,6-tetrahydropyran-4-yl)-8-[(2,4-difluorophenyl)amino]purin-2-yl}amino)thiane-1,1-dione

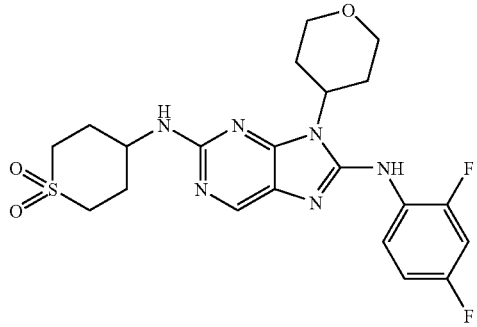

2H-3,4,5,6-Tetrahydropyran-4-yl[5-nitro-2-(thian-4-ylamino)pyrimidin-4-yl]amine 2H-3,4,5,6-Tetrahydropyran-4-yl(2-chloro-5-nitropyrimidin-4-yl)amine (3.14 mmol, 810.6 mg, obtained from 2,4-dichloro-5-nitropyrimidine and 4-aminotetrahydropyran following the method described in Example 5.1) and 4-aminotetrahydrothiopyran (3.77 mmol, 441 mg, obtained following the procedure described in PCT Int. Appl. WO 2002083642) were dissolved in DMF (20 mL). N,N-Diisopropylethylamine (3.77 mmol, 0.67 mL) was added and the reaction was stirred at room temperature overnight. DMF was removed in vacuo and the crude was sonicated with ethyl acetate. The precipitate was filtered to yield the title compound (992 mg, 93% yield). ES-MS: 340 (M+1).

2H-3,4,5,6-tetrahydropyran-4-yl[5-amino-2-(thian-4-ylamino)pyrimidin-4-yl]amine The title compound (760 mg, 93% yield) was obtained from 2H-3,4,5,6-tetrahydropyran-4-yl[5-nitro-2-(thian-4-ylamino)pyrimidin-4-yl]amine (2.63 mmol, 892 mg) by catalytic hydrogenation following the procedure described in Example 5.1, step 3. ES-MS: 310 (M+1).

[9-(2H-3,4,5,6-Tetrahydropyran-4-yl)-2-(thian-4-ylamino)purin-8-yl](2,4-difluorophenyl)amine The title compound (577.1 mg, 71% yield) was obtained from 2H-3,4,5,6-tetrahydropyran-4-yl[5-amino-2-(thian-4-ylamino)pyrimidin-4-yl]amine (1.81 mmol, 560 mg) and 2,4-difluorophenylisothiocyanate following the procedure described in Example 5.1 step 4. ES-MS: 447 (M+1).

4-({9-(2H-3,4,5,6-tetrahydropyran-4-yl)-8-[(2,4-difluorophenyl)amino]purin-2-yl}amino)thiane-1,1-dione

[9-(2H-3,4,5,6-tetrahydropyran-4-yl)-2-(thian-4-ylamino)purin-8-yl](2,4-difluorophenyl)amine (1.2 mmol, 537 mg) was dissolved in methylene chloride (15 mL) and 3-chloroperoxybenzoic acid (2.64 mmol, 591 mg) were added. The reaction was stirred at room temperature for 18 h. The reaction mixture was washed with saturated solution of sodium bicarbonate (10 mL) and extracted with chloroform (3×15 mL). The organic layer was dried over magnesium sulfate and filtered. Solvent was removed in vacuo and the residue was purified by column chromatography (SiO$_2$, 10% Methanol/ethyl acetate) and reverse-phase HPLC (20% acetonitrile/water (0.1% TFA) to 100% acetonitrile/water (0.1% TFA) over 30 min) to yield the title compound (146 mg, 25% yield). ES-MS: 479 (M+1).

Example 5.15

Synthesis of 4-{8-[(2,4-difluorophenyl)amino]-2-[(4-trans-hydroxycyclohexyl)amino]purin-9-yl}thiane-1,1-dione

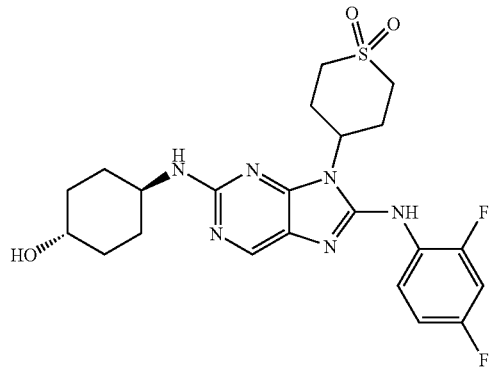

4-({8-[(2,4-Difluorophenyl)amino]-9-thian-4-ylpurin-2-yl}amino)-trans-cyclohexan-1-ol (0.49 mmol, 225 mg), obtained from 4-aminotetrahydrothiopyran (PCT Int. Appl. WO 2002083642), trans-4-aminocyclohexanol and 2,4-difluorophenyl isothiocyanate following the general procedure described in Example 5.1, were dissolved in methylene chloride (5 mL), and 3-chloroperoxybenzoic acid (1.08 mmol, 241 mg) was added. The reaction was stirred at room temperature for 18 h. The reaction mixture was washed with saturated solution of sodium bicarbonate (5 mL) and extracted with chloroform (3×10 mL). The organic layer was dried over magnesium sulfate and filtered. Solvent was removed in vacuo and the residue was purified by column chromatography (SiO$_2$, ethyl acetate to 2% methanol/ethyl acetate) and reverse-phase HPLC (20% acetonitrile/water (0.1% TFA) to 100% acetonitrile/water (0.1% TFA) over 30 min) to yield the title compound (88.4 mg, 36% yield). ES-MS: 493 (M+1).

Example 5.16

Building Block Involved in the Synthesis of

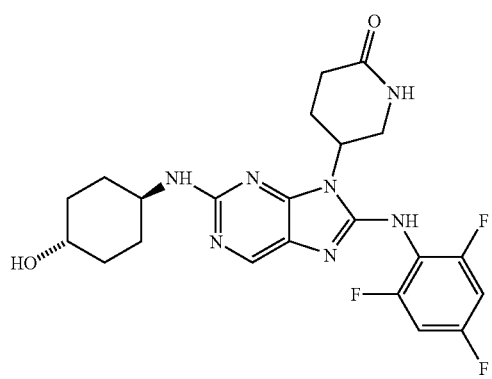

(5S)-5-aminopiperidin-2-one, hydrochloride

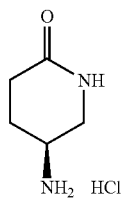

(2S)-2-[(tert-Butoxy)carbonylamino]-4-(methoxycarbonyl)butanoic acid

L-Glutamic acid 5-methyl ester (91.3 mmol, 14.7 g) was added to a solution of triethylamine (274 mmol, 38 mL) in DMF (350 mL). Di-t-butyl dicarbonate (183 mmol, 40 g) was added and the reaction was stirred at 50° C. for 1 hour and then at room temperature overnight. Solvent was removed in vacuo and the crude material was purified by column chromatography (SiO$_2$, 1:1 n-hexanes/ethyl acetate to ethyl acetate) to yield the title compound (20.36 g, 85% yield). ES-MS: 262 (M+1).

Methyl (4S)-4-[(tert-butoxy)carbonylamino]-5-hydroxypentanoate

In a round-bottom flask, (2S)-2-[(tert-butoxy)carbonylamino]-4-(methoxycarbonyl)butanoic acid (78 mmol, 20.36 g) was dissolved in THF (300 mL). The solution was cooled to −10° C. and N-methylmorpholine (78 mmol, 8.58 mL) and ethyl chloroformate (78 mmol, 7.48 mL) were added, followed by sodium borohydride (234 mmol, 8.85 g). The reaction was stirred for 30 min at this temperature and then quenched by slow addition of saturated solution of ammonium chloride until no further evolution of hydrogen was observed. The reaction mixture was then extracted with ethyl acetate and dried over magnesium sulfate. After filtration, solvent was evaporated and the crude material was purified by column chromatography (SiO$_2$, 1:1 n-hexanes/ethyl acetate) to yield the title compound (11.68 g, 61% yield). ES-MS: 248 (M+1).

Methyl (4S)-4-[(tert-butoxy)carbonylamino]-5-[(4-methylphenyl) sulfonyloxy]pentanoate Methyl (4S)-4-[(tert-butoxy)carbonylamino]-5-hydroxypentanoate (9.11 mmol, 2.25 g) was dissolved in 30 mL of methylene chloride. p-Toluenesulfonyl chloride (9.1 mmol, 1.7 g) and triethylamine (27.33 mmol, 3.8 mL) were added and the reaction was stirred at room temperature overnight. Solvent was removed in vacuo and crude was purified by column chromatography (SiO$_2$, 4:1 n-hexanes/ethyl acetate to 7:3 n-hexanes/ethyl acetate) to yield the title compound (1.98 g, 54% yield). ES-MS: 402 (M+1).

Methyl (4S)-5-azido-4-[(tert-butoxy)carbonylamino] pentanoate

Methyl (4S)-4-[(tert-butoxy)carbonylamino]-5-[(4-methylphenyl)sulfonyloxy]pentanoate (4.93 mmol, 1.98 g) was dissolved in DMF (15 mL) and sodium azide (14.8 mmol, 0.961 g) were added. The reaction was heated at 50° C. for 3 hours. The reaction mixture was filtered and the solvent was removed in vacuo. The crude was purified by flash chromatography (SiO$_2$, ethyl acetate) to yield the title compound (1.07 g, 80% yield). ES-MS: 273 (M+1).

N-((3S)-6-oxo(3-piperidyl))(tert-butoxy)carboxamide

Methyl (4S)-5-azido-4-[(tert-butoxy)carbonylamino]pentanoate (3.9 mmol, 1.07 g) was dissolved in methanol (10 mL), and 10% palladium on carbon (0.1 g) was added. The reaction was stirred overnight under 1 atm of hydrogen. The reaction was filtered and the solvent was removed in vacuo to yield the title compound (0.83 g, 99% yield). ES-MS: 215 (M+1).

(5S)-5-aminopiperidin-2-one, hydrochloride

N-((3S)-6-Oxo(3-piperidyl))(tert-butoxy)carboxamide (3.9 mmol, 0.83 g) were dissolved in ethanol (10 mL) and cooled to 0° C. Acetyl chloride (2 mL) was added and the reaction was allowed to reach room temperature. The reaction was stirred for 1 hour after which the solvent was removed in vacuo to yield the title compound (725 mg, 99% yield) as the dihydrochloride salt. ES-MS: 115 (M+1).

Example 5.17

Building Block Used for the Synthesis of

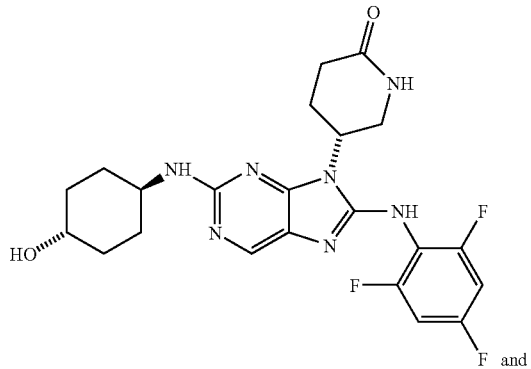

and

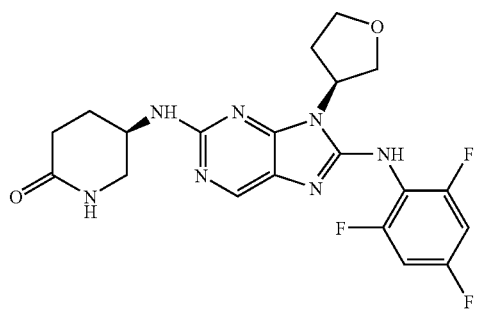

357

(5R)-5-aminopiperidin-2-one, hydrochloride

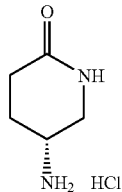

The title compound was prepared as described in Example 5.15, starting from D-glutamic acid 5-methyl ester.

Example 5.18

Building Block Used for the Synthesis of

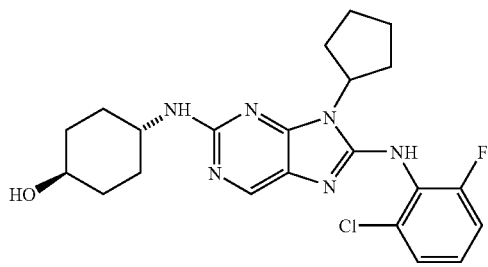

Synthesis of 6-chloro-2-fluorobenzeneisothiocyanate

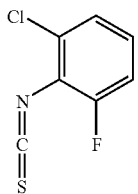

A solution of 2-chloro-6-fluoroaniline (767 mg, 5.29 mmol) in tetrahydrofuran (5 ml) was added drop wise with stirring to a solution of di-2-pyridyl thionocarbonate (2.46 g, 10.58 mmol) in tetrahydrofuran (7 ml) at room temperature. The reaction mixture was stirred for 60 hours at room temperature and then the solvent was evaporated. The resulting residue was purified by chromatography on a normal phase silica gel column with pentane. Fractions containing clean product were combined and the solvent evaporated to give the title compound (167 mg, 17%): $^1$H NMR (400 MHz, CDCl$_3$) δ 7.19-7.23 (m, 1H), 7.12-7.19 (m, 1H), 7.04-7.10 (m, 1H).

358

Example 5.19

Building Block Used for the Synthesis of

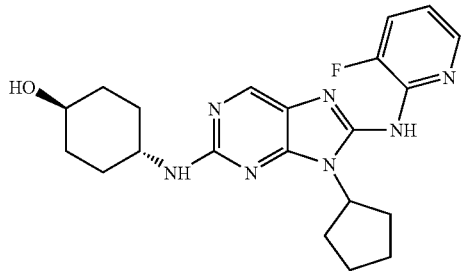

Synthesis of 3-fluoropyridin-2-isothiocyanate

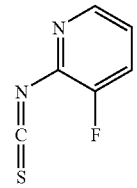

A solution of 3-fluoro-pyridin-2-ylamine (928 mg, 8.28 mmol) in dichloromethane (3 mL) was added dropwise with stirring to a solution of thiophosgene (1.9 mL, 24.83 mmol) in dichloromethane (6 mL) at 0° C. The reaction mixture was stirred for 1 hour at room temperature. The reaction was diluted with dichloromethane and saturated aqueous sodium bicarbonate. The organic layer was separated and the aqueous solution extracted 3 times with dichloromethane. The organic layers were combined and the solvent evaporated. The resulting residue was purified by chromatography on a normal phase silica gel column with 10% ethyl acetate in hexanes. Fractions containing clean product were combined and the solvent evaporated to give the title compound (479 mg, 37%): $^1$H NMR (400 MHz, CDCl$_3$) δ 8.22-8.23 (m, 1H), 7.48-7.52 (m, 1H), 7.21-7.26 (m, 1H).

Example 5.20

Building Block Used for the Synthesis of

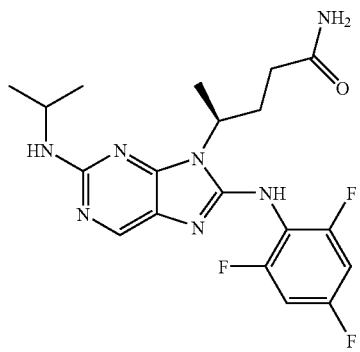

Synthesis of methyl (2E)(4S)-4-aminopent-2-enoate hydrochloride

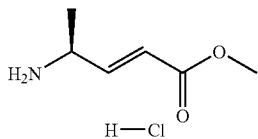

(2S)-2-[(tert-Butoxy)carbonylamino]-N-methoxy-N-methylpropanamide

To a solution of Boc-alanine (20 grams, 105.7 mmol) in dichloromethane (170 ml) was added HOBT (14.28 g, 105.7 mmol) and N,O-dimethylhydroxylamine hydrochloride (10.31 g, 105.7 mmol). The mixture was chilled with an ice water bath then triethylamine (30 ml, 211.4 mmol) and 1,3-dicyclohexylcarbodiimide (21.81 g, 105.7 mmol) were added. The reaction was stirred in the ice water bath for 1 hour and then allowed to warm to room temperature overnight. The crude reaction was then chilled in an ice water bath and the precipitate filtered. The resulting organic solution was then washed twice with 1N aqueous sodium hydroxide (50 mL), twice with 10% aqueous citric acid (50 mL), and once with brine. The solution was then dried over anhydrous sodium sulfate, filtered, and the solvent evaporated. The resulting residue was purified by chromatography on a normal phase silica gel column with 30-100% ethyl acetate in hexanes. Fractions containing clean product were combined and the solvent evaporated to give the title compound (20 g, 81%): ES-MS (m/z) 233.2 [M+1]$^+$.

Methyl (2E)(4S)-4-[(tert-butoxy)carbonylamino]pent-2-enoate

A solution of (2S)-2-[(tert-butoxy)carbonylamino]-N-methoxy-N-methylpropanamide (13.05 g, 56.18 mmol) in ethyl ether (560 mL) was chilled with an ice water bath and then 95% lithium aluminum hydride (2.80 g, 70.23 mmol) was added. The reaction was stirred at room temperature for 20 minutes and then a solution of aqueous potassium hydrogen sulfate (300 mL, 0.33M) was added. The resulting mixture was extracted three times with ethyl ether. The combined organic layers were washed three times with 1N hydrogen chloride, three times with saturated aqueous sodium hydrogen carbonate, and once with brine. The solution was then dried over anhydrous sodium sulfate, filtered, and the solvent evaporated. The resulting solid was dissolved in anhydrous tetrahydrofuran (430 mL) then added to a cold solution of trimethyl phosphonoacetate (27.3 mL, 168.5 mmol) and sodium hydride (112 mmol) in anhydrous tetrahydrofuran (130 mL) that had been previously stirred at room temperature for 30 minutes. The reaction was stirred for 5 minutes in a ice water bath, at room temperature for 20 minutes, and then water (500 mL) was added. The reaction mixture was diluted with brine and ethyl acetate, stirred, and the layers separated. The organic layer was dried over anhydrous sodium sulfate, filtered, and the solvent evaporated. The resulting residue was purified by chromatography on a normal phase silica gel column with 0-30% ethyl acetate in hexanes. Fractions containing clean product were combined and the solvent evaporated to give the title compound (8.85 g, 69%): ES-MS (m/z) 230.4 [M+1]$^+$.

Methyl (2E)(4S)-4-aminopent-2-enoate hydrochloride

A solution of methyl (2E)(4S)-4-[(tert-butoxy)carbonylamino]pent-2-enoate (3.083 g, 13.45 mmol) in 4N hydrogen chloride in dioxane was stirred at room temperature for 1 hour. The volatiles were evaporated to give the title compound (2.2 g, 98%): ES-MS (m/z) 130.3 [M+1]$^+$.

Methyl (4S)-4-({5-amino-2-[(methylethyl)amino]pyrimidin-4-yl}amino)pentanoate A solution of methyl (2E)(4S)-4-aminopent-2-enoate hydrochloride (1.7 g, 10.31 mmol) in tetrahydrofuran (7 mL) was added drop wise to a solution of 2,4-dichloro-5-nitropyrimidine (2.0 g, 10.31 mmol) and diisopropylethylamine (3.6 mL, 20.6 mmol) in tetrahydrofuran (17 mL) chilled at −78° C. The reaction was stirred at −78° C. for 1 hour and then at room temperature overnight. The was solvent was evaporated and the resulting residue was purified by chromatography on a normal phase silica gel column with 0-20% ethyl acetate in hexanes. Fractions containing clean product were combined and the solvent evaporated to give 2.35 g white solid. To the solid were added anhydrous N,N-dimethylformamide (40 mL), diisopropylethylamine (1.44 mL, 8.25 mmol), and isopropylamine (0.70 mL, 8.25 mmol). The mixture was stirred at room temperature for 70 hours, diluted with water, and extracted three times with dichloromethane. The organic layers were combined, dried over anhydrous sodium sulfate, filtered, and the solvent evaporated. To the resulting oil was added anhydrous ethanol (50 mL) and 10% palladium on carbon (200 mg). The solution was treated with hydrogen gas from a balloon and stirred at room temperature overnight. The reaction mixture was filtered and the solvent evaporated to provide the title compound (2.24 g, 77%): ES-MS (m/z) 282 [M+1]$^+$.

(4S)-4-{2-[(methylethyl)amino]-8-[(2,4,6-trifluorophenyl)aminopurin-9-yl}pentanamide A solution of methyl (4S)-4-{2-[(methylethyl)amino]-8-[(2,4,6-trifluorophenyl)amino]purin-9-yl}pentanoate (500 mg, 1.15 mmol) in anhydrous methanol (25 mL) at −78° C. was saturated with ammonia gas. The solution was sealed in a reaction tube and allowed to warm to room temperature followed by heating at 40° C. for 2 days. The solvent was evaporated and the resulting residue was purified by chromatography on a normal phase silica gel column with 70-100% ethyl acetate in hexanes. Fractions containing clean product were combined and the solvent evaporated to give the title compound (223 mg, 46%): ES-MS (m/z) 422.3 [M+1]$^+$.

Example 5.21

Building Block Used for the Synthesis of

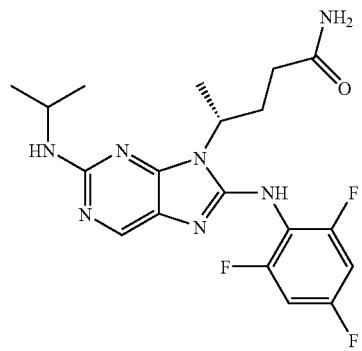

Synthesis of methyl (2E)(4R)-4-aminopent-2-enoate hydrochloride

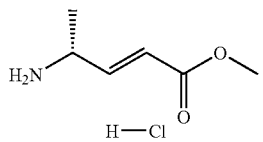

(2R)-2-[(tert-Butoxy)carbonylamino]-N-methoxy-N-methylpropanamide

The title compound was prepared as (2S)-2-[(tert-butoxy)carbonylamino]-N-methoxy-N-methylpropanamide with boc-D-alanine (20 grams, 105.7 mmol) to give the title compound (21.7 g, 88%): ES-MS (m/z) 233.2 [M+1]$^+$.

Methyl (2E)(4R)-4-[(tert-butoxy)carbonylamino]pent-2-enoate

The title compound was prepared as Methyl (2E)(4S)-4-[(tert-butoxy)carbonylamino]pent-2-enoate with (2R)-2-[(tert-butoxy)carbonylamino]-N-methoxy-N-methylpropanamide (13.05 grams, 56.18 mmol) to give the title compound (10.2 g, 79%): ES-MS (m/z) 230 [M+1]$^+$.

Methyl (2E)(4i)-4-aminopent-2-enoate hydrochloride

A solution of methyl (2E)(4R)-4-[(tert-butoxy)carbonylamino]pent-2-enoate (3.61 g, 15.75 mmol) in 4N hydrogen chloride in dioxane was stirred at room temperature for 1 hour. The volatiles were evaporated to give the title compound (2.6 g, 98%): ES-MS (m/z) 130.3 [M+1]$^+$.

Methyl (4R)-4-({5-amino-2-[(methylethyl)amino]pyrimidin-4-yl}amino)pentanoate The title compound was prepared as methyl (4S)-4-({5-amino-2-[(methylethyl)amino]pyrimidin-4-yl}amino)pentanoate with methyl (2E)(4R)-4-aminopent-2-enoate hydrochloride (1.7 g, 10.31 mmol) to give the title compound (2.17 g, 75%): ES-MS (m/z) 282 [M+1]$^+$.

(4R)-4-{2-[(Methylethyl)amino]-8-[(2,4,6-trifluorophenyl)amino]purin-9-yl}pentanamide The title compound was prepared as (4S)-4-{2-[(methylethyl)amino]-8-[(2,4,6-trifluorophenyl)amino]purin-9-yl}pentanamide with methyl (4R)-4-{2-[(methylethyl)amino]-8-[(2,4,6-trifluorophenyl)amino]purin-9-yl}pentanoate (500 mg, 1.15 mmol) to give the title compound (273 mg, 57%): ES-MS (m/z) 422.3 [M+1]$^+$.

Example 5.22

Building Block Used for the Synthesis of

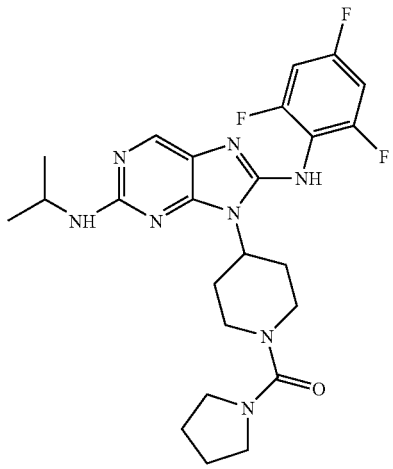

Synthesis of 4-Aminopiperidyl pyrrolidinyl ketone

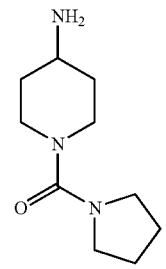

(tert-Butoxy)-N-[1-(pyrrolidinylcarbonyl)(4-piperidyl)]carboxamide

1-Pyrrolidine carbonylchloride (1.10 g, 9.99 mmol) was dissolved in 400 ml if dichloromethane under N$_2$. (Tert-butoxy)-N-(4-piperidyl)carboxamide (2.0 g, 9.99 mmol) and triethyl amine (1.40 mL, 9.99 mmol) were added and the reaction mixture was stirred for three days. The reaction was quenched with sat. NaHCO$_3$ solution and extracted with dichloromethane. The combined organic phases were dried over MgSO$_4$ and the solvent evaporated to give the product as a white solid. (2.63 g, 8.84 mmol, 89%).

4-Aminopiperidyl pyrrolidinyl ketone (tert-Butoxy)-N-[1-(pyrrolidinylcarbonyl)(4-piperidyl)]carboxamide (2.0 g, 6.73 mmol) was dissolved in 40 mL dichloromethane and trifluoroacetic acid (15 mL, 201.94 mmol) were added. The reaction mixture was stirred for 4 hours. The solvent was evaporated to give the product as a light brown semi-solid, which was used directly for the next step. (2.09 g, 6.73 mmol, 100%).

Example 5.23

Synthesis of 4-[(R)-8-(2,4-difluoro-phenylamino)-9-(4-hydroxy-cyclohexyl)-7H-purin-2-ylamino]-cyclohexanone

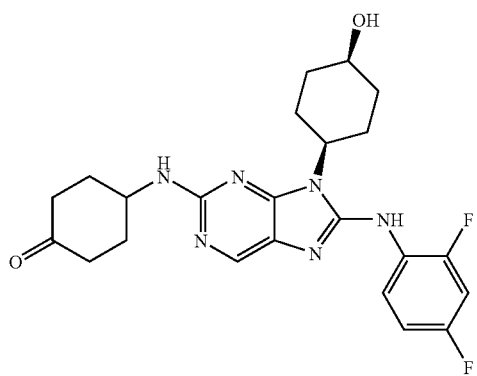

4-[(R)-8-(2,4-Difluoro-phenylamino)-2-(1,4-dioxa-spiro[4.5]dec-8-ylamino)-7H-purin-9-yl]-cyclohexanol (0.62 g, 1.7 mmol) was dissolved in 25 mL of methylene chloride under an N2 atmosphere. Trifluoroacetic acid (5 mL) was then added dropwise via addition funnel. After stirring for 24 h the resulting reaction mixture was concentrated under reduced pressure. Saturated sodium bicarbonate was added to the resulting residue until pH 12. The basic aqueous layer was then extracted using chloroform (2×75 mL). The combined organic layers were dried with MgSO4. The crude product was then purified on the preparatory HPLC using a 5-70% CH3CN/H2O over 39 minutes method. Fractions of greater then 98% purity via analytical HPLC were combined and concentrated. Excess trifluoroacetic acid was removed by washing the product with 1.75 M potassium carbonate (3×100 mL). The organic layers were then concentrated to dryness under vacuum to give the ketone (0.015 g 0.033 mmol, 12%) as a fine white powder: LC-MS (m/z) 457.1 [M+1]$^+$.

Example 5.24

Building Block Used for the Synthesis of

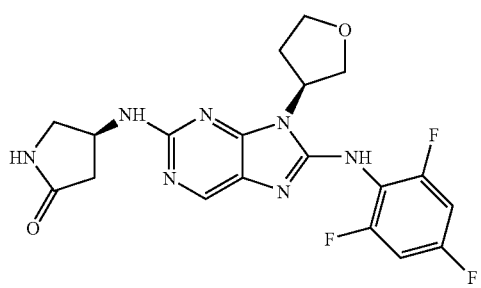

Synthesis of (S)-(−)-4-amino-2-pyrrolidinone

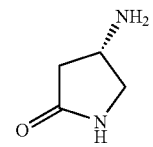

(S)-(−)-4-azido-2-pyrrolidinone

To an ice cooled solution of (R)-(+)-4-hydroxy-2-pyrrolidinone (25.0 g, 247 mmol) in dichloromethane (300 mL) was added triethylamine (17.0 g, 168.7 mmol) and methane sulfonyl chloride (21 mL, 272 mmol) dropwise. The solution was stirred at ambient temperature for one hour. The reaction was monitored via TLC (100% ethyl acetate using permanganate stain). The solution was then condensed under reduced pressure to give a solid. The solid was diluted with DMF (300 mL) followed by the addition of sodium azide (48.24 g, 742 mmol). The solution was heated to 60° C. for 3 hours. The reaction was monitored via TLC (100% ethyl acetate using permanganate stain). The solution was then condensed under reduced pressure and the resultant oil purified via silica gel chromatography (50-80% acetate/hexanes followed by 12% methanol/dichloromethane) to afford the title compound (10.2 g, 32%). $^1$H-NMR (CD$_3$OD) δ 4.43 (m, 1H), 3.71 (dd, 1H), 3.34 (m, 1H), 2.75 (dd, 1H), 2.29 (dd, 1H).

(S)-(−)-4-amino-2-pyrrolidinone

To a solution of (S)-(−)-4-azido-2-pyrrolidinone (10.2 g, 80.8 mmol) in THF (450 mL) was added triphenylphosphine resin bound (40.5 g, 3 mmol comp/1.0 g resin). The solution was heated to 60° C. for two hours. The evolution of nitrogen gas from the solution is an indicator of the reaction proceeding. The reaction is monitored via TLC and permanganate stain for completion. The solution was filtered through a glass frit and the resin bound product is then added to another reaction vessel and diluted with water (500 mL). The solution was heated to 70° C. for sixteen hours. The solution filtered through a glass frit and the aqueous filtrate was condensed under reduced pressure and chased with toluene (3×) to afford the title compound upon vacuum (5.62 g, 62%). $^1$H-NMR (CD$_3$OD) δ 3.68 (m, 1H), 3.56 (m, 1H), 3.04 (m, 1H), 2.54 (m, 1H), 2.05 (m, 1H).

Example 5.25

Synthesis of 5-[9-Cyclopentyl-8-(2,4,6-trifluorophenylamino)-9H-purin-2-ylamino]pyridine-2-ol

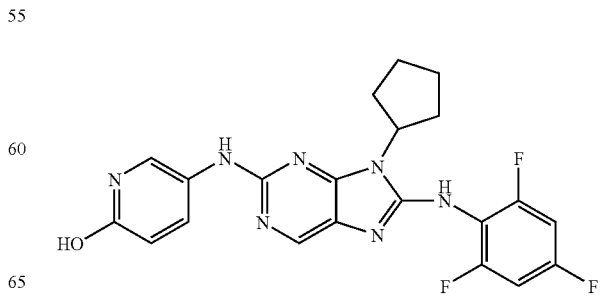

9-Cyclopentyl-N2-(6-methoxypyridin-3-yl)-N8-(2,4,6-trifluorophenyl)-9H-purine-2,8-diamine (0.350 g, 0.769 mmol) was dissolved in 30% HBr/acetic acid in a sealed tube and heated to 80° C. for 16 hours. Product confirmed by LC-MS. The solution was partitioned between 1.75 M potassium carbonate and ethyl acetate (3×). The organics were combined, dried over magnesium sulfate, filtered and solvent removed under reduced pressure. The resultant solid was purified via preparative HPLC (5-55% acetonitrile/water, 20 mL/min.) to afford the title compound (0.212 g, 34%). ES-MS (m/z) 442 [M+1]+. Melting point 257-260° C.

Example 5.26

Building block used for the synthesis of (S)-3-[8-(2,4-trifluoro-phenylamino)-2-isopropylamino-purin-9-yl]-butyramide

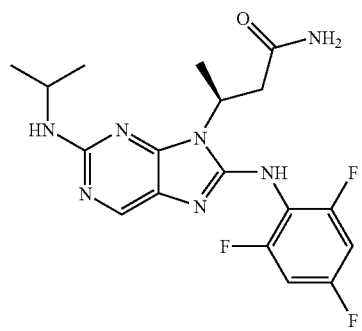

(S)-(−)-3-Aminobutyramide hydrochloride

To a solution of (3S)-3-[tert-butoxycarbonyl)amino]butanoic acid (2 g, 9.8 mmol) in acetonitrile (10 mL) was added HBTU (4.8 g, 12.7 mmol), ammonium chloride (2.6 g, 49 mmole) at room temperature. The reaction mixture was cooled to 0° C. and diisopropylethyl amine (10.0 g, 78 mmole). The ice-water bath was removed and the brown mixture was stirred under nitrogen for 12 hours. The solvent was removed in vacuo and the residue was dissolved in dichloromethane (100 mL). The organic phase was washed with sodium carbonate aqueous solution (saturated). The organic phase was dried with brine followed by sodium sulfate, which was subsequently filtered. The organic phase was concentrated and purified by normal phase silica gel chromatography (50% ethyl acetate/hexane followed by 10% methanol/dichloromethane) to afford partially purified fractions, which were combined and used in the next reaction. The crude amide was dissolved in 10 mL dry dioxane and cooled to 0° C. in an ice/water bath. 4N HCl in dioxane solution (12.2 mL, Aldrich) was added dropwise and the mixture was stirred for 3 hours at room temperature. The solvent was removed in-vacuo to afford oily solid which was not purified further but was suspended in THF (5 mL). Diisopropylethyl amine (2.53 g, 19.6 mmole) was added to create a slurry.

(S)-3-(2-Chloro-5-nitro-pyrimidin-4-ylamino)-butyramide 2,4-dichloro-5-nitropyrimidine (1.9 g, 9.8 mmole) was added to a oven-dried 100 ml round-bottomed flask and THF (27 mL) was added to afford a solution. The mixture was cooled to −78° C. under nitrogen atmosphere and the slurry (Step A) was added dropwise. The reaction mixture was stirred at −78° C. for 30 minutes and then warmed to room temperature over 3 h. Water (10 mL) was added to the mixture and the organic solvent was removed in vacuo. The aqueous phase was extracted with ethyl acetate (3×50 mL) and the resulting organic phase was dried with brine. The organic phase was concentrated to a residue. Normal phase silica gel chromatography (5-50% ethyl acetate/hexane) of the residue afforded the title compound (761 mg, 30% overall): ES-MS (m/z) 260.0 [M+1]+. The intermediate was employed according to the standard procedure to provide (S)-3-[8-(2,4,6-trifluoro-phenylamino)-2-isopropylamino-purin-9-yl]-butyramide.

Example 5.27

Building block used for the synthesis of (R)-3-[8-(2,4,6-trifluoro-phenylamino)-2-isopropylamino-purin-9-yl]-butyramide

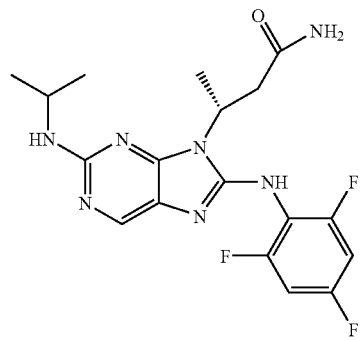

(R)-3-(2-Chloro-5-nitro-pyrimidin-4-ylamino)-butyramide was similarly prepared (586 mg, 23% overall yield): ES-MS (m/z) 260.0 [M+1]+. The intermediate was employed according to the standard procedure to provide (R)-3-[8-(2,4,6-trifluoro-phenylamino)-2-isopropylamino-purin-9-yl]-butyramide.

Example 5.28

Building block used for the synthesis of 4-[9-(R)-1,1-dioxo-tetrahydro-1λ6-thiophen-3-yl)-8-(2,4,6-trifluoro-phenylamino)-9H-purin-2-ylamino]-cyclohexanol

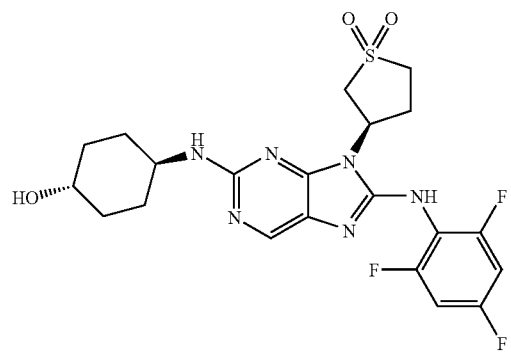

Preparation of (R)-tetrahydro-3-thiopheneamine hydrochloride

Synthesis of title compound was performed according to Dehmlow, E. V et al. *Synthesis* 1992, 10, 947-9. Amine hydrochloride was employed in usual manner to afford 4-[(R)-9-tetrahydro-thiophen-3-yl-8-(2,4,6-trifluoro-phenylamino)-9H-purin-2-ylamino]cyclohexanol.

Synthesis of 4-[9-(R)-1,1-dioxo-tetrahydro-1λ⁶-thiophen-3-yl)-8-(2,4,6-trifluoro-phenylamino)-9H-purin-2-ylamino]-cyclohexanol 4-[(R)-9-Tetrahydro-thiophen-3-yl-8-(2,4,6-trifluoro-phenylamino)-9H-purin-2-ylamino]cyclohexanol (100 mg, 0.21 mmole) was dissolved in MeOH (1 mL) and the mixture was cooled to 0° C. with ice/water bath. Oxone (338 mg, 0.52 mmole) was dissolved in water (1 mL) and the solution was added dropwise to the former mixture at 0° C. with vigorous stirring. The bath was then removed and the cloudy mixture was stirred at room temperature for 10 minutes. The mixture was added to dichloromethane (100 mL) and the organic phase was washed with sodium carbonate (aqueous), brine and dried over sodium sulfate. After filtration, the solvent was removed and the residue was subjected to silica gel chromatography (5-10% methylene chloride/methanol) to afford sulfone (59 mg, 57%): ES-MS (m/z) 497.0 [M+1]⁺.

Example 5.29

Building block used for the synthesis of 4-[9-(S)-1,1-dioxo-tetrahydro-1λ⁶-thiophen-3-yl)-8-(2,4,6-trifluoro-phenylamino)-9H-purin-2-ylamino]-cyclohexanol

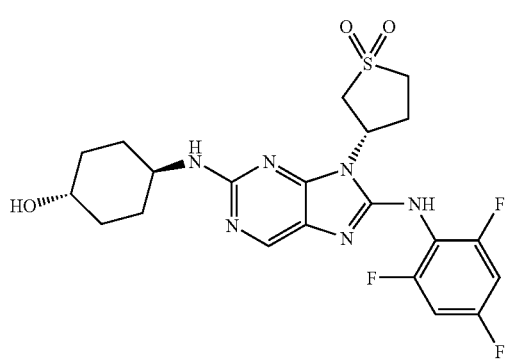

Preparation (S)-tetrahydro-3-thiopheneamine hydrochloride

Synthesis of title compound was performed according to Dehmlow, E. V.; Westerheide, R.; *Synthesis* 1992, 10, 947-9. Amine hydrochloride was employed in usual manner to afford 4-[(S-9-Tetrahydro-thiophen-3-yl-8-(2,4,6-trifluoro-phenylamino)-9H-purin-2-ylamino]cyclohexanol.

Synthesis of 4-[9-(S)-1,1-dioxo-tetrahydro-1λ⁶-thiophen-3-yl)-8-(2,4,6-trifluoro-phenylamino)-9H-purin-2-ylamino]-cyclohexanol Synthesis of sulfone was similarly performed to afford 4-[9-(S)-1,1-dioxo-tetrahydro-1λ⁶-thiophen-3-yl)-8-(2,4,6-trifluoro-phenylamino)-9H-purin-2-ylamino]-cyclohexanol (51 mg, 49%): ES-MS (m/z/) 497.0 [M+1]⁺.

Example 5.30

Building Block Used for the Synthesis of

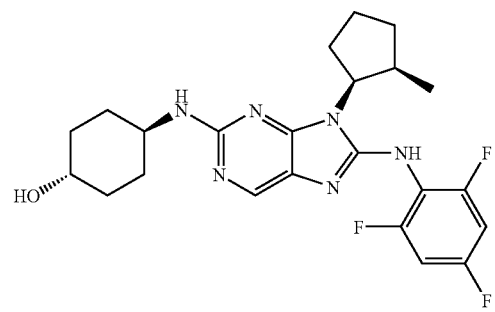

Synthesis of 4-[9-((1S,2R)-2-methyl-cyclopentyl)-8-(2,4,6-trifluoro-phenylamino)-9H-purin-2-ylamino]-cyclohexanol Preparation of cyclopentanamine, 2-methyl-, hydrochloride, (1S,2R)-(9CI)

Synthesis of title compound was performed according to Wiehl, W.; Frahm, A. W.; *Chemische Berichte* 1986 119(8), 2668-77. Amine hydrochloride was employed in usual manner.

Example 5.31

Building block used for the synthesis of 4-[9-((1R,2S)-2-Methyl-cyclopentyl)-8-(2,4,6-trifluoro-phenylamino)-9H-purin-2-ylamino]-cyclohexanol

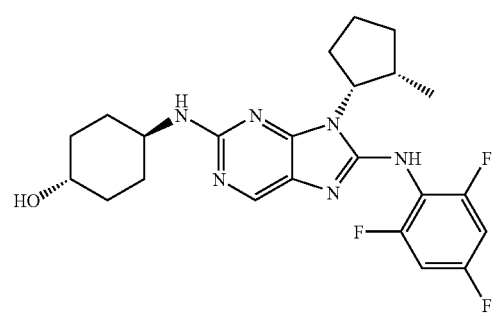

Preparation of cyclopentanamine, 2-methyl-, hydrochloride, (1R,2S)-(9CI)

Synthesis of title compound was performed according to Wiehl, W.; Frahm, A. W.; *Chemische Berichte* 1986 119(8), 2668-77. Amine hydrochloride was employed in usual manner.

Example 5.32

Building Block Used for the Synthesis of

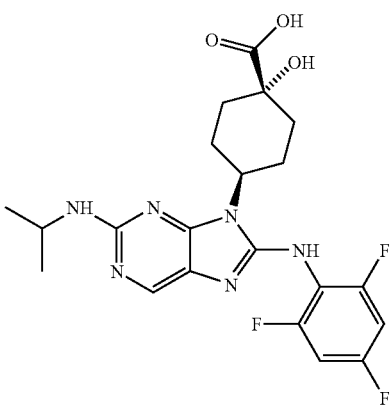

Synthesis of methyl 4-amino-1-hydroxycyclohexanecarboxylate hydrochloride

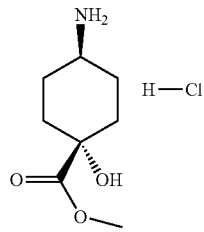

((1S)-1-Phenylethyl)(1,4-dioxaspiro[4.5]dec-8-yl)amine 1,4-Dioxaspiro[4.5]decan-8-one (10 g, 64.03 mmol) was dissolved in dry dichloroethane (300 mL) under an atmosphere of nitrogen. (1S)-1-phenylethylamine (8.96 mL, 70.43 mmol) was added neat at room temperature followed by sodium triacetoxyborohydride (20.36 g, 96.04 mmol) neat in small portions. The reaction was stirred at room temperature overnight. The reaction was quenched by the addition of distilled water (200 mL). The phases were separated and the aqueous phase was extracted with dichloromethane. The combined organic phases were dried over sodium sulfate. The filtrate was concentrated under reduced pressure. A yellow oil was obtained of satisfactory purity based on (11.2 g, 67% yield). M+1: 262.

N-((1S)-1-Phenylethyl)-N-(1,4-dioxaspiro[4.5]dec-8-yl)-2,2,2-trifluoroacetamide ((1S)-1-Phenylethyl)(1,4-dioxaspiro[4.5]dec-8-yl)amine (11.2 g, 42.85 mmol) was dissolved in dichloromethane (135 mL) at room temperature. The solution was treated with pyridine (3.81 mL, 47.14 mmol) and trifluoroacetic anhydride (7.15 mL, 51.42 mmol). The reaction was stirred over the week-end at room temperature. The completion of the reaction was ascertained by LC-MS. The reaction was washed with saturated ammonium chloride. After drying over sodium sulfate, the organic extracts were concentrated to a yellow oil. The crude was used without further purification.

N-((1S)-1-Phenylethyl)-2,2,2-trifluoro-N-(4-oxocyclohexyl)acetamide

N-((1S)-1-Phenylethyl)-N-(1,4-dioxaspiro[4.5]dec-8-yl)-2,2,2-trifluoroacetamide (15.31 g, 42.84 mmol) was dissolved in tetrahydrofuran (30 mL). The solution was treated with 30 mL of 3.0 N aqueous HCl. The reaction was heated to 50-60° C. over 48 h. The reaction was cooled to room temperature. THF was removed under reduced pressure. The crude product was extracted with dichloromethane and was purified by silica gel column (eluent 15-20% ethyl acetate in hexanes). The product was isolated as a yellow oil (5.49 g, 41% yield) M+1: 314.

N-((1S)-1-Phenylethyl)-N-[4-(1,1-dimethyl-1-silaethoxy)-4-cyanocyclohexyl]-2,2,2-trifluoroacetamide N-((1S)-1-Phenylethyl)-2,2,2-trifluoro-N-(4-oxocyclohexyl)acetamide (3.8 g, 12.13 mmol) was dissolved in 30 mL of dichloromethane. $ZnI_2$ (0.774 g, 2.42 mmol) was added to the solution as a solid at room temperature followed by trimethylsilyl chloride (3.25 mL, 24.25 mmol). The reaction mixture was heated to reflux temperature. The conversion was monitored by LC-MS. After 4 h, heating was stopped and the solvent was removed under reduced pressure. 50 mL of dry diethyl ether were added. The resulting cloudy suspension was evaporated to dryness. The resulting orange oil was re-suspended in 100 mL of diethyl ether. A small amount of white solid was removed by filtration and was washed with a small volume of diethyl ether. The combined filtrates were evaporated to dryness and the residue was maintained under high vacuum overnight. The product was used without further purification (5.64 g). M+1: 413.

4-[N-((1S)-1-Phenylethyl)-2,2,2-trifluoroacetylamino]-1-hydroxycyclohexanecarboxamide N-((1S)-1-Phenylethyl)-N-[4-(1,1-dimethyl-1-silaethoxy)-4-cyanocyclohexyl]-2,2,2-trifluoroacetamide (5.64 g, 13.67 mmol) was suspended in 15 mL of concentrated hydrochloric acid. The reaction was stirred at room temperature for 1.5 days resulting in the formation of a dark orange suspension. The solid was collected by filtration, dissolved in 10 mL of methanol under mild temperature and slowly was precipitated out with water. (lightly colored solid separating from orange solution). The mother liquor was collected concentrated and the precipitation conditions were reproduced. This isolation step yielded overall 2.6 g of light yellow solid (53%) clean by $^1H$ and $^{19}F$ NMR. M+1: 359.

Methyl-cis-4-amino-1-hydroxycyclohexanecarboxylate hydrochloride

4-[N-((1S)-1-Phenylethyl)-2,2,2-trifluoroacetylamino]-1-hydroxycyclohexaneboxamide (2.6 g, 7.25 mmol) was suspended in 30 mL of concentrated hydrochloric acid and the reaction mixture was heated to 80° C. for 6 h (light yellow solution). The completion of the reaction was assessed by LC-MS. The reaction mixture was cooled to room temperature and 40 mL of methanol were added. The solution was stirred at room temperature for 36 h. Methanol was removed under reduced pressure. Organic side products were removed by extraction in diethyl ether. The aqueous solution was concentrated under reduced pressure and the residue was dried overnight. Methyl-cis-4-amino-1-hydroxycyclohexanecarboxylate hydrochloride was isolated as a solid and was used without further purification. (quantitative yield).

Example 5.33

Synthesis of 1-hydroxy-4-{2-[(methylethyl)amino]-8-[(2,4,6-trifluorophenyl)amino]purin-9-yl}cyclohexanecarboxylic acid

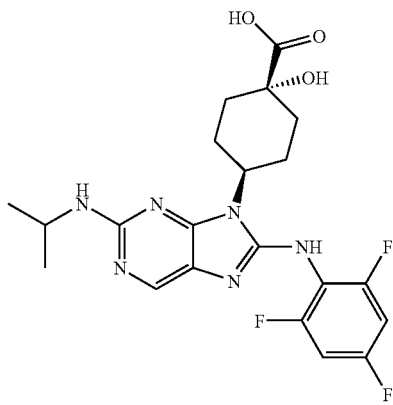

Methyl 1-hydroxy-4-{2-[(methylethyl)amino]-8-[(2,4,6-trifluorophenyl)amino]purin-9-yl}cyclohexanecarboxylate (1.858 g, 3.858 mmol) was dissolved in 27 mL of 4.0 N aqueous hydrochloric acid solution. The reaction mixture was heated to 60° C. for 24 h. The mixture was then concentrated under reduced pressure to an oil and purified by preparative HPLC (20-80% acetonitrile-water, 0.1% TFA). The product was isolated as a white solid by filtration after evaporating acetonitrile from the combined fractions and neutralizing with concentrated ammonium hydroxide. (1.325 g, 73% yield).

Example 5.34

Building block used for the synthesis of N-cyclopentyl(1-hydroxy-4-{2-[(methylethyl)amino]-8-[(2,4,6-trifluorophenyl)amino]purin-9-yl}cyclohexyl)carboxamide

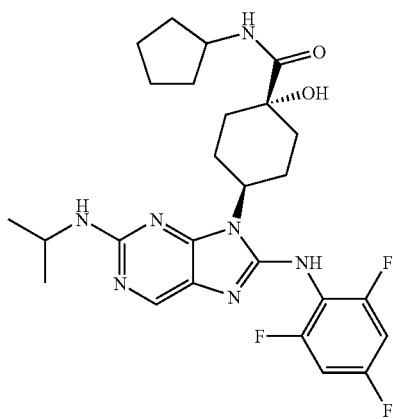

1-Hydroxy-4-{2-[(methylethyl)amino]-8-[(2,4,6-trifluorophenyl)amino]purin-9-yl}cyclohexanecarboxylic acid (0.200 g, 0.4 mmol) was dissolved in 4 mL of dry THF. Cyclopentyl amine (0.079 mL, 0.8 mmol) was added neat followed by di-isopropyl amine (0.105 mL, 0.6 mmol). Benzotriazol-1-yloxytris(dimethylamino)phosphonium hexafluorophosphate (BOP) was added last, as a solid in one portion at room temperature (0.177 g, 0.4 mmol). The reaction was complete within 10 min as confirmed by LC-MS. DMF was removed under reduced pressure. The residue was triturated in saturated aqueous sodium bicarbonate. The resulting beige solid was collected by filtration and washed with water. The crude product was re-crystallized from hot methanol-water. The crystals were dried in vacuum oven. (141 mg, 66% yield) M+1: 532.

Example 5.35

Building block used for the synthesis of 1-(hydroxymethyl)-4-{2-[(methylethyl)amino]-8-[(2,4,6-trifluorophenyl)amino]purin-9-yl}cyclohexan-1-ol

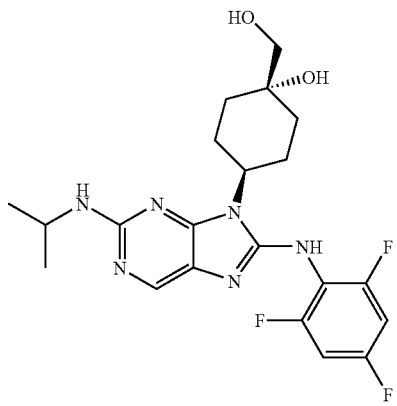

Methyl 1-hydroxy-4-{2-[(methylethyl)amino]-8-[(2,4,6-trifluorophenyl)amino]purin-9-yl}cyclohexanecarboxylate (0.300 g, 0.6 mmol) was dissolved in 3 mL of dry methanol. The solution was cooled to 0° C. before addition of solid sodium borohydride (0.300 g, 7.92 mmol). After 1 h at low temperature, the reaction was warmed to rt and stirred overnight. The reaction was quenched with 5 mL of a saturated solution of ammonium chloride. The crude product was extracted with dichloromethane (four times). The product was purified by column chromatography (75% ethyl acetate in hexanes) followed by semi-preparative HPLC. The fractions were neutralized using a resin-exchange column. (0.101 g, 37% yield). M+1: 451.

Example 5.36

Building Block Used for the Synthesis of

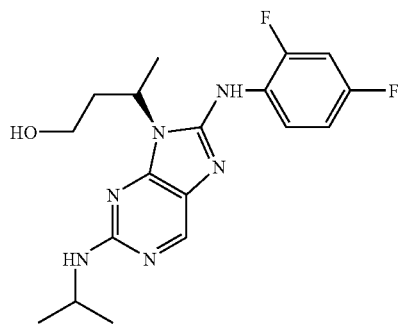

Synthesis of (3R)-3-aminobutanol

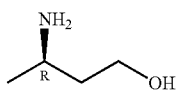

tert-Butyl (3R)-3-{benzyl[(1R)-1-phenylethyl]amino}butanoate n-BuLi (29.5 mL, 47.3 mmol) was added via canula to a solution of (R)—(N-benzyl)[N-(1-phenyl)ethyl]amine (10.0 g, 47.3 mmol) in THF (75 mL) at 0° C. under $N_2$. The reaction was stirred for 20 minutes, and subsequently cooled to −78° C. tert-Butyl crotonate (3.5 g, 24.6 mmol) dissolved in THF (30 mL) was added to the cooled reaction mixture over 20 minutes. After 75 minutes, the reaction was quenched with saturated aqueous $NH_4Cl$ and brine was then added. The layers were separated and the aqueous layer was further extracted with $Et_2O$. The organics were combined, dried with $MgSO_4$, filtered, and concentrated to a yellow crude oil. The crude product was dissolved in hexanes (100 mL) and washed with 10% aqueous citric acid solution (3×25 mL). The organics were pooled, dried with $MgSO_4$, filtered and condensed to yield 6.2 g (17.55 mmol, 37%) of the title compound.

(3R)-3-{benzyl[(1R)-1-phenylethyl]amino}butanol tert-Butyl (3R)-3-{benzyl[(1R)-1-phenylethyl]amino}butanoate (6.2 g, 17.6 mmol) was dissolved in THF (100 mL). The 1 L-flask was purged with $N_2$ and cooled to 0° C. Lithium aluminum hydride (2.7 g, 69.8 mmol) was slowly added over 5 minutes. The reaction was allowed to stir at 0° C. for 1 hour, and then heated to 60° C. for 1 hour. The reaction was cooled to room temperature and diluted with $Et_2O$ (500 mL). This solution was quenched with a mixture of celite:$Na_2SO_4 \cdot 10H_2O$ (1:1) added over 15 minutes. The solution was then filtered and the mother liquor condensed to yield 3.9 g (13.8 mmol, 78%) of the title compound.

(3R)-3-Aminobutanol (3R)-3-{benzyl[(1R)-1-phenylethyl]amino}butanol (3.9 g, 13.8 mmol), was dissolved in methanol (60 mL). Pearlman's catalyst was added to the reaction and subsequently pressurized to 30 psi with $H_2$ on a Parr shaker. After 24 hours, the reaction was filtered through celite and washed additionally with methanol (150 mL). This mixture was condensed to yield 1.2 g (13.4 mmol) of the title product.

Example 5.37

Building Block Used for the Synthesis of

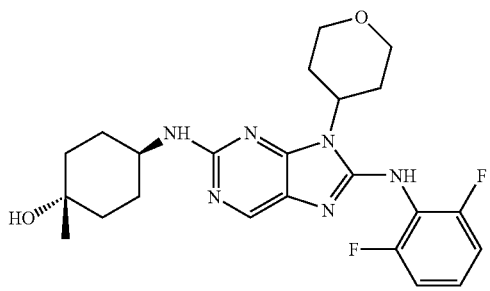

Synthesis of trans-4-amino-1-methylcyclohexanol

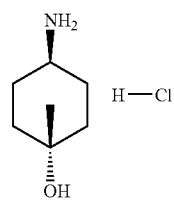

trans-4-Dibenzylaminocyclohexanol

To a solution of trans-4-aminocyclohexanol (7.90 g, 68.5 mmol) in acetonitrile (150 mL), was added cesium carbonate (51.4 g, 157.5 mmol) and benzyl bromide (18.2 g, 143.8 mmol). The solution was stirred at ambient temperature for 16 hours. The solution was complete by LC-MS and the mixture filtered through a frit, washed with additional acetonitrile, and condensed under reduced pressure. The solid was partitioned between water and dichloromethane (500 mL) and dried over sodium sulfate, filtered and solvent removed under reduced pressure to afford the title compound (17.14 g, 85%). ES-MS (m/z) 296.5 [M+1]$^+$.

trans-4-Dibenzylaminocyclohexanone

Oxalyl chloride (12.89 g, 101.1 mmol) in dichloromethane (200 mL) was cooled to −78° C. DMSO (14.5 mL) in dichloromethane (25 mL) was added by addition funnel slowly over 10 minutes until bubbling stopped. trans-4-Dibenzylaminocyclohexanol (17.14 g, 58.10 mmol) in dichloromethane (150 mL) as then dripped in slowly. After 30 minutes, triethylamine (56 mL) was then added dropwise and then the solution stirred at ambient temperature. The reaction was monitored via TLC to assure starting material consumption. The solution was then condensed under reduced pressure and partitioned between water and ethyl acetate. The organics were dried over magnesium sulfate, filtered and solvent removed under reduced pressure. The resultant oil was purified via silica gel chromatography (30% ethyl acetate/hexanes) to afford the title compound (13.71 g, 81%). ES-MS (m/z) 294 [M+1]$^+$.

trans-4-Dibenzylamino-1-methylcyclohexanol

To a solution of trans-4-dibenzylaminocyclexanone (1.40 g, 4.77 mmol) in THF at 0° C. (40 mL) was added a 3.0 M methylmagnesium bromide solution on THF (6.36 mL, 19.1 mmol) dropwise. The solution was allowed to warm to ambient temperature and allowed to stir for 16 hours. The solution was quenched with saturated ammonium chloride solution and partitioned between water and ethyl acetate (three times). The organics were combined, dried over magnesium sulfate, filtered and solvent removed under reduced pressure. The resultant oil was purified via silica gel chromatography (15% ethyl acetate/hexanes) to afford the title compound (2.21 g, 17%). ES-MS (m/z) 310.6 [M+1]$^+$.

trans-4-Amino-1-methylcyclohexanol

To a solution of trans-4-dibenzylamino-1-methylcyclohexanol (2.21 g, 7.15 mmol) in ethanol (50 mL) was added palladium hydroxide (0.663 g, 30% by wt.). The solution was flushed with fresh hydrogen gas and allowed to stir at ambient temperature for 16 hours. Starting material consumption was confirmed via LC-MS. The solution was filtered through celite and washed with additional ethyl acetate. The filtrate was condensed under reduced pressure to afford the title compound (quantitative). ES-MS (m/z) 130.4 [M+1]$^+$.

Example 5.38

Amide Coupling

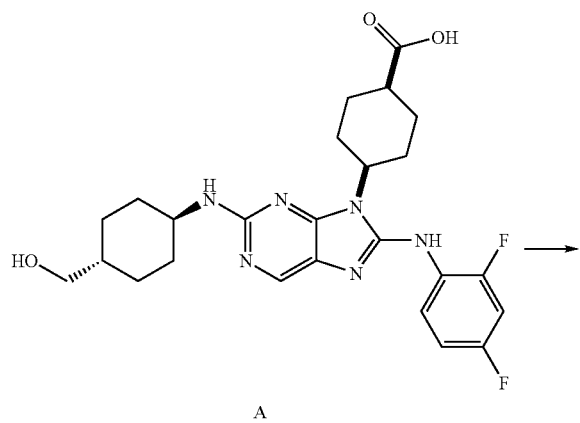

A

-continued

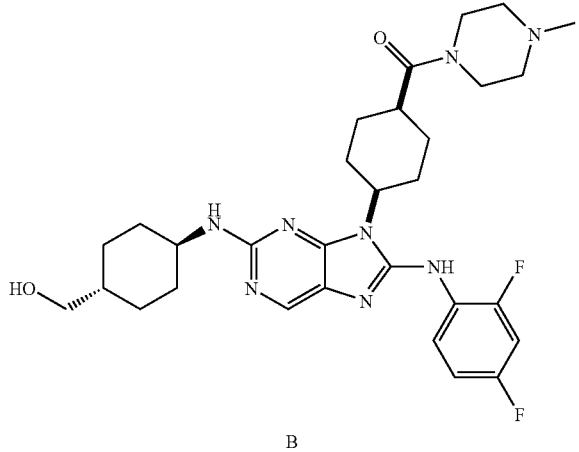

B

Amides coupling reactions as set forth above can be accomplished by Methods A-C described below.

Method A: HATU 0.164 g (0.30 mmol) of A was dissolved in 5 ml of DMF and 0.140 g (1.2 eq.) of HATU was added in one lot. The reaction was stirred at room temperature for about 0.5 h under a nitrogen atmosphere, 0.040 g (1.2 eq.) of N-methylpiperazine was added and stirring continued overnight. The reaction mixture was purified using preparative chromatography using a 15-40% gradient acetonitrile/water (0.1% TFA). After analyzing fractions by HPLC, pure fractions were combined and concentrated to the TFA salt. TFA was exchanged using 1N HCl and the TFA was extracted (10×10 ml) using ether. Upon neutralization of the aqueous layer, the freebase crashed out and was collected and dried to give 0.020 g of B in 10% yield.

Method B: HATU/HBTU

A solution of A (1 mmol) in 10 ml DMF (0.1 M) was treated with 1.2 eq. of HATU or HBTU (1.2 mmol) and stirred under a nitrogen atmosphere at room temperature for about 0.5 h and 1.2 eq of N-methylpiperazine (1.2 mmol) was added. The reaction mixture was stirred at room temperature overnight. After concentrating the reaction mixture, it was purified using preparative chromatography. The clean fractions were combined and concentrated to the TFA salt. TFA was exchanged using 1N HCl and the TFA was extracted with ether. Finally, the HCl salt was obtained upon concentration of the aqueous layer.

Method C: HOBT/EDCI

A solution of A (1 mmol) in 10 ml DMF (0.1 M) was treated with 2.0 eq. of HOBT (2.0 mmol), 2.4 eq of EDCI (2.4 mmol), 2.4 eq of the N-methylpiperazine (2.4 mmol) and stirred under a nitrogen atmosphere at room temperature overnight. After concentrating the reaction mixture, it was purified using preparative chromatography. The clean fractions were combined and concentrated to the TFA salt. TFA was exchanged using 1N HCl and the TFA was extracted with ether. Finally, the HCl salt was obtained upon concentration of the aqueous layer.

Certain intermediates and reactants useful in the preparation of the aminopurine compounds can be prepared as described in Examples 5.15 to 5.29, below.

Example 5.39

Electron-Poor Anilines

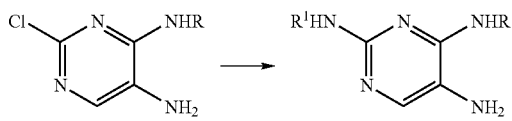

The chloropyrimidine compound is dissolved in acetic acid and the corresponding aniline is added. The reaction is stirred overnight at room temperature. Water is added to the reaction mixture until a precipitate forms. The precipitate is filtered out and dried under high vacuum.

Example 5.40

Acylation/Mesylation/Chloroformylation of Amines

An amine is suspended in methylene chloride and triethylamine is added. The mixture is stirred at room temperature until a clear solution is obtained. The corresponding acyl chloride, methanesulfonyl chloride or methyl chloroformate is added and the reaction mixture is stirred for about 2 h. Typically, mono and diacylated compounds are obtained. The desired monoacylated product is obtained in a pure form after purification using semi-preparative HPLC.

Example 5.41 cis-Ethyl-4-aminocyclohexanecarboxylate Hydrochloride

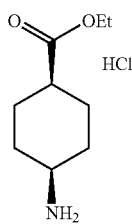

19.3 mL of concentrated hydrochloric acid (2.8 eq) was added to a solution of cis-4-aminocyclohexane carboxylic acid (10 g, 69.83 mmol) in anhydrous ethyl alcohol (250 mL). Mixture was stirred overnight at about 60° C. and then cooled to room temperature. Solvent was evaporated in vacuo. Crude material was then redissolved in acetonitrile, sonicated, and concentrated to a solid in vacuo. This acetonitrile wash was repeated three times to obtain 11.5 g of while solid (96% yield). Trans-ethyl 4-aminocyclohexanecarboxylate hydrochloride can be prepared following the same procedure using trans-4-aminocyclohexane carboxylic acid.

Example 5.42

Ester Hydrolysis (Basic Conditions)

The appropriate ester is added to a solution of 10 equivalent of LiOH in 1:1 THF/H$_2$O. Gradually, the reaction mixture is heated to about 60° C. and stirred overnight. After about 12 h, the presence of the desired compound is verified via LC/MS. The reaction mixture is concentrated and 1N HCl is added dropwise. The aqueous layers are extracted with 2-butanone (3×100 ml) and dried with MgSO$_4$. After filtering off the MgSO$_4$, the compound is concentrated under reduced pressure and purified using column chromatography or reverse-phase HPLC.

Example 5.43

Ester Hydrolysis (Acidic Conditions)

Carboxylic acid ethyl ester is dissolved in 2N hydrochloric acid. The resulting solution is heated to about 75° C. and stirred for about three hours. After cooling to room temperature, excess aqueous ammonium hydroxide is added and the solvent is evaporated under reduced pressure. Trituration of the residue with ethanol, followed by filtration, gives the corresponding carboxylic acid.

Example 5.44

Carboxamide Formation

Oxalyl chloride is added, under an N$_{2\,(g)}$ atmosphere, dropwise to a solution of the appropriate carboxylic acid in DCM. DMF is then added to the solution and bubbling is observed. After about 6 h, the reaction mixture is concentrated under reduced pressure and DCM and NH$_4$OH (conc) are added. The reaction mixture is stirred for about an additional 4 h before being concentrated and purified via reverse-phase preparative HPLC (20-80% acetonitrile/water (0.1% TFA)).

Example 5.45 trans-(4-Aminocyclohexyl)methan-1-ol

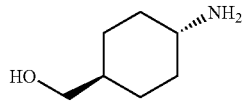

Trans-4-aminocyclohexane carboxylic acid hydrochloride (2.00 g, 14.3 mmol) was added in small portions to a stirred, hot (70-85° C.) solution of Red-Al (27.0 g) for 2 h (a semi-solid formed), and heating was continued overnight. After 24 h, the reaction mixture was cooled to room temperature and treated with a solution of NaOH (3.8 g) in H$_2$O (34 ml). Following the addition, the reaction was gradually heated to 80° C., and cooled. The toluene layer was separated and the aqueous layer was extracted with CHCl$_3$ (3×100 ml). The organic layers were dried with MgSO$_4$ and then concentrated under reduced pressure to provide the desired compound (1.81 g, 14.0 mmol) as a pure white solid in 50% yield. ES-MS: 130 (M+1).

Example 5.46 trans-2-(4-Aminocyclohexyl)propan-2-ol

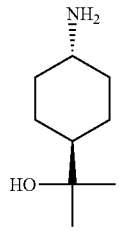

trans-Phenylmethyl 4-[N,N-dibenzylamino]cyclohexanecarboxylate

To an 80° C. heated mixture of trans-4-Aminocyclohexanecarboxylic acid (8 g, 55.97 mmol) and $K_2CO_3$ (23.4 g) in 112 mL of $CH_3CN$, was added dropwise a solution of BnBr (23.3 mL, 195.5 mmol) in 70 mL of $CH_3CN$ by addition funnel. Reaction stirred overnight at 80° C. The reaction was cooled to room temperature and filtered. Precipitate did not form in filtrate like it did with the cis-isomer so the filtrate was concentrated to an oil and carried on to next step (23.01 g, 99% yield).

trans-2-{4-[N,N-Dibisbenzylamino]cyclohexyl}propan-2-ol

Phenylmethyl 4-[bisbenzylamino]cyclohexanecarboxylate (6 g, 14.50 mmol) was combined with 460 mL of THF, flushed with $N_2$ and cooled to 0° C. Methylmagnesium bromide (48 ml, 145.08 mmol) was added to reaction and left to stir overnight. The reaction was quenched with 600 mL of saturated $NH_4Cl$. Layers were separated and organics were washed with saturated $NaHCO_3$ and brine (100 mL). Organics were dried with $Na_2SO_4$ and concentrated in vacuo. The mixture was dried overnight on high vacuum to afford 3.89 g of solid product (80% yield).

trans-2-(4-Aminocyclohexyl)propan-2-ol 3.85 g of trans-2-{4-[N,N-dibenzylamino]cyclohexyl}propan-2-ol (11.40 mmol) was combined with 3.3 g of 20 wt % palladium hydroxide and dissolved with 100 mL of anhydrous ethyl alcohol. The mixture was flushed with $H_2$ (4×) before a $H_2$ balloon was inserted into the reaction and allowed to stir overnight. $N_2$ was bubbled through for about 20 minutes and the catalyst was filtered off. The reaction was washed with methanol. The filtrate was concentrated in vacuo and redissolved in acetonitrile and sonicated which produced a white solid. The mixture was filtered and 0.67 g of white product was obtained (37% yield).

Example 5.47 trans-4-(N,N-Dibenzylamino)cyclohexanol

To a 1-L round bottom flask equipped with magnetic stirring, nitrogen inlet and dropping funnel was charged trans-4-aminocyclohexanol hydrochloride (50.0 g, 0.33 mol), sodium carbonate (139.9 g, 1.32 mol) and anhydrous DMF (400 mL). Stirring was initiated and benzyl bromide (82.3 mL, 0.69 mol) was added via dropping funnel over a period of about 15 minutes. A slight exotherm was observed following addition of benzyl bromide. The reaction was allowed to stir at ambient temperature for about 18 h, then a sample was taken for LCMS analysis. LCMS indicated complete conversion of starting material at this time.

The reaction mixture was filtered through a medium frit under vacuum to remove salts, and the filtrate was diluted with water (400 mL) and MTBE (400 mL). The mixture was agitated in a separatory funnel, then the lower aqueous layer was drained off. The organic layer was decanted, then the aqueous layer was extracted with MTBE (200 mL). The organic layers were combined and extracted twice with water (300 mL), then extracted with saturated brine (100 mL). The organic layer was dried (sodium sulfate), filtered and evaporated under reduce pressure to yield a white solid. The solid was further dried at 50° C. under vacuum. To the dry solid was added cyclohexane (400 mL) and the mixture was stirred in a water bath at 80° C. until most solids were in solution. The solution was quickly filtered using celite and a fritted funnel under vacuum. The resulting slurry was heated to boiling to redissolve solids and stirred while cooling slowly. The fine white crystals were filtered on a frit, then washed with two portions of cyclohexane (50 mL). The crystals were then dried for about 18 h at 60° C. under vacuum to yield 58.4 g (60%) of pure material. LRMS (ES) m/e 296.2 [MH]$^+$; HPLC (5→70% acetonitrile/water (0.1% TFA) over 20 minutes) RT=9.55 min.

Example 5.48 trans-N,N-Dibenzyl-4-(2-(piperidin-1-yl)ethoxy)cyclohexanamine

Into a nitrogen flushed 250-mL round bottom flask was charged 35% potassium hydride suspension in oil (16.27 g, 142 mmol) and hexanes (60 mL). The mixture was stirred briefly, then allowed to settle. The supernatant was drawn off via syringe, then trans-4-(dibenzylamino)cyclohexanol (10.0 g, 33.9 mmol), 1-(2-chloroethyl)piperidine hydrochloride (18.72 g, 101.7 mmol) and dioxane (120 mL) were added and the mixture stirred at ambient temperature. The reaction mixture tends to thicken. Once hydrogen evolution had ceased the mixture was brought to 90-100° C. for about 2 h, then cooled to ambient temperature. Methanol (20 mL) was added and the mixture was stirred until hydrogen evolution ceased. The solvents were evaporated under reduced pressure, and the residue partitioned between 5% sodium carbonate solution (100 mL) and dichloromethane (200 mL). The layers were separated and the aqueous layer extracted with dichloromethane (100 mL). The organic extracts were combined and dried (sodium sulfate), filtered and evaporated under reduced pressure. The residue was chromatographed (silica gel, 330 g, using a gradient of chloroform-ethanol-conc. ammonia soln. from (98:2:0) to (92:8:2)) to give 4.7 g of an oil (61%). LRMS (ES) m/e 407.3 [MH]$^+$; HPLC (5→70% acetonitrile/water (0.1% TFA) over 20 minutes) RT=9.23 min.

Example 5.49 trans-4-(2-(Piperidin-1-yl)ethoxy)cyclohexanamine

Trans-N,N-dibenzyl-4-(2-(piperidin-1-yl)ethoxy)cyclohexanamine (4.7 g, 11.6 mmol), 20% Pd(OH)$_2$/C (0.94 g) and methanol (40 mL) were charged into a septum-sealed flask. The reaction mixture was placed under balloon pressure of hydrogen for 18 h at ambient temperature, at which time LCMS indicated complete debenzylation to form the free amine. The catalyst was filtered off and the filtrate evaporated under reduced pressure to give 2.42 g of a crystalline material (93%). In some cases an additional portion of catalyst (ca. 50% of the initial charge) was needed in order to attain complete reaction. LRMS (ES) m/e 227.2 [MH]+; 1H NMR (300 MHz, CD3OD) δ 3.51 (t, 2H), 3.12 (m, 1H), 2.61 (m, 1H), 2.42 (t, 2H), 2.18 (m, 4H), 1.93 (m, 2H), 1.80 (m, 2H), 1.50 (m, 4H), 1.33 (m, 2H), 1.12 (m, 4H).

Example 5.50

1-Methylsulfonylpyrrolidin-3S-amine Hydrochloride

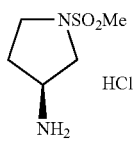

(3S)-3-(tert-Butylcarbonylamino)pyrrolidine (10.0 mmol, 1 eq.) and N,N-diisopropylethylamine (25.0 mmol, 2.5 eq.) were dissolved in 20 ml DCM. Methanesulfonylchloride (10.0 mmol, 1 eq.) was added dropwise and the reaction mixture was stirred overnight at rt. After adding water the phases were separated and the organic phase was dried over MgSO4 and evaporated to give the desired product. This compound was dissolved in 12 ml dioxane and 23 ml 4N HCl in dioxane was added, The reaction mixture was stirred overnight. Evaporation of the solvent and additional coevaporation with toluene gave the desired product. This reaction can also be performed with the R-enantiomer.

Example 5.51 cis-4-[(2-piperidylethoxy)methyl]cyclohexylamine

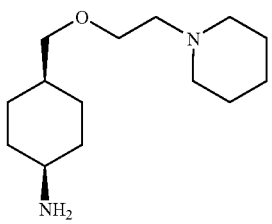

Benzyl cis-4-[N,N-dibenzylamino]cyclohexane carboxylate cis-4-Aminocyclohexanecarboxylic acid (10.0 g, 67.48 mmol) was dissolved in 140 mL of dry acetonitrile. Solid potassium carbonate (28.0 g, 202.6 mmol) was added. The suspension was heated to about 80° C. To this solution, was added benzyl bromide (28.09 mL, 236.2 mmol) in 70 mL of acetonitrile, dropwise via addition funnel. The reaction mixture was stirred at about 80° C. under nitrogen for about 2 hours then about 40° C. overnight. The reaction was cooled to room temperature and the suspension was filtered. The filtrate was concentrated under reduced pressure. The compound was purified using column chromatography on silica gel (100% hexanes to remove excess benzyl bromide, then 10% ethyl acetate in hexanes). The product was isolated as a white solid (14.35 g, 51% yield): ES-MS (m/z) 414.

cis-{4-[N,N-Dibenzylamino]cyclohexyl}methan-1-ol

A solution of benzyl cis-4-[N,N-dibenzylamino]cyclohexane carboxylate (14.35 g, 34.70 mmol) in dry THF (180 mL) was prepared and then cooled down to −78° C. A solution of lithium aluminum hydride (104.0 mL, 1.0 M solution in diethyl ether) was added dropwise. At the end of the addition, the reaction temperature was raised to about −50° C. (acetonitrile/dry ice) and the temperature was maintained for about 3 hours. The completion of the reaction was monitored by LC-MS. The reaction was quenched by dropwise addition of saturated aqueous sodium sulfate. Saturated aqueous sodium bicarbonate (10 mL) and diethyl ether (50 mL) were then added. A white solid formed and was removed by filtration and washed with THF. The organic phase was separated and concentrated under reduced pressure. The product was purified by slow precipitation. The residue was dissolved in 5 mL of diethyl ether and the solution was layered with 50 mL of hexanes. Clear large crystals were obtained after overnight diffusion. (7.279 g, 67% yield) ES-MS (m/z) 310.

cis-N,N-Dibenzyl-N-{4-[(2-piperidylethoxy)methyl] cyclohexyl}amine cis-{4-[N,N-Dibenzylamino]cyclohexyl}methan-1-ol (2.851 g, 9.21 mmol) and (2-chloroethyl)piperidine hydrochloride were suspended in 50 mL of dioxane. Potassium hydride (3.16 g, 35% by weight in mineral oil) was added dropwise in suspension in 20 mL of dioxane. The reaction mixture was stirred at room temperature for about 1 hour. The reaction mixture was then warmed to about 70° C. and one equivalent of potassium hydride (1.05 g, 35% by weight in mineral oil) was added dropwise. The temperature was maintained for about 2 hours, after which the conversion was complete. The reaction was cooled to room temperature and quenched with methanol. Solvents were removed under reduced pressure. Acetonitrile was added (200 mL) and the gray brown solid was removed by filtration. The crude was purified by column chromatography on silica gel using 3% (ethanol/ammonium hydroxide=8:1) in dichloromethane. The product was isolated as an orange oil that solidified under vacuum. (2.84 g, 72% yield): ES-MS (m/z) 421.

cis-4-[(2-Piperidylethoxy)methyl]cyclohexylamine cis-N,N-Dibenzyl-N-{4-[(2-piperidylethoxy)methyl] cyclohexyl}amine (2.84 g, 6.65 mmol) was dissolved in 20 mL of ethanol. Palladium hydroxide (20% weight) was added (50 mg) and the reaction was stirred overnight under an atmosphere of hydrogen. The catalyst was removed by filtration and washed with small portions of ethanol. The filtrate was concentrated and used without further purification. (quantitative yield): ES-MS (m/z) 241.

Example 5.52 cis-4-(Methoxymethyl)cyclohexyl amine

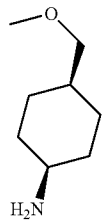

cis-4-[(tert-Butoxy)carbonylamino]cyclohexane carboxylic acid cis-4-Aminocyclohexyl carboxylic acid (2.0 g, 13.96 mmol) was dissolved in 40 mL of 1,4-dioxane. Two equivalents of di-tert-butyl-dicarbonate (6.094 g, 27.92 mmol) were added followed by 3 equivalents of sodium bicarbonate (4.06 g, 41.88 mmol) dissolved in 40 mL of water. The reaction mixture was stirred at room temperature for about 12 hours. The completion of the reaction was monitored by LC-MS. Saturated aqueous KHSO$_4$ was added dropwise, until gas evolution stopped. The solvent was then removed under reduced pressure and the crude product was extracted in ethyl acetate. The combined organic extracts were washed with aqueous saturated KHSO$_4$ and dried over Na$_2$SO$_4$. The solvent was removed under reduced pressure, yielding 2.6 g of product. Based on $^1$H NMR, the product was pure and used in subsequent steps without further purification ES-MS (m/z) 244.

cis-(tert-Butoxy)-N-[4-(hydroxymethyl)cyclohexyl] carboxamide cis-4-[(tert-Butoxy)carbonylamino]cyclohexane carboxylic acid (2.6 g, 10.68 mmol) was dissolved in THF (20 mL) and cooled to −10° C. (MeOH-ice). N-Methyl morpholine was added followed by isobutyl chloroformate (1.175 mL, 10.68 mmol). After 10 min, NaBH$_4$ was added as a solid in one portion (1.213 g, 32.06 mmol). The reaction mixture was warmed to 0° C. and methanol was added dropwise (13.35 mL). After about 30 min, the reaction was quenched with 5% aqueous KHSO$_4$. The reaction monitored by LC-MS was complete. The crude product was extracted with ethyl acetate and the combined extracts were dried over Na$_2$SO$_4$. A colorless oil was obtained and solidified slowly at room temperature. The product and purity were assessed by LC-MS and $^1$H NMR. No further purification was necessary. (quantitative yield) ES-MS (m/z) 230.

cis-4-(Methoxymethyl)cyclohexyl amine

Sodium hydride (72 mg, 1.78 mmol, 60% by weight suspended in mineral oil) was washed three times with 10 mL portions of hexanes, and suspended in dry THF (12 mL). The suspension was cooled to 0° C. To this suspension, cis-(tert-butoxy)-N-[4-(hydroxymethyl)cyclohexyl]carboxamide (0.273 g, 1.20 mmol) and 15-crown-5 (0.250 mL, 1.25 mmol) were added. The reaction mixture was then stirred at 0° C. for about 30 min. Methyl iodide was then added dropwise (75 µL, 1.20 mmol). Since the reaction was not complete after overnight stirring at room temperature, the mixture was cooled to 0° C. and reacted with 100 mg of sodium hydride and 0.250 mL of 15-crown-5. After about 2 hours at room temperature, the reaction was complete. The reaction was quenched by the slow addition of water and the crude product was extracted with ethyl acetate. Purification was effected by column chromatography on silica gel using 20% ethyl acetate in hexanes as the eluent. ES-MS (m/z) 244. cis-(Tert-butoxy)-N-[4-(methoxymethyl)cyclohexyl]carboxamide was dissolved in ethanol (5 mL) and the solution was treated with 1 mL of acetyl chloride at room temperature. The reaction mixture was stirred at room temperature overnight. The solvent was removed under reduced pressure and the resulting solid was used without further purification. (79% yield) ES-MS (m/z) 144.

Example 5.53 trans-4-Methoxycyclohexylamine

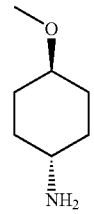

trans-(tert-Butoxy)-N-(4-methoxycyclohexyl)carboxamide

Sodium hydride (60% in mineral oil, 278 mg, 6.96 mmol) was suspended in THF (5 mL) and cooled to 0° C. trans-tert-Butoxy-N-(4-hydroxycyclohexyl)carboxamide (1 g, 4.64 mmol) and 15-crown-5 (0.965 mL, 4.88 mmol) were added and the reaction mixture was stirred at 0° C. for about 30 minutes. Iodomethane (0.289 mL, 4.64 mmol) was added and the reaction stirred at 0° C. for about 1 hour after which the LCMS showed it was complete. The reaction was quenched with methanol, the solvents removed in vacuo and the crude purified by column chromatography (SiO$_2$, 8:2 n-hexanes/ethyl acetate) to afford 642 mg of the methyl ether. ES-MS: 230 (M+1).

trans-4-Methoxycyclohexylamine trans-(tert-Butoxy)-N-(4-methoxycyclohexyl)carboxamide (642 mg, 2.80 mmol) was dissolved in ethanol (5 mL) and cooled to 0° C. Acetyl chloride (1.5 mL) was added and the reaction was allowed to reach room temperature and stirred overnight. Solvent was removed in vacuo to give the desired product (458 mg, quantitative yield) as a hydrochloride salt. ES-MS: 130 (M+1).

The Aminopurine Compounds can be assayed for their activity according to the following procedures.

JNK1 Assay

To 10 µL of an Aminopurine Compound in 20% DMSO/80% dilution buffer consisting of 20 mM HEPES (pH 7.6), 0.1 mM EDTA, 2.5 mM magnesium chloride, 0.004% Triton x 100, 2 µg/mL leupeptin, 20 mM β-glycerolphosphate, 0.1 mM sodium vanadate, and 2 mM DTT in water is added 30 µL of 50 ng His6-JNK1 in the same dilution buffer. The mixture is preincubated for 30 minutes at room temperature. Sixty microliter of 10 μg GST-c-Jun(1-79) in assay buffer consisting of 20 mM HEPES (pH 7.6), 50 mM sodium chloride, 0.1 mM EDTA, 24 mM magnesium chloride, 1 mM DTT, 25 mM PNPP, 0.05% Triton x 100, 11 μM ATP, and 0.5 μCi γ-$^{32}$P ATP in water is added and the reaction is allowed to proceed for 1 hour at room temperature. The c-Jun phosphorylation is terminated by addition of 150 μL of 12.5% trichloroacetic acid. After 30 minutes, the precipitate is harvested onto a filter plate, diluted with 50 μL of the scintillation fluid and quantified by a counter. The $IC_{50}$ values are calculated as the concentration of the Aminopurine Compound at which the c-Jun phosphorylation is reduced to 50% of the control value. Certain compounds have an $IC_{50}$ value ranging from 0.01-10 μM in this assay.

JNK2 Assay

To 10 μL of an Aminopurine Compound in 20% DMSO/80% dilution buffer consisting of 20 mM HEPES (pH 7.6), 0.1 mM EDTA, 2.5 mM magnesium chloride, 0.004% Triton x 100, 2 μg/mL leupeptin, 20 mM β-glycerolphosphate, 0.1 mM sodium vanadate, and 2 mM DTT in water is added 30 μL of 50 ng His6-JNK2 in the same dilution buffer. The mixture is preincubated for 30 minutes at room temperature. Sixty microliter of 10 μg GST-c-Jun(1-79) in assay buffer consisting of 20 mM HEPES (pH 7.6), 50 mM sodium chloride, 0.1 mM EDTA, 24 mM magnesium chloride, 1 mM DTT, 25 mM PNPP, 0.05% Triton x 100, 11 μM ATP, and 0.5 μCi γ-$^{32}$P ATP in water is added and the reaction is allowed to proceed for 1 hour at room temperature. The c-Jun phosphorylation is terminated by addition of 150 μL of 12.5% trichloroacetic acid. After 30 minutes, the precipitate is harvested onto a filter plate, diluted with 50 μL of the scintillation fluid and quantified by a counter. The $IC_{50}$ values are calculated as the concentration of the Aminopurine Compound at which the c-Jun phosphorylation is reduced to 50% of the control value. Certain compounds have an $IC_{50}$ value ranging from 0.01-10 μM in this assay.

JNK3 Assay

To 10 μL of an Aminopurine Compound in 20% DMSO/80% dilution buffer consisting of 20 mM HEPES (pH 7.6), 0.1 mM EDTA, 2.5 mM magnesium chloride, 0.004% Triton x 100, 2 μg/mL leupeptin, 20 mM β-glycerolphosphate, 0.1 mM sodium vanadate, and 2 mM DTT in water is added 30 μL of 200 ng His6-JNK3 in the same dilution buffer. The mixture is preincubated for 30 minutes at room temperature. Sixty microliter of 10 μg GST-c-Jun(1-79) in assay buffer consisting of 20 mM HEPES (pH 7.6), 50 mM sodium chloride, 0.1 mM EDTA, 24 mM magnesium chloride, 1 mM DTT, 25 mM PNPP, 0.05% Triton x 100, 11 μM ATP, and 0.5 μCi γ-$^{32}$P ATP in water is added and the reaction is allowed to proceed for 1 hour at room temperature. The c-Jun phosphorylation is terminated by addition of 150 μL of 12.5% trichloroacetic acid. After 30 minutes, the precipitate is harvested onto a filter plate, diluted with 50 μL of the scintillation fluid and quantified by a counter. The $IC_{50}$ values are calculated as the concentration of the Aminopurine Compound at which the c-Jun phosphorylation is reduced to 50% of the control value. Certain compounds have an $IC_{50}$ value ranging from 0.001-10 μM in this assay.

p38α Assay

The p38α kinase assay is carried out in 96-well plate format at a final volume of 100 μl. ATP is used at a final concentration of 340 μM, three fold the apparent $K_m$. Kinase is diluted in Dilution Buffer (20 mM HEPES pH 7.6, 0.1 mM EDTA, 2.5 mM $MgCl_2$, 0.004% (w/v) Triton x 100, 2 μg/ml Leupeptin, 20 mM B-glycerol phosphate, 0.1 mM $Na_3VO_4$, 2 mM dithiothreitol) and pre-mixed with MBP diluted in Substrate Solution Buffer (20 mM HEPES pH 7.6, 50 mM NaCl, 0.1 mM EDTA, 2.5 mM $MgCl_2$, 0.05% (w/v) Triton x 100) to give final assay concentrations of 50 ng/well (7.8 nM) for p38α and 30 μg/well (16 μM, $2 \times K_m$) for MBP. The p38α/MBP mix (85 μl) is added to an Aminopurine Compound (5 μl) diluted in 100% DMSO to give a final DMSO assay concentration of 5% (v/v). Enzyme, substrate and Aminopurine Compound are allowed to equilibrate at room temperature for about 15 minutes. The reaction is started by addition of 10 μl 10×ATP in kinase buffer (130 mM $MgCl_2$ 6 mM dithiothreitol, 150 mM para-nitrophenyl phosphate, 100 μCi/ml γ-[$^{33}$P]-ATP). Reactions are allowed to proceed for 60 minutes before precipitation of protein via trichloroacetic acid (7.2% TCA final). After a 30 minute incubation with TCA, reaction products are collected onto glass microfilter 96-well plates (Millipore MAHF CIH60) using a Packard Filtermate. The precipitate is washed with Phosphate Buffered Saline and the amount of phosphate incorporated into MBP is quantified by scintillation counting using a Packard Topcount-NXT.

Jurkat T-Cell Il-2 Production Assay

Jurkat T cells (clone E6-1) are purchased from the American Tissue Culture Collection and maintained in growth media consisting of RPMI 1640 medium containing 2 mM L-glutamine (Mediatech), with 10% fetal bovine serum (Hyclone) and penicillin/streptomycin. All cells are cultured at 37° C. in 95% air and 5% $CO_2$. Cells are plated at a density of $0.2 \times 10^6$ cells per well in 200 μL of media. Aminopurine Compound stock (20 mM) is diluted in growth media and added to each well as a 10× concentrated solution in a volume of 25 μL, mixed, and allowed to pre-incubate with cells for 30 minutes. The compound vehicle (dimethylsulfoxide) is maintained at a final concentration of 0.5% in all samples. After 30 minutes the cells are activated with PHA (phorbol myristate acetate; final concentration 50 μg/mL) and PHA (phytohaemagglutinin; final concentration 2 μg/mL). PMA and PHA are added as a 10× concentrated solution made up in growth media and added in a volume of 25 μL per well. Cell plates are cultured for 10 hours. Cells are pelleted by centrifugation and the media removed and stored at −20° C. Media aliquots are analyzed by sandwich ELISA for the presence of IL-2 as per the manufacturers instructions (Endogen). The $IC_{50}$ values are calculated as the concentration of the Aminopurine Compound at which the Il-2 production was reduced to 50% of the control value. Certain compounds have an $IC_{50}$ value ranging from 0.01-10 μM in this assay.

Rat In Vivo LPS-Induced TNF-α Production Assay

Male CD rats procured from Charles River Laboratories at 7 weeks of age are allowed to acclimate for one week prior to use. A lateral tail vein is cannulated percutaneously with a 22-gage over-the-needle catheter under brief isoflurane anesthesia. Rats are administered an Aminopurine Compound either by intravenous injection via the tail vein catheter or oral gavage 15 to 180 min prior to injection of 0.05 mg/kg LPS (*E. Coli* 055:BS). Catheters are flushed with 2.5 mL/kg of normal injectable saline. Blood is collected via cardiac puncture 90 minutes after LPS challenge. Plasma is prepared using lithium heparin separation tubes and frozen at −80° C. until analyzed. TNF-α levels are determined using a rat specific TNF-α ELISA kit (Biosource). The $ED_{50}$ values are calculated as the dose of the Aminopurine Compound at which the TNF-α production is reduced to 50% of the control value. Certain compounds have an $ED_{50}$ value ranging from 1-30 mg/kg in this assay.

Abl LANCE HTRF Tyrosine Kinase Assay

The day prior to performing the assay, the following are prepared:

(1) 2 mg/ml BSA/0.4% Triton x 100/50 mM HEPES pH 7.6 (kept at 4° C.);

(2) Streptavidin-APC (PerkinElmer Life Sciences CR130-100) diluted in $nH_2O$ according to instructions (kept at 4° C., up to 2 weeks maximum);

(3) Tyrosine Kinase Biotinylated Peptide Substrate 2 (Pierce 29914) diluted in $nH_2O$ (kept at 4°);

(4) Aminopurine Compound dilutions in DMSO.

The following mixtures are prepared the day on which the assay is performed:

(5) 2 mM DTT/50 mM HEPES pH 7.6;

(6) 2 mM Staurosporine for Background Control and 1:3 serial dilutions for Reference Control in DMSO;

(7) LANCE Mixture in 2 mg/ml BSA/0.2% Triton x 100/50 mM HEPES pH 7.6 prepared as follows: 250 nM Streptavidin-APC (PerkinElmer Life Sciences CR130-100), 250 nM Tyrosine Kinase Biotinylated Peptide Substrate 2 (Pierce 29914), and 250 ng/ml Eu-anti-phosphoTyrosine (PerkinElmer Life Sciences AD0066);

(8) Kinase/detection mixture prepared as follows: 18.7 ng/ml Abl (Calbiochem 102555), 5.9 mM $MgCl_2$, and 58.8% LANCE Mixture from (7), brought to final volume with 2 mM DTT/50 mM HEPES pH 7.6;

(9) 240 µM ATP in 2 mM DTT/25 mM HEPES pH 7.4.

To a black 384 well microtiter plate (Corning 3710) is added 2.5 µl/well compound dilutions/DMSO and 42.5 µl/well kinase/detection mixture. The plate is incubated for 5 minutes on shaker followed by 10 minutes static incubation at room temperature.

5 µl/well ATP is added to the plate and the plate is incubated for 5 minutes on shaker followed by 55 minutes static incubation at room temperature.

30 µl/well 16.7 mM EDTA is added to the plate and the plate is incubated for at least 2 minutes on a shaker followed by 30 minutes static incubation at room temperature. The plate is then read (TR-FRET) on Packard Fusion instrument.

Certain compounds have an $IC_{50}$ value ranging from 0.01-10 µM in this assay.

Alamar Blue Assay for K562 Cells

Chronic myelogenous leukemia K562 is routinely maintained in RPMI 1640 with 10% heat inactivated FBS and 1% Penicillin-Streptomycin. For cell proliferation assay, K562 cells are plated in 96-well round bottom plates. Cells are treated with an Aminopurine Compound the same day of plating. For dose response experiments, a 30 mM solution of an Aminopurine Compound is diluted to give final concentrations of 30 µM, 3 µM, 0.3 µM, 0.03 µM, and 0.003 µM. The final DMSO concentration is 0.2% in each well. Alamar Blue is used to quantify cell number after a 72 hour incubation with an Aminopurine Compound. Certain compounds have an $IC_{50}$ value ranging from 0.1-10 µM in this assay.

Ozone-Induced Effects in Mice

The following protocol can be used to assay an Aminopurine Compound for activity against ozone-induced effects in vivo.

Mice: Pathogen free 6-8 week old male BALB/c mice (Harlan, UK) are housed within 'maximiser' filter-topped cages (Maximiser, Theseus caging system Inc., Hazelton, Pa., USA).

Aminopurine Compound: The Aminopurine Compound is prepared as a 30 mg/kg solution in a vehicle of 10% Ethanol, 15% Cremophor-El, 30% Polyethylene Glycol-400 and 20% Propylene Glycol (Sigma, Dorset, UK) in sterile saline. Mice are injected intraperitoneally with the Aminopurine Compound (30 mg/kg; 0.16 ml volume). Control animals receive vehicle alone, in the same volume as the Aminopurine Compound.

Aminopurine Compound Administration Protocol: The effect of the Aminopurine Compound or of vehicle alone in air or ozone-exposed mice is studied at two time-points. Three hours following exposure, lung tissues are collected for Affymetrix microarray, real-time polymerase chain reaction, Western blot analysis and bronchioalveolar (BAL) are performed. Twenty to twenty-four hours following exposure, lung resistance ($R_L$) is measured and BAL is performed. Mice are exposed to ozone produced by an ozonizer (Model 500 Sander Ozoniser, Germany), mixed with air for 3 h at a concentration of 3 parts per million (ppm) within a sealed Perspex container. Ozone concentration is continually monitored with an ozone probe (ATi Technologies, Oldham, UK). Control animals receive medical air only. Mice receive either the Aminopurine Compound or vehicle two hours prior to air- or ozone-exposure, eight hours after exposure and two hours prior to measurement of $R_L$.

Measurement of Lung Resistance ($R_L$): Twenty-four hours following exposure, mice are anesthetized with an intraperitoneal injection of anesthetic solution containing midazolam (Roche Products Ltd., Welwyn Garden City, UK) and Hypnorm (0.315 mg/ml fentanyl citrate and 10 mg/ml fluanisone; Janssen Animal Health, Wantage, UK). Mice are tracheostomised and ventilated (Mini Vent type 845, Hugo Sach Electronic, Germany; rate: 250 breaths/min and tidal volume: 250 µl). Mice are monitored in a whole body plethysmograph with a pneumotachograph connected to a transducer (EMMS, Hants, UK). Transpulmonary pressure is assessed via an esophageal catheter (EMMS, Hants, UK). Instantaneous calculation of pulmonary resistance ($R_L$) is obtained. Increasing concentrations of acetylcholine chloride (ACh) (Sigma, Dorset, UK) (4-256 mg/ml) are administered with an ultrasonic nebulizer, and $R_L$ is recorded for a 5-min period following each concentration. $R_L$ after each concentration is expressed as percentage change from baseline $R_L$ measured following nebulized phosphate buffered saline (PBS) (Sigma, Dorset, UK). The concentration of acetylcholine required to increase $R_L$ by 150% from baseline is calculated ($PC_{150}$).

Bronchioalveolar Lavage: A previously-published method is used (Nath P. et al., *European Journal of Pharmacology* 506: 273-283 (2005)). Briefly, following an overdose of anaesthetic, mice are lavaged with a six 0.5 ml aliquots of PBS via the endrotracheal tube, and retrieved as the bronchioalveolar lavage fluid. Total cell counts and differential cell counts from cytospin preparations stained by May-Grunwald-Giemsa stain are determined under an optical microscope (Olympus BH2, Olympus Optical Company Ltd., Tokyo, Japan). At least 400 cells are counted per mouse and identified as macrophages, eosinophils, lymphocytes and neutrophils according to standard morphology under x400 magnification.

DNA Microarray: Total RNA is extracted from frozen lung tissue using TriZol reagent (GIBCO, Paisley, UK) followed by RNeasy columns (Qiagen, Crawley, UK) for additional purity. Quantitation and quality assessment of the RNA preparations are performed on a spectrophotometer (Nanodrop Technologies, Wilmington, Del., USA) and Agilent Bioanalyzer (Foster City, Calif., USA), respectively. Biotinylated antisense-RNA is generated with the MessageAmp II Kit (Ambion, Austin, Tex., USA). Briefly, first strand cDNA is synthesized from 1 µg total RNA with T7-oligo(dT) primers for 2 hours at 42° C. Second-strand cDNA is synthesized at 16° C. for 2 hours and then purified on Ambion cDNA filter cartridges. In vitro transcription is conducted at 37° C. for 14 hours with T7 RNA polymerase and biotinylated CTP and UTP (Enzo, Farmingdale, N.Y., USA). The biotinylated antisense-RNA is purified on filter cartridges (Ambion, Tex., USA) and fragmented at 94° C. for 30 minutes prior to use on DNA Microarray. Fragmented antisense-RNA (10 g) is hybridized to Affymetrix 430A v.2 mouse GeneChips for 16 hrs at 45° C. according to manufacturer's instructions (Affymetrix, Calif., USA). Mouse GeneChips are washed on the Fluidics Station and imaged on a high-resolution Scanner 3000 (Affymetrix, Calif., USA). The above procedures are performed in duplicate for each sample. Gene expression data analysis is performed using GeneSpring software version 7.2 (Agilent, Palo Alto, Pa., USA). Data normalization includes the following steps, as recommended by Affymetrix: (i) values below 0.01 are set to 0.01 (ii) each gene measurement is divided by the 50th percentile of all measurements in that sample (iii) each gene measurement is divided by the median of its measurements in all samples. Fold-change analysis is performed on average values from each pair of replicates. Clustering and generation of a condition tree are performed using the Standard Correlation parameter within GeneSpring.

cDNA synthesis, reverse transcription and real-time polymerase chain reaction (PCR): RNA extracted from each sample in the previous step is used for the following experiment. RNA (5 µg per sample) is used to synthesize single-stranded complementary DNA (cDNA) using random hexamers and an avian myeloblastosis virus reverse transcriptase (Promega, Southampton, UK). The cDNA generated is used as a template in subsequent real-time PCR analyses. Transcript levels are determined by real-time PCR (Rotor Gene 3000, Corbett Research, Sydney, AUS) using SYBR Green PCR Master Mix Reagent (Qiagen, Crawley, UK). Cycling conditions are as follows: step 1: 15 min at 95° C.; step 2: 20 s at 94° C.; step 3: 20 s at 60° C.; step 4: 20 s at 72° C., with step 2 to step 4 repeated 45 times. The standard curves used to determine relative expression for each primer are obtained by running real-time PCR for a diluted sample, for example, to 1:1, 1:10, 1:100 and 1:1000. Gene expression is normalized to GAPDH.

Measurement of JNK activity in lung tissue: JNK activity is measured in the lung tissue, using a previously-published method (Eynott P. R. et al., *Immunology* 112: 446-453 (2004). Briefly, 30 µg of total lung protein per lane are separated through 12% denaturing-polyacrylamide gels and transferred to nitrocellulose membranes. The membranes are blocked with 5% non-fat dry milk in the following buffer (Tris 20 mM, pH 7.6, NaCl 140 mM and 0.1% Tween) and then incubated overnight with affinity-purified rabbit polyclonal antibodies, anti-non-phosphorylated c-jun anti-phosphoserine-63 (Cell Signaling Technology, Beverly, Mass., USA) and anti-phosphorylated c-jun (p-c-jun) (Cell Signaling Technology) as markers of JNK activity. Horseradish peroxidase-conjugated anti-rabbit (diluted to 1:2,000 from Cell Signalling Technology) is used as a secondary antibody and Enhanced Chemiluminescence (Amersham, Bucks, UK) reagent is used for detection. The bands, which are visualised by autoradiography, are quantified using a densitometer with Grab-It and GelWorks software (UVP, Cambridge, UK).

Data analysis: Data are presented as the mean±S.E.M. For multiple comparisons of different groups, the Kruskall-Wallis test for analysis of variance is used. The Dunn's test for comparison between two individual groups is then performed. A p value of less than 0.05 is accepted as significant.

The embodiments disclosed herein are not to be limited in scope by the specific embodiments disclosed in the examples which are intended as illustrations of a few aspects of the disclosed embodiments and any embodiments that are functionally equivalent are encompassed by the present disclosure. Indeed, various modifications of the embodiments disclosed herein are in addition to those shown and described herein will become apparent to those skilled in the art and are intended to fall within the scope of the appended claims.

A number of references have been cited, the disclosures of which are incorporated herein by reference in their entirety.

What is claimed is:

1. A method for inhibiting neutrophil accumulation in bronchoalveolar lavage fluid of a patient, comprising administering to a patient an effective amount of a compound having the formula (I):

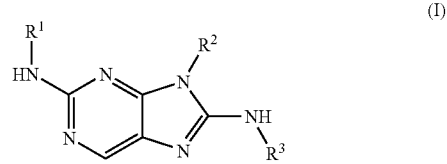

or a pharmaceutically acceptable salt thereof, wherein:

$R^1$ is substituted or unsubstituted $C_{1-6}$alkyl, substituted or unsubstituted $C_{3-10}$cycloalkyl or substituted or unsubstituted $C_{3-10}$heterocycle;

$R^2$ is substituted or unsubstituted $C_{3-10}$cycloalkyl or substituted or unsubstituted $C_{3-10}$heterocycle; and $R^3$ is aryl substituted with one or more halogens.

2. The method of claim 1, wherein $R^1$ is substituted or unsubstituted $C_{3-10}$cycloalkyl.

3. The method of claim 1, wherein $R^1$ is $C_{3-10}$cycloalkyl substituted with one or more $C_{1-6}$alkyl, hydroxy, hydroxyalkyl, alkoxy, alkoxyalkyl, amino, alkylamino, carboxy, aminocarbonyl, cyano, acylamino, alkanesulfonylamino, tetrazolyl, triazolyl or imidazolyl groups.

4. The method of claim 1, wherein $R^2$ is substituted or unsubstituted $C_{3-10}$cycloalkyl.

5. The method of claim 1, wherein $R^2$ is substituted or unsubstituted $C_{3-10}$heterocycle.

6. The method of claim 1, wherein $R^3$ is halogen substituted aryl.

7. The method of claim 6, wherein $R^3$ is fluoro substituted aryl.

* * * * *